US008987210B2

(12) United States Patent
Lillard, Jr.

(10) Patent No.: US 8,987,210 B2
(45) Date of Patent: Mar. 24, 2015

(54) CHEMOKINE-IMMUNOGLOBULIN FUSION POLYPEPTIDES, COMPOSITIONS, METHOD OF MAKING AND USE THEREOF

(71) Applicant: Jyant Technologies, Marietta, GA (US)

(72) Inventor: James W. Lillard, Jr., Smyrna, GA (US)

(73) Assignee: Jyant Technologies, Inc., Marietta, GA (US)

( * ) Notice: Subject to any disclaimer, the term of this patent is extended or adjusted under 35 U.S.C. 154(b) by 0 days.

(21) Appl. No.: 13/962,401

(22) Filed: Aug. 8, 2013

(65) Prior Publication Data

US 2013/0315909 A1 Nov. 28, 2013

Related U.S. Application Data

(63) Continuation of application No. 13/962,110, filed on Aug. 8, 2013, now Pat. No. 8,796,422, which is a continuation-in-part of application No. 13/480,526, filed on May 25, 2012, now Pat. No. 8,541,564.

(60) Provisional application No. 61/492,260, filed on Jun. 1, 2011.

(51) Int. Cl.

| | |
|---|---|
| ***A61K 38/00*** | (2006.01) |
| ***A61K 38/16*** | (2006.01) |
| ***C07K 1/00*** | (2006.01) |
| ***C07K 16/28*** | (2006.01) |
| ***C07K 14/52*** | (2006.01) |

(52) U.S. Cl.

CPC ............. *C07K 16/2866* (2013.01); *A61K 38/00* (2013.01); *C07K 2319/30* (2013.01); *C07K 14/521* (2013.01)

USPC ......... 514/19.4; 514/19.3; 514/21.2; 530/351

(58) Field of Classification Search

None

See application file for complete search history.

(56) References Cited

U.S. PATENT DOCUMENTS

| | | | | |
|---|---|---|---|---|
| 5,766,897 | A | 6/1998 | Braxton | |
| 7,279,460 | B2 * | 10/2007 | Wang et al. | 424/94.61 |
| 2005/0053579 | A1 | 3/2005 | Galipeau et al. | |
| 2007/0036750 | A1 * | 2/2007 | Chou et al. | 424/85.1 |
| 2007/0116669 | A1 | 5/2007 | Merzouk et al. | |
| 2009/0098101 | A1 | 4/2009 | Raines et al. | |
| 2010/0196406 | A1 | 8/2010 | Karin et al. | |

OTHER PUBLICATIONS

Nextprot Beta, CCL25—C—C motif chemokine 25, 2011.*

The International Search Report and the Written Opinion of the International Searching Authority (Application No. PCT/US2012/039550, International Filing Date: May 25, 2012), mailed Dec. 18, 2012.

Biragyn, A. et al., "Mediators of Innate Immunity That Target Immature, But Not Mature, Dendritic Cells Induce Antitumor Immunity When Genetically Fused with Nonimmunogenic Tumor Antigens", The Journal of Immunology, Dec. 1, 2001, vol. 167, No. 11, pp. 6644-6653.

Fagète, S., et al., "Specificity tuning of antibody fragments to neutralize two human chemokines with a single agent", MAbs, May-Jun. 2009, vol. 1, No. 3, pp. 288-296.

Van Heeke, G., et al., "Expression of Human Asparagine Synthetase in *Escherichia coli*," The Journal of Biological Chemistry, vol. 264, No. 10, Apr. 5, 1989, pp. 5503-5509.

Allen, S.J., et al., "Chemokine: Receptor Structure, Interactions, and Antagonism," Annu. Rev. Immunol., 2007. 25: 787-820.

File history of U.S. Appl. No. 13/480,526, filed May 25, 2012.

* cited by examiner

*Primary Examiner* — Shulamith H Shafer

(74) *Attorney, Agent, or Firm* — Ping Wang; Andrews Kurth LLP

(57) ABSTRACT

This application is directed to chemokine-immunoglobulin fusion polypeptides and chemokine-polymer conjugates. The fusion polypeptides and conjugates can be used for treating chemokine receptor-mediated disorders and modulating inflammation, inflammatory cell motility, cancer cell motility, or cancer cell survival.

18 Claims, 70 Drawing Sheets

FIG.1A
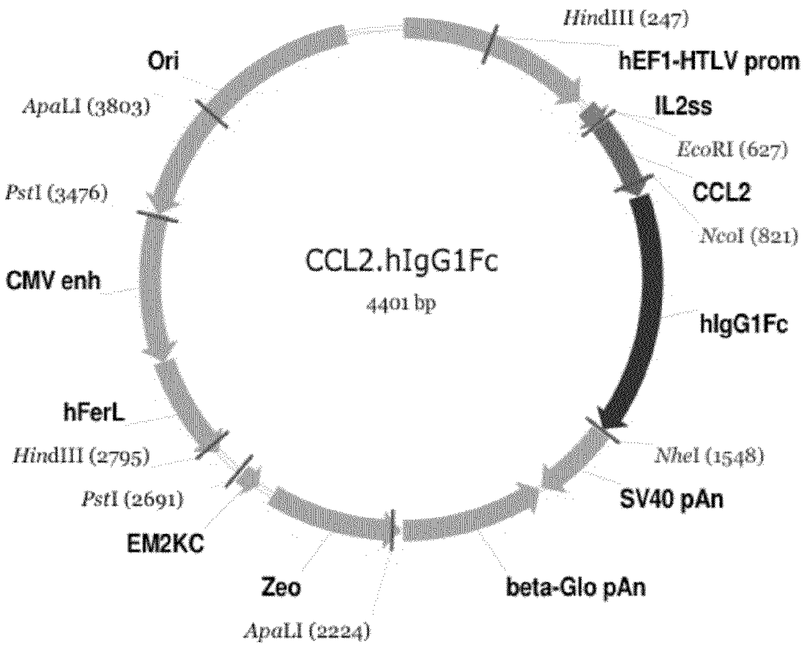
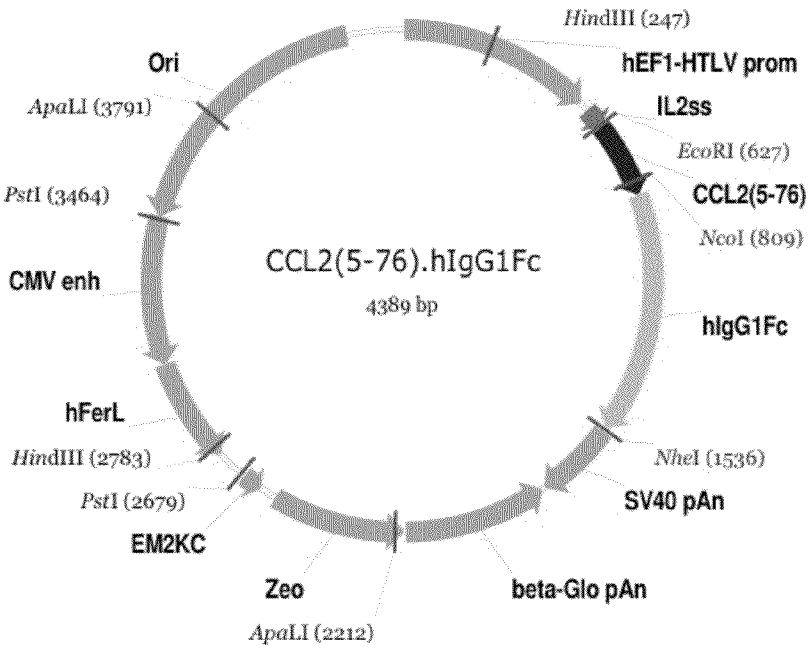
FIG.1B

FIG.1C

IL2ss.CCL2.hIgG1Fc GAGless plasmid sequence

```
1     GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                          KasI
                                          NarI
                                          SfoI
                                          BbeI
                                         ~~~~~~~                                  IL-2 secretion signal (SEQ ID NO:106)
                                                                                   MetTyrArg MetGlnLeu LeuSerCysIle
501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                            EcoRI
                            ~~~~~~~ CCL2 (1-76)
        AlaLeuSer LeuAlaLeu ValThrAsnSer GlnProAsp AlaIleAsn AlaProValThr CysCysTyr AsnPheThr AsnArgLysIle SerValGln
601   TTGCACTAAG TCTTGCACTT GTCACGAATT CGCAGCCAGA TGCAATCAAT GCCCCAGTCA CCTGCTGTTA TAACTTCACC AATAGGAAGA TCTCAGTGCA
       ArgLeuAla SerTyrArgArg IleThrSer SerLysCys ProLysGluAla ValIlePhe LysThrIle ValAlaLysGlu IleCysAla AspProLys
701   GAGGCTCGCG AGCTATAGAA GAATCACCAG CAGCAAGTGT CCCAAAGAAG CTGTGATCTT CAAGACCATT GTGCCAAGG AGATCTGTGC TGACCCCAAG
                                                                   human IgG1 Fc (constant region)
      GlnLysTrpVal GlnAspSer MetAspHis LeuAspLysGln ThrGlnThr ProLysThr AspLysThrHis ThrCysPro ProCysPro AlaProGluLeu
801   CAGAAGTGGG TTCAGGATTC CATGGACCAC CTGGACAAGC AAACCCAAAC TCCGAAGACT GACAAAACTC ACACATGCCC ACCGTGCCCA GCACCTGAAC
        LeuGlyGly ProSerVal PheLeuPhePro ProLysPro LysAspThr LeuMetIleSer ArgThrPro GluValThr CysValValVal AspValSer
901   TCCTGGGGGG ACCGTCAGTC TTCCTCTTCC CCCCAAAACC CAAGGACACC CTCATGATCT CCCGGACCCC TGAGGTCACA TGCGTGGTGG TGGACGTGAG
       HisGluAsp ProGluValLys PheAsnTrp TyrValAsp GlyValGluVal HisAsnAla LysThrLys ProArgGluGlu GlnTyrAsn SerThrTyr
1001  CCACGAAGAC CCTGAGGTCA AGTTCAACTG GTACGTGGAC GGCGTGGAGG TGCATAATGC CAAGACAAAG CCGCGGGAGG AGCAGTACAA CAGCACGTAC
      ArgValValSer ValLeuThr ValLeuHis GlnAspTrpLeu AsnGlyLys GluTyrLys CysLysValSer AsnLysAla LeuProAla ProIleGluLys
1101  CGTGTGGTCA GCGTCCTCAC CGTCCTGCAC CAGGACTGGC TGAATGGCAA GGAGTACAAG TGCAAGGTCT CCAACAAAGC CCTCCCAGCC CCCATCGAGA
        ThrIleSer LysAlaLys GlyGlnProArg GluProGln ValTyrThr LeuProProSer ArgGluGlu MetThrLys AsnGlnValSer LeuThrCys
1201  AAACCATCTC CAAAGCCAAA GGGCAGCCCC GAGAACCACA GGTGTACACC CTGCCCCCAT CCCGGGAGGA GATGACCAAG AACCAGGTCA GCCTGACCTG
       LeuValLys GlyPheTyrPro SerAspIle AlaValGlu TrpGluSerAsn GlyGlnPro GluAsnAsn TyrLysThrThr ProProVal LeuAspSer
1301  CCTGGTCAAA GGCTTCTATC CCAGCGACAT CGCCGTGGAG TGGGAGAGCA ATGGGCAGCC GGAGAACAAC TACAAGACCA CGCCTCCCGT GCTGGACTCC
      AspGlySerPhe PheLeuTyr SerLysLeu ThrValAspLys SerArgTrp GlnGlnGly AsnValPheSer CysSerVal MetHisGlu AlaLeuHisAsn
1401  GACGGCTCCT TCTTCCTCTA CAGCAAGCTC ACCGTGGACA AGAGCAGGTG GCAGCAGGGG AACGTCTTCT CATGCTCCGT GATGCACGAG GCTCTGCACA
                                                        BmtI
                                                        NheI
        HisTyrThr GlnLysSer LeuSerLeuSer ProGlyLys ***(SEQ ID NO: 52)
1501  ACCACTACAC GCAGAAGAGC CTCTCCCTGT CTCCGGGTAA ATGAGTGCTA GCTGGCCAGA CATGATAAGA TACATTGATG AGTTTGGACA AACCACAACT
1601  AGAATGCAGT GAAAAAAATG CTTTATTTGT GAAATTTGTG ATGCTATTGC TTTATTTGTA ACCATTATAA GCTGCAATAA ACAAGTTAAC AACAACAATT
                                                                                                AseI
1701  GCATTCATTT TATGTTTCAG GTTCAGGGGG AGGTGTGGGA GGTTTTTTAA AGCAAGTAAA ACCTCTACAA ATGTGGTATG GAATTAATTC TAAAATACAG
1801  CATAGCAAAA CTTTAACCTC CAAATCAAGC CTCTACTTGA ATCCTTTTCT GAGGGATGAA TAAGGCATAG GCATCAGGGG CTGTTGCCAA TGTGCATTAG
```

```
1901   CTGTTTGCAG CCTCACCTTC TTTCATGGAG TTTAAGATAT AGTGTATTTT CCCAAGGTTT GAACTAGCTC TTCATTTCTT TATGTTTTAA ATGCACTGAC
2001   CTCCCACATT CCCTTTTTAG TAAAATATTC AGAAATAATT TAAATACATC ATTGCAATGA AAATAAATGT TTTTTATTAG GCAGAATCCA GATGCTCAAG
2101   GCCCTTCATA ATATCCCCCA GTTTAGTAGT TGGACTTAGG GAACAAAGGA ACCTTTAATA GAAATTGGAC AGCAAGAAAG CGAGCTTCTA GCTTATCCTC
2201   AGTCCTGCTC CTCTGCCACA AAGTGCACGC AGTTGCCGGC CGGGTCGCGC AGGGCGAACT CCCGCCCCCA CGGCTGCTCG CCGATCTCGG TCATGGCCGG
2301   CCCGGAGGCG TCCCGGAAGT TCGTGGACAC GACCTCCGAC CACTCGGCGT ACAGCTCGTC CAGGCCGCGC ACCCACACCC AGGCCAGGGT GTTGTCCGGC
2401   ACCACCTGGT CCTGGACCGC GCTGATGAAC AGGGTCACGT CGTCCCGGAC CACACCGGCG AAGTCGTCCT CCACGAAGTC CCGGGAGAAC CCGAGCCGGT
2501   CGGTCCAGAA CTCGACCGCT CCGGCGACGT CGCGCGCGGT GAGCACCGGA ACGGCACTGG TCAACTTGGC CATGATGGCT CCTCCTGTCA GGAGAGGAAA
                                                                                AseI
                                                                               ~~~~~~~
2601   GAGAAGAAGG TTAGTACAAT TGCTATAGTG AGTTGTATTA TACTATGCAG ATATACTATG CCAATGATTA ATTGTCAAAC TAGGGCTGCA GGGTTCATAG
2701   TGCCACTTTT CCTGCACTGC CCCATCTCCT GCCCACCCTT TCCCAGGCAT AGACAGTCAG TGACTTACCA AACTCACAGG AGGGAGAAGG CAGAAGCTTG
2801   AGACAGACCC GCGGGACCGC CGAACTGCGA GGGGACGTGG CTAGGGCGGC TTCTTTTATG GTGCGCCGGC CCTCGGAGGC AGGGCGCTCG GGGAGGCCTA
2901   GCGGCCAATC TGCGGTGGCA GGAGGCGGGG CCGAAGGCCG TGCCTGACCA ATCCGGAGCA CATAGGAGTC TCAGCCCCCC GCCCCAAAGC AAGGGGAAGT
3001   CACGCGCCTG TAGCGCCAGC GTGTTGTGAA ATGGGGGCTT GGGGGGGTTG GGGCCCTGAC TAGTCAAAAC AAACTCCCAT TGACGTCAAT GGGGTGGAGA
3101   CTTGGAAATC CCCGTGAGTC AAACCGCTAT CCACGCCCAT TGATGTACTG CCAAAACCGC ATCATCATGG TAATAGCGAT GACTAATACG TAGATGTACT
3201   GCCAAGTAGG AAAGTCCCAT AAGGTCATGT ACTGGGCATA ATGCCAGGCG GGCCATTTAC CGTCATTGAC GTCAATAGGG GGCGTACTTG GCATATGATA
3301   CACTTGATGT ACTGCCAAGT GGGCAGTTTA CCGTAAATAC TCCACCCATT GACGTCAATG GAAAGTCCCT ATTGGCGTTA CTATGGGAAC ATACGTCATT
3401   ATTGACGTCA ATGGGCGGGG GTCGTTGGGC GGTCAGCCAG GCGGGCCATT TACCGTAAGT TATGTAACGC CTGCAGGTTA ATTAAGAACA TGTGAGCAAA
3501   AGGCCAGCAA AAGGCCAGGA ACCGTAAAAA GGCCGCGTTG CTGGCGTTTT TCCATAGGCT CCGCCCCCCT GACGAGCATC ACAAAAATCG ACGCTCAAGT
3601   CAGAGGTGGC GAAACCCGAC AGGACTATAA AGATACCAGG CGTTTCCCCC TGGAAGCTCC CTCGTGCGCT CTCCTGTTCC GACCCTGCCG CTTACCGGAT
3701   ACCTGTCCGC CTTTCTCCCT TCGGGAAGCG TGGCGCTTTC TCATAGCTCA CGCTGTAGGT ATCTCAGTTC GGTGTAGGTC GTTCGCTCCA AGCTGGGCTG
3801   TGTGCACGAA CCCCCCGTTC AGCCCGACCG CTGCGCCTTA TCCGGTAACT ATCGTCTTGA GTCCAACCCG GTAAGACACG ACTTATCGCC ACTGGCAGCA
3901   GCCACTGGTA ACAGGATTAG CAGAGCGAGG TATGTAGGCG GTGCTACAGA GTTCTTGAAG TGGTGGCCTA ACTACGGCTA CACTAGAAGA ACAGTATTTG
4001   GTATCTGCGC TCTGCTGAAG CCAGTTACCT TCGGAAAAAG AGTTGGTAGC TCTTGATCCG GCAAACAAAC CACCGCTGGT AGCGGTGGTT TTTTTGTTTG
4101   CAAGCAGCAG ATTACGCGCA GAAAAAAAGG ATCTCAAGAA GATCCTTTGA TCTTTTCTAC GGGGTCTGAC GCTCAGTGGA ACGAAAACTC ACGTTAAGGG
4201   ATTTTGGTCA TGGCTAGTTA ATTAACATTT AAATCAGCGG CCGCAATAAA ATATCTTTAT TTTCATTACA TCTGTGTGTT GGTTTTTTGT GTGAATCGTA
4301   ACTAACATAC GCTCTCCATC AAAACAAAAC GAAACAAAAC AAACTAGCAA AATAGGCTGT CCCCAGTGCA AGTGCAGGTG CCAGAACATT TCTCTATCGA
4401   A (SEQ ID NO: 79)
```

IL2ss.CCL2(5-76).hIgG1Fc GAGless plasmid sequence

```
 1     GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                           KasI
                                           NarI
                                           SfoI
                                           BbeI
                                          ~~~~~~~                                  IL-2 secretion signal
                                                                                   MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                EcoRI
                                ~~~~~~  CCL2(5-76
        AlaLeuSer LeuAlaLeu ValThrAsnSer IleAsnAla ProValThr CysCysTyrAsn PheThrAsn ArgLysIle SerValGlnArg LeuAlaSer
 601   TTGCACTAAG TCTTGCACTT GTCACGAATT CGATCAATGC CCCAGTCACC TGCTGTTATA ACTTCACCAA TAGGAAGATC TCAGTGCAGA GGCTCGCGAG
       TyrArgArg IleThrSerSer LysCysPro LysGluAla ValIlePheLys ThrIleVal AlaLysGlu IleCysAlaAsp ProLysGln LysTrpVal
 701   CTATAGAAGA ATCACCAGCA GCAAGTGTCC CAAAGAAGCT GTGATCTTCA AGACCATTGT GGCCAAGGAG ATCTGTGCTG ACCCCAAGCA GAAGTGGGTT
                                                        human IgG1 Fc (constant region)
      GlnAspSerMet AspHisLeu AspLysGln ThrGlnThrPro LysThrAsp LysThrHis ThrCysProPro CysProAla ProGluLeu LeuGlyGlyPro
 801   CAGGATTCCA TGGACCACCT GGACAAGCAA ACCCAAACTC CGAAGACTGA CAAAACTCAC ACATGCCCAC CGTGCCCAGC ACCTGAACTC CTGGGGGGAC
        SerValPhe LeuPhePro ProLysProLys AspThrLeu MetIleSer ArgThrProGlu ValThrCys ValValVal AspValSerHis GluAspPro
 901   CGTCAGTCTT CCTCTTCCCC CCAAAACCCA AGGACACCCT CATGATCTCC CGGACCCCTG AGGTCACATG CGTGGTGGTG GACGTGAGCC ACGAAGACCC
       GluValLys PheAsnTrpTyr ValAspGly ValGluVal HisAsnAlaLys ThrLysPro ArgGluGlu GlnTyrAsnSer ThrTyrArg ValValSer
 1001  TGAGGTCAAG TTCAACTGGT ACGTGGACGG CGTGGAGGTG CATAATGCCA AGACAAAGCC GCGGGAGGAG CAGTACAACA GCACGTACCG TGTGGTCAGC
      ValLeuThrVal LeuHisGln AspTrpLeu AsnGlyLysGlu TyrLysCys LysValSer AsnLysAlaLeu ProAlaPro IleGluLys ThrIleSerLys
 1101  GTCCTCACCG TCCTGCACCA GGACTGGCTG AATGGCAAGG AGTACAAGTG CAAGGTCTCC AACAAAGCCC TCCCAGCCCC CATCGAGAAA ACCATCTCCA
        AlaLysGly GlnProArg GluProGlnVal TyrThrLeu ProProSer ArgGluGluMet ThrLysAsn GlnValSer LeuThrCysLeu ValLysGly
 1201  AAGCCAAAGG GCAGCCCCGA GAACCACAGG TGTACACCCT GCCCCCATCC CGGGAGGAGA TGACCAAGAA CCAGGTCAGC CTGACCTGCC TGGTCAAAGG
        PheTyrPro SerAspIleAla ValGluTrp GluSerAsn GlyGlnProGlu AsnAsnTyr LysThrThr ProProValLeu AspSerAsp GlySerPhe
 1301  CTTCTATCCC AGCGACATCG CCGTGGAGTG GGAGAGCAAT GGGCAGCCGG AGAACAACTA CAAGACCACG CCTCCCGTGC TGGACTCCGA CGGCTCCTTC
      PheLeuTyrSer LysLeuThr ValAspLys SerArgTrpGln GlnGlyAsn ValPheSer CysSerValMet HisGluAla LeuHisAsn HisTyrThrGln
 1401  TTCCTCTACA GCAAGCTCAC CGTGGACAAG AGCAGGTGGC AGCAGGGGAA CGTCTTCTCA TGCTCCGTGA TGCACGAGGC TCTGCACAAC CACTACACGC
                                           BmtI
                                           NheI
        LysSerLeu SerLeuSer ProGlyLys***(SEQ ID NO:  53)
 1501  AGAAGAGCCT CTCCCTGTCT CCGGGTAAAT GAGTGCTAGC TGGCCAGACA TGATAAGATA CATTGATGAG TTTGGACAAA CCACAACTAG AATGCAGTGA
 1601  AAAAAATGCT TTATTTGTGA AATTTGTGAT GCTATTGCTT TATTTGTAAC CATTATAAGC TGCAATAAAC AAGTTAACAA CAACAATTGC ATTCATTTTA
                                                                                 AseI
 1701  TGTTTCAGGT TCAGGGGGAG GTGTGGGAGG TTTTTTAAAG CAAGTAAAAC CTCTACAAAT GTGGTATGGA ATTAATTCTA AAATACAGCA TAGCAAAACT
 1801  TTAACCTCCA AATCAAGCCT CTACTTGAAT CCTTTTCTGA GGGATGAATA AGGCATAGGC ATCAGGGGCT GTTGCCAATG TGCATTAGCT GTTTGCAGCC
```

```
1901   TCACCTTCTT TCATGGAGTT TAAGATATAG TGTATTTTCC CAAGGTTTGA ACTAGCTCTT CATTTCTTTA TGTTTTAAAT GCACTGACCT CCCACATTCC
2001   CTTTTTAGTA AAATATTCAG AAATAATTTA AATACATCAT TGCAATGAAA ATAAATGTTT TTTATTAGGC AGAATCCAGA TGCTCAAGGC CCTTCATAAT

2101   ATCCCCCAGT TTAGTAGTTG GACTTAGGGA ACAAAGGAAC CTTTAATAGA AATTGGACAG CAAGAAAGCG AGCTTCTAGC TTATCCTCAG TCCTGCTCCT
2201   CTGCCACAAA GTGCACGCAG TTGCCGGCCG GGTCGCGCAG GGCGAACTCC CGCCCCCACG GCTGCTCGCC GATCTCGGTC ATGGCCGGCC CGGAGGCGTC
2301   CCGGAAGTTC GTGGACACGA CCTCCGACCA CTCGGCGTAC AGCTCGTCCA GGCCGCGCAC CCACACCCAG GCCAGGGTGT TGTCCGGCAC CACCTGGTCC
2401   TGGACCGCGC TGATGAACAG GGTCACGTCG TCCCGGACCA CACCGGCGAA GTCGTCCTCC ACGAAGTCCC GGGAGAACCC GAGCCGGTCG GTCCAGAACT
2501   CGACCGCTCC GGCGACGTCG CGCGCGGTGA GCACCGGAAC GGCACTGGTC AACTTGGCCA TGATGGCTCC TCCTGTCAGG AGAGGAAAGA GAAGAAGGTT
                                                                          AseI
2601   AGTACAATTG CTATAGTGAG TTGTATTATA CTATGCAGAT ATACTATGCC AATGATTAAT TGTCAAACTA GGGCTGCAGG GTTCATAGTG CCACTTTTCC
2701   TGCACTGCCC CATCTCCTGC CCACCCTTTC CCAGGCATAG ACAGTCAGTG ACTTACCAAA CTCACAGGAG GGAGAAGGCA GAAGCTTGAG ACAGACCCGC
2801   GGGACCGCCG AACTGCGAGG GGACGTGGCT AGGGCGGCTT CTTTTATGGT GCGCCGGCCC TCGGAGGCAG GGCGCTCGGG GAGGCCTAGC GGCCAATCTG
2901   CGGTGGCAGG AGGCGGGGCC GAAGGCCGTG CCTGACCAAT CCGGAGCACA TAGGAGTCTC AGCCCCCCGC CCCAAAGCAA GGGGAAGTCA CGCGCCTGTA
3001   GCGCCAGCGT GTTGTGAAAT GGGGGCTTGG GGGGGTTGGG GCCCTGACTA GTCAAAACAA ACTCCCATTG ACGTCAATGG GGTGGAGACT TGGAAATCCC
3101   CGTGAGTCAA ACCGCTATCC ACGCCCATTG ATGTACTGCC AAAACCGCAT CATCATGGTA ATAGCGATGA CTAATACGTA GATGTACTGC CAAGTAGGAA
3201   AGTCCCATAA GGTCATGTAC TGGGCATAAT GCCAGGCGGG CCATTTACCG TCATTGACGT CAATAGGGGG CGTACTTGGC ATATGATACA CTTGATGTAC
3301   TGCCAAGTGG GCAGTTTACC GTAAATACTC CACCCATTGA CGTCAATGGA AAGTCCCTAT TGGCGTTACT ATGGGAACAT ACGTCATTAT TGACGTCAAT
3401   GGGCGGGGGT CGTTGGGCGG TCAGCCAGGC GGGCCATTTA CCGTAAGTTA TGTAACGCCT GCAGGTTAAT TAAGAACATG TGAGCAAAAG GCCAGCAAAA
3501   GGCCAGGAAC CGTAAAAAGG CCGCGTTGCT GGCGTTTTTC CATAGGCTCC GCCCCCCTGA CGAGCATCAC AAAAATCGAC GCTCAAGTCA GAGGTGGCGA
3601   AACCCGACAG GACTATAAAG ATACCAGGCG TTTCCCCCTG GAAGCTCCCT CGTGCGCTCT CCTGTTCCGA CCCTGCCGCT TACCGGATAC CTGTCCGCCT
3701   TTCTCCCTTC GGGAAGCGTG GCGCTTTCTC ATAGCTCACG CTGTAGGTAT CTCAGTTCGG TGTAGGTCGT TCGCTCCAAG CTGGGCTGTG TGCACGAACC
3801   CCCCGTTCAG CCCGACCGCT GCGCCTTATC CGGTAACTAT CGTCTTGAGT CCAACCCGGT AAGACACGAC TTATCGCCAC TGGCAGCAGC CACTGGTAAC
3901   AGGATTAGCA GAGCGAGGTA TGTAGGCGGT GCTACAGAGT TCTTGAAGTG GTGGCCTAAC TACGGCTACA CTAGAAGAAC AGTATTTGGT ATCTGCGCTC
4001   TGCTGAAGCC AGTTACCTTC GGAAAAAGAG TTGGTAGCTC TTGATCCGGC AAACAAACCA CCGCTGGTAG CGGTGGTTTT TTTGTTTGCA AGCAGCAGAT
4101   TACGCGCAGA AAAAAAGGAT CTCAAGAAGA TCCTTTGATC TTTTCTACGG GGTCTGACGC TCAGTGGAAC GAAAACTCAC GTTAAGGGAT TTTGGTCATG
4201   GCTAGTTAAT TAACATTTAA ATCAGCGGCC GCAATAAAAT ATCTTTATTT TCATTACATC TGTGTGTTGG TTTTTTGTGT GAATCGTAAC TAACATACGC
4301   TCTCCATCAA AACAAAACGA AACAAAACAA ACTAGCAAAA TAGGCTGTCC CCAGTGCAAG TGCAGGTGCC AGAACATTTC TCTATCGAA (SEQ ID NO: 80)
```

IL2ss.CCL2(5-76).hIgG1Fc sequence [Alanine substitutions for removal of GAG binding sites – Lys & His]

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                          KasI
                                          NarI
                                          SfoI
                                          BbeI
                                         ~~~~~~~                                    IL-2 secretion signal
                                                                                    MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                              EcoRI
                              ~~~~~~  CCL2(5-76
        AlaLeuSer LeuAlaLeu ValThrAsnSer IleAsnAla ProValThr CysCysTyrAsn PheThrAsn ArgLysIle SerValGlnArg LeuAlaSer
 601   TTGCACTAAG TCTTGCACTT GTCACGAATT CGATCAATGC CCCAGTCACC TGCTGTTATA ACTTCACCAA TAGGAAGATC TCAGTGCAGA GGCTCGCGAG
       TyrArgArg IleThrSerSer LysCysPro LysGluAla ValIlePheLys ThrIleVal AlaAlaGlu IleCysAlaAsp ProAlaGln AlaTrpVal
 701   CTATAGAAGA ATCACCAGCA GCAAGTGTCC CAAAGAAGCT GTGATCTTCA AGACCATTGT GGCCgcgGAG ATCTGTGCTG ACCCCgctCA GgccTGGGTT
                                                            human IgG1 Fc (constant region)
       GlnAspSerMet AspAlaLeu AspAlaGln ThrGlnThrPro AlaThrAsp LysThrHis ThrCysProPro CysProAla ProGluLeu LeuGlyGlyPro
 801   CAGGATTCCA TGGACgctCT GGACgccCAA ACCCAAACTC CGgcgACTGA CAAAACTCAC ACATGCCCAC CGTGCCCAGC ACCTGAACTC CTGGGGGGAC
        SerValPhe LeuPhePro ProLysProLys AspThrLeu MetIleSer ArgThrProGlu ValThrCys ValValVal AspValSerHis GluAspPro
 901   CGTCAGTCTT CCTCTTCCCC CCAAAACCCA AGGACACCCT CATGATCTCC CGGACCCCTG AGGTCACATG CGTGGTGGTG GACGTGAGCC ACGAAGACCC
        GluValLys PheAsnTrpTyr ValAspGly ValGluVal HisAsnAlaLys ThrLysPro ArgGluGlu GlnTyrAsnSer ThrTyrArg ValValSer
1001   TGAGGTCAAG TTCAACTGGT ACGTGGACGG CGTGGAGGTG CATAATGCCA AGACAAAGCC GCGGGAGGAG CAGTACAACA GCACGTACCG TGTGGTCAGC
       ValLeuThrVal LeuHisGln AspTrpLeu AsnGlyLysGlu TyrLysCys LysValSer AsnLysAlaLeu ProAlaPro IleGluLys ThrIleSerLys
1101   GTCCTCACCG TCCTGCACCA GGACTGGCTG AATGGCAAGG AGTACAAGTG CAAGGTCTCC AACAAAGCCC TCCCAGCCCC CATCGAGAAA ACCATCTCCA
        AlaLysGly GlnProArg GluProGlnVal TyrThrLeu ProProSer ArgGluGluMet ThrLysAsn GlnValSer LeuThrCysLeu ValLysGly
1201   AAGCCAAAGG GCAGCCCCGA GAACCACAGG TGTACACCCT GCCCCCATCC CGGGAGGAGA TGACCAAGAA CCAGGTCAGC CTGACCTGCC TGGTCAAAGG
        PheTyrPro SerAspIleAla ValGluTrp GluSerAsn GlyGlnProGlu AsnAsnTyr LysThrThr ProProValLeu AspSerAsp GlySerPhe
1301   CTTCTATCCC AGCGACATCG CCGTGGAGTG GGAGAGCAAT GGGCAGCCGG AGAACAACTA CAAGACCACG CCTCCCGTGC TGGACTCCGA CGGCTCCTTC
       PheLeuTyrSer LysLeuThr ValAspLys SerArgTrpGln GlnGlyAsn ValPheSer CysSerValMet HisGluAla LeuHisAsn HisTyrThrGln
1401   TTCCTCTACA GCAAGCTCAC CGTGGACAAG AGCAGGTGGC AGCAGGGGAA CGTCTTCTCA TGCTCCGTGA TGCACGAGGC TCTGCACAAC CACTACACGC
                                          BmtI
                                          NheI
        LysSerLeu SerLeuSer ProGlyLys***(SEQ ID NO: 54)
1501   AGAAGAGCCT CTCCCTGTCT CCGGGTAAAT GAGTGCTAGC TGGCCAGACA TGATAAGATA CATTGATGAG TTTGGACAAA CCACAACTAG AATGCAGTGA
1601   AAAAAATGCT TTATTTGTGA AATTTGTGAT GCTATTGCTT TATTTGTAAC CATTATAAGC TGCAATAAAC AAGTTAACAA CAACAATTGC ATTCATTTTA
                                                                                    AseI
1701   TGTTTCAGGT TCAGGGGGAG GTGTGGGAGG TTTTTTAAAG CAAGTAAAAC CTCTACAAAT GTGGTATGGA ATTAATTCTA AAATACAGCA TAGCAAAACT
1801   TTAACCTCCA AATCAAGCCT CTACTTGAAT CCTTTTCTGA GGGATGAATA AGGCATAGGC ATCAGGGGCT GTTGCCAATG TGCATTAGCT GTTTGCAGCC
```

```
1901  TCACCTTCTT TCATGGAGTT TAAGATATAG TGTATTTTCC CAAGGTTTGA ACTAGCTCTT CATTTCTTTA TGTTTTAAAT GCACTGACCT CCCACATTCC
2001  CTTTTTAGTA AAATATTCAG AAATAATTTA AATACATCAT TGCAATGAAA ATAAATGTTT TTTATTAGGC AGAATCCAGA TGCTCAAGGC CCTTCATAAT
2101  ATCCCCCAGT TTAGTAGTTG GACTTAGGGA ACAAAGGAAC CTTTAATAGA AATTGGACAG CAAGAAAGCG AGCTTCTAGC TTATCCTCAG TCCTGCTCCT
2201  CTGCCACAAA GTGCACGCAG TTGCCGGCCG GGTCGCGCAG GGCGAACTCC CGCCCCCACG GCTGCTCGCC GATCTCGGTC ATGGCCGGCC CGGAGGCGTC
2301  CCGGAAGTTC GTGGACACGA CCTCCGACCA CTCGGCGTAC AGCTCGTCCA GGCCGCGCAC CCACACCCAG GCCAGGGTGT TGTCCGGCAC CACCTGGTCC
2401  TGGACCGCGC TGATGAACAG GGTCACGTCG TCCCGGACCA CACCGGCGAA GTCGTCCTCC ACGAAGTCCC GGGAGAACCC GAGCCGGTCG GTCCAGAACT
2501  CGACCGCTCC GGCGACGTCG CGCGCGGTGA GCACCGGAAC GGCACTGGTC AACTTGGCCA TGATGGCTCC TCCTGTCAGG AGAGGAAAGA GAAGAAGGTT
                                                                    AseI
2601  AGTACAATTG CTATAGTGAG TTGTATTATA CTATGCAGAT ATACTATGCC AATGATTAAT TGTCAAACTA GGGCTGCAGG GTTCATAGTG CCACTTTTCC
2701  TGCACTGCCC CATCTCCTGC CCACCCTTTC CCAGGCATAG ACAGTCAGTG ACTTACCAAA CTCACAGGAG GGAGAAGGCA GAAGCTTGAG ACAGACCCGC
2801  GGGACCGCCG AACTGCGAGG GGACGTGGCT AGGGCGGCTT CTTTTATGGT GCGCCGGCCC TCGGAGGCAG GGCGCTCGGG GAGGCCTAGC GGCCAATCTG
2901  CGGTGGCAGG AGGCGGGGCC GAAGGCCGTG CCTGACCAAT CCGGAGCACA TAGGAGTCTC AGCCCCCCGC CCCAAAGCAA GGGGAAGTCA CGCGCCTGTA
3001  GCGCCAGCGT GTTGTGAAAT GGGGGCTTGG GGGGGTTGGG GCCCTGACTA GTCAAAACAA ACTCCCATTG ACGTCAATGG GGTGGAGACT TGGAAATCCC
3101  CGTGAGTCAA ACCGCTATCC ACGCCCATTG ATGTACTGCC AAAACCGCAT CATCATGGTA ATAGCGATGA CTAATACGTA GATGTACTGC CAAGTAGGAA
3201  AGTCCCATAA GGTCATGTAC TGGGCATAAT GCCAGGCGGG CCATTTACCG TCATTGACGT CAATAGGGGG CGTACTTGGC ATATGATACA CTTGATGTAC
3301  TGCCAAGTGG GCAGTTTACC GTAAATACTC CACCCATTGA CGTCAATGGA AAGTCCCTAT TGGCGTTACT ATGGGAACAT ACGTCATTAT TGACGTCAAT
3401  GGGCGGGGGT CGTTGGGCGG TCAGCCAGGC GGGCCATTTA CCGTAAGTTA TGTAACGCCT GCAGGTTAAT TAAGAACATG TGAGCAAAAG GCCAGCAAAA
3501  GGCCAGGAAC CGTAAAAAGG CCGCGTTGCT GGCGTTTTTC CATAGGCTCC GCCCCCCTGA CGAGCATCAC AAAAATCGAC GCTCAAGTCA GAGGTGGCGA
3601  AACCCGACAG GACTATAAAG ATACCAGGCG TTTCCCCCTG GAAGCTCCCT CGTGCGCTCT CCTGTTCCGA CCCTGCCGCT TACCGGATAC CTGTCCGCCT
3701  TTCTCCCTTC GGGAAGCGTG GCGCTTTCTC ATAGCTCACG CTGTAGGTAT CTCAGTTCGG TGTAGGTCGT TCGCTCCAAG CTGGGCTGTG TGCACGAACC
3801  CCCCGTTCAG CCCGACCGCT GCGCCTTATC CGGTAACTAT CGTCTTGAGT CCAACCCGGT AAGACACGAC TTATCGCCAC TGGCAGCAGC CACTGGTAAC
3901  AGGATTAGCA GAGCGAGGTA TGTAGGCGGT GCTACAGAGT TCTTGAAGTG GTGGCCTAAC TACGGCTACA CTAGAAGAAC AGTATTTGGT ATCTGCGCTC
4001  TGCTGAAGCC AGTTACCTTC GGAAAAAGAG TTGGTAGCTC TTGATCCGGC AAACAAACCA CCGCTGGTAG CGGTGGTTTT TTTGTTTGCA AGCAGCAGAT
4101  TACGCGCAGA AAAAAAGGAT CTCAAGAAGA TCCTTTGATC TTTTCTACGG GGTCTGACGC TCAGTGGAAC GAAAACTCAC GTTAAGGGAT TTTGGTCATG
4201  GCTAGTTAAT TAACATTTAA ATCAGCGGCC GCAATAAAAT ATCTTTATTT TCATTACATC TGTGTGTTGG TTTTTTGTGT GAATCGTAAC TAACATACGC
4301  TCTCCATCAA AACAAAACGA AACAAAACAA ACTAGCAAAA TAGGCTGTCC CCAGTGCAAG TGCAGGTGCC AGAACATTTC TCTATCGAA (SEQ ID NO: 81)
```

FIG. 1E (CONT)

FIG.2A
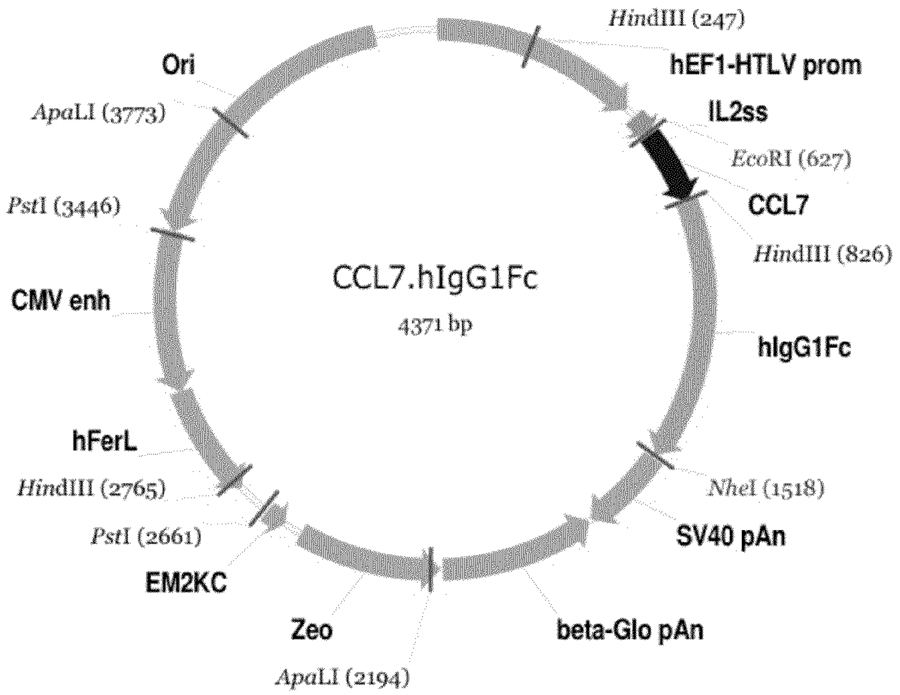
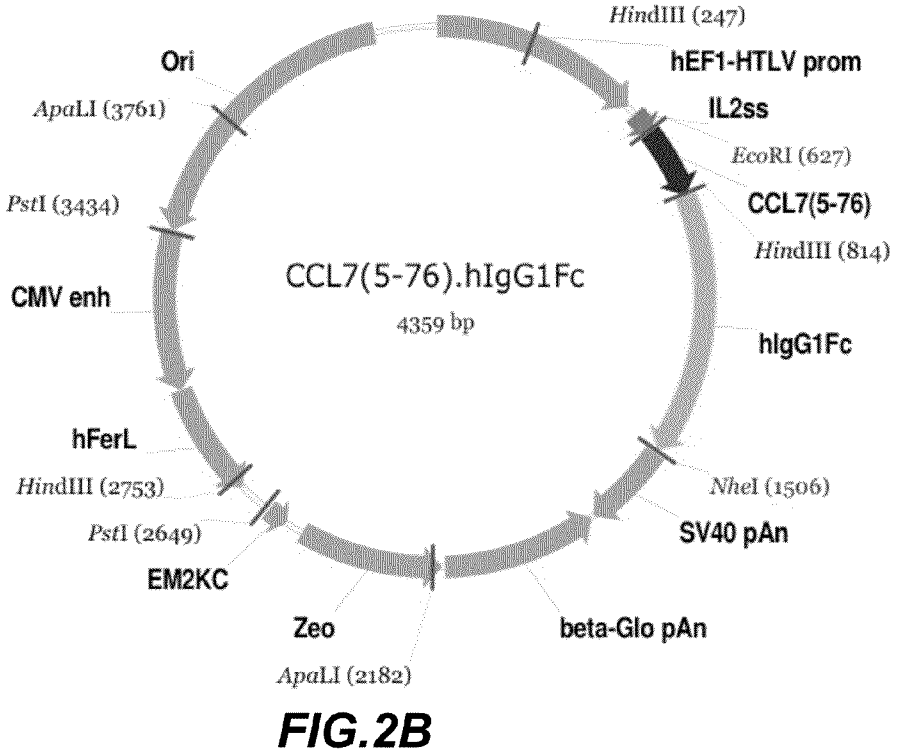
FIG.2B

FIG. 2C

IL2ss.CCL7.hIgG1Fc sequence

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                        KasI
                                        NarI
                                        SfoI
                                        BbeI
                                       ~~~~~~~                                       IL-2 secretion signal
                                                                                     MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                              EcoRI
                              ~~~~~~~ CCL7 (1-76)
        AlaLeuSer LeuAlaLeu ValThrAsnSer CysCysTyr ArgPheIle AsnLysLysIle ProLysGln ArgLeuGlu SerTyrArgArg ThrThrSer
 601   TTGCACTAAG TCTTGCACTT GTCACGAATT CGTGCTGCTA CAGATTTATC AATAAGAAAA TCCCTAAGCA GAGGCTGGAG AGCTACAGAA GGACCACCAG
        SerHisCys ProArgGluAla ValIlePhe LysThrLys LeuAspLysGlu IleCysAla AspProThr GlnLysTrpVal GlnAspPhe MetLysHis
 701   TAGCCACTGT CCCCGGGAAG CTGTAATCTT CAAGACCAAA CTGGACAAGG AGATCTGTGC TGACCCCACA CAGAAGTGGG TCCAGGACTT TATGAAGCAC
                                        human IgG1 Fc (constant region)
       LeuAspLysLys ThrGlnThr ProLysLeu AspLysThrHis ThrCysPro ProCysPro AlaProGluLeu LeuGlyGly ProSerVal PheLeuPhePro
 801   CTGGACAAGA AAACCCAAAC TCCAAAGCTT GACAAAACTC ACACATGCCC ACCGTGCCCA GCACCTGAAC TCCTGGGGGG ACCGTCAGTC TTCCTCTTCC
        ProLysPro LysAspThr LeuMetIleSer ArgThrPro GluValThr CysValValVal AspValSer HisGluAsp ProGluValLys PheAsnTrp
 901   CCCCAAAACC CAAGGACACC CTCATGATCT CCCGGACCCC TGAGGTCACA TGCGTGGTGG TGGACGTGAG CCACGAAGAC CCTGAGGTCA AGTTCAACTG
        TyrValAsp GlyValGluVal HisAsnAla LysThrLys ProArgGluGlu GlnTyrAsn SerThrTyr ArgValValSer ValLeuThr ValLeuHis
1001   GTACGTGGAC GGCGTGGAGG TGCATAATGC CAAGACAAAG CCGCGGGAGG AGCAGTACAA CAGCACGTAC CGTGTGGTCA GCGTCCTCAC CGTCCTGCAC
       GlnAspTrpLeu AsnGlyLys GluTyrLys CysLysValSer AsnLysAla LeuProAla ProIleGluLys ThrIleSer LysAlaLys GlyGlnProArg
1101   CAGGACTGGC TGAATGGCAA GGAGTACAAG TGCAAGGTCT CCAACAAAGC CCTCCCAGCC CCCATCGAGA AAACCATCTC CAAAGCCAAA GGGCAGCCCC
        GluProGln ValTyrThr LeuProProSer ArgGluGlu MetThrLys AsnGlnValSer LeuThrCys LeuValLys GlyPheTyrPro SerAspIle
1201   GAGAACCACA GGTGTACACC CTGCCCCCAT CCCGGGAGGA GATGACCAAG AACCAGGTCA GCCTGACCTG CCTGGTCAAA GGCTTCTATC CCAGCGACAT
        AlaValGlu TrpGluSerAsn GlyGlnPro GluAsnAsn TyrLysThrThr ProProVal LeuAspSer AspGlySerPhe PheLeuTyr SerLysLeu
1301   CGCCGTGGAG TGGGAGAGCA ATGGGCAGCC GGAGAACAAC TACAAGACCA CGCCTCCCGT GCTGGACTCC GACGGCTCCT TCTTCCTCTA CAGCAAGCTC
       ThrValAspLys SerArgTrp GlnGlnGly AsnValPheSer CysSerVal MetHisGlu AlaLeuHisAsn HisTyrThr GlnLysSer LeuSerLeuSer
1401   ACCGTGGACA AGAGCAGGTG GCAGCAGGGG AACGTCTTCT CATGCTCCGT GATGCACGAG GCTCTGCACA ACCACTACAC GCAGAAGAGC CTCTCCCTGT
                          BmtI
                          NheI
        ProGlyLys ***(SEQ ID NO: 55)
1501   CTCCGGGTAA ATGAGTGCTA GCTGGCCAGA CATGATAAGA TACATTGATG AGTTTGGACA AACCACAACT AGAATGCAGT GAAAAAAATG CTTTATTTGT
1601   GAAATTTGTG ATGCTATTGC TTTATTTGTA ACCATTATAA GCTGCAATAA ACAAGTTAAC AACAACAATT GCATTCATTT TATGTTTCAG GTTCAGGGGG
                                                             AseI
1701   AGGTGTGGGA GGTTTTTTAA AGCAAGTAAA ACCTCTACAA ATGTGGTATG GAATTAATTC TAAAATACAG CATAGCAAAA CTTTAACCTC CAAATCAAGC
1801   CTCTACTTGA ATCCTTTTCT GAGGGATGAA TAAGGCATAG GCATCAGGGG CTGTTGCCAA TGTGCATTAG CTGTTTGCAG CCTCACCTTC TTTCATGGAG
```

```
1901   TTTAAGATAT AGTGTATTTT CCCAAGGTTT GAACTAGCTC TTCATTTCTT TATGTTTTAA ATGCACTGAC CTCCCACATT CCCTTTTTAG TAAAATATTC
2001   AGAAATAATT TAAATACATC ATTGCAATGA AAATAAATGT TTTTTATTAG GCAGAATCCA GATGCTCAAG GCCCTTCATA ATATCCCCCA GTTTAGTAGT
2101   TGGACTTAGG GAACAAAGGA ACCTTTAATA GAAATTGGAC AGCAAGAAAG CGAGCTTCTA GCTTATCCTC AGTCCTGCTC CTCTGCCACA AAGTGCACGC
2201   AGTTGCCGGC CGGGTCGCGC AGGGCGAACT CCCGCCCCCA CGGCTGCTCG CCGATCTCGG TCATGGCCGG CCCGGAGGCG TCCCGGAAGT TCGTGGACAC
2301   GACCTCCGAC CACTCGGCGT ACAGCTCGTC CAGGCCGCGC ACCCACACCC AGGCCAGGGT GTTGTCCGGC ACCACCTGGT CCTGGACCGC GCTGATGAAC
2401   AGGGTCACGT CGTCCCGGAC CACACCGGCG AAGTCGTCCT CCACGAAGTC CCGGGAGAAC CCGAGCCGGT CGGTCCAGAA CTCGACCGCT CCGGCGACGT
2501   CGCGCGCGGT GAGCACCGGA ACGGCACTGG TCAACTTGGC CATGATGGCT CCTCCTGTCA GGAGAGGAAA GAGAAGAAGG TTAGTACAAT TGCTATAGTG
                                      AseI
2601   AGTTGTATTA TACTATGCAG ATATACTATG CCAATGATTA ATTGTCAAAC TAGGGCTGCA GGGTTCATAG TGCCACTTTT CCTGCACTGC CCCATCTCCT
2701   GCCCACCCTT TCCCAGGCAT AGACAGTCAG TGACTTACCA AACTCACAGG AGGGAGAAGG CAGAAGCTTG AGACAGACCC GCGGGACCGC CGAACTGCGA
2801   GGGGACGTGG CTAGGGCGGC TTCTTTTATG GTGCGCCGGC CCTCGGAGGC AGGGCGCTCG GGGAGGCCTA GCGGCCAATC TGCGGTGGCA GGAGGCGGGG
2901   CCGAAGGCCG TGCCTGACCA ATCCGGAGCA CATAGGAGTC TCAGCCCCCC GCCCCAAAGC AAGGGGAAGT CACGCGCCTG TAGCGCCAGC GTGTTGTGAA
3001   ATGGGGGCTT GGGGGGGTTG GGGCCCTGAC TAGTCAAAAC AAACTCCCAT TGACGTCAAT GGGGTGGAGA CTTGGAAATC CCCGTGAGTC AAACCGCTAT
3101   CCACGCCCAT TGATGTACTG CCAAAACCGC ATCATCATGG TAATAGCGAT GACTAATACG TAGATGTACT GCCAAGTAGG AAAGTCCCAT AAGGTCATGT
3201   ACTGGGCATA ATGCCAGGCG GGCCATTTAC CGTCATTGAC GTCAATAGGG GGCGTACTTG GCATATGATA CACTTGATGT ACTGCCAAGT GGGCAGTTTA
3301   CCGTAAATAC TCCACCCATT GACGTCAATG GAAAGTCCCT ATTGGCGTTA CTATGGGAAC ATACGTCATT ATTGACGTCA ATGGGCGGGG GTCGTTGGGC
3401   GGTCAGCCAG GCGGGCCATT TACCGTAAGT TATGTAACGC CTGCAGGTTA ATTAAGAACA TGTGAGCAAA AGGCCAGCAA AAGGCCAGGA ACCGTAAAAA
3501   GGCCGCGTTG CTGGCGTTTT TCCATAGGCT CCGCCCCCCT GACGAGCATC ACAAAAATCG ACGCTCAAGT CAGAGGTGGC GAAACCCGAC AGGACTATAA
3601   AGATACCAGG CGTTTCCCCC TGGAAGCTCC CTCGTGCGCT CTCCTGTTCC GACCCTGCCG CTTACCGGAT ACCTGTCCGC CTTTCTCCCT TCGGGAAGCG
3701   TGGCGCTTTC TCATAGCTCA CGCTGTAGGT ATCTCAGTTC GGTGTAGGTC GTTCGCTCCA AGCTGGGCTG TGTGCACGAA CCCCCCGTTC AGCCCGACCG
3801   CTGCGCCTTA TCCGGTAACT ATCGTCTTGA GTCCAACCCG GTAAGACACG ACTTATCGCC ACTGGCAGCA GCCACTGGTA ACAGGATTAG CAGAGCGAGG
3901   TATGTAGGCG GTGCTACAGA GTTCTTGAAG TGGTGGCCTA ACTACGGCTA CACTAGAAGA ACAGTATTTG GTATCTGCGC TCTGCTGAAG CCAGTTACCT
4001   TCGGAAAAAG AGTTGGTAGC TCTTGATCCG GCAAACAAAC CACCGCTGGT AGCGGTGGTT TTTTTGTTTG CAAGCAGCAG ATTACGCGCA GAAAAAAAGG
4101   ATCTCAAGAA GATCCTTTGA TCTTTTCTAC GGGGTCTGAC GCTCAGTGGA ACGAAAACTC ACGTTAAGGG ATTTTGGTCA TGGCTAGTTA ATTAACATTT
4201   AAATCAGCGG CCGCAATAAA ATATCTTTAT TTTCATTACA TCTGTGTGTT GGTTTTTTGT GTGAATCGTA ACTAACATAC GCTCTCCATC AAAACAAAAC
4301   GAAACAAAAC AAACTAGCAA AATAGGCTGT CCCCAGTGCA AGTGCAGGTG CCAGAACATT TCTCTATCGA A  (SEQ ID NO: 82)
```

IL2ss.CCL7(5-76).hIgG1Fc sequence

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                          KasI
                                          NarI
                                          SfoI
                                          BbeI
                                         ~~~~~~~                                     IL-2 secretion signal
                                                                                      MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                              EcoRI
                              ~~~~~~~ CCL7 (5-76)
        AlaLeuSer LeuAlaLeu ValThrAsnSer PheIleAsn LysLysIle ProLysGlnArg LeuGluSer TyrArgArg ThrThrSerSer HisCysPro
 601   TTGCACTAAG TCTTGCACTT GTCACGAATT CGTTTATCAA TAAGAAAATC CCTAAGCAGA GGCTGGAGAG CTACAGAAGG ACCACCAGTA GCCACTGTCC
       ArgGluAla ValIlePheLys ThrLysLeu AspLysGlu IleCysAlaAsp ProThrGln LysTrpVal GlnAspPheMet LysHisLeu AspLysLys
 701   CCGGGAAGCT GTAATCTTCA AGACCAAACT GGACAAGGAG ATCTGTGCTG ACCCCACACA GAAGTGGGTC CAGGACTTTA TGAAGCACCT GGACAAGAAA
                       human IgG1 Fc (constant region)
       ThrGlnThrPro LysLeuAsp LysThrHis ThrCysProPro CysProAla ProGluLeu LeuGlyGlyPro SerValPhe LeuPhePro ProLysProLys
 801   ACCCAAACTC CAAAGCTTGA CAAAACTCAC ACATGCCCAC CGTGCCCAGC ACCTGAACTC CTGGGGGGAC CGTCAGTCTT CCTCTTCCCC CCAAAACCCA
        AspThrLeu MetIleSer ArgThrProGlu ValThrCys ValValVal AspValSerHis GluAspPro GluValLys PheAsnTrpTyr ValAspGly
 901   AGGACACCCT CATGATCTCC CGGACCCCTG AGGTCACATG CGTGGTGGTG GACGTGAGCC ACGAAGACCC TGAGGTCAAG TTCAACTGGT ACGTGGACGG
       ValGluVal HisAsnAlaLys ThrLysPro ArgGluGlu GlnTyrAsnSer ThrTyrArg ValValSer ValLeuThrVal LeuHisGln AspTrpLeu
1001   CGTGGAGGTG CATAATGCCA AGACAAAGCC GCGGGAGGAG CAGTACAACA GCACGTACCG TGTGGTCAGC GTCCTCACCG TCCTGCACCA GGACTGGCTG
       AsnGlyLysGlu TyrLysCys LysValSer AsnLysAlaLeu ProAlaPro IleGluLys ThrIleSerLys AlaLysGly GlnProArg GluProGlnVal
1101   AATGGCAAGG AGTACAAGTG CAAGGTCTCC AACAAAGCCC TCCCAGCCCC CATCGAGAAA ACCATCTCCA AAGCCAAAGG GCAGCCCCGA GAACCACAGG
        TyrThrLeu ProProSer ArgGluGluMet ThrLysAsn GlnValSer LeuThrCysLeu ValLysGly PheTyrPro SerAspIleAla ValGluTrp
1201   TGTACACCCT GCCCCCATCC CGGGAGGAGA TGACCAAGAA CCAGGTCAGC CTGACCTGCC TGGTCAAAGG CTTCTATCCC AGCGACATCG CCGTGGAGTG
       GluSerAsn GlyGlnProGlu AsnAsnTyr LysThrThr ProProValLeu AspSerAsp GlySerPhe PheLeuTyrSer LysLeuThr ValAspLys
1301   GGAGAGCAAT GGGCAGCCGG AGAACAACTA CAAGACCACG CCTCCCGTGC TGGACTCCGA CGGCTCCTTC TTCCTCTACA GCAAGCTCAC CGTGGACAAG
       SerArgTrpGln GlnGlyAsn ValPheSer CysSerValMet HisGluAla LeuHisAsn HisTyrThrGln LysSerLeu SerLeuSer ProGlyLys***
                                                                                                      (SEQ ID NO: 56)
1401   AGCAGGTGGC AGCAGGGGAA CGTCTTCTCA TGCTCCGTGA TGCACGAGGC TCTGCACAAC CACTACACGC AGAAGAGCCT CTCCCTGTCT CCGGGTAAAT

           BmtI
       **   NheI
1501   GAGTGCTAGC TGGCCAGACA TGATAAGATA CATTGATGAG TTTGGACAAA CCACAACTAG AATGCAGTGA AAAAAATGCT TTATTTGTGA AATTTGTGAT
1601   GCTATTGCTT TATTTGTAAC CATTATAAGC TGCAATAAAC AAGTTAACAA CAACAATTGC ATTCATTTTA TGTTTCAGGT TCAGGGGGAG GTGTGGGAGG
                                                AseI
1701   TTTTTTAAAG CAAGTAAAAC CTCTACAAAT GTGGTATGGA ATTAATTCTA AAATACAGCA TAGCAAAACT TTAACCTCCA AATCAAGCCT CTACTTGAAT
```

```
1801  CCTTTTCTGA GGGATGAATA AGGCATAGGC ATCAGGGGCT GTTGCCAATG TGCATTAGCT GTTTGCAGCC TCACCTTCTT TCATGGAGTT TAAGATATAG
1901  TGTATTTTCC CAAGGTTTGA ACTAGCTCTT CATTTCTTTA TGTTTTAAAT GCACTGACCT CCCACATTCC CTTTTTAGTA AAATATTCAG AAATAATTTA
2001  AATACATCAT TGCAATGAAA ATAAATGTTT TTTATTAGGC AGAATCCAGA TGCTCAAGGC CCTTCATAAT ATCCCCCAGT TTAGTAGTTG GACTTAGGGA
2101  ACAAAGGAAC CTTTAATAGA AATTGGACAG CAAGAAAGCG AGCTTCTAGC TTATCCTCAG TCCTGCTCCT CTGCCACAAA GTGCACGCAG TTGCCGGCCG
2201  GGTCGCGCAG GGCGAACTCC CGCCCCCACG GCTGCTCGCC GATCTCGGTC ATGGCCGGCC CGGAGGCGTC CCGGAAGTTC GTGGACACGA CCTCCGACCA
2301  CTCGGCGTAC AGCTCGTCCA GGCCGCGCAC CCACACCCAG GCCAGGGTGT TGTCCGGCAC CACCTGGTCC TGGACCGCGC TGATGAACAG GGTCACGTCG
2401  TCCCGGACCA CACCGGCGAA GTCGTCCTCC ACGAAGTCCC GGGAGAACCC GAGCCGGTCG GTCCAGAACT CGACCGCTCC GGCGACGTCG CGCGCGGTGA
2501  GCACCGGAAC GGCACTGGTC AACTTGGCCA TGATGGCTCC TCCTGTCAGG AGAGGAAAGA GAAGAAGGTT AGTACAATTG CTATAGTGAG TTGTATTATA
                                 AseI
2601  CTATGCAGAT ATACTATGCC AATGATTAAT TGTCAAACTA GGGCTGCAGG GTTCATAGTG CCACTTTTCC TGCACTGCCC CATCTCCTGC CCACCCTTTC
2701  CCAGGCATAG ACAGTCAGTG ACTTACCAAA CTCACAGGAG GGAGAAGGCA GAAGCTTGAG ACAGACCCGC GGGACCGCCG AACTGCGAGG GGACGTGGCT
2801  AGGGCGGCTT CTTTTATGGT GCGCCGGCCC TCGGAGGCAG GGCGCTCGGG GAGGCCTAGC GGCCAATCTG CGGTGGCAGG AGGCGGGGCC GAAGGCCGTG
2901  CCTGACCAAT CCGGAGCACA TAGGAGTCTC AGCCCCCCGC CCCAAAGCAA GGGGAAGTCA CGCGCCTGTA GCGCCAGCGT GTTGTGAAAT GGGGGCTTGG
3001  GGGGGTTGGG GCCCTGACTA GTCAAAACAA ACTCCCATTG ACGTCAATGG GGTGGAGACT TGGAAATCCC CGTGAGTCAA ACCGCTATCC ACGCCCATTG
3101  ATGTACTGCC AAAACCGCAT CATCATGGTA ATAGCGATGA CTAATACGTA GATGTACTGC CAAGTAGGAA AGTCCCATAA GGTCATGTAC TGGGCATAAT
3201  GCCAGGCGGG CCATTTACCG TCATTGACGT CAATAGGGGG CGTACTTGGC ATATGATACA CTTGATGTAC TGCCAAGTGG GCAGTTTACC GTAAATACTC
3301  CACCCATTGA CGTCAATGGA AAGTCCCTAT TGGCGTTACT ATGGGAACAT ACGTCATTAT TGACGTCAAT GGGCGGGGGT CGTTGGGCGG TCAGCCAGGC
3401  GGGCCATTTA CCGTAAGTTA TGTAACGCCT GCAGGTTAAT TAAGAACATG TGAGCAAAAG GCCAGCAAAA GGCCAGGAAC CGTAAAAAGG CCGCGTTGCT
3501  GGCGTTTTTC CATAGGCTCC GCCCCCCTGA CGAGCATCAC AAAAATCGAC GCTCAAGTCA GAGGTGGCGA AACCCGACAG GACTATAAAG ATACCAGGCG
3601  TTTCCCCCTG GAAGCTCCCT CGTGCGCTCT CCTGTTCCGA CCCTGCCGCT TACCGGATAC CTGTCCGCCT TTCTCCCTTC GGGAAGCGTG GCGCTTTCTC
3701  ATAGCTCACG CTGTAGGTAT CTCAGTTCGG TGTAGGTCGT TCGCTCCAAG CTGGGCTGTG TGCACGAACC CCCCGTTCAG CCCGACCGCT GCGCCTTATC
3801  CGGTAACTAT CGTCTTGAGT CCAACCCGGT AAGACACGAC TTATCGCCAC TGGCAGCAGC CACTGGTAAC AGGATTAGCA GAGCGAGGTA TGTAGGCGGT
3901  GCTACAGAGT TCTTGAAGTG GTGGCCTAAC TACGGCTACA CTAGAAGAAC AGTATTTGGT ATCTGCGCTC TGCTGAAGCC AGTTACCTTC GGAAAAAGAG
4001  TTGGTAGCTC TTGATCCGGC AAACAAACCA CCGCTGGTAG CGGTGGTTTT TTTGTTTGCA AGCAGCAGAT TACGCGCAGA AAAAAAGGAT CTCAAGAAGA
4101  TCCTTTGATC TTTTCTACGG GGTCTGACGC TCAGTGGAAC GAAAACTCAC GTTAAGGGAT TTTGGTCATG GCTAGTTAAT TAACATTTAA ATCAGCGGCC
4201  GCAATAAAAT ATCTTTATTT TCATTACATC TGTGTGTTGG TTTTTTGTGT GAATCGTAAC TAACATACGC TCTCCATCAA AACAAAACGA AACAAAACAA
4301  ACTAGCAAAA TAGGCTGTCC CCAGTGCAAG TGCAGGTGCC AGAACATTTC TCTATCGAA  (SEQ ID NO:83)
```

IL2ss.CCL7(5-76).hIgG1Fc sequence
[Alanine substitutions for removal of GAG binding sites – Lys & His]

```
   1     GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101     GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201     GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301     GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401     GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                             KasI
                                             NarI
                                             SfoI
                                             BbeI
                                            ~~~~~~~                                 IL-2 secretion signal
                                                                                     MetTyrArg MetGlnLeu LeuSerCysIle
 501     TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                               EcoRI
                               ~~~~~~~ CCL7 (5-76)
          AlaLeuSer LeuAlaLeu ValThrAsnSer PheIleAsn LysLysIle ProLysGlnArg LeuGluSer TyrArgArg ThrThrSerSer HisCysPro
 601     TTGCACTAAG TCTTGCACTT GTCACGAATT CGTTTATCAA TAAGAAAATC CCTAAGCAGA GGCTGGAGAG CTACAGAAGG ACCACCAGTA GCCACTGTCC
         ArgGluAla ValIlePheAla ThrAlaLeu AspAlaGlu IleCysAlaAsp ProThrGln AlaTrpVal GlnAspPheMet AlaAlaLeu AspAlaAla
 701     CCGGGAAGCT GTAATCTTCg ccACCgcgCT GGACgctGAG ATCTGTGCTG ACCCCACACA GgccTGGGTC CAGGACTTTA TGgctgccCT GGACgcggct
                         human IgG1 Fc (constant region)
         ThrGlnThrPro AlaLeuAsp LysThrHis ThrCysProPro CysProAla ProGluLeu LeuGlyGlyPro SerValPhe LeuPhePro ProLysProLys
 801     ACCCAAACTC CAgccCTTGA CAAAACTCAC ACATGCCCAC CGTGCCCAGC ACCTGAACTC CTGGGGGGAC CGTCAGTCTT CCTCTTCCCC CCAAAACCCA
          AspThrLeu MetIleSer ArgThrProGlu ValThrCys ValValVal AspValSerHis GluAspPro GluValLys PheAsnTrpTyr ValAspGly
 901     AGGACACCCT CATGATCTCC CGGACCCCTG AGGTCACATG CGTGGTGGTG GACGTGAGCC ACGAAGACCC TGAGGTCAAG TTCAACTGGT ACGTGGACGG
         ValGluVal HisAsnAlaLys ThrLysPro ArgGluGlu GlnTyrAsnSer ThrTyrArg ValValSer ValLeuThrVal LeuHisGln AspTrpLeu
1001     CGTGGAGGTG CATAATGCCA AGACAAAGCC GCGGGAGGAG CAGTACAACA GCACGTACCG TGTGGTCAGC GTCCTCACCG TCCTGCACCA GGACTGGCTG
         AsnGlyLysGlu TyrLysCys LysValSer AsnLysAlaLeu ProAlaPro IleGluLys ThrIleSerLys AlaLysGly GlnProArg GluProGlnVal
1101     AATGGCAAGG AGTACAAGTG CAAGGTCTCC AACAAAGCCC TCCCAGCCCC CATCGAGAAA ACCATCTCCA AAGCCAAAGG GCAGCCCCGA GAACCACAGG
          TyrThrLeu ProProSer ArgGluGluMet ThrLysAsn GlnValSer LeuThrCysLeu ValLysGly PheTyrPro SerAspIleAla ValGluTrp
1201     TGTACACCCT GCCCCCATCC CGGGAGGAGA TGACCAAGAA CCAGGTCAGC CTGACCTGCC TGGTCAAAGG CTTCTATCCC AGCGACATCG CCGTGGAGTG
         GluSerAsn GlyGlnProGlu AsnAsnTyr LysThrThr ProProValLeu AspSerAsp GlySerPhe PheLeuTyrSer LysLeuThr ValAspLys
1301     GGAGAGCAAT GGGCAGCCGG AGAACAACTA CAAGACCACG CCTCCCGTGC TGGACTCCGA CGGCTCCTTC TTCCTCTACA GCAAGCTCAC CGTGGACAAG
         SerArgTrpGln GlnGlyAsn ValPheSer CysSerValMet HisGluAla LeuHisAsn HisTyrThrGln LysSerLeu SerLeuSer ProGlyLys***
                                                                                                   (SEQ ID NO: 57)
1401     AGCAGGTGGC AGCAGGGGAA CGTCTTCTCA TGCTCCGTGA TGCACGAGGC TCTGCACAAC CACTACACGC AGAAGAGCCT CTCCCTGTCT CCGGGTAAAT

              BmtI
         **   NheI
1501     GAGTGCTAGC TGGCCAGACA TGATAAGATA CATTGATGAG TTTGGACAAA CCACAACTAG AATGCAGTGA AAAAAATGCT TTATTTGTGA AATTTGTGAT
1601     GCTATTGCTT TATTTGTAAC CATTATAAGC TGCAATAAAC AAGTTAACAA CAACAATTGC ATTCATTTTA TGTTTCAGGT TCAGGGGGAG GTGTGGGAGG
                                                           AseI
```

```
1701    TTTTTTAAAG CAAGTAAAAC CTCTACAAAT GTGGTATGGA ATTAATTCTA AAATACAGCA TAGCAAAACT TTAACCTCCA AATCAAGCCT CTACTTGAAT
1801    CCTTTTCTGA GGGATGAATA AGGCATAGGC ATCAGGGGCT GTTGCCAATG TGCATTAGCT GTTTGCAGCC TCACCTTCTT TCATGGAGTT TAAGATATAG
1901    TGTATTTTCC CAAGGTTTGA ACTAGCTCTT CATTTCTTTA TGTTTTAAAT GCACTGACCT CCCACATTCC CTTTTTAGTA AAATATTCAG AAATAATTTA
2001    AATACATCAT TGCAATGAAA ATAAATGTTT TTTATTAGGC AGAATCCAGA TGCTCAAGGC CCTTCATAAT ATCCCCCAGT TTAGTAGTTG GACTTAGGGA
2101    ACAAAGGAAC CTTTAATAGA AATTGGACAG CAAGAAAGCG AGCTTCTAGC TTATCCTCAG TCCTGCTCCT CTGCCACAAA GTGCACGCAG TTGCCGGCCG
2201    GGTCGCGCAG GGCGAACTCC CGCCCCCACG GCTGCTCGCC GATCTCGGTC ATGGCCGGCC CGGAGGCGTC CCGGAAGTTC GTGGACACGA CCTCCGACCA
2301    CTCGGCGTAC AGCTCGTCCA GGCCGCGCAC CCACACCCAG GCCAGGGTGT TGTCCGGCAC CACCTGGTCC TGGACCGCGC TGATGAACAG GGTCACGTCG
2401    TCCCGGACCA CACCGGCGAA GTCGTCCTCC ACGAAGTCCC GGGAGAACCC GAGCCGGTCG GTCCAGAACT CGACCGCTCC GGCGACGTCG CGCGCGGTGA
2501    GCACCGGAAC GGCACTGGTC AACTTGGCCA TGATGGCTCC TCCTGTCAGG AGAGGAAAGA GAAGAAGGTT AGTACAATTG CTATAGTGAG TTGTATTATA
                                 AseI
2601    CTATGCAGAT ATACTATGCC AATGATTAAT TGTCAAACTA GGGCTGCAGG GTTCATAGTG CCACTTTTCC TGCACTGCCC CATCTCCTGC CCACCCCTTTC
2701    CCAGGCATAG ACAGTCAGTG ACTTACCAAA CTCACAGGAG GGAGAAGGCA GAAGCTTGAG ACAGACCCGC GGGACCGCCG AACTGCGAGG GGACGTGGCT
2801    AGGGCGGCTT CTTTTATGGT GCGCCGGCCC TCGGAGGCAG GGCGCTCGGG GAGGCCTAGC GGCCAATCTG CGGTGGCAGG AGGCGGGGCC GAAGGCCGTG
2901    CCTGACCAAT CCGGAGCACA TAGGAGTCTC AGCCCCCCGC CCCAAAGCAA GGGGAAGTCA CGCGCCTGTA GCGCCAGCGT GTTGTGAAAT GGGGGCTTGG
3001    GGGGGTTGGG GCCCTGACTA GTCAAAACAA ACTCCCATTG ACGTCAATGG GGTGGAGACT TGGAAATCCC CGTGAGTCAA ACCGCTATCC ACGCCCATTG
3101    ATGTACTGCC AAAACCGCAT CATCATGGTA ATAGCGATGA CTAATACGTA GATGTACTGC CAAGTAGGAA AGTCCCATAA GGTCATGTAC TGGGCATAAT
3201    GCCAGGCGGG CCATTTACCG TCATTGACGT CAATAGGGGG CGTACTTGGC ATATGATACA CTTGATGTAC TGCCAAGTGG GCAGTTTACC GTAAATACTC
3301    CACCCATTGA CGTCAATGGA AAGTCCCTAT TGGCGTTACT ATGGGAACAT ACGTCATTAT TGACGTCAAT GGGCGGGGGT CGTTGGGCGG TCAGCCAGGC
3401    GGGCCATTTA CCGTAAGTTA TGTAACGCCT GCAGGTTAAT TAAGAACATG TGAGCAAAAG GCCAGCAAAA GGCCAGGAAC CGTAAAAAGG CCGCGTTGCT
3501    GGCGTTTTTC CATAGGCTCC GCCCCCCTGA CGAGCATCAC AAAAATCGAC GCTCAAGTCA GAGGTGGCGA AACCCGACAG GACTATAAAG ATACCAGGCG
3601    TTTCCCCCTG GAAGCTCCCT CGTGCGCTCT CCTGTTCCGA CCCTGCCGCT TACCGGATAC CTGTCCGCCT TTCTCCCTTC GGGAAGCGTG GCGCTTTCTC
3701    ATAGCTCACG CTGTAGGTAT CTCAGTTCGG TGTAGGTCGT TCGCTCCAAG CTGGGCTGTG TGCACGAACC CCCCGTTCAG CCCGACCGCT GCGCCTTATC
3801    CGGTAACTAT CGTCTTGAGT CCAACCCGGT AAGACACGAC TTATCGCCAC TGGCAGCAGC CACTGGTAAC AGGATTAGCA GAGCGAGGTA TGTAGGCGGT
3901    GCTACAGAGT TCTTGAAGTG GTGGCCTAAC TACGGCTACA CTAGAAGAAC AGTATTTGGT ATCTGCGCTC TGCTGAAGCC AGTTACCTTC GGAAAAAGAG
4001    TTGGTAGCTC TTGATCCGGC AAACAAACCA CCGCTGGTAG CGGTGGTTTT TTTGTTTGCA AGCAGCAGAT TACGCGCAGA AAAAAGGAT CTCAAGAAGA
4101    TCCTTTGATC TTTTCTACGG GGTCTGACGC TCAGTGGAAC GAAAACTCAC GTTAAGGGAT TTTGGTCATG GCTAGTTAAT TAACATTTAA ATCAGCGGCC
4201    GCAATAAAAT ATCTTTATTT TCATTACATC TGTGTGTTGG TTTTTTGTGT GAATCGTAAC TAACATACGC TCTCCATCAA AACAAAACGA AACAAAACAA
4301    ACTAGCAAAA TAGGCTGTCC CCAGTGCAAG TGCAGGTGCC AGAACATTTC TCTATCGAA (SEQ ID NO: 84)
```

FIG. 2E (CONT)

FIG.3A
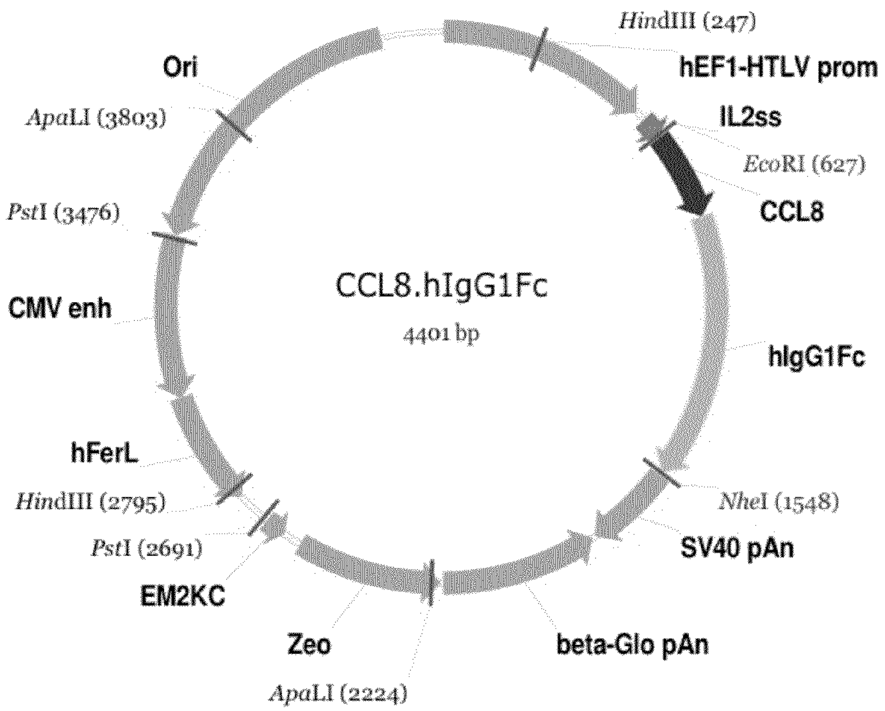
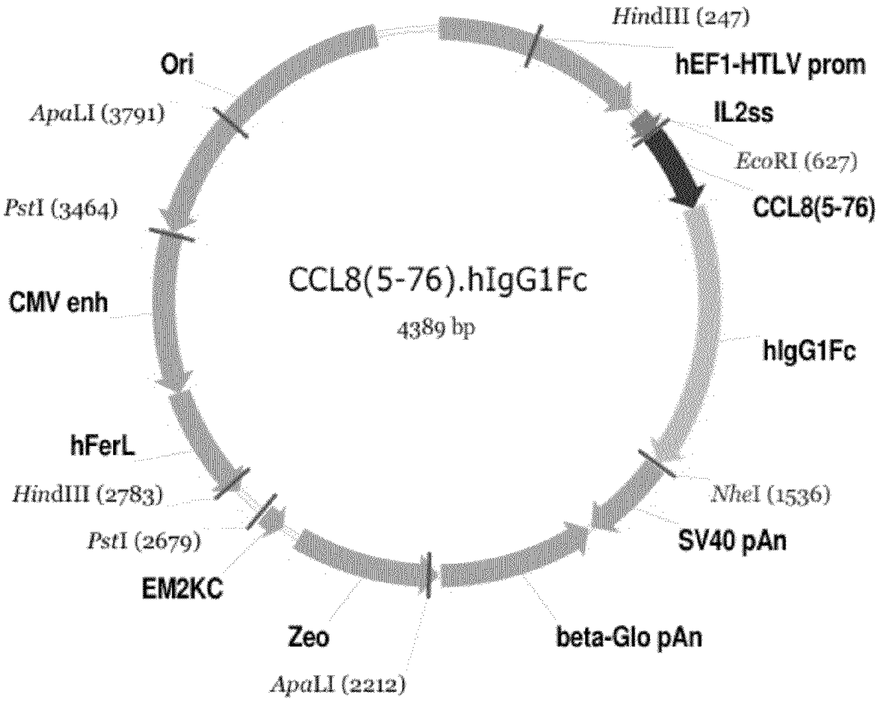
FIG.3B

FIG. 3C

IL2ss.CCL8.hIgG1Fc sequence

```
   1     GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101     GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201     GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301     GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401     GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                                  KasI
                                                  NarI
                                                  SfoI
                                                  BbeI
                                                 ~~~~~~~                                       IL-2 secretion signal
                                                                                               MetTyrArg MetGlnLeu LeuSerCysIle
 501     TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                 EcoRI
                                 ~~~~~~~ CCL8 (1-76)
           AlaLeuSer LeuAlaLeu ValThrAsnSer GlnProAsp SerValSer IleProIleThr CysCysPhe AsnValIle AsnArgLysIle ProIleGln
 601     TTGCACTAAG TCTTGCACTT GTCACGAATT CGCAGCCAGA TTCAGTTTCC ATTCCAATCA CCTGCTGCTT TAACGTGATC AATAGGAAAA TTCCTATCCA
          ArgLeuGlu SerTyrThrArg IleThrAsn IleGlnCys ProLysGluAla ValIlePhe LysThrLys ArgGlyLysGlu ValCysAla AspProLys
 701     GAGGCTGGAG AGCTACACAA GAATCACCAA CATCCAATGT CCCAAGGAAG CTGTGATCTT CAAGACCAAA CGGGGCAAGG AGGTCTGTGC TGACCCCAAG
                                                                                   human IgG1 Fc (constant region)
         GluArgTrpVal ArgAspSer MetLysHis LeuAspGlnIle PheGlnAsn LeuLysPro AspLysThrHis ThrCysPro ProCysPro AlaProGluLeu
 801     GAGAGATGGG TCAGGGATTC CATGAAGCAT CTGGACCAAA TATTTCAAAA TCTGAAGCCA GACAAAACTC ACACATGCCC ACCGTGCCCA GCACCTGAAC
           LeuGlyGly ProSerVal PheLeuPhePro ProLysPro LysAspThr LeuMetIleSer ArgThrPro GluValThr CysValValVal AspValSer
 901     TCCTGGGGGG ACCGTCAGTC TTCCTCTTCC CCCCAAAACC CAAGGACACC CTCATGATCT CCCGGACCCC TGAGGTCACA TGCGTGGTGG TGGACGTGAG
          HisGluAsp ProGluValLys PheAsnTrp TyrValAsp GlyValGluVal HisAsnAla LysThrLys ProArgGluGlu GlnTyrAsn SerThrTyr
1001     CCACGAAGAC CCTGAGGTCA AGTTCAACTG GTACGTGGAC GGCGTGGAGG TGCATAATGC CAAGACAAAG CCGCGGGAGG AGCAGTACAA CAGCACGTAC
         ArgValValSer ValLeuThr ValLeuHis GlnAspTrpLeu AsnGlyLys GluTyrLys CysLysValSer AsnLysAla LeuProAla ProIleGluLys
1101     CGTGTGGTCA GCGTCCTCAC CGTCCTGCAC CAGGACTGGC TGAATGGCAA GGAGTACAAG TGCAAGGTCT CCAACAAAGC CCTCCCAGCC CCCATCGAGA
           ThrIleSer LysAlaLys GlyGlnProArg GluProGln ValTyrThr LeuProProSer ArgGluGlu MetThrLys AsnGlnValSer LeuThrCys
1201     AAACCATCTC CAAAGCCAAA GGGCAGCCCC GAGAACCACA GGTGTACACC CTGCCCCCAT CCCGGGAGGA GATGACCAAG AACCAGGTCA GCCTGACCTG
          LeuValLys GlyPheTyrPro SerAspIle AlaValGlu TrpGluSerAsn GlyGlnPro GluAsnAsn TyrLysThrThr ProProVal LeuAspSer
1301     CCTGGTCAAA GGCTTCTATC CCAGCGACAT CGCCGTGGAG TGGGAGAGCA ATGGGCAGCC GGAGAACAAC TACAAGACCA CGCCTCCCGT GCTGGACTCC
         AspGlySerPhe PheLeuTyr SerLysLeu ThrValAspLys SerArgTrp GlnGlnGly AsnValPheSer CysSerVal MetHisGlu AlaLeuHisAsn
1401     GACGGCTCCT TCTTCCTCTA CAGCAAGCTC ACCGTGGACA AGAGCAGGTG GCAGCAGGGG AACGTCTTCT CATGCTCCGT GATGCACGAG GCTCTGCACA
                                                                        BmtI
                                                                        NheI
           HisTyrThr GlnLysSer LeuSerLeuSer ProGlyLys ***(SEQ ID NO: 58)
1501     ACCACTACAC GCAGAAGAGC CTCTCCCTGT CTCCGGGTAA ATGAGTGCTA GCTGGCCAGA CATGATAAGA TACATTGATG AGTTTGGACA AACCACAACT
1601     AGAATGCAGT GAAAAAAATG CTTTATTTGT GAAATTTGTG ATGCTATTGC TTTATTTGTA ACCATTATAA GCTGCAATAA ACAAGTTAAC AACAACAATT
                                                                                                         AseI
1701     GCATTCATTT TATGTTTCAG GTTCAGGGGG AGGTGTGGGA GGTTTTTTAA AGCAAGTAAA ACCTCTACAA ATGTGGTATG GAATTAATTC TAAAATACAG
1801     CATAGCAAAA CTTTAACCTC CAAATCAAGC CTCTACTTGA ATCCTTTTCT GAGGGATGAA TAAGGCATAG GCATCAGGGG CTGTTGCCAA TGTGCATTAG
```

```
1901   CTGTTTGCAG CCTCACCTTC TTTCATGGAG TTTAAGATAT AGTGTATTTT CCCAAGGTTT GAACTAGCTC TTCATTTCTT TATGTTTTAA ATGCACTGAC
2001   CTCCCACATT CCCTTTTTAG TAAAATATTC AGAAATAATT TAAATACATC ATTGCAATGA AAATAAATGT TTTTTATTAG GCAGAATCCA GATGCTCAAG
2101   GCCCTTCATA ATATCCCCCA GTTTAGTAGT TGGACTTAGG GAACAAAGGA ACCTTTAATA GAAATTGGAC AGCAAGAAAG CGAGCTTCTA GCTTATCCTC
2201   AGTCCTGCTC CTCTGCCACA AAGTGCACGC AGTTGCCGGC CGGGTCGCGC AGGGCGAACT CCCGCCCCCA CGGCTGCTCG CCGATCTCGG TCATGGCCGG
2301   CCCGGAGGCG TCCCGGAAGT TCGTGGACAC GACCTCCGAC CACTCGGCGT ACAGCTCGTC CAGGCCGCGC ACCCACACCC AGGCCAGGGT GTTGTCCGGC
2401   ACCACCTGGT CCTGGACCGC GCTGATGAAC AGGGTCACGT CGTCCCGGAC CACACCGGCG AAGTCGTCCT CCACGAAGTC CCGGGAGAAC CCGAGCCGGT
2501   CGGTCCAGAA CTCGACCGCT CCGGCGACGT CGCGCGCGGT GAGCACCGGA ACGGCACTGG TCAACTTGGC CATGATGGCT CCTCCTGTCA GGAGAGGAAA

                                                                                AseI
2601   GAGAAGAAGG TTAGTACAAT TGCTATAGTG AGTTGTATTA TACTATGCAG ATATACTATG CCAATGATTA ATTGTCAAAC TAGGGCTGCA GGGTTCATAG
2701   TGCCACTTTT CCTGCACTGC CCCATCTCCT GCCCACCCTT TCCCAGGCAT AGACAGTCAG TGACTTACCA AACTCACAGG AGGGAGAAGG CAGAAGCTTG
2801   AGACAGACCC GCGGGACCGC CGAACTGCGA GGGGACGTGG CTAGGGCGGC TTCTTTTATG GTGCGCCGGC CCTCGGAGGC AGGGCGCTCG GGGAGGCCTA
2901   GCGGCCAATC TGCGGTGGCA GGAGGCGGGG CCGAAGGCCG TGCCTGACCA ATCCGGAGCA CATAGGAGTC TCAGCCCCCC GCCCCAAAGC AAGGGGAAGT
3001   CACGCGCCTG TAGCGCCAGC GTGTTGTGAA ATGGGGGCTT GGGGGGGTTG GGGCCCTGAC TAGTCAAAAC AAACTCCCAT TGACGTCAAT GGGGTGGAGA
3101   CTTGGAAATC CCCGTGAGTC AAACCGCTAT CCACGCCCAT TGATGTACTG CCAAAACCGC ATCATCATGG TAATAGCGAT GACTAATACG TAGATGTACT
3201   GCCAAGTAGG AAAGTCCCAT AAGGTCATGT ACTGGGCATA ATGCCAGGCG GGCCATTTAC CGTCATTGAC GTCAATAGGG GGCGTACTTG GCATATGATA
3301   CACTTGATGT ACTGCCAAGT GGGCAGTTTA CCGTAAATAC TCCACCCATT GACGTCAATG GAAAGTCCCT ATTGGCGTTA CTATGGGAAC ATACGTCATT
3401   ATTGACGTCA ATGGGCGGGG GTCGTTGGGC GGTCAGCCAG GCGGGCCATT TACCGTAAGT TATGTAACGC CTGCAGGTTA ATTAAGAACA TGTGAGCAAA
3501   AGGCCAGCAA AAGGCCAGGA ACCGTAAAAA GGCCGCGTTG CTGGCGTTTT TCCATAGGCT CCGCCCCCCT GACGAGCATC ACAAAAATCG ACGCTCAAGT
3601   CAGAGGTGGC GAAACCCGAC AGGACTATAA AGATACCAGG CGTTTCCCCC TGGAAGCTCC CTCGTGCGCT CTCCTGTTCC GACCCTGCCG CTTACCGGAT
3701   ACCTGTCCGC CTTTCTCCCT TCGGGAAGCG TGGCGCTTTC TCATAGCTCA CGCTGTAGGT ATCTCAGTTC GGTGTAGGTC GTTCGCTCCA AGCTGGGCTG
3801   TGTGCACGAA CCCCCCGTTC AGCCCGACCG CTGCGCCTTA TCCGGTAACT ATCGTCTTGA GTCCAACCCG GTAAGACACG ACTTATCGCC ACTGGCAGCA
3901   GCCACTGGTA ACAGGATTAG CAGAGCGAGG TATGTAGGCG GTGCTACAGA GTTCTTGAAG TGGTGGCCTA ACTACGGCTA CACTAGAAGA ACAGTATTTG
4001   GTATCTGCGC TCTGCTGAAG CCAGTTACCT TCGGAAAAAG AGTTGGTAGC TCTTGATCCG GCAAACAAAC CACCGCTGGT AGCGGTGGTT TTTTTGTTTG
4101   CAAGCAGCAG ATTACGCGCA GAAAAAAAGG ATCTCAAGAA GATCCTTTGA TCTTTTCTAC GGGGTCTGAC GCTCAGTGGA ACGAAAACTC ACGTTAAGGG
4201   ATTTTGGTCA TGGCTAGTTA ATTAACATTT AAATCAGCGG CCGCAATAAA ATATCTTTAT TTTCATTACA TCTGTGTGTT GGTTTTTTGT GTGAATCGTA
4301   ACTAACATAC GCTCTCCATC AAAACAAAAC GAAACAAAAC AAACTAGCAA AATAGGCTGT CCCCAGTGCA AGTGCAGGTG CCAGAACATT TCTCTATCGA
4401   A (SEQ ID NO: 85)
```

IL2ss.CCL8(5-76).hIgG1Fc sequence

```
 1      GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101    GAGAAGGTGG CGCGGGGTAA ACTCGGAAAG TGATGTCGTG TACTGGCTCC GCCTTTTTCC CGAGGGTGGG GGAGAACCGT ATATAAGTGC AGTAGTCGCC
 201    GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301    GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401    GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                           KasI
                                           NarI
                                           SfoI
                                           BbeI
                                          ~~~~~~~                                   IL-2 secretion signal
                                                                                    MetTyrArg MetGlnLeu LeuSerCysIle
 501    TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                EcoRI
                                ~~~~~~~ CCL8 (5-76)
         AlaLeuSer LeuAlaLeu ValThrAsnSer ValSerIle ProIleThr CysCysPheAsn ValIleAsn ArgLysIle ProIleGlnArg LeuGluSer
 601    TTGCACTAAG TCTTGCACTT GTCACGAATT CGGTTTCCAT TCCAATCACC TGCTGCTTTA ACGTGATCAA TAGGAAAATT CCTATCCAGA GGCTGGAGAG
        TyrThrArg IleThrAsnIle GlnCysPro LysGluAla ValIlePheLys ThrLysArg GlyLysGlu ValCysAlaAsp ProLysGlu ArgTrpVal
 701    CTACACAAGA ATCACCAACA TCCAATGTCC CAAGGAAGCT GTGATCTTCA AGACCAAACG GGGCAAGGAG GTCTGTGCTG ACCCCAAGGA GAGATGGGTC
                                                      human IgG1 Fc (constant region)
        ArgAspSerMet LysHisLeu AspGlnIle PheGlnAsnLeu LysProAsp LysThrHis ThrCysProPro CysProAla ProGluLeu LeuGlyGlyPro
 801    AGGGATTCCA TGAAGCATCT GGACCAAATA TTTCAAAATC TGAAGCCAGA CAAAACTCAC ACATGCCCAC CGTGCCCAGC ACCTGAACTC CTGGGGGGAC
         SerValPhe LeuPhePro ProLysProLys AspThrLeu MetIleSer ArgThrProGlu ValThrCys ValValVal AspValSerHis GluAspPro
 901    CGTCAGTCTT CCTCTTCCCC CCAAAACCCA AGGACACCCT CATGATCTCC CGGACCCCTG AGGTCACATG CGTGGTGGTG GACGTGAGCC ACGAAGACCC
        GluValLys PheAsnTrpTyr ValAspGly ValGluVal HisAsnAlaLys ThrLysPro ArgGluGlu GlnTyrAsnSer ThrTyrArg ValValSer
 1001   TGAGGTCAAG TTCAACTGGT ACGTGGACGG CGTGGAGGTG CATAATGCCA AGACAAAGCC GCGGGAGGAG CAGTACAACA GCACGTACCG TGTGGTCAGC
        ValLeuThrVal LeuHisGln AspTrpLeu AsnGlyLysGlu TyrLysCys LysValSer AsnLysAlaLeu ProAlaPro IleGluLys ThrIleSerLys
 1101   GTCCTCACCG TCCTGCACCA GGACTGGCTG AATGGCAAGG AGTACAAGTG CAAGGTCTCC AACAAAGCCC TCCCAGCCCC CATCGAGAAA ACCATCTCCA
         AlaLysGly GlnProArg GluProGlnVal TyrThrLeu ProProSer ArgGluGluMet ThrLysAsn GlnValSer LeuThrCysLeu ValLysGly
 1201   AAGCCAAAGG GCAGCCCCGA GAACCACAGG TGTACACCCT GCCCCCATCC CGGGAGGAGA TGACCAAGAA CCAGGTCAGC CTGACCTGCC TGGTCAAAGG
        PheTyrPro SerAspIleAla ValGluTrp GluSerAsn GlyGlnProGlu AsnAsnTyr LysThrThr ProProValLeu AspSerAsp GlySerPhe
 1301   CTTCTATCCC AGCGACATCG CCGTGGAGTG GGAGAGCAAT GGGCAGCCGG AGAACAACTA CAAGACCACG CCTCCCGTGC TGGACTCCGA CGGCTCCTTC
        PheLeuTyrSer LysLeuThr ValAspLys SerArgTrpGln GlnGlyAsn ValPheSer CysSerValMet HisGluAla LeuHisAsn HisTyrThrGln
 1401   TTCCTCTACA GCAAGCTCAC CGTGGACAAG AGCAGGTGGC AGCAGGGGAA CGTCTTCTCA TGCTCCGTGA TGCACGAGGC TCTGCACAAC CACTACACGC
                                          BmtI
                                          NheI
         LysSerLeu SerLeuSer ProGlyLys***(SEQ ID NO. 59)
 1501   AGAAGAGCCT CTCCCTGTCT CCGGGTAAAT GAGTGCTAGC TGGCCAGACA TGATAAGATA CATTGATGAG TTTGGACAAA CCACAACTAG AATGCAGTGA
 1601   AAAAAATGCT TTATTTGTGA AATTTGTGAT GCTATTGCTT TATTTGTAAC CATTATAAGC TGCAATAAAC AAGTTAACAA CAACAATTGC ATTCATTTTA
                                                                                    AseI
 1701   TGTTTCAGGT TCAGGGGGAG GTGTGGGAGG TTTTTTAAAG CAAGTAAAAC CTCTACAAAT GTGGTATGGA ATTAATTCTA AAATACAGCA TAGCAAAACT
 1801   TTAACCTCCA AATCAAGCCT CTACTTGAAT CCTTTTCTGA GGGATGAATA AGGCATAGGC ATCAGGGGCT GTTGCCAATG TGCATTAGCT GTTTGCAGCC
```

1901 TCACCTTCTT TCATGGAGTT TAAGATATAG TGTATTTTCC CAAGGTTTGA ACTAGCTCTT CATTTCTTTA TGTTTTAAAT GCACTGACCT CCCACATTCC
2001 CTTTTTAGTA AAATATTCAG AAATAATTTA AATACATCAT TGCAATGAAA ATAAATGTTT TTTATTAGGC AGAATCCAGA TGCTCAAGGC CCTTCATAAT
2101 ATCCCCCAGT TTAGTAGTTG GACTTAGGGA ACAAAGGAAC CTTTAATAGA AATTGGACAG CAAGAAAGCG AGCTTCTAGC TTATCCTCAG TCCTGCTCCT
2201 CTGCCACAAA GTGCACGCAG TTGCCGGCCG GGTCGCGCAG GGCGAACTCC CGCCCCCACG GCTGCTCGCC GATCTCGGTC ATGGCCGGCC CGGAGGCGTC
2301 CCGGAAGTTC GTGGACACGA CCTCCGACCA CTCGGCGTAC AGCTCGTCCA GGCCGCGCAC CCACACCCAG GCCAGGGTGT TGTCCGGCAC CACCTGGTCC
2401 TGGACCGCGC TGATGAACAG GGTCACGTCG TCCCGGACCA CACCGGCGAA GTCGTCCTCC ACGAAGTCCC GGGAGAACCC GAGCCGGTCG GTCCAGAACT
2501 CGACCGCTCC GGCGACGTCG CGCGCGGTGA GCACCGGAAC GGCACTGGTC AACTTGGCCA TGATGGCTCC TCCTGTCAGG AGAGGAAAGA GAAGAAGGTT

AseI
2601 AGTACAATTG CTATAGTGAG TTGTATTATA CTATGCAGAT ATACTATGCC AATGATTAAT TGTCAAACTA GGGCTGCAGG GTTCATAGTG CCACTTTTCC
2701 TGCACTGCCC CATCTCCTGC CCACCCTTTC CCAGGCATAG ACAGTCAGTG ACTTACCAAA CTCACAGGAG GGAGAAGGCA GAAGCTTGAG ACAGACCCGC
2801 GGGACCGCCG AACTGCGAGG GGACGTGGCT AGGGCGGCTT CTTTTATGGT GCGCCGGCCC TCGGAGGCAG GGCGCTCGGG GAGGCCTAGC GGCCAATCTG
2901 CGGTGGCAGG AGGCGGGGCC GAAGGCCGTG CCTGACCAAT CCGGAGCACA TAGGAGTCTC AGCCCCCCGC CCCAAAGCAA GGGGAAGTCA CGCGCCTGTA
3001 GCGCCAGCGT GTTGTGAAAT GGGGGCTTGG GGGGGTTGGG GCCCTGACTA GTCAAAACAA ACTCCCATTG ACGTCAATGG GGTGGAGACT TGGAAATCCC
3101 CGTGAGTCAA ACCGCTATCC ACGCCCATTG ATGTACTGCC AAAACCGCAT CATCATGGTA ATAGCGATGA CTAATACGTA GATGTACTGC CAAGTAGGAA
3201 AGTCCCATAA GGTCATGTAC TGGGCATAAT GCCAGGCGGG CCATTTACCG TCATTGACGT CAATAGGGGG CGTACTTGGC ATATGATACA CTTGATGTAC
3301 TGCCAAGTGG GCAGTTTACC GTAAATACTC CACCCATTGA CGTCAATGGA AAGTCCCTAT TGGCGTTACT ATGGGAACAT ACGTCATTAT TGACGTCAAT
3401 GGGCGGGGGT CGTTGGGCGG TCAGCCAGGC GGGCCATTTA CCGTAAGTTA TGTAACGCCT GCAGGTTAAT TAAGAACATG TGAGCAAAAG GCCAGCAAAA
3501 GGCCAGGAAC CGTAAAAAGG CCGCGTTGCT GGCGTTTTTC CATAGGCTCC GCCCCCCTGA CGAGCATCAC AAAAATCGAC GCTCAAGTCA GAGGTGGCGA
3601 AACCCGACAG GACTATAAAG ATACCAGGCG TTTCCCCCTG GAAGCTCCCT CGTGCGCTCT CCTGTTCCGA CCCTGCCGCT TACCGGATAC CTGTCCGCCT
3701 TTCTCCCTTC GGGAAGCGTG GCGCTTTCTC ATAGCTCACG CTGTAGGTAT CTCAGTTCGG TGTAGGTCGT TCGCTCCAAG CTGGGCTGTG TGCACGAACC
3801 CCCCGTTCAG CCCGACCGCT GCGCCTTATC CGGTAACTAT CGTCTTGAGT CCAACCCGGT AAGACACGAC TTATCGCCAC TGGCAGCAGC CACTGGTAAC
3901 AGGATTAGCA GAGCGAGGTA TGTAGGCGGT GCTACAGAGT TCTTGAAGTG GTGGCCTAAC TACGGCTACA CTAGAAGAAC AGTATTTGGT ATCTGCGCTC
4001 TGCTGAAGCC AGTTACCTTC GGAAAAAGAG TTGGTAGCTC TTGATCCGGC AAACAAACCA CCGCTGGTAG CGGTGGTTTT TTTGTTTGCA AGCAGCAGAT
4101 TACGCGCAGA AAAAAAGGAT CTCAAGAAGA TCCTTTGATC TTTTCTACGG GGTCTGACGC TCAGTGGAAC GAAAACTCAC GTTAAGGGAT TTTGGTCATG
4201 GCTAGTTAAT TAACATTTAA ATCAGCGGCC GCAATAAAAT ATCTTTATTT TCATTACATC TGTGTGTTGG TTTTTTGTGT GAATCGTAAC TAACATACGC
4301 TCTCCATCAA AACAAAACGA AACAAAACAA ACTAGCAAAA TAGGCTGTCC CCAGTGCAAG TGCAGGTGCC AGAACATTTC TCTATCGAA (SEQ ID NO: 86)

IL2ss.CCL8(5-76).hIgG1Fc sequence

[Alanine substitutions for GAG binding sites – Lys, Arg & His]

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                             KasI
                                             NarI
                                             SfoI
                                             BbeI
                                            ~~~~~~~                                     IL-2 secretion signal
                                                                                        MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                 EcoRI
                                 ~~~~~~~ CCL8 (5-76)
         AlaLeuSer LeuAlaLeu ValThrAsnSer ValSerIle ProIleThr CysCysPheAsn ValIleAsn ArgLysIle ProIleGlnArg LeuGluSer
 601   TTGCACTAAG TCTTGCACTT GTCACGAATT CGGTTTCCAT TCCAATCACC TGCTGCTTTA ACGTGATCAA TAGGAAAATT CCTATCCAGA GGCTGGAGAG
        TyrThrArg IleThrAsnIle GlnCysPro LysGluAla ValIlePheLys ThrAlaAla GlyAlaGlu ValCysAlaAsp ProAlaGlu AlaTrpVal
 701   CTACACAAGA ATCACCAACA TCCAATGTCC CAAGGAAGCT GTGATCTTCA AGACCgccgc gGGCgctGAG GTCTGTGCTG ACCCCgccGA GgcgTGGGTC
                                                                  human IgG1 Fc (constant region)
       AlaAspSerMet AlaAlaLeu AspGlnIle PheGlnAsnLeu AlaProAsp LysThrHis ThrCysProPro CysProAla ProGluLeu LeuGlyGlyPro
 801   gctGATTCCA TGgccgcgCT GGACCAAATA TTTCAAAATC TGgctCCAGA CAAAACTCAC ACATGCCCAC CGTGCCCAGC ACCTGAACTC CTGGGGGGAC
         SerValPhe LeuPhePro ProLysProLys AspThrLeu MetIleSer ArgThrProGlu ValThrCys ValValVal AspValSerHis GluAspPro
 901   CGTCAGTCTT CCTCTTCCCC CCAAAACCCA AGGACACCCT CATGATCTCC CGGACCCCTG AGGTCACATG CGTGGTGGTG GACGTGAGCC ACGAAGACCC
        GluValLys PheAsnTrpTyr ValAspGly ValGluVal HisAsnAlaLys ThrLysPro ArgGluGlu GlnTyrAsnSer ThrTyrArg ValValSer
1001   TGAGGTCAAG TTCAACTGGT ACGTGGACGG CGTGGAGGTG CATAATGCCA AGACAAAGCC GCGGGAGGAG CAGTACAACA GCACGTACCG TGTGGTCAGC
       ValLeuThrVal LeuHisGln AspTrpLeu AsnGlyLysGlu TyrLysCys LysValSer AsnLysAlaLeu ProAlaPro IleGluLys ThrIleSerLys
1101   GTCCTCACCG TCCTGCACCA GGACTGGCTG AATGGCAAGG AGTACAAGTG CAAGGTCTCC AACAAAGCCC TCCCAGCCCC CATCGAGAAA ACCATCTCCA
         AlaLysGly GlnProArg GluProGlnVal TyrThrLeu ProProSer ArgGluGluMet ThrLysAsn GlnValSer LeuThrCysLeu ValLysGly
1201   AAGCCAAAGG GCAGCCCCGA GAACCACAGG TGTACACCCT GCCCCCATCC CGGGAGGAGA TGACCAAGAA CCAGGTCAGC CTGACCTGCC TGGTCAAAGG
        PheTyrPro SerAspIleAla ValGluTrp GluSerAsn GlyGlnProGlu AsnAsnTyr LysThrThr ProProValLeu AspSerAsp GlySerPhe
1301   CTTCTATCCC AGCGACATCG CCGTGGAGTG GGAGAGCAAT GGGCAGCCGG AGAACAACTA CAAGACCACG CCTCCCGTGC TGGACTCCGA CGGCTCCTTC
       PheLeuTyrSer LysLeuThr ValAspLys SerArgTrpGln GlnGlyAsn ValPheSer CysSerValMet HisGluAla LeuHisAsn HisTyrThrGln
1401   TTCCTCTACA GCAAGCTCAC CGTGGACAAG AGCAGGTGGC AGCAGGGGAA CGTCTTCTCA TGCTCCGTGA TGCACGAGGC TCTGCACAAC CACTACACGC
                                            BmtI
                                            NheI
         LysSerLeu SerLeuSer ProGlyLys***(SEQ ID NO: 60)
1501   AGAAGAGCCT CTCCCTGTCT CCGGGTAAAT GAGTGCTAGC TGGCCAGACA TGATAAGATA CATTGATGAG TTTGGACAAA CCACAACTAG AATGCAGTGA
1601   AAAAAATGCT TTATTTGTGA AATTTGTGAT GCTATTGCTT TATTTGTAAC CATTATAAGC TGCAATAAAC AAGTTAACAA CAACAATTGC ATTCATTTTA
                                                                                      AseI
1701   TGTTTCAGGT TCAGGGGGAG GTGTGGGAGG TTTTTTAAAG CAAGTAAAAC CTCTACAAAT GTGGTATGGA ATTAATTCTA AAATACAGCA TAGCAAAACT
```

```
1801  TTAACCTCCA AATCAAGCCT CTACTTGAAT CCTTTTCTGA GGGATGAATA AGGCATAGGC ATCAGGGGCT GTTGCCAATG TGCATTAGCT GTTTGCAGCC
1901  TCACCTTCTT TCATGGAGTT TAAGATATAG TGTATTTTCC CAAGGTTTGA ACTAGCTCTT CATTTCTTTA TGTTTTAAAT GCACTGACCT CCCACATTCC
2001  CTTTTTAGTA AAATATTCAG AAATAATTTA AATACATCAT TGCAATGAAA ATAAATGTTT TTTATTAGGC AGAATCCAGA TGCTCAAGGC CCTTCATAAT
2101  ATCCCCCAGT TTAGTAGTTG GACTTAGGGA ACAAAGGAAC CTTTAATAGA AATTGGACAG CAAGAAAGCG AGCTTCTAGC TTATCCTCAG TCCTGCTCCT
2201  CTGCCACAAA GTGCACGCAG TTGCCGGCCG GGTCGCGCAG GGCGAACTCC CGCCCCCACG GCTGCTCGCC GATCTCGGTC ATGGCCGGCC CGGAGGCGTC
2301  CCGGAAGTTC GTGGACACGA CCTCCGACCA CTCGGCGTAC AGCTCGTCCA GGCCGCGCAC CCACACCCAG GCCAGGGTGT TGTCCGGCAC CACCTGGTCC
2401  TGGACCGCGC TGATGAACAG GGTCACGTCG TCCCGGACCA CACCGGCGAA GTCGTCCTCC ACGAAGTCCC GGGAGAACCC GAGCCGGTCG GTCCAGAACT
2501  CGACCGCTCC GGCGACGTCG CGCGCGGTGA GCACCGGAAC GGCACTGGTC AACTTGGCCA TGATGGCTCC TCCTGTCAGG AGAGGAAAGA GAAGAAGGTT
                                                                      AseI
2601  AGTACAATTG CTATAGTGAG TTGTATTATA CTATGCAGAT ATACTATGCC AATGATTAAT TGTCAAACTA GGGCTGCAGG GTTCATAGTG CCACTTTTCC
2701  TGCACTGCCC CATCTCCTGC CCACCCTTTC CCAGGCATAG ACAGTCAGTG ACTTACCAAA CTCACAGGAG GGAGAAGGCA GAAGCTTGAG ACAGACCCGC
2801  GGGACCGCCG AACTGCGAGG GGACGTGGCT AGGGCGGCTT CTTTTATGGT GCGCCGGCCC TCGGAGGCAG GGCGCTCGGG GAGGCCTAGC GGCCAATCTG
2901  CGGTGGCAGG AGGCGGGGCC GAAGGCCGTG CCTGACCAAT CCGGAGCACA TAGGAGTCTC AGCCCCCCGC CCCAAAGCAA GGGGAAGTCA CGCGCCTGTA
3001  GCGCCAGCGT GTTGTGAAAT GGGGGCTTGG GGGGGTTGGG GCCCTGACTA GTCAAAACAA ACTCCCATTG ACGTCAATGG GGTGGAGACT TGGAAATCCC
3101  CGTGAGTCAA ACCGCTATCC ACGCCCATTG ATGTACTGCC AAAACCGCAT CATCATGGTA ATAGCGATGA CTAATACGTA GATGTACTGC CAAGTAGGAA
3201  AGTCCCATAA GGTCATGTAC TGGGCATAAT GCCAGGCGGG CCATTTACCG TCATTGACGT CAATAGGGGG CGTACTTGGC ATATGATACA CTTGATGTAC
3301  TGCCAAGTGG GCAGTTTACC GTAAATACTC CACCCATTGA CGTCAATGGA AAGTCCCTAT TGGCGTTACT ATGGGAACAT ACGTCATTAT TGACGTCAAT
3401  GGGCGGGGGT CGTTGGGCGG TCAGCCAGGC GGGCCATTTA CCGTAAGTTA TGTAACGCCT GCAGGTTAAT TAAGAACATG TGAGCAAAAG GCCAGCAAAA
3501  GGCCAGGAAC CGTAAAAAGG CCGCGTTGCT GGCGTTTTTC CATAGGCTCC GCCCCCCTGA CGAGCATCAC AAAAATCGAC GCTCAAGTCA GAGGTGGCGA
3601  AACCCGACAG GACTATAAAG ATACCAGGCG TTTCCCCCTG GAAGCTCCCT CGTGCGCTCT CCTGTTCCGA CCCTGCCGCT TACCGGATAC CTGTCCGCCT
3701  TTCTCCCTTC GGGAAGCGTG GCGCTTTCTC ATAGCTCACG CTGTAGGTAT CTCAGTTCGG TGTAGGTCGT TCGCTCCAAG CTGGGCTGTG TGCACGAACC
3801  CCCCGTTCAG CCCGACCGCT GCGCCTTATC CGGTAACTAT CGTCTTGAGT CCAACCCGGT AAGACACGAC TTATCGCCAC TGGCAGCAGC CACTGGTAAC
3901  AGGATTAGCA GAGCGAGGTA TGTAGGCGGT GCTACAGAGT TCTTGAAGTG GTGGCCTAAC TACGGCTACA CTAGAAGAAC AGTATTTGGT ATCTGCGCTC
4001  TGCTGAAGCC AGTTACCTTC GGAAAAAGAG TTGGTAGCTC TTGATCCGGC AAACAAACCA CCGCTGGTAG CGGTGGTTTT TTTGTTTGCA AGCAGCAGAT
4101  TACGCGCAGA AAAAAAGGAT CTCAAGAAGA TCCTTTGATC TTTTCTACGG GGTCTGACGC TCAGTGGAAC GAAAACTCAC GTTAAGGGAT TTTGGTCATG
4201  GCTAGTTAAT TAACATTTAA ATCAGCGGCC GCAATAAAAT ATCTTTATTT TCATTACATC TGTGTGTTGG TTTTTTGTGT GAATCGTAAC TAACATACGC
4301  TCTCCATCAA AACAAAACGA AACAAAACAA ACTAGCAAAA TAGGCTGTCC CCAGTGCAAG TGCAGGTGCC AGAACATTTC TCTATCGAA (SEQ ID NO:87)
```

FIG. 3E (CONT)

FIG.4A
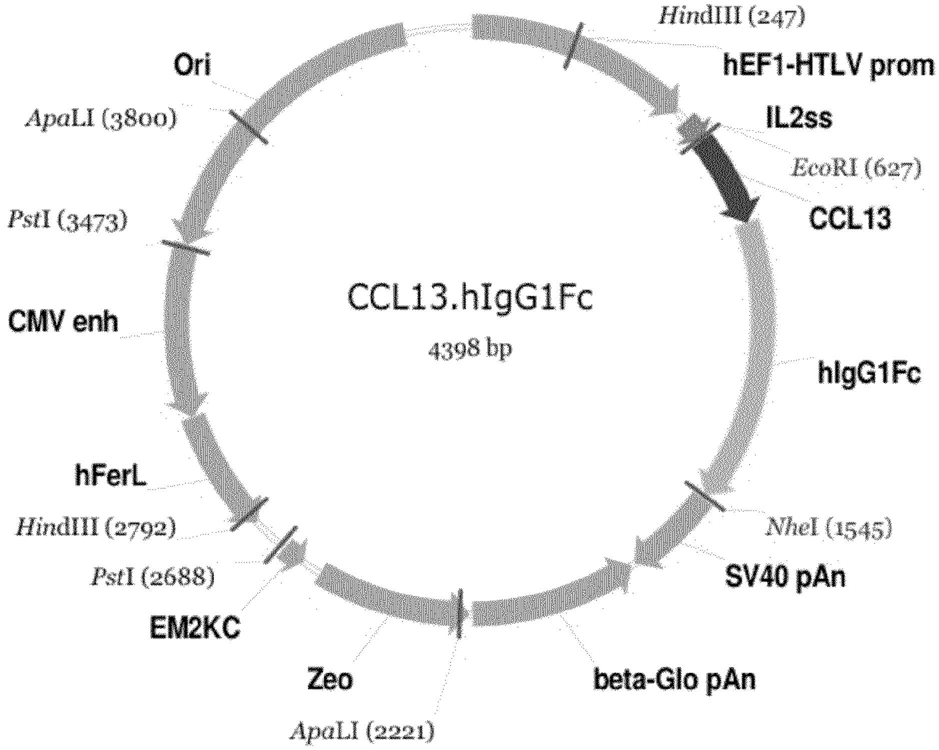
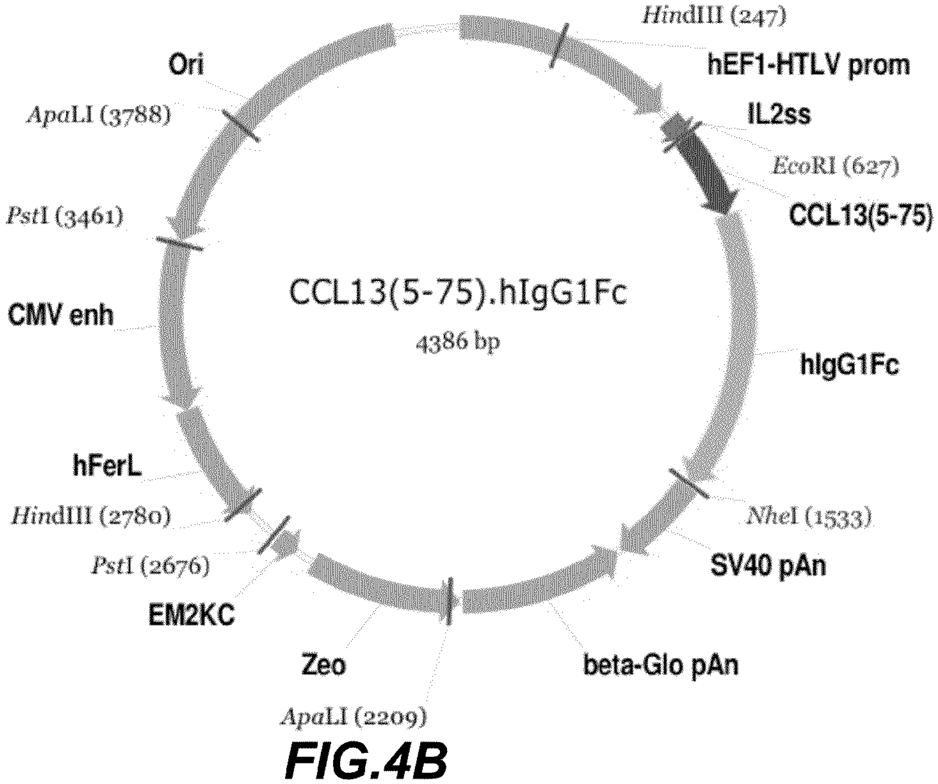
FIG.4B

FIG. 4C

IL2ss.CCL13.hIgG1Fc sequence

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                         SfoI
                                         NarI
                                         KasI
                                         BbeI
                                        ~~~~~~~                                    IL-2 secretion signal
                                                                                   MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                 EcoRI
                                 ~~~~~~~ CCL13 (1-75)
        AlaLeuSer LeuAlaLeu ValThrAsnSer GlnProAsp AlaLeuAsn ValProSerThr CysCysPhe ThrPheSer SerLysLysIle SerLeuGln
 601   TTGCACTAAG TCTTGCACTT GTCACGAATT CGCAGCCAGA TGCACTCAAC GTCCCATCTA CTTGCTGCTT CACATTTAGC AGTAAGAAGA TCTCCTTGCA
       ArgLeuLys SerTyrValIle ThrThrSer ArgCysPro GlnLysAlaVal IlePheArg ThrLysLeu GlyLysGluIle CysAlaAsp ProLysGlu
 701   GAGGCTGAAG AGCTATGTGA TCACCACCAG CAGGTGTCCC CAGAAGGCTG TCATCTTCAG AACCAAACTG GGCAAGGAGA TCTGTGCTGA CCCAAAGGAG
                                                                  human IgG1 Fc (constant region)
       LysTrpValGln AsnTyrMet LysHisLeu GlyArgLysAla HisThrLeu LysThrAsp LysThrHisThr CysProPro CysProAla ProGluLeuLeu
 801   AAGTGGGTCC AGAATTATAT GAAACACCTG GGCCGGAAAG CTCACACCCT GAAGACTGAC AAAACTCACA CATGCCCACC GTGCCCAGCA CCTGAACTCC
        GlyGlyPro SerValPhe LeuPheProPro LysProLys AspThrLeu MetIleSerArg ThrProGlu ValThrCys ValValValAsp ValSerHis
 901   TGGGGGGACC GTCAGTCTTC CTCTTCCCCC CAAAACCCAA GGACACCCTC ATGATCTCCC GGACCCCTGA GGTCACATGC GTGGTGGTGG ACGTGAGCCA
        GluAspPro GluValLysPhe AsnTrpTyr ValAspGly ValGluValHis AsnAlaLys ThrLysPro ArgGluGluGln TyrAsnSer ThrTyrArg
1001   CGAAGACCCT GAGGTCAAGT TCAACTGGTA CGTGGACGGC GTGGAGGTGC ATAATGCCAA GACAAAGCCG CGGGAGGAGC AGTACAACAG CACGTACCGT
       ValValSerVal LeuThrVal LeuHisGln AspTrpLeuAsn GlyLysGlu TyrLysCys LysValSerAsn LysAlaLeu ProAlaPro IleGluLysThr
1101   GTGGTCAGCG TCCTCACCGT CCTGCACCAG GACTGGCTGA ATGGCAAGGA GTACAAGTGC AAGGTCTCCA ACAAAGCCCT CCCAGCCCCC ATCGAGAAAA
        IleSerLys AlaLysGly GlnProArgGlu ProGlnVal TyrThrLeu ProProSerArg GluGluMet ThrLysAsn GlnValSerLeu ThrCysLeu
1201   CCATCTCCAA AGCCAAAGGG CAGCCCCGAG AACCACAGGT GTACACCCTG CCCCCATCCC GGGAGGAGAT GACCAAGAAC CAGGTCAGCC TGACCTGCCT
       ValLysGly PheTyrProSer AspIleAla ValGluTrp GluSerAsnGly GlnProGlu AsnAsnTyr LysThrThrPro ProValLeu AspSerAsp
1301   GGTCAAAGGC TTCTATCCCA GCGACATCGC CGTGGAGTGG GAGAGCAATG GGCAGCCGGA GAACAACTAC AAGACCACGC CTCCCGTGCT GGACTCCGAC
       GlySerPhePhe LeuTyrSer LysLeuThr ValAspLysSer ArgTrpGln GlnGlyAsn ValPheSerCys SerValMet HisGluAla LeuHisAsnHis
1401   GGCTCCTTCT TCCTCTACAG CAAGCTCACC GTGGACAAGA GCAGGTGGCA GCAGGGGAAC GTCTTCTCAT GCTCCGTGAT GCACGAGGCT CTGCACAACC
                                                         BmtI
                                                         NheI
        TyrThrGln LysSerLeu SerLeuSerPro GlyLys***(SEQ ID NO:61)
1501   ACTACACGCA GAAGAGCCTC TCCCTGTCTC CGGGTAAATG AGTGCTAGCT GGCCAGACAT GATAAGATAC ATTGATGAGT TTGGACAAAC CACAACTAGA
1601   ATGCAGTGAA AAAAATGCTT TATTTGTGAA ATTTGTGATG CTATTGCTTT ATTTGTAACC ATTATAAGCT GCAATAAACA AGTTAACAAC AACAATTGCA
                                                                                                  AseI
1701   TTCATTTTAT GTTTCAGGTT CAGGGGGAGG TGTGGGAGGT TTTTTAAAGC AAGTAAAACC TCTACAAATG TGGTATGGAA TTAATTCTAA AATACAGCAT
1801   AGCAAAACTT TAACCTCCAA ATCAAGCCTC TACTTGAATC CTTTTCTGAG GGATGAATAA GGCATAGGCA TCAGGGGCTG TTGCCAATGT GCATTAGCTG
```

```
1901   TTTGCAGCCT CACCTTCTTT CATGGAGTTT AAGATATAGT GTATTTTCCC AAGGTTTGAA CTAGCTCTTC ATTTCTTTAT GTTTTAAATG CACTGACCTC
2001   CCACATTCCC TTTTTAGTAA AATATTCAGA AATAATTTAA ATACATCATT GCAATGAAAA TAAATGTTTT TTATTAGGCA GAATCCAGAT GCTCAAGGCC
2101   CTTCATAATA TCCCCCAGTT TAGTAGTTGG ACTTAGGGAA CAAAGGAACC TTTAATAGAA ATTGGACAGC AAGAAAGCGA GCTTCTAGCT TATCCTCAGT
2201   CCTGCTCCTC TGCCACAAAG TGCACGCAGT TGCCGGCCGG GTCGCGCAGG GCGAACTCCC GCCCCCACGG CTGCTCGCCG ATCTCGGTCA TGGCCGGCCC
2301   GGAGGCGTCC CGGAAGTTCG TGGACACGAC CTCCGACCAC TCGGCGTACA GCTCGTCCAG GCCGCGCACC CACACCCAGG CCAGGGTGTT GTCCGGCACC
2401   ACCTGGTCCT GGACCGCGCT GATGAACAGG GTCACGTCGT CCCGGACCAC ACCGGCGAAG TCGTCCTCCA CGAAGTCCCG GGAGAACCCG AGCCGGTCGG
2501   TCCAGAACTC GACCGCTCCG GCGACGTCGC GCGCGGTGAG CACCGGAACG GCACTGGTCA ACTTGGCCAT GATGGCTCCT CCTGTCAGGA GAGGAAAGAG

                                                                    AseI
2601   AAGAAGGTTA GTACAATTGC TATAGTGAGT TGTATTATAC TATGCAGATA TACTATGCCA ATGATTAATT GTCAAACTAG GGCTGCAGGG TTCATAGTGC
2701   CACTTTTCCT GCACTGCCCC ATCTCCTGCC CACCCTTTCC CAGGCATAGA CAGTCAGTGA CTTACCAAAC TCACAGGAGG GAGAAGGCAG AAGCTTGAGA
2801   CAGACCCGCG GGACCGCCGA ACTGCGAGGG GACGTGGCTA GGGCGGCTTC TTTTATGGTG CGCCGGCCCT CGGAGGCAGG GCGCTCGGGG AGGCCTAGCG
2901   GCCAATCTGC GGTGGCAGGA GGCGGGGCCG AAGGCCGTGC CTGACCAATC CGGAGCACAT AGGAGTCTCA GCCCCCCGCC CCAAAGCAAG GGGAAGTCAC
3001   GCGCCTGTAG CGCCAGCGTG TTGTGAAATG GGGGCTTGGG GGGGTTGGGG CCCTGACTAG TCAAAACAAA CTCCCATTGA CGTCAATGGG GTGGAGACTT
3101   GGAAATCCCC GTGAGTCAAA CCGCTATCCA CGCCCATTGA TGTACTGCCA AAACCGCATC ATCATGGTAA TAGCGATGAC TAATACGTAG ATGTACTGCC
3201   AAGTAGGAAA GTCCCATAAG GTCATGTACT GGGCATAATG CCAGGCGGGC CATTTACCGT CATTGACGTC AATAGGGGGC GTACTTGGCA TATGATACAC
3301   TTGATGTACT GCCAAGTGGG CAGTTTACCG TAAATACTCC ACCCATTGAC GTCAATGGAA AGTCCCTATT GGCGTTACTA TGGGAACATA CGTCATTATT
3401   GACGTCAATG GGCGGGGGTC GTTGGGCGGT CAGCCAGGCG GGCCATTTAC CGTAAGTTAT GTAACGCCTG CAGGTTAATT AAGAACATGT GAGCAAAAGG
3501   CCAGCAAAAG GCCAGGAACC GTAAAAAGGC CGCGTTGCTG GCGTTTTTCC ATAGGCTCCG CCCCCCTGAC GAGCATCACA AAAATCGACG CTCAAGTCAG
3601   AGGTGGCGAA ACCCGACAGG ACTATAAAGA TACCAGGCGT TTCCCCCTGG AAGCTCCCTC GTGCGCTCTC CTGTTCCGAC CCTGCCGCTT ACCGGATACC
3701   TGTCCGCCTT TCTCCCTTCG GGAAGCGTGG CGCTTTCTCA TAGCTCACGC TGTAGGTATC TCAGTTCGGT GTAGGTCGTT CGCTCCAAGC TGGGCTGTGT
3801   GCACGAACCC CCCGTTCAGC CCGACCGCTG CGCCTTATCC GGTAACTATC GTCTTGAGTC CAACCCGGTA AGACACGACT TATCGCCACT GGCAGCAGCC
3901   ACTGGTAACA GGATTAGCAG AGCGAGGTAT GTAGGCGGTG CTACAGAGTT CTTGAAGTGG TGGCCTAACT ACGGCTACAC TAGAAGAACA GTATTTGGTA
4001   TCTGCGCTCT GCTGAAGCCA GTTACCTTCG GAAAAAGAGT TGGTAGCTCT TGATCCGGCA AACAAACCAC CGCTGGTAGC GGTGGTTTTT TTGTTTGCAA
4101   GCAGCAGATT ACGCGCAGAA AAAAAGGATC TCAAGAAGAT CCTTTGATCT TTTCTACGGG GTCTGACGCT CAGTGGAACG AAAACTCACG TTAAGGGATT
4201   TTGGTCATGG CTAGTTAATT AACATTTAAA TCAGCGGCCG CAATAAAATA TCTTTATTTT CATTACATCT GTGTGTTGGT TTTTTGTGTG AATCGTAACT
4301   AACATACGCT CTCCATCAAA ACAAAACGAA ACAAAACAAA CTAGCAAAAT AGGCTGTCCC CAGTGCAAGT GCAGGTGCCA GAACATTTCT CTATCGAA
                                                                                                  (SEQ ID NO:88)
```

IL2ss.CCL13(5-75).hIgG1Fc sequence

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                                 SfoI
                                                 NarI
                                                 KasI
                                                 BbeI
                                                ~~~~~~~                               IL-2 secretion signal
                                                                                      MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                EcoRI
                                ~~~~~~~ CCL13 (5-75)
        AlaLeuSer LeuAlaLeu ValThrAsnSer LeuAsnVal ProSerThr CysCysPheThr PheSerSer LysLysIle SerLeuGlnArg LeuLysSer
 601   TTGCACTAAG TCTTGCACTT GTCACGAATT CGCTCAACGT CCCATCTACT TGCTGCTTCA CATTTAGCAG TAAGAAGATC TCCTTGCAGA GGCTGAAGAG
        TyrValIle ThrThrSerArg CysProGln LysAlaVal IlePheArgThr LysLeuGly LysGluIle CysAlaAspPro LysGluLys TrpValGln
 701   CTATGTGATC ACCACCAGCA GGTGTCCCCA GAAGGCTGTC ATCTTCAGAA CCAAACTGGG CAAGGAGATC TGTGCTGACC CAAAGGAGAA GTGGGTCCAG
                                                     human IgG1 Fc (constant region)
       AsnTyrMetLys HisLeuGly ArgLysAla HisThrLeuLys ThrAspLys ThrHisThr CysProProCys ProAlaPro GluLeuLeu GlyGlyProSer
 801   AATTATATGA AACACCTGGG CCGGAAAGCT CACACCCTGA AGACTGACAA AACTCACACA TGCCCACCGT GCCCAGCACC TGAACTCCTG GGGGGACCGT
        ValPheLeu PheProPro LysProLysAsp ThrLeuMet IleSerArg ThrProGluVal ThrCysVal ValValAsp ValSerHisGlu AspProGlu
 901   CAGTCTTCCT CTTCCCCCCA AAACCCAAGG ACACCCTCAT GATCTCCCGG ACCCCTGAGG TCACATGCGT GGTGGTGGAC GTGAGCCACG AAGACCCTGA
        ValLysPhe AsnTrpTyrVal AspGlyVal GluValHis AsnAlaLysThr LysProArg GluGluGln TyrAsnSerThr TyrArgVal ValSerVal
1001   GGTCAAGTTC AACTGGTACG TGGACGGCGT GGAGGTGCAT AATGCCAAGA CAAAGCCGCG GGAGGAGCAG TACAACAGCA CGTACCGTGT GGTCAGCGTC
       LeuThrValLeu HisGlnAsp TrpLeuAsn GlyLysGluTyr LysCysLys ValSerAsn LysAlaLeuPro AlaProIle GluLysThr IleSerLysAla
1101   CTCACCGTCC TGCACCAGGA CTGGCTGAAT GGCAAGGAGT ACAAGTGCAA GGTCTCCAAC AAAGCCCTCC CAGCCCCCAT CGAGAAAACC ATCTCCAAAG
        LysGlyGln ProArgGlu ProGlnValTyr ThrLeuPro ProSerArg GluGluMetThr LysAsnGln ValSerLeu ThrCysLeuVal LysGlyPhe
1201   CCAAAGGGCA GCCCCGAGAA CCACAGGTGT ACACCCTGCC CCCATCCCGG GAGGAGATGA CCAAGAACCA GGTCAGCCTG ACCTGCCTGG TCAAAGGCTT
        TyrProSer AspIleAlaVal GluTrpGlu SerAsnGly GlnProGluAsn AsnTyrLys ThrThrPro ProValLeuAsp SerAspGly SerPhePhe
1301   CTATCCCAGC GACATCGCCG TGGAGTGGGA GAGCAATGGG CAGCCGGAGA ACAACTACAA GACCACGCCT CCCGTGCTGG ACTCCGACGG CTCCTTCTTC
       LeuTyrSerLys LeuThrVal AspLysSer ArgTrpGlnGln GlyAsnVal PheSerCys SerValMetHis GluAlaLeu HisAsnHis TyrThrGlnLys
1401   CTCTACAGCA AGCTCACCGT GGACAAGAGC AGGTGGCAGC AGGGGAACGT CTTCTCATGC TCCGTGATGC ACGAGGCTCT GCACAACCAC TACACGCAGA
                                              NheI
                                              BmtI
        SerLeuSer LeuSerPro GlyLys***(SEQ ID NO:62)
1501   AGAGCCTCTC CCTGTCTCCG GGTAAATGAG TGCTAGCTGG CCAGACATGA TAAGATACAT TGATGAGTTT GGACAAACCA CAACTAGAAT GCAGTGAAAA
1601   AAATGCTTTA TTTGTGAAAT TTGTGATGCT ATTGCTTTAT TTGTAACCAT TATAAGCTGC AATAAACAAG TTAACAACAA CAATTGCATT CATTTTATGT
                                                                                   AseI
1701   TTCAGGTTCA GGGGGAGGTG TGGGAGGTTT TTTAAAGCAA GTAAAACCTC TACAAATGTG GTATGGAATT AATTCTAAAA TACAGCATAG CAAAACTTTA
1801   ACCTCCAAAT CAAGCCTCTA CTTGAATCCT TTTCTGAGGG ATGAATAAGG CATAGGCATC AGGGGCTGTT GCCAATGTGC ATTAGCTGTT TGCAGCCTCA
```

```
1901  CCTTCTTTCA TGGAGTTTAA GATATAGTGT ATTTTCCCAA GGTTTGAACT AGCTCTTCAT TTCTTTATGT TTTAAATGCA CTGACCTCCC ACATTCCCTT
2001  TTTAGTAAAA TATTCACAAA TAATTTAAAT ACATCATTGC AATGAAAATA AATGTTTTTT ATTAGGCACA ATCCAGATGC TCAAGGCCCT TCATAATATC
2101  CCCCAGTTTA GTAGTTGGAC TTAGGGAACA AAGGAACCTT TAATAGAAAT TGGACAGCAA GAAAGCGAGC TTCTAGCTTA TCCTCAGTCC TGCTCCTCTG
2201  CCACAAAGTG CACGCAGTTG CCGGCCGGGT CGCGCAGGGC GAACTCCCGC CCCCACGGCT GCTCGCCGAT CTCGGTCATG GCCGGCCCGG AGGCGTCCCG
2301  GAAGTTCGTG GACACGACCT CCGACCACTC GGCGTACAGC TCGTCCAGGC CGCGCACCCA CACCCAGGCC AGGGTGTTGT CCGGCACCAC CTGGTCCTGG
2401  ACCGCGCTGA TGAACAGGGT CACGTCGTCC CGGACCACAC CGGCGAAGTC GTCCTCCACG AAGTCCCGGG AGAACCCGAG CCGGTCGGTC CAGAACTCGA
2501  CCGCTCCGGC GACGTCGCGC GCGGTGAGCA CCGGAACGGC ACTGGTCAAC TTGGCCATGA TGGCTCCTCC TGTCAGGAGA GGAAAGAGAA GAAGGTTAGT

                                                                      AseI
2601  ACAATTGCTA TAGTGACTTG TATTATACTA TGCAGATATA CTATGCCAAT GATTAATTGT CAAACTAGGG CTCCAGGGTT CATAGTGCCA CTTTTCCTGC
2701  ACTGCCCCAT CTCCTGCCCA CCCTTTCCCA GGCATAGACA GTCAGTGACT TACCAAACTC ACAGGAGGGA GAAGGCAGAA GCTTGAGACA GACCCGCGGG
2801  ACCGCCGAAC TGCGAGGGGA CGTGGCTAGG GCGGCTTCTT TTATGGTGCG CCGGCCCTCG GAGGCAGGGC GCTCGGGGAG GCCTAGCGGC CAATCTGCGG
2901  TGGCAGGAGG CGGGGCCGAA GGCCGTGCCT GACCAATCCG GAGCACATAG GAGTCTCAGC CCCCCGCCCC AAAGCAAGGG GAAGTCACGC GCCTGTAGCG
3001  CCAGCGTGTT GTGAAATGGG GGCTTGGGGG GGTTGGGGCC CTGACTAGTC AAAACAAACT CCCATTGACG TCAATGGGGT GGAGACTTGG AAATCCCCGT
3101  GAGTCAAACC GCTATCCACG CCCATTGATG TACTGCCAAA ACCGCATCAT CATGGTAATA GCGATGACTA ATACGTAGAT GTACTGCCAA GTAGGAAAGT
3201  CCCATAAGGT CATGTACTGG GCATAATGCC AGGCGGGCCA TTTACCGTCA TTGACGTCAA TAGGGGGCGT ACTTGGCATA TGATACACTT GATGTACTGC
3301  CAAGTGGGCA GTTTACCGTA AATACTCCAC CCATTGACGT CAATGGAAAG TCCCTATTGG CGTTACTATG GGAACATACG TCATTATTGA CGTCAATGGG
3401  CGGGGGTCGT TGGGCGGTCA GCCAGGCGGG CCATTTACCG TAAGTTATGT AACGCCTGCA GGTTAATTAA GAACATGTGA GCAAAAGGCC AGCAAAAGGC
3501  CAGGAACCGT AAAAAGGCCG CGTTGCTGGC GTTTTTCCAT AGGCTCCGCC CCCCTGACGA GCATCACAAA AATCGACGCT CAAGTCAGAG GTGGCGAAAC
3601  CCGACAGGAC TATAAAGATA CCAGGCGTTT CCCCCTGGAA GCTCCCTCGT GCGCTCTCCT GTTCCGACCC TGCCGCTTAC CGGATACCTG TCCGCCTTTC
3701  TCCCTTCGGG AAGCGTGGCG CTTTCTCATA GCTCACGCTG TAGGTATCTC AGTTCGGTGT AGGTCGTTCG CTCCAAGCTG GGCTGTGTGC ACGAACCCCC
3801  CGTTCAGCCC GACCGCTGCG CCTTATCCGG TAACTATCGT CTTGAGTCCA ACCCGGTAAG ACACGACTTA TCGCCACTGG CAGCAGCCAC TGGTAACAGG
3901  ATTAGCAGAG CGAGGTATGT AGGCGGTGCT ACAGAGTTCT TGAAGTGGTG GCCTAACTAC GGCTACACTA GAAGAACAGT ATTTGGTATC TGCGCTCTGC
4001  TGAAGCCAGT TACCTTCGGA AAAAGAGTTG GTAGCTCTTG ATCCGGCAAA CAAACCACCG CTGGTAGCGG TGGTTTTTTT GTTTGCAAGC AGCAGATTAC
4101  GCGCAGAAAA AAAGGATCTC AAGAAGATCC TTTGATCTTT TCTACGGGGT CTGACGCTCA GTGGAACGAA AACTCACGTT AAGGGATTTT GGTCATGGCT
4201  AGTTAATTAA CATTTAAATC AGCGGCCGCA ATAAAATATC TTTATTTTCA TTACATCTGT GTGTTGGTTT TTTGTGTGAA TCGTAACTAA CATACGCTCT
4301  CCATCAAAAC AAAACGAAAC AAAACAAACT AGCAAAATAG GCTGTCCCCA GTGCAAGTGC AGGTGCCAGA ACATTTCTCT ATCGAA (SEQ ID NO:89)
```

IL2ss.CCL13(5-75).hIgG1Fc sequence
[Alanine substitutions for removal of GAG binding sites – Lys & His]

```
   1     GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101     GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201     GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301     GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401     GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                          SfoI
                                          NarI
                                          KasI
                                          BbeI
                                         ~~~~~~~                                  IL-2 secretion signal
                                                                                  MetTyrArg MetGlnLeu LeuSerCysIle
 501     TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                              EcoRI
                              ~~~~~~~ CCL13 (5-75)
           AlaLeuSer LeuAlaLeu ValThrAsnSer LeuAsnVal ProSerThr CysCysPheThr PheSerSer LysLysIle SerLeuGlnArg LeuLysSer
 601     TTGCACTAAG TCTTGCACTT GTCACGAATT CGCTCAACGT CCCATCTACT TGCTGCTTCA CATTTAGCAG TAAGAAGATC TCCTTGCAGA GGCTGAAGAG
          TyrValIle ThrThrSerArg CysProGln LysAlaVal IlePheArgThr AlaLeuGly AlaGluIle CysAlaAspPro AlaGluAla TrpValGln
 701     CTATGTGATC ACCACCAGCA GGTGTCCCCA GAAGGCTGTC ATCTTCAGAA CCgcccTGGG CgcgGAGATC TGTGCTGACC CAgccGAGgc cTGGGTCCAG
                                                       human IgG1 Fc (constant region)
         AsnTyrMetAla AlaLeuGly ArgLysAla AlaThrLeuAla ThrAspLys ThrHisThr CysProProCys ProAlaPro GluLeuLeu GlyGlyProSer
 801     AATTATATGg cggctCTGGG CCGGAAAGCT gccACCCTGg ctACTGACAA AACTCACACA TGCCCACCGT GCCCAGCACC TGAACTCCTG GGGGGACCGT
           ValPheLeu PheProPro LysProLysAsp ThrLeuMet IleSerArg ThrProGluVal ThrCysVal ValValAsp ValSerHisGlu AspProGlu
 901     CAGTCTTCCT CTTCCCCCCA AAACCCAAGG ACACCCTCAT GATCTCCCGG ACCCCTGAGG TCACATGCGT GGTGGTGGAC GTGAGCCACG AAGACCCTGA
          ValLysPhe AsnTrpTyrVal AspGlyVal GluValHis AsnAlaLysThr LysProArg GluGluGln TyrAsnSerThr TyrArgVal ValSerVal
1001     GGTCAAGTTC AACTGGTACG TGGACGGCGT GGAGGTGCAT AATGCCAAGA CAAAGCCGCG GGAGGAGCAG TACAACAGCA CGTACCGTGT GGTCAGCGTC
         LeuThrValLeu HisGlnAsp TrpLeuAsn GlyLysGluTyr LysCysLys ValSerAsn LysAlaLeuPro AlaProIle GluLysThr IleSerLysAla
1101     CTCACCGTCC TGCACCAGGA CTGGCTGAAT GGCAAGGAGT ACAAGTGCAA GGTCTCCAAC AAAGCCCTCC CAGCCCCCAT CGAGAAAACC ATCTCCAAAG
           LysGlyGln ProArgGlu ProGlnValTyr ThrLeuPro ProSerArg GluGluMetThr LysAsnGln ValSerLeu ThrCysLeuVal LysGlyPhe
1201     CCAAAGGGCA GCCCCGAGAA CCACAGGTGT ACACCCTGCC CCCATCCCGG GAGGAGATGA CCAAGAACCA GGTCAGCCTG ACCTGCCTGG TCAAAGGCTT
          TyrProSer AspIleAlaVal GluTrpGlu SerAsnGly GlnProGluAsn AsnTyrLys ThrThrPro ProValLeuAsp SerAspGly SerPhePhe
1301     CTATCCCAGC GACATCGCCG TGGAGTGGGA GAGCAATGGG CAGCCGGAGA ACAACTACAA GACCACGCCT CCCGTGCTGG ACTCCGACGG CTCCTTCTTC
         LeuTyrSerLys LeuThrVal AspLysSer ArgTrpGlnGln GlyAsnVal PheSerCys SerValMetHis GluAlaLeu HisAsnHis TyrThrGlnLys
1401     CTCTACAGCA AGCTCACCGT GGACAAGAGC AGGTGGCAGC AGGGGAACGT CTTCTCATGC TCCGTGATGC ACGAGGCTCT GCACAACCAC TACACGCAGA
                                          NheI
                                          BmtI
           SerLeuSer LeuSerPro GlyLys***(SEQ ID NO:63)
1501     AGAGCCTCTC CCTGTCTCCG GGTAAATGAG TGCTAGCTGG CCAGACATGA TAAGATACAT TGATGAGTTT GGACAAACCA CAACTAGAAT GCAGTGAAAA
1601     AAATGCTTTA TTTGTGAAAT TTGTGATGCT ATTGCTTTAT TTGTAACCAT TATAAGCTGC AATAAACAAG TTAACAACAA CAATTGCATT CATTTTATGT
                                                                                   AseI
1701     TTCAGGTTCA GGGGGAGGTG TGGGAGGTTT TTTAAAGCAA GTAAAACCTC TACAAATGTG GTATGGAATT AATTCTAAAA TACAGCATAG CAAAACTTTA
```

```
1801  ACCTCCAAAT CAAGCCTCTA CTTGAATCCT TTTCTGAGGG ATGAATAAGG CATAGGCATC AGGGGCTGTT GCCAATGTGC ATTAGCTGTT TGCAGCCTCA
1901  CCTTCTTTCA TGGAGTTTAA GATATAGTGT ATTTTCCCAA GGTTTGAACT AGCTCTTCAT TTCTTTATGT TTTAAATGCA CTGACCTCCC ACATTCCCTT
2001  TTTAGTAAAA TATTCAGAAA TAATTTAAAT ACATCATTGC AATGAAAATA AATGTTTTTT ATTAGGCAGA ATCCAGATGC TCAAGGCCCT TCATAATATC
2101  CCCCAGTTTA GTAGTTGGAC TTAGGGAACA AAGGAACCTT TAATAGAAAT TGGACAGCAA GAAAGCGAGC TTCTAGCTTA TCCTCAGTCC TGCTCCTCTG
2201  CCACAAAGTG CACGCAGTTG CCGGCCGGGT CGCGCAGGGC GAACTCCCGC CCCCACGGCT GCTCGCCGAT CTCGGTCATG GCCGGCCCGG AGGCGTCCCG
2301  GAAGTTCGTG GACACGACCT CCGACCACTC GGCGTACAGC TCGTCCAGGC CGCGCACCCA CACCCAGGCC AGGGTGTTGT CCGGCACCAC CTGGTCCTGG
2401  ACCGCGCTGA TGAACAGGGT CACGTCGTCC CGGACCACAC CGGCGAAGTC GTCCTCCACG AAGTCCCGGG AGAACCCGAG CCGGTCGGTC CAGAACTCGA
2501  CCGCTCCGGC GACGTCGCGC GCGGTGAGCA CCGGAACGGC ACTGGTCAAC TTGGCCATGA TGGCTCCTCC TGTCAGGAGA GGAAAGAGAA GAAGGTTAGT
                                                            AseI
2601  ACAATTGCTA TAGTGAGTTG TATTATACTA TGCAGATATA CTATGCCAAT GATTAATTGT CAAACTAGGG CTGCAGGGTT CATAGTGCCA CTTTTCCTGC
2701  ACTGCCCCAT CTCCTGCCCA CCCTTTCCCA GGCATAGACA GTCAGTGACT TACCAAACTC ACAGGAGGGA GAAGGCAGAA GCTTGAGACA GACCCGCGGG
2801  ACCGCCGAAC TGCGAGGGGA CGTGGCTAGG GCGGCTTCTT TTATGGTGCG CCGGCCCTCG GAGGCAGGGC GCTCGGGGAG GCCTAGCGGC CAATCTGCGG
2901  TGGCAGGAGG CGGGGCCGAA GGCCGTGCCT GACCAATCCG GAGCACATAG GAGTCTCAGC CCCCCGCCCC AAAGCAAGGG GAAGTCACGC GCCTGTAGCG
3001  CCAGCGTGTT GTGAAATGGG GGCTTGGGGG GGTTGGGGCC CTGACTAGTC AAAACAAACT CCCATTGACG TCAATGGGGT GGAGACTTGG AAATCCCCGT
3101  GAGTCAAACC GCTATCCACG CCCATTGATG TACTGCCAAA ACCGCATCAT CATGGTAATA GCGATGACTA ATACGTAGAT GTACTGCCAA GTAGGAAAGT
3201  CCCATAAGGT CATGTACTGG GCATAATGCC AGGCGGGCCA TTTACCGTCA TTGACGTCAA TAGGGGGCGT ACTTGGCATA TGATACACTT GATGTACTGC
3301  CAAGTGGGCA GTTTACCGTA AATACTCCAC CCATTGACGT CAATGGAAAG TCCCTATTGG CGTTACTATG GGAACATACG TCATTATTGA CGTCAATGGG
3401  CGGGGGTCGT TGGGCGGTCA GCCAGGCGGG CCATTTACCG TAAGTTATGT AACGCCTGCA GGTTAATTAA GAACATGTGA GCAAAAGGCC AGCAAAAGGC
3501  CAGGAACCGT AAAAAGGCCG CGTTGCTGGC GTTTTTCCAT AGGCTCCGCC CCCCTGACGA GCATCACAAA AATCGACGCT CAAGTCAGAG GTGGCGAAAC
3601  CCGACAGGAC TATAAAGATA CCAGGCGTTT CCCCCTGGAA GCTCCCTCGT GCGCTCTCCT GTTCCGACCC TGCCGCTTAC CGGATACCTG TCCGCCTTTC
3701  TCCCTTCGGG AAGCGTGGCG CTTTCTCATA GCTCACGCTG TAGGTATCTC AGTTCGGTGT AGGTCGTTCG CTCCAAGCTG GGCTGTGTGC ACGAACCCCC
3801  CGTTCAGCCC GACCGCTGCG CCTTATCCGG TAACTATCGT CTTGAGTCCA ACCCGGTAAG ACACGACTTA TCGCCACTGG CAGCAGCCAC TGGTAACAGG
3901  ATTAGCAGAG CGAGGTATGT AGGCGGTGCT ACAGAGTTCT TGAAGTGGTG GCCTAACTAC GGCTACACTA GAAGAACAGT ATTTGGTATC TGCGCTCTGC
4001  TGAAGCCACT TACCTTCGGA AAAAGAGTTG GTAGCTCTTG ATCCGGCAAA CAAACCACCG CTGGTAGCGG TGGTTTTTTT GTTTGCAAGC AGCAGATTAC
4101  GCGCAGAAAA AAAGGATCTC AAGAAGATCC TTTGATCTTT TCTACGGGGT CTGACGCTCA GTGGAACGAA AACTCACGTT AAGGGATTTT GGTCATGGCT
4201  AGTTAATTAA CATTTAAATC AGCGGCCGCA ATAAAATATC TTTATTTTCA TTACATCTGT GTGTTGGTTT TTTGTGTGAA TCGTAACTAA CATACGCTCT
4301  CCATCAAAAC AAAACGAAAC AAAACAAACT AGCAAAATAG GCTGTCCCCA GTGCAAGTGC AGGTGCCAGA ACATTTCTCT ATCGAA  (SEQ ID NO:90)
```

FIG.4E (CONT)

FIG.5A
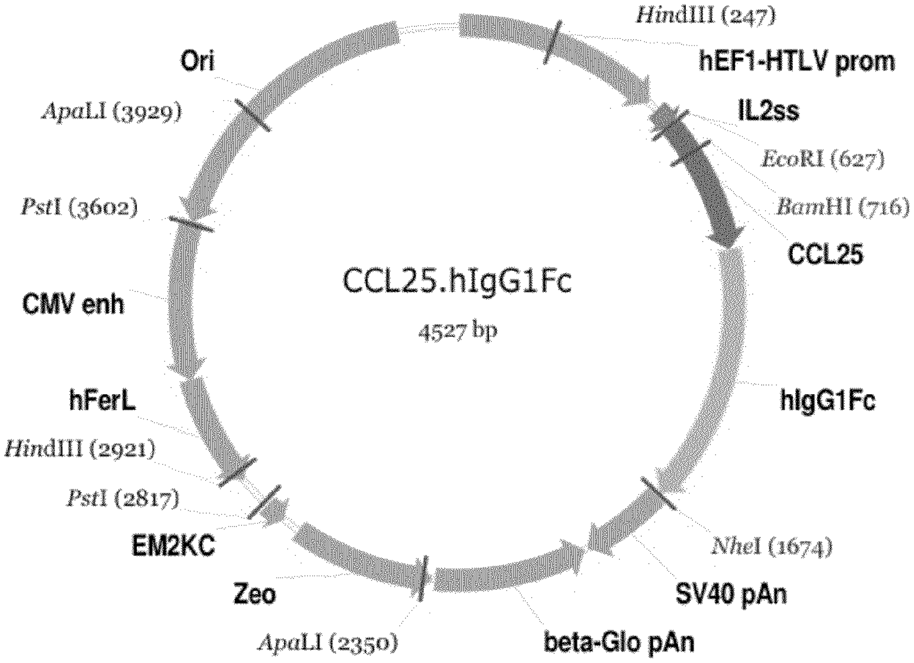
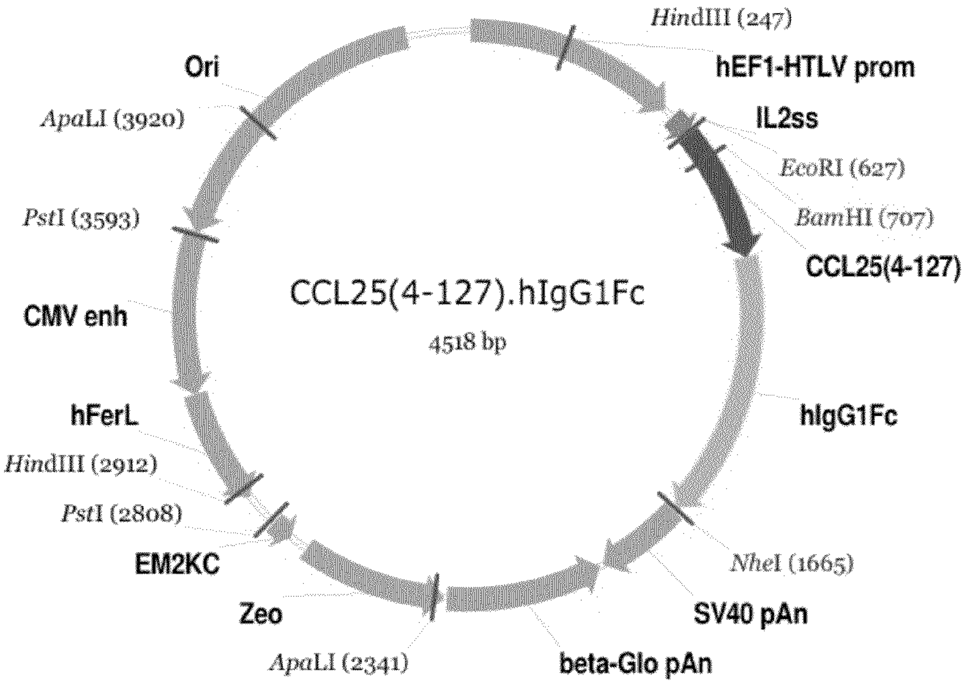
FIG.5B

FIG. 5C

IL2ss.CCL25.hIgG1Fc sequence

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                         SfoI
                                         NarI
                                         KasI
                                         BbeI
                                        ~~~~~~~                                        IL-2 secretion signal
                                                                                       MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                             EcoRI
                             ~~~~~~~ CCL25 (1-127)
        AlaLeuSer LeuAlaLeu ValThrAsnSer ThrGlnGly ValPheGlu AspCysCysLeu AlaTyrHis TyrProIle GlyTrpAlaVal LeuArgHis
 601   TTGCACTAAG TCTTGCACTT GTCACGAATT CGACCCAAGG TGTCTTTGAG GACTGCTGCC TGGCCTACCA CTACCCCATT GGGTGGGCTG TGCTCCGGCA
        AlaTrpThr TyrArgIleGln GluValSer GlySerCys AsnLeuProAla AlaIlePhe TyrLeuPro LysArgHisArg LysValCys GlyAsnPro
 701   CGCCTGGACT TACCGGATCC AGGAGGTGAG CGGGAGCTGC AATCTGCCTG CTGCGATATT CTACCTCCCC AAGAGACACA GGAAGGTGTG TGGGAACCCC
       LysSerArgGlu ValGlnArg AlaMetLys LeuLeuAspAla ArgAsnLys ValPheAla LysLeuArgHis AsnThrGln ThrPheGln GlyProHisAla
 801   AAAAGCAGGG AGGTGCAGAG AGCCATGAAG CTCCTGGATG CTCGAAATAA GGTTTTTGCA AAGCTCCGCC ACAACACGCA GACCTTCCAA GGCCCTCATG
                                                                                                human IgG1 Fc
                                                                                                (constant region)
        ValLysLys LeuSerSer GlyAsnSerLys LeuSerSer SerLysPhe SerAsnProIle SerSerSer LysArgAsn ValSerAspLys ThrHisThr
 901   CTGTAAAGAA GTTGAGTTCT GGAAACTCCA AGTTATCATC GTCCAAGTTT AGCAATCCCA TCAGCAGCAG CAAGAGGAAT GTCTCCGACA AAACTCACAC
        CysProPro CysProAlaPro GluLeuLeu GlyGlyPro SerValPheLeu PheProPro LysProLys AspThrLeuMet IleSerArg ThrProGlu
1001   ATGCCCACCG TGCCCAGCAC CTGAACTCCT GGGGGGACCG TCAGTCTTCC TCTTCCCCCC AAAACCCAAG GACACCCTCA TGATCTCCCG GACCCCTGAG
          AleI
       ValThrCysVal ValValAsp ValSerHis GluAspProGlu ValLysPhe AsnTrpTyr ValAspGlyVal GluValHis AsnAlaLys ThrLysProArg
1101   GTCACATGCG TGGTGGTGGA CGTGAGCCAC GAAGACCCTG AGGTCAAGTT CAACTGGTAC GTGGACGGCG TGGAGGTGCA TAATGCCAAG ACAAAGCCGC
        GluGluGln TyrAsnSer ThrTyrArgVal ValSerVal LeuThrVal LeuHisGlnAsp TrpLeuAsn GlyLysGlu TyrLysCysLys ValSerAsn
1201   GGGAGGAGCA GTACAACAGC ACGTACCGTG TGGTCAGCGT CCTCACCGTC CTGCACCAGG ACTGGCTGAA TGGCAAGGAG TACAAGTGCA AGGTCTCCAA
        LysAlaLeu ProAlaProIle GluLysThr IleSerLys AlaLysGlyGln ProArgGlu ProGlnVal TyrThrLeuPro ProSerArg GluGluMet
1301   CAAAGCCCTC CCAGCCCCCA TCGAGAAAAC CATCTCCAAA GCCAAAGGGC AGCCCCGAGA ACCACAGGTG TACACCCTGC CCCCATCCCG GGAGGAGATG
       ThrLysAsnGln ValSerLeu ThrCysLeu ValLysGlyPhe TyrProSer AspIleAla ValGluTrpGlu SerAsnGly GlnProGlu AsnAsnTyrLys
1401   ACCAAGAACC AGGTCAGCCT GACCTGCCTG GTCAAAGGCT TCTATCCCAG CGACATCGCC GTGGAGTGGG AGAGCAATGG GCAGCCGGAG AACAACTACA
        ThrThrPro ProValLeu AspSerAspGly SerPhePhe LeuTyrSer LysLeuThrVal AspLysSer ArgTrpGln GlnGlyAsnVal PheSerCys
1501   AGACCACGCC TCCCGTGCTG GACTCCGACG GCTCCTTCTT CCTCTACAGC AAGCTCACCG TGGACAAGAG CAGGTGGCAG CAGGGGAACG TCTTCTCATG
                                                                                      BmtI
                                                                                      NheI
        SerValMet HisGluAlaLeu HisAsnHis TyrThrGln LysSerLeuSer LeuSerPro GlyLys***(SEQ ID NO:64)
1601   CTCCGTGATG CACGAGGCTC TGCACAACCA CTACACGCAG AAGAGCCTCT CCCTGTCTCC GGGTAAATGA GTGCTAGCTG GCCAGACATG ATAAGATACA
```

```
1701   TTGATGAGTT TGGACAAACC ACAACTAGAA TGCAGTGAAA AAAATGCTTT ATTTGTGAAA TTTGTGATGC TATTGCTTTA TTTGTAACCA TTATAAGCTG
1801   CAATAAACAA GTTAACAACA ACAATTGCAT TCATTTTATG TTTCAGGTTC AGGGGGAGGT GTGGGAGGTT TTTTAAAGCA AGTAAAACCT CTACAAATGT
                 AseI
1901   GGTATGGAAT TAATTCTAAA ATACAGCATA GCAAAACTTT AACCTCCAAA TCAAGCCTCT ACTTGAATCC TTTTCTGAGG GATGAATAAG GCATAGGCAT
2001   CAGGGGCTGT TGCCAATGTG CATTAGCTGT TTGCAGCCTC ACCTTCTTTC ATGGAGTTTA AGATATAGTG TATTTTCCCA AGGTTTGAAC TAGCTCTTCA
2101   TTTCTTTATG TTTTAAATGC ACTGACCTCC CACATTCCCT TTTTAGTAAA ATATTCAGAA ATAATTTAAA TACATCATTG CAATGAAAAT AAATGTTTTT
2201   TATTAGGCAG AATCCAGATG CTCAAGGCCC TTCATAATAT CCCCCAGTTT AGTAGTTGGA CTTAGGGAAC AAAGGAACCT TTAATAGAAA TTGGACAGCA
2301   AGAAAGCGAG CTTCTAGCTT ATCCTCAGTC CTGCTCCTCT GCCACAAAGT GCACGCAGTT GCCGGCCGGG TCGCGCAGGG CGAACTCCCG CCCCCACGGC
2401   TGCTCGCCGA TCTCGGTCAT GGCCGGCCCG GAGGCGTCCC GGAAGTTCGT GGACACGACC TCCGACCACT CGGCGTACAG CTCGTCCAGG CCGCGCACCC
2501   ACACCCAGGC CAGGGTGTTG TCCGGCACCA CCTGGTCCTG GACCGCGCTG ATGAACAGGG TCACGTCGTC CCGGACCACA CCGGCGAAGT CGTCCTCCAC
2601   GAAGTCCCGG GAGAACCCGA GCCGGTCGGT CCAGAACTCG ACCGCTCCGG CGACGTCGCG CGCGGTGAGC ACCGGAACGG CACTGGTCAA CTTGGCCATG
                                                                                                                AseI
2701   ATGGCTCCTC CTGTCAGGAG AGGAAAGAGA AGAAGGTTAG TACAATTGCT ATAGTGAGTT GTATTATACT ATGCAGATAT ACTATGCCAA TGATTAATTG
2801   TCAAACTAGG GCTGCAGGGT TCATAGTGCC ACTTTTCCTG CACTGCCCCA TCTCCTGCCC ACCCTTTCCC AGGCATAGAC AGTCAGTGAC TTACCAAACT
2901   CACAGGAGGG AGAAGGCAGA AGCTTGAGAC AGACCCGCGG GACCGCCGAA CTGCGAGGGG ACGTGGCTAG GGCGGCTTCT TTTATGGTGC GCCGGCCCTC
3001   GGAGGCAGGG CGCTCGGGGA GGCCTAGCGG CCAATCTGCG GTGGCAGGAG GCGGGGCCGA AGGCCGTGCC TGACCAATCC GGAGCACATA GGAGTCTCAG
3101   CCCCCCGCCC CAAAGCAAGG GGAAGTCACG CGCCTGTAGC GCCAGCGTGT TGTGAAATGG GGGCTTGGGG GGGTTGGGGC CCTGACTAGT CAAAACAAAC
3201   TCCCATTGAC GTCAATGGGG TGGAGACTTG GAAATCCCCG TGAGTCAAAC CGCTATCCAC GCCCATTGAT GTACTGCCAA AACCGCATCA TCATGGTAAT
3301   AGCGATGACT AATACGTAGA TGTACTGCCA AGTAGGAAAG TCCCATAAGG TCATGTACTG GGCATAATGC CAGGCGGGCC ATTTACCGTC ATTGACGTCA
3401   ATAGGGGGCG TACTTGGCAT ATGATACACT TGATGTACTG CCAAGTGGGC AGTTTACCGT AAATACTCCA CCCATTGACG TCAATGGAAA GTCCCTATTG
3501   GCGTTACTAT GGGAACATAC GTCATTATTG ACGTCAATGG GCGGGGGTCG TTGGGCGGTC AGCCAGGCGG GCCATTTACC GTAAGTTATG TAACGCCTGC
3601   AGGTTAATTA AGAACATGTG AGCAAAAGGC CAGCAAAAGG CCAGGAACCG TAAAAAGGCC GCGTTGCTGG CGTTTTTCCA TAGGCTCCGC CCCCCTGACG
3701   AGCATCACAA AAATCGACGC TCAAGTCAGA GGTGGCGAAA CCCGACAGGA CTATAAAGAT ACCAGGCGTT TCCCCCTGGA AGCTCCCTCG TGCGCTCTCC
3801   TGTTCCGACC CTGCCGCTTA CCGGATACCT GTCCGCCTTT CTCCCTTCGG GAAGCGTGGC GCTTTCTCAT AGCTCACGCT GTAGGTATCT CAGTTCGGTG
3901   TAGGTCGTTC GCTCCAAGCT GGGCTGTGTG CACGAACCCC CCGTTCAGCC CGACCGCTGC GCCTTATCCG GTAACTATCG TCTTGAGTCC AACCCGGTAA
4001   GACACGACTT ATCGCCACTG GCAGCAGCCA CTGGTAACAG GATTAGCAGA GCGAGGTATG TAGGCGGTGC TACAGAGTTC TTGAAGTGGT GGCCTAACTA
4101   CGGCTACACT AGAAGAACAG TATTTGGTAT CTGCGCTCTG CTGAAGCCAG TTACCTTCGG AAAAAGAGTT GGTAGCTCTT GATCCGGCAA ACAAACCACC
4201   GCTGGTAGCG GTGGTTTTTT TGTTTGCAAG CAGCAGATTA CGCGCAGAAA AAAAGGATCT CAAGAAGATC CTTTGATCTT TTCTACGGGG TCTGACGCTC
4301   AGTGGAACGA AAACTCACGT TAAGGGATTT TGGTCATGGC TAGTTAATTA ACATTTAAAT CAGCGGCCGC AATAAAATAT CTTTATTTTC ATTACATCTG
4401   TGTGTTGGTT TTTTGTGTGA ATCGTAACTA ACATACGCTC TCCATCAAAA CAAAACGAAA CAAAACAAAC TAGCAAAATA GGCTGTCCCC AGTGCAAGTG
4501   CAGGTGCCAG AACATTTCTC TATCGAA  (SEQ ID NO:  91)
```

IL2ss.CCL25(4-127).hIgG1Fc sequence

```
   1     GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101     GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201     GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301     GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401     GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                           SfoI
                                           NarI
                                           KasI
                                           BbeI
                                          ~~~~~~~                                  IL-2 secretion signal
                                                                                   MetTyrArg MetGlnLeu LeuSerCysIle
 501     TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                              EcoRI
                              ~~~~~~~ CCL25 (4-127)
          AlaLeuSer LeuAlaLeu ValThrAsnSer ValPheGlu AspCysCys LeuAlaTyrHis TyrProIle GlyTrpAla ValLeuArgHis AlaTrpThr
 601     TTGCACTAAG TCTTGCACTT GTCACGAATT CGGTCTTTGA GGACTGCTGC CTGGCCTACC ACTACCCCAT TGGGTGGGCT GTGCTCCGGC ACGCCTGGAC
          TyrArgIle GlnGluValSer GlySerCys AsnLeuPro AlaAlaIlePhe TyrLeuPro LysArgHis ArgLysValCys GlyAsnPro LysSerArg
 701     TTACCGGATC CAGGAGGTGA GCGGGAGCTG CAATCTGCCT GCTGCGATAT TCTACCTCCC CAAGAGACAC AGGAAGGTGT GTGGGAACCC CAAAAGCAGG
         GluValGlnArg AlaMetLys LeuLeuAsp AlaArgAsnLys ValPheAla LysLeuArg HisAsnThrGln ThrPheGln GlyProHis AlaValLysLys
 801     GAGGTGCAGA GAGCCATGAA GCTCCTGGAT GCTCGAAATA AGGTTTTTGC AAAGCTCCGC CACAACACGC AGACCTTCCA AGGCCCTCAT GCTGTAAAGA
                                                                                        human IgG1 Fc (constant region)
          LeuSerSer GlyAsnSer LysLeuSerSer SerLysPhe SerAsnPro IleSerSerSer LysArgAsn ValSerAsp LysThrHisThr CysProPro
 901     AGTTGAGTTC TGGAAACTCC AAGTTATCAT CGTCCAAGTT TAGCAATCCC ATCAGCAGCA GCAAGAGGAA TGTCTCCGAC AAAACTCACA CATGCCCACC
          CysProAla ProGluLeuLeu GlyGlyPro SerValPhe LeuPheProPro LysProLys AspThrLeu MetIleSerArg ThrProGlu ValThrCys
1001     GTGCCCAGCA CCTGAACTCC TGGGGGGACC GTCAGTCTTC CTCTTCCCCC CAAAACCCAA GGACACCCTC ATGATCTCCC GGACCCCTGA GGTCACATGC
         ValValValAsp ValSerHis GluAspPro GluValLysPhe AsnTrpTyr ValAspGly ValGluValHis AsnAlaLys ThrLysPro ArgGluGluGln
1101     GTGGTGGTGG ACGTGAGCCA CGAAGACCCT GAGGTCAAGT TCAACTGGTA CGTGGACGGC GTGGAGGTGC ATAATGCCAA GACAAAGCCG CGGGAGGAGC
          TyrAsnSer ThrTyrArg ValValSerVal LeuThrVal LeuHisGln AspTrpLeuAsn GlyLysGlu TyrLysCys LysValSerAsn LysAlaLeu
1201     AGTACAACAG CACGTACCGT GTGGTCAGCG TCCTCACCGT CCTGCACCAG GACTGGCTGA ATGGCAAGGA GTACAAGTGC AAGGTCTCCA ACAAAGCCCT
          ProAlaPro IleGluLysThr IleSerLys AlaLysGly GlnProArgGlu ProGlnVal TyrThrLeu ProProSerArg GluGluMet ThrLysAsn
1301     CCCAGCCCCC ATCGAGAAAA CCATCTCCAA AGCCAAAGGG CAGCCCCGAG AACCACAGGT GTACACCCTG CCCCCATCCC GGGAGGAGAT GACCAAGAAC
         GlnValSerLeu ThrCysLeu ValLysGly PheTyrProSer AspIleAla ValGluTrp GluSerAsnGly GlnProGlu AsnAsnTyr LysThrThrPro
1401     CAGGTCAGCC TGACCTGCCT GGTCAAAGGC TTCTATCCCA GCGACATCGC CGTGGAGTGG GAGAGCAATG GGCAGCCGGA GAACAACTAC AAGACCACGC
          ProValLeu AspSerAsp GlySerPhePhe LeuTyrSer LysLeuThr ValAspLysSer ArgTrpGln GlnGlyAsn ValPheSerCys SerValMet
1501     CTCCCGTGCT GGACTCCGAC GGCTCCTTCT TCCTCTACAG CAAGCTCACC GTGGACAAGA GCAGGTGGCA GCAGGGGAAC GTCTTCTCAT GCTCCGTGAT
                                                                               BmtI
                                                                               NheI
          HisGluAla LeuHisAsnHis TyrThrGln LysSerLeu SerLeuSerPro GlyLys***(SEQ ID NO:65)
1601     GCACGAGGCT CTGCACAACC ACTACACGCA GAAGAGCCTC TCCCTGTCTC CGGGTAAATG AGTGCTAGCT GGCCAGACAT GATAAGATAC ATTGATGAGT
1701     TTGGACAAAC CACAACTAGA ATGCAGTGAA AAAAATGCTT TATTTGTGAA ATTTGTGATG CTATTGCTTT ATTTGTAACC ATTATAAGCT GCAATAAACA
                                                                                                          AseI
```

```
1801   AGTTAACAAC AACAATTGCA TTCATTTTAT GTTTCAGGTT CAGGGGGAGG TGTGGGAGGT TTTTTAAAGC AAGTAAAACC TCTACAAATG TGGTATGGAA
       AseI
1901   TTAATTCTAA AATACAGCAT AGCAAAACTT TAACCTCCAA ATCAAGCCTC TACTTGAATC CTTTTCTGAG GGATGAATAA GGCATAGGCA TCAGGGGCTG
2001   TTGCCAATGT GCATTAGCTG TTTGCAGCCT CACCTTCTTT CATGGAGTTT AAGATATAGT GTATTTTCCC AAGGTTTGAA CTAGCTCTTC ATTTCTTTAT
2101   GTTTTAAATG CACTGACCTC CCACATTCCC TTTTTAGTAA AATATTCAGA AATAATTTAA ATACATCATT GCAATGAAAA TAAATGTTTT TTATTAGGCA
2201   GAATCCAGAT GCTCAAGGCC CTTCATAATA TCCCCCAGTT TAGTAGTTGG ACTTAGGGAA CAAAGGAACC TTTAATAGAA ATTGGACAGC AAGAAAGCGA
2301   GCTTCTAGCT TATCCTCAGT CCTGCTCCTC TGCCACAAAG TGCACGCAGT TGCCGGCCGG GTCGCGCAGG GCGAACTCCC GCCCCCACGG CTGCTCGCCG
2401   ATCTCGGTCA TGGCCGGCCC GGAGGCGTCC CGGAAGTTCG TGGACACGAC CTCCGACCAC TCGGCGTACA GCTCGTCCAG GCCGCGCACC CACACCCAGG
2501   CCAGGGTGTT GTCCGGCACC ACCTGGTCCT GGACCGCGCT GATGAACAGG GTCACGTCGT CCCGGACCAC ACCGGCGAAG TCGTCCTCCA CGAAGTCCCG
2601   GGAGAACCCG AGCCGGTCGG TCCAGAACTC GACCGCTCCG GCGACGTCGC GCGCGGTGAG CACCGGAACG GCACTGGTCA ACTTGGCCAT GATGGCTCCT
                                                                                                    AseI
2701   CCTGTCAGGA GAGGAAAGAG AAGAAGGTTA GTACAATTGC TATAGTGAGT TGTATTATAC TATGCAGATA TACTATGCCA ATGATTAATT GTCAAACTAG
2801   GGCTGCAGGG TTCATAGTGC CACTTTTCCT GCACTGCCCC ATCTCCTGCC CACCCTTTCC CAGGCATAGA CAGTCAGTGA CTTACCAAAC TCACAGGAGG
2901   GAGAAGGCAG AAGCTTGAGA CAGACCCGCG GGACCGCCGA ACTGCGAGGG GACGTGGCTA GGGCGGCTTC TTTTATGGTG CGCCGGCCCT CGGAGGCAGG
3001   GCGCTCGGGG AGGCCTAGCG GCCAATCTGC GGTGGCAGGA GGCGGGGCCG AAGGCCGTGC CTGACCAATC CGGAGCACAT AGGAGTCTCA GCCCCCCGCC
3101   CCAAAGCAAG GGGAAGTCAC GCGCCTGTAG CGCCAGCGTG TTGTGAAATG GGGGCTTGGG GGGGTTGGGG CCCTGACTAG TCAAAACAAA CTCCCATTGA
3201   CGTCAATGGG GTGGAGACTT GGAAATCCCC GTGAGTCAAA CCGCTATCCA CGCCCATTGA TGTACTGCCA AAACCGCATC ATCATGGTAA TAGCGATGAC
3301   TAATACGTAG ATGTACTGCC AAGTAGGAAA GTCCCATAAG GTCATGTACT GGGCATAATG CCAGGCGGGC CATTTACCGT CATTGACGTC AATAGGGGGC
3401   GTACTTGGCA TATGATACAC TTGATGTACT GCCAAGTGGG CAGTTTACCG TAAATACTCC ACCCATTGAC GTCAATGGAA AGTCCCTATT GGCGTTACTA
3501   TGGGAACATA CGTCATTATT GACGTCAATG GGCGGGGGTC GTTGGGCGGT CAGCCAGGCG GGCCATTTAC CGTAAGTTAT GTAACGCCTG CAGGTTAATT
3601   AAGAACATGT GAGCAAAAGG CCAGCAAAAG GCCAGGAACC GTAAAAAGGC CGCGTTGCTG GCGTTTTTCC ATAGGCTCCG CCCCCCTGAC GAGCATCACA
3701   AAAATCGACG CTCAAGTCAG AGGTGGCGAA ACCCGACAGG ACTATAAAGA TACCAGGCGT TTCCCCCTGG AAGCTCCCTC GTGCGCTCTC CTGTTCCGAC
3801   CCTGCCGCTT ACCGGATACC TGTCCGCCTT TCTCCCTTCG GGAAGCGTGG CGCTTTCTCA TAGCTCACGC TGTAGGTATC TCAGTTCGGT GTAGGTCGTT
3901   CGCTCCAAGC TGGGCTGTGT GCACGAACCC CCCGTTCAGC CCGACCGCTG CGCCTTATCC GGTAACTATC GTCTTGAGTC CAACCCGGTA AGACACGACT
4001   TATCGCCACT GGCAGCAGCC ACTGGTAACA GGATTAGCAG AGCGAGGTAT GTAGGCGGTG CTACAGAGTT CTTGAAGTGG TGGCCTAACT ACGGCTACAC
4101   TAGAAGAACA GTATTTGGTA TCTGCGCTCT GCTGAAGCCA GTTACCTTCG GAAAAAGAGT TGGTAGCTCT TGATCCGGCA AACAAACCAC CGCTGGTAGC
4201   GGTGGTTTTT TTGTTTGCAA GCAGCAGATT ACGCGCAGAA AAAAAGGATC TCAAGAAGAT CCTTTGATCT TTTCTACGGG GTCTGACGCT CAGTGGAACG
4301   AAAACTCACG TTAAGGGATT TTGGTCATGG CTAGTTAATT AACATTTAAA TCAGCGGCCG CAATAAAATA TCTTTATTTT CATTACATCT GTGTGTTGGT
4401   TTTTTGTGTG AATCGTAACT AACATACGCT CTCCATCAAA ACAAAACGAA ACAAAACAAA CTAGCAAAAT AGGCTGTCCC CAGTGCAAGT GCAGGTGCCA
4501   GAACATTTCT CTATCGAA  (SEQ ID NO:92)
```

IL2ss.CCL25(4-127).hIgG1Fc sequence

[Alanine substitutions for GAG binding sites – Lys, Arg & His]

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                             SfoI
                                             NarI
                                             KasI
                                             BbeI
                                            ~~~~~~~                                     IL-2 secretion signal
                                                                                        MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                  EcoRI
                                 ~~~~~~~    CCL25 (4-127)
         AlaLeuSer LeuAlaLeu ValThrAsnSer ValPheGlu AspCysCys LeuAlaTyrHis TyrProIle GlyTrpAla ValLeuArgHis AlaTrpThr
 601   TTGCACTAAG TCTTGCACTT GTCACGAATT CGGTCTTTGA GGACTGCTGC CTGGCCTACC ACTACCCCAT TGGGTGGGCT GTGCTCCGGC ACGCCTGGAC
        TyrArgIle GlnGluValSer GlySerCys AsnLeuPro AlaAlaIlePhe TyrLeuPro AlaAlaAla AlaAlaValCys GlyAsnPro AlaSerAla
 701   TTACCGGATC CAGGAGGTGA GCGGGAGCTG CAATCTGCCT GCTGCGATAT TCTACCTCCC Cgctgccgct gccgcgGTGT GTGGGAACCC CgctAGCgcc
       GluValGlnAla AlaMetAla LeuLeuAsp AlaAlaAsnAla ValPheAla AlaLeuAla AlaAsnThrGln ThrPheGln GlyProAla AlaValAlaAla
 801   GAGGTGCAGg ctGCCATGgc cCTCCTGGAT GCTgctAATg ccGTTTTTGC AgcgCTCgct gccAACACGC AGACCTTCCA AGGCCCTgcg GCTGTAgccg
                                                                                       human IgG1 Fc (constant region)
         LeuSerSer GlyAsnSer AlaLeuSerSer SerAlaPhe SerAsnPro IleSerSerSer AlaAlaAsn ValSerAsp LysThrHisThr CysProPro
 901   ctTTGAGTTC TGGAAACTCC gccTTATCAT CGTCCgcgTT TAGCAATCCC ATCAGCAGCA GCgctgccAA TGTCTCCGAC AAAACTCACA CATGCCCACC
        CysProAla ProGluLeuLeu GlyGlyPro SerValPhe LeuPheProPro LysProLys AspThrLeu MetIleSerArg ThrProGlu ValThrCys
1001   GTGCCCAGCA CCTGAACTCC TGGGGGGACC GTCAGTCTTC CTCTTCCCCC CAAAACCCAA GGACACCCTC ATGATCTCCC GGACCCCTGA GGTCACATGC
       ValValValAsp ValSerHis GluAspPro GluValLysPhe AsnTrpTyr ValAspGly ValGluValHis AsnAlaLys ThrLysPro ArgGluGluGln
1101   GTGGTGGTGG ACGTGAGCCA CGAAGACCCT GAGGTCAAGT TCAACTGGTA CGTGGACGGC GTGGAGGTGC ATAATGCCAA GACAAAGCCG CGGGAGGAGC
         TyrAsnSer ThrTyrArg ValValSerVal LeuThrVal LeuHisGln AspTrpLeuAsn GlyLysGlu TyrLysCys LysValSerAsn LysAlaLeu·
1201   AGTACAACAG CACGTACCGT GTGGTCAGCG TCCTCACCGT CCTGCACCAG GACTGGCTGA ATGGCAAGGA GTACAAGTGC AAGGTCTCCA ACAAAGCCCT
        ProAlaPro IleGluLysThr IleSerLys AlaLysGly GlnProArgGlu ProGlnVal TyrThrLeu ProProSerArg GluGluMet ThrLysAsn
1301   CCCAGCCCCC ATCGAGAAAA CCATCTCCAA AGCCAAAGGG CAGCCCCGAG AACCACAGGT GTACACCCTG CCCCCATCCC GGGAGGAGAT GACCAAGAAC
       GlnValSerLeu ThrCysLeu ValLysGly PheTyrProSer AspIleAla ValGluTrp GluSerAsnGly GlnProGlu AsnAsnTyr LysThrThrPro
1401   CAGGTCAGCC TGACCTGCCT GGTCAAAGGC TTCTATCCCA GCGACATCGC CGTGGAGTGG GAGAGCAATG GGCAGCCGGA GAACAACTAC AAGACCACGC
         ProValLeu AspSerAsp GlySerPhePhe LeuTyrSer LysLeuThr ValAspLysSer ArgTrpGln GlnGlyAsn ValPheSerCys SerValMet·
1501   CTCCCGTGCT GGACTCCGAC GGCTCCTTCT TCCTCTACAG CAAGCTCACC GTGGACAAGA GCAGGTGGCA GCAGGGGAAC GTCTTCTCAT GCTCCGTGAT
                                                                              BmtI
                                                                              NheI
        HisGluAla LeuHisAsnHis TyrThrGln LysSerLeu SerLeuSerPro GlyLys***(SEQ ID NO:66)
1601   GCACGAGGCT CTGCACAACC ACTACACGCA GAAGAGCCTC TCCCTGTCTC CGGGTAAATG AGTGCTAGCT GGCCAGACAT GATAAGATAC ATTGATGAGT
```

```
1701   TTGGACAAAC CACAACTAGA ATGCAGTGAA AAAAATGCTT TATTTGTGAA ATTTGTGATG CTATTGCTTT ATTTGTAACC ATTATAAGCT GCAATAAACA
                                                                                                                    AseI
1801   AGTTAACAAC AACAATTGCA TTCATTTTAT GTTTCAGGTT CAGGGGGAGG TGTGGGAGGT TTTTTAAAGC AAGTAAAACC TCTACAAATG TGGTATGGAA
       AseI
1901   TTAATTCTAA AATACAGCAT AGCAAAACTT TAACCTCCAA ATCAAGCCTC TACTTGAATC CTTTTCTGAG GGATGAATAA GGCATAGGCA TCAGGGGCTG
2001   TTGCCAATGT GCATTAGCTG TTTGCAGCCT CACCTTCTTT CATGGAGTTT AAGATATAGT GTATTTTCCC AAGGTTTGAA CTAGCTCTTC ATTTCTTTAT
2101   GTTTTAAATG CACTGACCTC CCACATTCCC TTTTTAGTAA AATATTCAGA AATAATTTAA ATACATCATT GCAATGAAAA TAAATGTTTT TTATTAGGCA
2201   GAATCCAGAT GCTCAAGGCC CTTCATAATA TCCCCCAGTT TAGTAGTTGG ACTTAGGGAA CAAAGGAACC TTTAATAGAA ATTGGACAGC AAGAAAGCGA
2301   GCTTCTAGCT TATCCTCAGT CCTGCTCCTC TGCCACAAAG TGCACGCAGT TGCCGGCCGG GTCGCGCAGG GCGAACTCCC GCCCCCACGG CTGCTCGCCG
2401   ATCTCGGTCA TGGCCGGCCC GGAGGCGTCC CGGAAGTTCG TGGACACGAC CTCCGACCAC TCGGCGTACA GCTCGTCCAG GCCGCGCACC CACACCCAGG
2501   CCAGGGTGTT GTCCGGCACC ACCTGGTCCT GGACCGCGCT GATGAACAGG GTCACGTCGT CCCGGACCAC ACCGGCGAAG TCGTCCTCCA CGAAGTCCCG
2601   GGAGAACCCG AGCCGGTCGG TCCAGAACTC GACCGCTCCG GCGACGTCGC GCGCGGTGAG CACCGGAACG GCACTGGTCA ACTTGGCCAT GATGGCTCCT
                                                                                                   AseI
2701   CCTGTCAGGA GAGGAAAGAG AAGAAGGTTA GTACAATTGC TATAGTGAGT TGTATTATAC TATGCAGATA TACTATGCCA ATGATTAATT GTCAAACTAG
2801   GGCTGCAGGG TTCATAGTGC CACTTTTCCT GCACTGCCCC ATCTCCTGCC CACCCTTTCC CAGGCATAGA CAGTCAGTGA CTTACCAAAC TCACAGGAGG
2901   GAGAAGGCAG AAGCTTGAGA CAGACCCGCG GGACCGCCGA ACTGCGAGGG GACGTGGCTA GGGCGGCTTC TTTTATGGTG CGCCGGCCCT CGGAGGCAGG
3001   GCGCTCGGGG AGGCCTAGCG GCCAATCTGC GGTGGCAGGA GGCGGGGCCG AAGGCCGTGC CTGACCAATC CGGAGCACAT AGGAGTCTCA GCCCCCCGCC
3101   CCAAAGCAAG GGGAAGTCAC GCGCCTGTAG CGCCAGCGTG TTGTGAAATG GGGGCTTGGG GGGGTTGGGG CCCTGACTAG TCAAAACAAA CTCCCATTGA
3201   CGTCAATGGG GTGGAGACTT GGAAATCCCC GTGAGTCAAA CCGCTATCCA CGCCCATTGA TGTACTGCCA AAACCGCATC ATCATGGTAA TAGCGATGAC
3301   TAATACGTAG ATGTACTGCC AAGTAGGAAA GTCCCATAAG GTCATGTACT GGGCATAATG CCAGGCGGGC CATTTACCGT CATTGACGTC AATAGGGGGC
3401   GTACTTGGCA TATGATACAC TTGATGTACT GCCAAGTGGG CAGTTTACCG TAAATACTCC ACCCATTGAC GTCAATGGAA AGTCCCTATT GGCGTTACTA
3501   TGGGAACATA CGTCATTATT GACGTCAATG GGCGGGGGTC GTTGGGCGGT CAGCCAGGCG GGCCATTTAC CGTAAGTTAT GTAACGCCTG CAGGTTAATT
3601   AAGAACATGT GAGCAAAAGG CCAGCAAAAG GCCAGGAACC GTAAAAAGGC CGCGTTGCTG GCGTTTTTCC ATAGGCTCCG CCCCCCTGAC GAGCATCACA
3701   AAAATCGACG CTCAAGTCAG AGGTGGCGAA ACCCGACAGG ACTATAAAGA TACCAGGCGT TTCCCCCTGG AAGCTCCCTC GTGCGCTCTC CTGTTCCGAC
3801   CCTGCCGCTT ACCGGATACC TGTCCGCCTT TCTCCCTTCG GGAAGCGTGG CGCTTTCTCA TAGCTCACGC TGTAGGTATC TCAGTTCGGT GTAGGTCGTT
3901   CGCTCCAAGC TGGGCTGTGT GCACGAACCC CCCGTTCAGC CCGACCGCTG CGCCTTATCC GGTAACTATC GTCTTGAGTC CAACCCGGTA AGACACGACT
4001   TATCGCCACT GGCAGCAGCC ACTGGTAACA GGATTAGCAG AGCGAGGTAT GTAGGCGGTG CTACAGAGTT CTTGAAGTGG TGGCCTAACT ACGGCTACAC
4101   TAGAAGAACA GTATTTGGTA TCTGCGCTCT GCTGAAGCCA GTTACCTTCG GAAAAAGAGT TGGTAGCTCT TGATCCGGCA AACAAACCAC CGCTGGTAGC
4201   GGTGGTTTTT TTGTTTGCAA GCAGCAGATT ACGCGCAGAA AAAAAGGATC TCAAGAAGAT CCTTTGATCT TTTCTACGGG GTCTGACGCT CAGTGGAACG
4301   AAAACTCACG TTAAGGGATT TTGGTCATGG CTAGTTAATT AACATTTAAA TCAGCGGCCG CAATAAAATA TCTTTATTTT CATTACATCT GTGTGTTGGT
4401   TTTTTGTGTG AATCGTAACT AACATACGCT CTCCATCAAA ACAAAACGAA ACAAAACAAA CTAGCAAAAT AGGCTGTCCC CAGTGCAAGT GCAGGTGCCA
4501   GAACATTTCT CTATCGAA  (SEQ ID NO:93)
```

FIG.5E (CONT)

FIG.6A
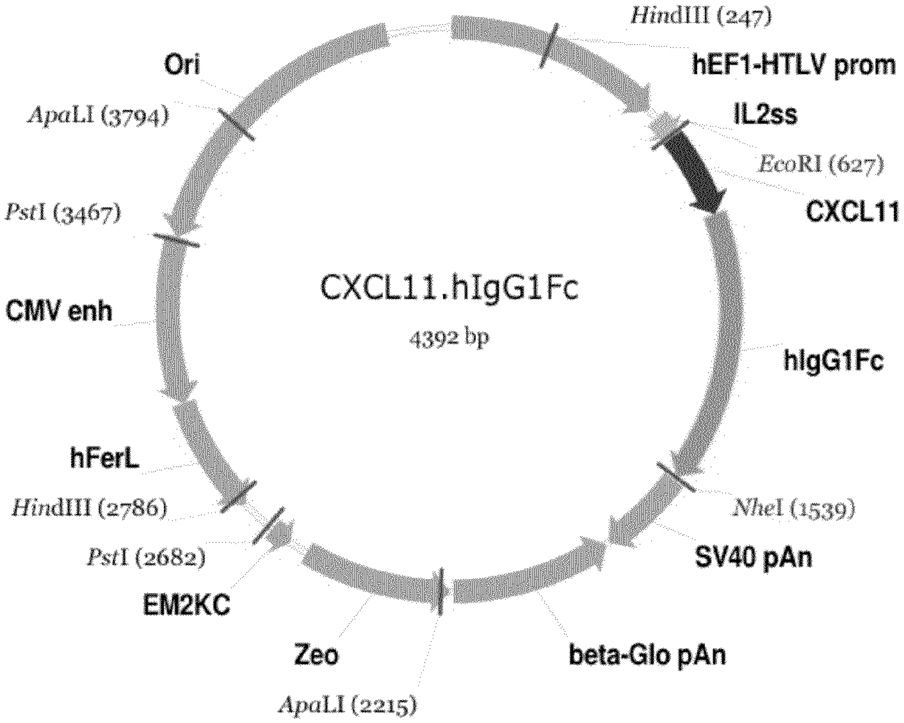
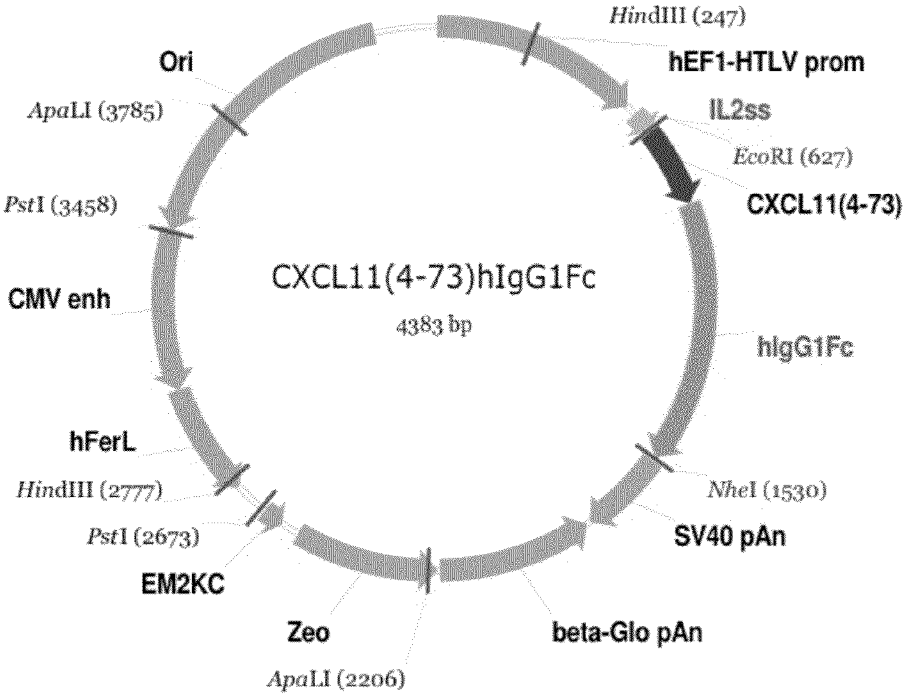
FIG.6B

FIG. 6C

IL2ss.CXCL11.hIgG1Fc sequence

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                              KasI
                                              NarI
                                              SfoI
                                              BbeI
                                              ~~~~~~~                                  IL-2 secretion signal
                                                                                       MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                 EcoRI
                                 ~~~~~~~ CXCL11 (1-73)
        AlaLeuSer LeuAlaLeu ValThrAsnSer PheProMet PheLysArg GlyArgCysLeu CysIleGly ProGlyVal LysAlaValLys ValAlaAsp
 601   TTGCACTAAG TCTTGCACTT GTCACGAATT CGTTCCCCAT GTTCAAAAGA GGACGCTGTC TTTGCATAGG CCCTGGGGTA AAAGCAGTGA AAGTGGCAGA
       IleGluLys AlaSerIleMet TyrProSer AsnAsnCys AspLysIleGlu ValIleIle ThrLeuLys GluAsnLysGly GlnArgCys LeuAsnPro
 701   TATTGAGAAA GCCTCCATAA TGTACCCAAG TAACAACTGT GACAAAATAG AAGTGATTAT TACCCTGAAA GAAAATAAAG GACAACGATG CCTAAATCCC
                                                                   human IgG1 Fc (constant region)
       LysSerLysGln AlaArgLeu IleIleLys LysValGluArg LysAsnPhe AspLysThr HisThrCysPro ProCysPro AlaProGlu LeuLeuGlyGly
 801   AAATCGAAGC AAGCAAGGCT TATAATCAAA AAAGTTGAAA GAAAGAATTT TGACAAAACT CACACATGCC CACCGTGCCC AGCACCTGAA CTCCTGGGGG
        ProSerVal PheLeuPhe ProProLysPro LysAspThr LeuMetIle SerArgThrPro GluValThr CysValVal ValAspValSer HisGluAsp
 901   GACCGTCAGT CTTCCTCTTC CCCCCAAAAC CCAAGGACAC CCTCATGATC TCCCGGACCC CTGAGGTCAC ATGCGTGGTG GTGGACGTGA GCCACGAAGA
       ProGluVal LysPheAsnTrp TyrValAsp GlyValGlu ValHisAsnAla LysThrLys ProArgGlu GluGlnTyrAsn SerThrTyr ArgValVal
1001   CCCTGAGGTC AAGTTCAACT GGTACGTGGA CGGCGTGGAG GTGCATAATG CCAAGACAAA GCCGCGGGAG GAGCAGTACA ACAGCACGTA CCGTGTGGTC
       SerValLeuThr ValLeuHis GlnAspTrp LeuAsnGlyLys GluTyrLys CysLysVal SerAsnLysAla LeuProAla ProIleGlu LysThrIleSer
1101   AGCGTCCTCA CCGTCCTGCA CCAGGACTGG CTGAATGGCA AGGAGTACAA GTGCAAGGTC TCCAACAAAG CCCTCCCAGC CCCCATCGAG AAAACCATCT
        LysAlaLys GlyGlnPro ArgGluProGln ValTyrThr LeuProPro SerArgGluGlu MetThrLys AsnGlnVal SerLeuThrCys LeuValLys
1201   CCAAAGCCAA AGGGCAGCCC CGAGAACCAC AGGTGTACAC CCTGCCCCCA TCCCGGGAGG AGATGACCAA GAACCAGGTC AGCCTGACCT GCCTGGTCAA
       GlyPheTyr ProSerAspIle AlaValGlu TrpGluSer AsnGlyGlnPro GluAsnAsn TyrLysThr ThrProProVal LeuAspSer AspGlySer
1301   AGGCTTCTAT CCCAGCGACA TCGCCGTGGA GTGGGAGAGC AATGGGCAGC CGGAGAACAA CTACAAGACC ACGCCTCCCG TGCTGGACTC CGACGGCTCC
       PhePheLeuTyr SerLysLeu ThrValAsp LysSerArgTrp GlnGlnGly AsnValPhe SerCysSerVal MetHisGlu AlaLeuHis AsnHisTyrThr
1401   TTCTTCCTCT ACAGCAAGCT CACCGTGGAC AAGAGCAGGT GGCAGCAGGG GAACGTCTTC TCATGCTCCG TGATGCACGA GGCTCTGCAC AACCACTACA
                                                BmtI
                                                NheI
        GlnLysSer LeuSerLeu SerProGlyLys ***(SEQ ID NO:67)
1501   CGCAGAAGAG CCTCTCCCTG TCTCCGGGTA AATGAGTGCT AGCTGGCCAG ACATGATAAG ATACATTGAT GAGTTTGGAC AAACCACAAC TAGAATGCAG
1601   TGAAAAAAAT GCTTTATTTG TGAAATTTGT GATGCTATTG CTTTATTTGT AACCATTATA AGCTGCAATA AACAAGTTAA CAACAACAAT TGCATTCATT
                                                                                          AseI
1701   TTATGTTTCA GGTTCAGGGG GAGGTGTGGG AGGTTTTTTA AAGCAAGTAA AACCTCTACA AATGTGGTAT GGAATTAATT CTAAAATACA GCATAGCAAA
1801   ACTTTAACCT CCAAATCAAG CCTCTACTTG AATCCTTTTC TGAGGGATGA ATAAGGCATA GGCATCAGGG GCTGTTGCCA ATGTGCATTA GCTGTTTGCA
```

```
1901   GCCTCACCTT CTTTCATGGA GTTTAAGATA TAGTGTATTT TCCCAAGGTT TGAACTAGCT CTTCATTTCT TTATGTTTTA AATGCACTGA CCTCCCACAT
2001   TCCCTTTTTA GTAAAATATT CAGAAATAAT TTAAATACAT CATTGCAATG AAAATAAATG TTTTTTATTA GGCAGAATCC AGATGCTCAA GGCCCTTCAT
2101   AATATCCCCC AGTTTAGTAG TTGGACTTAG GGAACAAAGG AACCTTTAAT AGAAATTGGA CAGCAAGAAA GCGAGCTTCT AGCTTATCCT CAGTCCTGCT
2201   CCTCTGCCAC AAAGTGCACG CAGTTGCCGG CCGGGTCGCG CAGGGCGAAC TCCCGCCCCC ACGGCTGCTC GCCGATCTCG GTCATGGCCG GCCCGGAGGC
2301   GTCCCGGAAG TTCGTGGACA CGACCTCCGA CCACTCGGCG TACAGCTCGT CCAGGCCGCG CACCCACACC CAGGCCAGGG TGTTGTCCGG CACCACCTGG
2401   TCCTGGACCG CGCTGATGAA CAGGGTCACG TCGTCCCGGA CCACACCGGC GAAGTCGTCC TCCACGAAGT CCCGGGAGAA CCCGAGCCGG TCGGTCCAGA
2501   ACTCGACCGC TCCGGCGACG TCGCGCGCGG TGAGCACCGG AACGGCACTG GTCAACTTGG CCATGATGGC TCCTCCTGTC AGGAGAGGAA AGAGAAGAAG

                                                                         AseI
2601   GTTAGTACAA TTGCTATAGT GAGTTGTATT ATACTATGCA GATATACTAT GCCAATGATT AATTGTCAAA CTAGGGCTGC AGGGTTCATA GTGCCACTTT
2701   TCCTGCACTG CCCCATCTCC TGCCCACCCT TTCCCAGGCA TAGACAGTCA GTGACTTACC AAACTCACAG GAGGGAGAAG GCAGAAGCTT GAGACAGACC
2801   CGCGGGACCG CCGAACTGCG AGGGGACGTG GCTAGGGCGG CTTCTTTTAT GGTGCGCCGG CCCTCGGAGG CAGGGCGCTC GGGGAGGCCT AGCGGCCAAT
2901   CTGCGGTGGC AGGAGGCGGG GCCGAAGGCC GTGCCTGACC AATCCGGAGC ACATAGGAGT CTCAGCCCCC CGCCCCAAAG CAAGGGGAAG TCACGCGCCT
3001   GTAGCGCCAG CGTGTTGTGA AATGGGGGCT TGGGGGGGTT GGGGCCCTGA CTAGTCAAAA CAAACTCCCA TTGACGTCAA TGGGGTGGAG ACTTGGAAAT
3101   CCCCGTGAGT CAAACCGCTA TCCACGCCCA TTGATGTACT GCCAAAACCG CATCATCATG GTAATAGCGA TGACTAATAC GTAGATGTAC TGCCAAGTAG
3201   GAAAGTCCCA TAAGGTCATG TACTGGGCAT AATGCCAGGC GGGCCATTTA CCGTCATTGA CGTCAATAGG GGGCGTACTT GGCATATGAT ACACTTGATG
3301   TACTGCCAAG TGGGCAGTTT ACCGTAAATA CTCCACCCAT TGACGTCAAT GGAAAGTCCC TATTGGCGTT ACTATGGGAA CATACGTCAT TATTGACGTC
3401   AATGGGCGGG GGTCGTTGGG CGGTCAGCCA GGCGGGCCAT TTACCGTAAG TTATGTAACG CCTGCAGGTT AATTAAGAAC ATGTGAGCAA AAGGCCAGCA
3501   AAAGGCCAGG AACCGTAAAA AGGCCGCGTT GCTGGCGTTT TTCCATAGGC TCCGCCCCCC TGACGAGCAT CACAAAAATC GACGCTCAAG TCAGAGGTGG
3601   CGAAACCCGA CAGGACTATA AAGATACCAG GCGTTTCCCC CTGGAAGCTC CCTCGTGCGC TCTCCTGTTC CGACCCTGCC GCTTACCGGA TACCTGTCCG
3701   CCTTTCTCCC TTCGGGAAGC GTGGCGCTTT CTCATAGCTC ACGCTGTAGG TATCTCAGTT CGGTGTAGGT CGTTCGCTCC AAGCTGGGCT GTGTGCACGA
3801   ACCCCCCGTT CAGCCCGACC GCTGCGCCTT ATCCGGTAAC TATCGTCTTG AGTCCAACCC GGTAAGACAC GACTTATCGC CACTGGCAGC AGCCACTGGT
3901   AACAGGATTA GCAGAGCGAG GTATGTAGGC GGTGCTACAG AGTTCTTGAA GTGGTGGCCT AACTACGGCT ACACTAGAAG AACAGTATTT GGTATCTGCG
4001   CTCTGCTGAA GCCAGTTACC TTCGGAAAAA GAGTTGGTAG CTCTTGATCC GGCAAACAAA CCACCGCTGG TAGCGGTGGT TTTTTTGTTT GCAAGCAGCA
4101   GATTACGCGC AGAAAAAAAG GATCTCAAGA AGATCCTTTG ATCTTTTCTA CGGGGTCTGA CGCTCAGTGG AACGAAAACT CACGTTAAGG GATTTTGGTC
4201   ATGGCTAGTT AATTAACATT TAAATCAGCG GCCGCAATAA AATATCTTTA TTTTCATTAC ATCTGTGTGT TGGTTTTTTG TGTGAATCGT AACTAACATA
4301   CGCTCTCCAT CAAAACAAAA CGAAACAAAA CAAACTAGCA AAATAGGCTG TCCCCAGTGC AAGTGCAGGT GCCAGAACAT TTCTCTATCG AA (SEQ ID NO:94)
```

IL2ss.CXCL11(4-73).hIgG1Fc sequence

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCT\CC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                           KasI
                                           NarI
                                           SfoI
                                           BbeI
                                           ~~~~~~~                                      IL-2 secretion signal
                                                                                        MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                 EcoRI
                                 ~~~~~~~ CXCL11 (4-73)
        AlaLeuSer LeuAlaLeu ValThrAsnSer PheLysArg GlyArgCys LeuCysIleGly ProGlyVal LysAlaVal LysValAlaAsp IleGluLys
 601   TTGCACTAAG TCTTGCACTT GTCACGAATT CGTTCAAAAG AGGACGCTGT CTTTGCATAG GCCCTGGGGT AAAAGCAGTG AAAGTGGCAG ATATTGAGAA
        AlaSerIle MetTyrProSer AsnAsnCys AspLysIle GluValIleIle ThrLeuLys GluAsnLys GlyGlnArgCys LeuAsnPro LysSerLys
 701   AGCCTCCATA ATGTACCCAA GTAACAACTG TGACAAAATA GAAGTGATTA TTACCCTGAA AGAAAATAAA GGACAACGAT GCCTAAATCC CAAATCGAAG
                                                            human IgG1 Fc (constant region)
       GlnAlaArgLeu IleIleLys LysValGlu ArgLysAsnPhe AspLysThr HisThrCys ProProCysPro AlaProGlu LeuLeuGly GlyProSerVal
 801   CAAGCAAGGC TTATAATCAA AAAAGTTGAA AGAAAGAATT TTGACAAAAC TCACACATGC CCACCGTGCC CAGCACCTGA ACTCCTGGGG GGACCGTCAG
        PheLeuPhe ProProLys ProLysAspThr LeuMetIle SerArgThr ProGluValThr CysValVal ValAspVal SerHisGluAsp ProGluVal
 901   TCTTCCTCTT CCCCCCAAAA CCCAAGGACA CCCTCATGAT CTCCCGGACC CCTGAGGTCA CATGCGTGGT GGTGGACGTG AGCCACGAAG ACCCTGAGGT
        LysPheAsn TrpTyrValAsp GlyValGlu ValHisAsn AlaLysThrLys ProArgGlu GluGlnTyr AsnSerThrTyr ArgValVal SerValLeu
1001   CAAGTTCAAC TGGTACGTGG ACGGCGTGGA GGTGCATAAT GCCAAGACAA AGCCGCGGGA GGAGCAGTAC AACAGCACGT ACCGTGTGGT CAGCGTCCTC
       ThrValLeuHis GlnAspTrp LeuAsnGly LysGluTyrLys CysLysVal SerAsnLys AlaLeuProAla ProIleGlu LysThrIle SerLysAlaLys
1101   ACCGTCCTGC ACCAGGACTG GCTGAATGGC AAGGAGTACA AGTGCAAGGT CTCCAACAAA GCCCTCCCAG CCCCCATCGA GAAAACCATC TCCAAAGCCA
        GlyGlnPro ArgGluPro GlnValTyrThr LeuProPro SerArgGlu GluMetThrLys AsnGlnVal SerLeuThr CysLeuValLys GlyPheTyr
1201   AAGGGCAGCC CCGAGAACCA CAGGTGTACA CCCTGCCCCC ATCCCGGGAG GAGATGACCA AGAACCAGGT CAGCCTGACC TGCCTGGTCA AAGGCTTCTA
        ProSerAsp IleAlaValGlu TrpGluSer AsnGlyGln ProGluAsnAsn TyrLysThr ThrProPro ValLeuAspSer AspGlySer PhePheLeu
1301   TCCCAGCGAC ATCGCCGTGG AGTGGGAGAG CAATGGGCAG CCGGAGAACA ACTACAAGAC CACGCCTCCC GTGCTGGACT CCGACGGCTC CTTCTTCCTC
       TyrSerLysLeu ThrValAsp LysSerArg TrpGlnGlnGly AsnValPhe SerCysSer ValMetHisGlu AlaLeuHis AsnHisTyr ThrGlnLysSer
1401   TACAGCAAGC TCACCGTGGA CAAGAGCAGG TGGCAGCAGG GGAACGTCTT CTCATGCTCC GTGATGCACG AGGCTCTGCA CAACCACTAC ACGCAGAAGA
                                     BmtI
                                     NheI
        LeuSerLeu SerProGly Lys***(SEQ ID NO:68)
1501   GCCTCTCCCT GTCTCCGGGT AAATGAGTGC TAGCTGGCCA GACATGATAA GATACATTGA TGAGTTTGGA CAAACCACAA CTAGAATGCA GTGAAAAAAA
1601   TGCTTTATTT GTGAAATTTG TGATGCTATT GCTTTATTTG TAACCATTAT AAGCTGCAAT AAACAAGTTA ACAACAACAA TTGCATTCAT TTTATGTTTC
                                                                              AseI
1701   AGGTTCAGGG GGAGGTGTGG GAGGTTTTTT AAAGCAAGTA AAACCTCTAC AAATGTGGTA TGGAATTAAT TCTAAAATAC AGCATAGCAA AACTTTAACC
1801   TCCAAATCAA GCCTCTACTT GAATCCTTTT CTGAGGGATG AATAAGGCAT AGGCATCAGG GGCTGTTGCC AATGTGCATT AGCTGTTTGC AGCCTCACCT
```

```
1901   TCTTTCATGG AGTTTAAGAT ATAGTGTATT TTCCCAAGGT TTGAACTAGC TCTTCATTTC TTTATGTTTT AAATGCACTG ACCTCCCACA TTCCCTTTTT
2001   AGTAAAATAT TCAGAAATAA TTTAAATACA TCATTGCAAT GAAAATAAAT GTTTTTTATT AGGCAGAATC CAGATGCTCA AGGCCCTTCA TAATATCCCC
2101   CAGTTTAGTA GTTGGACTTA GGGAACAAAG GAACCTTTAA TAGAAATTGG ACAGCAAGAA AGCGAGCTTC TAGCTTATCC TCAGTCCTGC TCCTCTGCCA
2201   CAAAGTGCAC GCAGTTGCCG GCCGGGTCGC GCAGGGCGAA CTCCCGCCCC CACGGCTGCT CGCCGATCTC GGTCATGGCC GGCCCGGAGG CGTCCCGGAA
2301   GTTCGTGGAC ACGACCTCCG ACCACTCGGC GTACAGCTCG TCCAGGCCGC GCACCCACAC CCAGGCCAGG GTGTTGTCCG GCACCACCTG GTCCTGGACC
2401   GCGCTGATGA ACAGGGTCAC GTCGTCCCGG ACCACACCGG CGAAGTCGTC CTCCACGAAG TCCCGGGAGA ACCCGAGCCG GTCGGTCCAG AACTCGACCG
2501   CTCCGGCGAC GTCGCGCGCG GTGAGCACCG GAACGGCACT GGTCAACTTG GCCATGATGG CTCCTCCTGT CAGGAGAGGA AAGAGAAGAA GGTTAGTACA

                                                    AseI
2601   ATTGCTATAG TGAGTTGTAT TATACTATGC AGATATACTA TGCCAATGAT TAATTGTCAA ACTAGGGCTG CAGGGTTCAT AGTGCCACTT TTCCTGCACT
2701   GCCCCATCTC CTGCCCACCC TTTCCCAGGC ATAGACAGTC AGTGACTTAC CAAACTCACA GGAGGGAGAA GGCAGAAGCT TGAGACAGAC CCGCGGGACC
2801   GCCGAACTGC GAGGGGACGT GGCTAGGGCG GCTTCTTTTA TGGTGCGCCG GCCCTCGGAG GCAGGGCGCT CGGGGAGGCC TAGCGGCCAA TCTGCGGTGG
2901   CAGGAGGCGG GGCCGAAGGC CGTGCCTGAC CAATCCGGAG CACATAGGAG TCTCAGCCCC CCGCCCCAAA GCAAGGGGAA GTCACGCGCC TGTAGCGCCA
3001   GCGTGTTGTG AAATGGGGGC TTGGGGGGGT TGGGGCCCTG ACTAGTCAAA ACAAACTCCC ATTGACGTCA ATGGGGTGGA GACTTGGAAA TCCCCGTGAG
3101   TCAAACCGCT ATCCACGCCC ATTGATGTAC TGCCAAAACC GCATCATCAT GGTAATAGCG ATGACTAATA CGTAGATGTA CTGCCAAGTA GGAAAGTCCC
3201   ATAAGGTCAT GTACTGGGCA TAATGCCAGG CGGGCCATTT ACCGTCATTG ACGTCAATAG GGGGCGTACT TGGCATATGA TACACTTGAT GTACTGCCAA
3301   GTGGGCAGTT TACCGTAAAT ACTCCACCCA TTGACGTCAA TGGAAAGTCC CTATTGGCGT TACTATGGGA ACATACGTCA TTATTGACGT CAATGGGCGG
3401   GGGTCGTTGG GCGGTCAGCC AGGCGGGCCA TTTACCGTAA GTTATGTAAC GCCTGCAGGT TAATTAAGAA CATGTGAGCA AAAGGCCAGC AAAAGGCCAG
3501   GAACCGTAAA AAGGCCGCGT TGCTGGCGTT TTTCCATAGG CTCCGCCCCC CTGACGAGCA TCACAAAAAT CGACGCTCAA GTCAGAGGTG GCGAAACCCG
3601   ACAGGACTAT AAAGATACCA GGCGTTTCCC CCTGGAAGCT CCCTCGTGCG CTCTCCTGTT CCGACCCTGC CGCTTACCGG ATACCTGTCC GCCTTTCTCC
3701   CTTCGGGAAG CGTGGCGCTT TCTCATAGCT CACGCTGTAG GTATCTCAGT TCGGTGTAGG TCGTTCGCTC CAAGCTGGGC TGTGTGCACG AACCCCCCGT
3801   TCAGCCCGAC CGCTGCGCCT TATCCGGTAA CTATCGTCTT GAGTCCAACC CGGTAAGACA CGACTTATCG CCACTGGCAG CAGCCACTGG TAACAGGATT
3901   AGCAGAGCGA GGTATGTAGG CGGTGCTACA GAGTTCTTGA AGTGGTGGCC TAACTACGGC TACACTAGAA GAACAGTATT TGGTATCTGC GCTCTGCTGA
4001   AGCCAGTTAC CTTCGGAAAA AGAGTTGGTA GCTCTTGATC CGGCAAACAA ACCACCGCTG GTAGCGGTGG TTTTTTTGTT TGCAAGCAGC AGATTACGCG
4101   CAGAAAAAAA GGATCTCAAG AAGATCCTTT GATCTTTTCT ACGGGGTCTG ACGCTCAGTG GAACGAAAAC TCACGTTAAG GGATTTTGGT CATGGCTAGT
4201   TAATTAACAT TTAAATCAGC GGCCGCAATA AAATATCTTT ATTTTCATTA CATCTGTGTG TTGGTTTTTT GTGTGAATCG TAACTAACAT ACGCTCTCCA
4301   TCAAAACAAA ACGAAACAAA ACAAACTAGC AAAATAGGCT GTCCCCAGTG CAAGTGCAGG TGCCAGAACA TTTCTCTATC GAA (SEQ ID NO:95)
```

IL2ss.CXCL11(4-73).hIgG1Fc sequence [Alanine substitutions for removal of GAG binding sites – Lys & His]

```
   1  GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101  GAGAAGGTGG CGCGGGGTAA ACTGGGAAAG TGATGTCGTG TACTGGCT\CC GCCTTTTTCC CGAGGGTGGG GGAGAACCGT ATATAAGTGC AGTAGTCGCC
 201  GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301  GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401  GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                             KasI
                                             NarI
                                             SfoI
                                             BbeI
                                            ~~~~~~~                                    IL-2 secretion signal
                                                                                       MetTyrArg MetGlnLeu LeuSerCysIle
 501  TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                 EcoRI
                                 ~~~~~~~ CXCL11 (4-73)
        AlaLeuSer LeuAlaLeu ValThrAsnSer PheLysArg GlyArgCys LeuCysIleGly ProGlyVal LysAlaVal LysValAlaAsp IleGluAla
 601  TTGCACTAAG TCTTGCACTT GTCACGAATT CGTTCAAAAG AGGACGCTGT CTTTGCATAG GCCCTGGGGT AAAAGCAGTG AAAGTGGCAG ATATTGAGgc
       AlaSerIle MetTyrProSer AsnAsnCys AspLysIle GluValIleIle ThrLeuAla GluAsnAla GlyGlnAlaCys LeuAsnPro AlaSerAla
 701  cGCCTCCATA ATGTACCCAA GTAACAACTG TGACAAAATA GAAGTGATTA TTACCCTGgc aGAAAATgcc GGACAAgcaT GCCTAAATCC CgccTCGgca
                                                       human IgG1 Fc (constant region)
      GlnAlaAlaLeu IleIleAla AlaValGlu AlaAlaAsnPhe AspLysThr HisThrCys ProProCysPro AlaProGlu LeuLeuGly GlyProSerVal
 801  CAAGCAgccC TTATAATCgc agccGTTGAA gcagccAATT TTGACAAAAC TCACACATGC CCACCGTGCC CAGCACCTGA ACTCCTGGGG GGACCGTCAG
        PheLeuPhe ProProLys ProLysAspThr LeuMetIle SerArgThr ProGluValThr CysValVal ValAspVal SerHisGluAsp ProGluVal
 901  TCTTCCTCTT CCCCCCAAAA CCCAAGGACA CCCTCATGAT CTCCCGGACC CCTGAGGTCA CATGCGTGGT GGTGGACGTG AGCCACGAAG ACCCTGAGGT
       LysPheAsn TrpTyrValAsp GlyValGlu ValHisAsn AlaLysThrLys ProArgGlu GluGlnTyr AsnSerThrTyr ArgValVal SerValLeu
1001  CAAGTTCAAC TGGTACGTGG ACGGCGTGGA GGTGCATAAT GCCAAGACAA AGCCGCGGGA GGAGCAGTAC AACAGCACGT ACCGTGTGGT CAGCGTCCTC
      ThrValLeuHis GlnAspTrp LeuAsnGly LysGluTyrLys CysLysVal SerAsnLys AlaLeuProAla ProIleGlu LysThrIle SerLysAlaLys
1101  ACCGTCCTGC ACCAGGACTG GCTGAATGGC AAGGAGTACA AGTGCAAGGT CTCCAACAAA GCCCTCCCAG CCCCCATCGA GAAAACCATC TCCAAAGCCA
        GlyGlnPro ArgGluPro GlnValTyrThr LeuProPro SerArgGlu GluMetThrLys AsnGlnVal SerLeuThr CysLeuValLys GlyPheTyr
1201  AAGGGCAGCC CCGAGAACCA CAGGTGTACA CCCTGCCCCC ATCCCGGGAG GAGATGACCA AGAACCAGGT CAGCCTGACC TGCCTGGTCA AAGGCTTCTA
       ProSerAsp IleAlaValGlu TrpGluSer AsnGlyGln ProGluAsnAsn TyrLysThr ThrProPro ValLeuAspSer AspGlySer PhePheLeu
1301  TCCCAGCGAC ATCGCCGTGG AGTGGGAGAG CAATGGGCAG CCGGAGAACA ACTACAAGAC CACGCCTCCC GTGCTGGACT CCGACGGCTC CTTCTTCCTC
      TyrSerLysLeu ThrValAsp LysSerArg TrpGlnGlnGly AsnValPhe SerCysSer ValMetHisGlu AlaLeuHis AsnHisTyr ThrGlnLysSer
1401  TACAGCAAGC TCACCGTGGA CAAGAGCAGG TGGCAGCAGG GGAACGTCTT CTCATGCTCC GTGATGCACG AGGCTCTGCA CAACCACTAC ACGCAGAAGA
                                   BmtI
                                   NheI
        LeuSerLeu SerProGly Lys***(SEQ ID NO:69)
1501  GCCTCTCCCT GTCTCCGGGT AAATGAGTGC TAGCTGGCCA GACATGATAA GATACATTGA TGAGTTTGGA CAAACCACAA CTAGAATGCA GTGAAAAAAA
1601  TGCTTTATTT GTGAAATTTG TGATGCTATT GCTTTATTTG TAACCATTAT AAGCTGCAAT AAACAAGTTA ACAACAACAA TTGCATTCAT TTTATGTTTC
                                                                            AseI
1701  AGGTTCAGGG GGAGGTGTGG GAGGTTTTTT AAAGCAAGTA AAACCTCTAC AAATGTGGTA TGGAATTAAT TCTAAAATAC AGCATAGCAA AACTTTAACC
1801  TCCAAATCAA GCCTCTACTT GAATCCTTTT CTGAGGGATG AATAAGGCAT AGGCATCAGG GGCTGTTGCC AATGTGCATT AGCTGTTTGC AGCCTCACCT
```

```
1901   TCTTTCATGG AGTTTAAGAT ATAGTGTATT TTCCCAAGGT TTGAACTAGC TCTTCATTTC TTTATGTTTT AAATGCACTG ACCTCCCACA TTCCCTTTTT
2001   AGTAAAATAT TCAGAAATAA TTTAAATACA TCATTGCAAT GAAAATAAAT GTTTTTTATT AGGCAGAATC CAGATGCTCA AGGCCCTTCA TAATATCCCC
2101   CAGTTTAGTA GTTGGACTTA GGGAACAAAG GAACCTTTAA TAGAAATTGG ACAGCAAGAA AGCGAGCTTC TAGCTTATCC TCAGTCCTGC TCCTCTGCCA
2201   CAAAGTGCAC GCAGTTGCCG GCCGGGTCGC GCAGGGCGAA CTCCCGCCCC CACGGCTGCT CGCCGATCTC GGTCATGGCC GGCCCGGAGG CGTCCCGGAA
2301   GTTCGTGGAC ACGACCTCCG ACCACTCGGC GTACAGCTCG TCCAGGCCGC GCACCCACAC CCAGGCCAGG GTGTTGTCCG GCACCACCTG GTCCTGGACC
2401   GCGCTGATGA ACAGGGTCAC GTCGTCCCGG ACCACACCGG CGAAGTCGTC CTCCACGAAG TCCCGGGAGA ACCCGAGCCG GTCGGTCCAG AACTCGACCG
2501   CTCCGGCGAC GTCGCGCGCG GTGAGCACCG GAACGGCACT GGTCAACTTG GCCATGATGG CTCCTCCTGT CAGGAGAGGA AAGAGAAGAA GGTTAGTACA

                                                   AseI
2601   ATTGCTATAG TGAGTTGTAT TATACTATGC AGATATACTA TGCCAATGAT TAATTGTCAA ACTAGGGCTG CAGGGTTCAT AGTGCCACTT TTCCTGCACT
2701   GCCCCATCTC CTGCCCACCC TTTCCCAGGC ATAGACAGTC AGTGACTTAC CAAACTCACA GGAGGGAGAA GGCAGAAGCT TGAGACAGAC CCGCGGGACC
2801   GCCGAACTGC GAGGGGACGT GGCTAGGGCG GCTTCTTTTA TGGTGCGCCG GCCCTCGGAG GCAGGGCGCT CGGGGAGGCC TAGCGGCCAA TCTGCGGTGG
2901   CAGGAGGCGG GGCCGAAGGC CGTGCCTGAC CAATCCGGAG CACATAGGAG TCTCAGCCCC CCGCCCCAAA GCAAGGGGAA GTCACGCGCC TGTAGCGCCA
3001   GCGTGTTGTG AAATGGGGGC TTGGGGGGGT TGGGGCCCTG ACTAGTCAAA ACAAACTCCC ATTGACGTCA ATGGGGTGGA GACTTGGAAA TCCCCGTGAG
3101   TCAAACCGCT ATCCACGCCC ATTGATGTAC TGCCAAAACC GCATCATCAT GGTAATAGCG ATGACTAATA CGTAGATGTA CTGCCAAGTA GGAAAGTCCC
3201   ATAAGGTCAT GTACTGGGCA TAATGCCAGG CGGGCCATTT ACCGTCATTG ACGTCAATAG GGGGCGTACT TGGCATATGA TACACTTGAT GTACTGCCAA
3301   GTGGGCAGTT TACCGTAAAT ACTCCACCCA TTGACGTCAA TGGAAAGTCC CTATTGGCGT TACTATGGGA ACATACGTCA TTATTGACGT CAATGGGCGG
3401   GGGTCGTTGG GCGGTCAGCC AGGCGGGCCA TTTACCGTAA GTTATGTAAC GCCTGCAGGT TAATTAAGAA CATGTGAGCA AAAGGCCAGC AAAAGGCCAG
3501   GAACCGTAAA AAGGCCGCGT TGCTGGCGTT TTTCCATAGG CTCCGCCCCC CTGACGAGCA TCACAAAAAT CGACGCTCAA GTCAGAGGTG GCGAAACCCG
3601   ACAGGACTAT AAAGATACCA GGCGTTTCCC CCTGGAAGCT CCCTCGTGCG CTCTCCTGTT CCGACCCTGC CGCTTACCGG ATACCTGTCC GCCTTTCTCC
3701   CTTCGGGAAG CGTGGCGCTT TCTCATAGCT CACGCTGTAG GTATCTCAGT TCGGTGTAGG TCGTTCGCTC CAAGCTGGGC TGTGTGCACG AACCCCCCGT
3801   TCAGCCCGAC CGCTGCGCCT TATCCGGTAA CTATCGTCTT GAGTCCAACC CGGTAAGACA CGACTTATCG CCACTGGCAG CAGCCACTGG TAACAGGATT
3901   AGCAGAGCGA GGTATGTAGG CGGTGCTACA GAGTTCTTGA AGTGGTGGCC TAACTACGGC TACACTAGAA GAACAGTATT TGGTATCTGC GCTCTGCTGA
4001   AGCCAGTTAC CTTCGGAAAA AGAGTTGGTA GCTCTTGATC CGGCAAACAA ACCACCGCTG GTAGCGGTGG TTTTTTTGTT TGCAAGCAGC AGATTACGCG
4101   CAGAAAAAAA GGATCTCAAG AAGATCCTTT GATCTTTTCT ACGGGGTCTG ACGCTCAGTG GAACGAAAAC TCACGTTAAG GGATTTTGGT CATGGCTAGT
4201   TAATTAACAT TTAAATCAGC GGCCGCAATA AAATATCTTT ATTTTCATTA CATCTGTGTG TTGGTTTTTT GTGTGAATCG TAACTAACAT ACGCTCTCCA
4301   TCAAAACAAA ACGAAACAAA ACAAACTAGC AAAATAGGCT GTCCCCAGTG CAAGTGCAGG TGCCAGAACA TTTCTCTATC GAA (SEQ ID NO:96)
```

*FIG.6E (CONT)*

*FIG.7A*
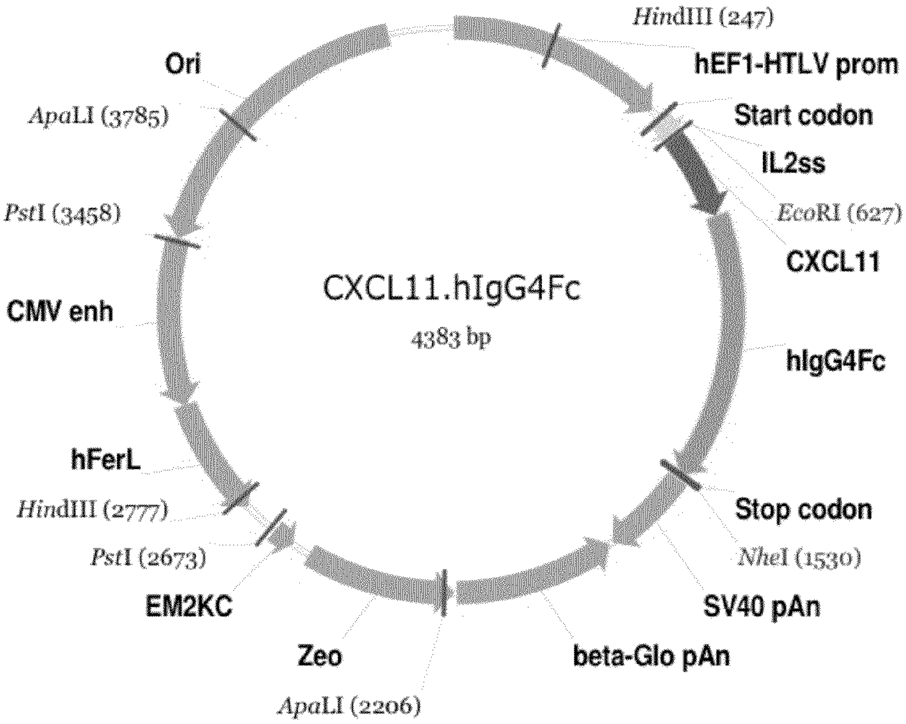
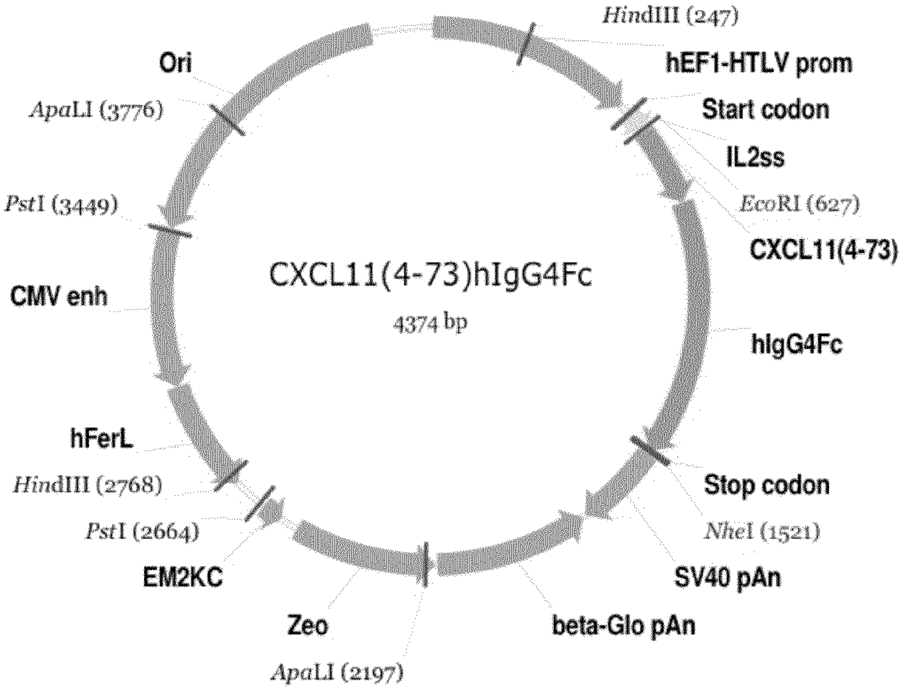
*FIG.7B*

FIG. 7C

IL2ss.CXCL11.hIgG4Fc sequence

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                            NarI
                                            SfoI
                                            KasI
                                            BbeI
                                           ~~~~~~~                                  IL-2 secretion signal
                                                                                    MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                 EcoRI
                                 ~~~~~~~ CXCL11 (1-73)
        AlaLeuSer LeuAlaLeu ValThrAsnSer PheProMet PheLysArg GlyArgCysLeu CysIleGly ProGlyVal LysAlaValLys ValAlaAsp
 601   TTGCACTAAG TCTTGCACTT GTCACGAATT CGTTCCCCAT GTTCAAAAGA GGACGCTGTC TTTGCATAGG CCCTGGGGTA AAAGCAGTGA AAGTGGCAGA
        IleGluLys AlaSerIleMet TyrProSer AsnAsnCys AspLysIleGlu ValIleIle ThrLeuLys GluAsnLysGly GlnArgCys LeuAsnPro
 701   TATTGAGAAA GCCTCCATAA TGTACCCAAG TAACAACTGT GACAAAATAG AAGTGATTAT TACCCTGAAA GAAAATAAAG GACAACGATG CCTAAATCCC
                                                         human IgG4 Fc (constant region)
       LysSerLysGln AlaArgLeu IleIleLys LysValGluArg LysAsnPhe ProProCys ProSerCysPro AlaProGlu PheLeuGly GlyProSerVal
 801   AAATCGAAGC AAGCAAGGCT TATAATCAAA AAAGTTGAAA GAAAGAATTT TCCCCCATGC CCATCATGCC CAGCACCTGA GTTCCTGGGG GGACCATCAG
        PheLeuPhe ProProLys ProLysAspThr LeuMetIle SerArgThr ProGluValThr CysValVal ValAspVal SerGlnGluAsp ProGluVal
 901   TCTTCCTGTT CCCCCCAAAA CCCAAGGACA CTCTCATGAT CTCCCGGACC CCTGAGGTCA CGTGCGTGGT GGTGGACGTG AGCCAGGAAG ACCCCGAGGT
       GlnPheAsn TrpTyrValAsp GlyValGlu ValHisAsn AlaLysThrLys ProArgGlu GluGlnPhe AsnSerThrTyr ArgValVal SerValLeu
1001   CCAGTTCAAC TGGTACGTGG ATGGCGTGGA GGTGCATAAT GCCAAGACAA AGCCGCGGGA GGAGCAGTTC AACAGCACGT ACCGTGTGGT CAGCGTCCTC
       ThrValLeuHis GlnAspTrp LeuAsnGly LysGluTyrLys CysLysVal SerAsnLys GlyLeuProSer SerIleGlu LysThrIle SerLysAlaLys
1101   ACCGTCCTGC ACCAGGACTG GCTGAACGGC AAGGAGTACA AGTGCAAGGT CTCCAACAAA GGCCTCCCGT CCTCCATCGA GAAAACCATC TCCAAAGCCA
        GlyGlnPro ArgGluPro GlnValTyrThr LeuProPro SerGlnGlu GluMetThrLys AsnGlnVal SerLeuThr CysLeuValLys GlyPheTyr
1201   AAGGGCAGCC CCGAGAGCCA CAGGTGTACA CCCTGCCCCC ATCCCAGGAG GAGATGACCA AGAACCAGGT CAGCCTGACC TGCCTGGTCA AAGGCTTCTA
        ProSerAsp IleAlaValGlu TrpGluSer AsnGlyGln ProGluAsnAsn TyrLysThr ThrProPro ValLeuAspSer AspGlySer PhePheLeu
1301   CCCCAGCGAC ATCGCCGTGG AGTGGGAGAG CAATGGGCAG CCGGAGAACA ACTACAAGAC CACGCCTCCC GTGCTGGACT CCGACGGCTC CTTCTTCCTC
       TyrSerArgLeu ThrValAsp LysSerArg TrpGlnGluGly AsnValPhe SerCysSer ValMetHisGlu AlaLeuHis AsnHisTyr ThrGlnLysSer
1401   TACAGCAGGC TAACCGTGGA CAAGAGCAGG TGGCAGGAGG GGAATGTCTT CTCATGCTCC GTGATGCATG AGGCTCTGCA CAACCACTAC ACACAGAAGA
                                     BmtI
                                     NheI
        LeuSerLeu SerProGly Lys***(SEQ ID NO:70)
1501   GCCTCTCCCT GTCTCCGGGT AAATGAGTGC TAGCTGGCCA GACATGATAA GATACATTGA TGAGTTTGGA CAAACCACAA CTAGAATGCA GTGAAAAAAA
1601   TGCTTTATTT GTGAAATTTG TGATGCTATT GCTTTATTTG TAACCATTAT AAGCTGCAAT AAACAAGTTA ACAACAACAA TTGCATTCAT TTTATGTTTC
                                                                               AseI
1701   AGGTTCAGGG GGAGGTGTGG GAGGTTTTTT AAAGCAAGTA AAACCTCTAC AAATGTGGTA TGGAATTAAT TCTAAAATAC AGCATAGCAA AACTTTAACC
1801   TCCAAATCAA GCCTCTACTT GAATCCTTTT CCGAGGCATG AATAAGGCAT AGGCATCAGG GGCTGTTGCC AATGTGCATT AGCTGTTTGC AGCCTCACCT
```

```
1901  TCTTTCATGG AGTTTAAGAT ATAGTGTATT TTCCCAAGGT TTGAACTAGC TCTTCATTTC TTTATGTTTT AAATGCACTG ACCTCCCACA TTCCCTTTTT
2001  AGTAAAATAT TCAGAAATAA TTTAAATACA TCATTGCAAT GAAAATAAAT GTTTTTTATT AGGCAGAATC CAGATGCTCA AGGCCCTTCA TAATATCCCC
2101  CAGTTTAGTA GTTGGACTTA GGGAACAAAG GAACCTTTAA TAGAAATTGG ACAGCAAGAA AGCGAGCTTC TAGCTTATCC TCAGTCCTGC TCCTCTGCCA
2201  CAAAGTGCAC GCAGTTGCCG GCCGGGTCGC GCAGGGCGAA CTCCCGCCCC CACGGCTGCT CGCCGATCTC GGTCATGGCC GGCCCGGAGG CGTCCCGGAA
2301  GTTCGTGGAC ACGACCTCCG ACCACTCGGC GTACAGCTCG TCCAGGCCGC GCACCCACAC CCAGGCCAGG GTGTTGTCCG GCACCACCTG GTCCTGGACC
2401  GCGCTGATGA ACAGGGTCAC GTCGTCCCGG ACCACACCGG CGAAGTCGTC CTCCACGAAG TCCCGGGAGA ACCCGAGCCG GTCGGTCCAG AACTCGACCG
2501  CTCCGGCGAC GTCGCGCGCG GTGAGCACCG GAACGGCACT GGTCAACTTG GCCATGATGG CTCCTCCTGT CAGGAGAGGA AAGAGAAGAA GGTTAGTACA
                                                       AseI
2601  ATTGCTATAG TGAGTTGTAT TATACTATGC AGATATACTA TGCCAATGAT TAATTGTCAA ACTAGGGCTG CAGGGTTCAT AGTGCCACTT TTCCTGCACT
2701  GCCCCATCTC CTGCCCACCC TTTCCCAGGC ATAGACAGTC AGTGACTTAC CAAACTCACA GGAGGGAGAA GGCAGAAGCT TGAGACAGAC CCGCGGGACC
2801  GCCGAACTGC GAGGGGACGT GGCTAGGGCG GCTTCTTTTA TGGTGCGCCG GCCCTCGGAG GCAGGGCGCT CGGGGAGGCC TAGCGGCCAA TCTGCGGTGG
2901  CAGGAGGCGG GGCCGAAGGC CGTGCCTGAC CAATCCGGAG CACATAGGAG TCTCAGCCCC CCGCCCCAAA GCAAGGGGAA GTCACGCGCC TGTAGCGCCA
3001  GCGTGTTGTG AAATGGGGGC TTGGGGGGGT TGGGGCCCTG ACTAGTCAAA ACAAACTCCC ATTGACGTCA ATGGGGTGGA GACTTGGAAA TCCCCGTGAG
3101  TCAAACCGCT ATCCACGCCC ATTGATGTAC TGCCAAAACC GCATCATCAT GGTAATAGCG ATGACTAATA CGTAGATGTA CTGCCAAGTA GGAAAGTCCC
3201  ATAAGGTCAT GTACTGGGCA TAATGCCAGG CGGGCCATTT ACCGTCATTG ACGTCAATAG GGGGCGTACT TGGCATATGA TACACTTGAT GTACTGCCAA
3301  GTGGGCAGTT TACCGTAAAT ACTCCACCCA TTGACGTCAA TGGAAAGTCC CTATTGGCGT TACTATGGGA ACATACGTCA TTATTGACGT CAATGGGCGG
3401  GGGTCGTTGG GCGGTCAGCC AGGCGGGCCA TTTACCGTAA GTTATGTAAC GCCTGCAGGT TAATTAAGAA CATGTGAGCA AAAGGCCAGC AAAAGGCCAG
3501  GAACCGTAAA AAGGCCGCGT TGCTGGCGTT TTTCCATAGG CTCCGCCCCC CTGACGAGCA TCACAAAAAT CGACGCTCAA GTCAGAGGTG GCGAAACCCG
3601  ACAGGACTAT AAAGATACCA GGCGTTTCCC CCTGGAAGCT CCCTCGTGCG CTCTCCTGTT CCGACCCTGC CGCTTACCGG ATACCTGTCC GCCTTTCTCC
3701  CTTCGGGAAG CGTGGCGCTT TCTCATAGCT CACGCTGTAG GTATCTCAGT TCGGTGTAGG TCGTTCGCTC CAAGCTGGGC TGTGTGCACG AACCCCCCGT
3801  TCAGCCCGAC CGCTGCGCCT TATCCGGTAA CTATCGTCTT GAGTCCAACC CGGTAAGACA CGACTTATCG CCACTGGCAG CAGCCACTGG TAACAGGATT
3901  AGCAGAGCGA GGTATGTAGG CGGTGCTACA GAGTTCTTGA AGTGGTGGCC TAACTACGGC TACACTAGAA GAACAGTATT TGGTATCTGC GCTCTGCTGA
4001  AGCCAGTTAC CTTCGGAAAA AGAGTTGGTA GCTCTTGATC CGGCAAACAA ACCACCGCTG GTAGCGGTGG TTTTTTTGTT TGCAAGCAGC AGATTACGCG
4101  CAGAAAAAAA GGATCTCAAG AAGATCCTTT GATCTTTTCT ACGGGGTCTG ACGCTCAGTG GAACGAAAAC TCACGTTAAG GGATTTTGGT CATGGCTAGT
4201  TAATTAACAT TTAAATCAGC GGCCGCAATA AAATATCTTT ATTTTCATTA CATCTGTGTG TTGGTTTTTT GTGTGAATCG TAACTAACAT ACGCTCTCCA
4301  TCAAAACAAA ACGAAACAAA ACAAACTAGC AAAATAGGCT GTCCCCAGTG CAAGTGCAGG TGCCAGAACA TTTCTCTATC GAA  (SEQ ID NO:97)
```

IL2ss.CXCL11(4-73).hIgG4Fc sequence

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                         KasI
                                         SfoI
                                         NarI
                                         BbeI
                                        ~~~~~~~                                      IL-2 secretion signal
                                                                                     MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                            EcoRI
                            ~~~~~~~ CXCL11 (4-73)
         AlaLeuSer LeuAlaLeu ValThrAsnSer PheLysArg GlyArgCys LeuCysIleGly ProGlyVal LysAlaVal LysValAlaAsp IleGluLys
 601   TTGCACTAAG TCTTGCACTT GTCACGAATT CGTTCAAAAG AGGACGCTGT CTTTGCATAG GCCCTGGGGT AAAAGCAGTG AAAGTGGCAG ATATTGAGAA
        AlaSerIle MetTyrProSer AsnAsnCys AspLysIle GluValIleIle ThrLeuLys GluAsnLys GlyGlnArgCys LeuAsnPro LysSerLys
 701   AGCCTCCATA ATGTACCCAA GTAACAACTG TGACAAAATA GAAGTGATTA TTACCCTGAA AGAAAATAAA GGACAACGAT GCCTAAATCC CAAATCGAAG
                                                  human IgG4 Fc (constant region)
       GlnAlaArgLeu IleIleLys LysValGlu ArgLysAsnPhe ProProCys ProSerCys ProAlaProGlu PheLeuGly GlyProSer ValPheLeuPhe
 801   CAAGCAAGGC TTATAATCAA AAAAGTTGAA AGAAAGAATT TTCCCCCATG CCCATCATGC CCAGCACCTG AGTTCCTGGG GGGACCATCA GTCTTCCTGT
         ProProLys ProLysAsp ThrLeuMetIle SerArgThr ProGluVal ThrCysValVal ValAspVal SerGlnGlu AspProGluVal GlnPheAsn
 901   TCCCCCCAAA ACCCAAGGAC ACTCTCATGA TCTCCCGGAC CCCTGAGGTC ACGTGCGTGG TGGTGGACGT GAGCCAGGAA GACCCCGAGG TCCAGTTCAA
        TrpTyrVal AspGlyValGlu ValHisAsn AlaLysThr LysProArgGlu GluGlnPhe AsnSerThr TyrArgValVal SerValLeu ThrValLeu
1001   CTGGTACGTG GATGGCGTGG AGGTGCATAA TGCCAAGACA AAGCCGCGGG AGGAGCAGTT CAACAGCACG TACCGTGTGG TCAGCGTCCT CACCGTCCTG
       HisGlnAspTrp LeuAsnGly LysGluTyr LysCysLysVal SerAsnLys GlyLeuPro SerSerIleGlu LysThrIle SerLysAla LysGlyGlnPro
1101   CACCAGGACT GGCTGAACGG CAAGGAGTAC AAGTGCAAGG TCTCCAACAA AGGCCTCCCG TCCTCCATCG AGAAAACCAT CTCCAAAGCC AAAGGGCAGC
         ArgGluPro GlnValTyr ThrLeuProPro SerGlnGlu GluMetThr LysAsnGlnVal SerLeuThr CysLeuVal LysGlyPheTyr ProSerAsp
1201   CCCGAGAGCC ACAGGTGTAC ACCCTGCCCC CATCCCAGGA GGAGATGACC AAGAACCAGG TCAGCCTGAC CTGCCTGGTC AAAGGCTTCT ACCCCAGCGA
        IleAlaVal GluTrpGluSer AsnGlyGln ProGluAsn AsnTyrLysThr ThrProPro ValLeuAsp SerAspGlySer PhePheLeu TyrSerArg
1301   CATCGCCGTG GAGTGGGAGA GCAATGGGCA GCCGGAGAAC AACTACAAGA CCACGCCTCC CGTGCTGGAC TCCGACGGCT CCTTCTTCCT CTACAGCAGG
       LeuThrValAsp LysSerArg TrpGlnGlu GlyAsnValPhe SerCysSer ValMetHis GluAlaLeuHis AsnHisTyr ThrGlnLys SerLeuSerLeu
1401   CTAACCGTGG ACAAGAGCAG GTGGCAGGAG GGGAATGTCT TCTCATGCTC CGTGATGCAT GAGGCTCTGC ACAACCACTA CACACAGAAG AGCCTCTCCC
                                BmtI
                                NheI
                               ~~~~~~~
         SerProGly Lys***(SEQ ID NO:71)
1501   TGTCTCCGGG TAAATGAGTG CTAGCTGGCC AGACATGATA AGATACATTG ATGAGTTTGG ACAAACCACA ACTAGAATGC AGTGAAAAAA ATGCTTTATT
1601   TGTGAAATTT GTGATGCTAT TGCTTTATTT GTAACCATTA TAAGCTGCAA TAAACAAGTT AACAACAACA ATTGCATTCA TTTTATGTTT CAGGTTCAGG
                                                                   AseI
                                                                  ~~~~~~~
```

```
1701    GGGAGGTGTG GGAGGTTTTT TAAAGCAAGT AAAACCTCTA CAAATGTGGT ATGGAATTAA TTCTAAAATA CAGCATAGCA AAACTTTAAC CTCCAAATCA
1801    AGCCTCTACT TGAATCCTTT TCTGAGGGAT GAATAAGGCA TAGGCATCAG GGGCTGTTGC CAATGTGCAT TAGCTGTTTG CAGCCTCACC TTCTTTCATG
1901    GAGTTTAAGA TATAGTGTAT TTTCCCAAGG TTTGAACTAG CTCTTCATTT CTTTATGTTT TAAATGCACT GACCTCCCAC ATTCCCTTTT TAGTAAAATA
2001    TTCAGAAATA ATTTAAATAC ATCATTGCAA TGAAAATAAA TGTTTTTTAT TAGGCAGAAT CCAGATGCTC AAGGCCCTTC ATAATATCCC CCAGTTTAGT
2101    AGTTGGACTT AGGGAACAAA GGAACCTTTA ATAGAAATTG GACAGCAAGA AAGCGAGCTT CTAGCTTATC CTCAGTCCTG CTCCTCTGCC ACAAAGTGCA
2201    CGCAGTTGCC GGCCGGGTCG CGCAGGGCGA ACTCCCGCCC CCACGGCTGC TCGCCGATCT CGGTCATGGC CGGCCCGGAG GCGTCCCGGA AGTTCGTGGA
2301    CACGACCTCC GACCACTCGG CGTACAGCTC GTCCAGGCCG CGCACCCACA CCCAGGCCAG GGTGTTGTCC GGCACCACCT GGTCCTGGAC CGCGCTGATG
2401    AACAGGGTCA CGTCGTCCCG GACCACACCG GCGAAGTCGT CCTCCACGAA GTCCCGGGAG AACCCGAGCC GGTCGGTCCA GAACTCGACC GCTCCGGCGA
2501    CGTCGCGCGC GGTGAGCACC GGAACGGCAC TGGTCAACTT GGCCATGATG GCTCCTCCTG TCAGGAGAGG AAAGAGAAGA AGGTTAGTAC AATTGCTATA
                                                  AseI
                                                ~~~~~~~
2601    GTGAGTTGTA TTATACTATG CAGATATACT ATGCCAATGA TTAATTGTCA AACTAGGGCT GCAGGGTTCA TAGTGCCACT TTTCCTGCAC TGCCCCATCT
2701    CCTGCCCACC CTTTCCCAGG CATAGACAGT CAGTGACTTA CCAAACTCAC AGGAGGGAGA AGGCAGAAGC TTGAGACAGA CCCGCGGGAC CGCCGAACTG
2801    CGAGGGGACG TGGCTAGGGC GGCTTCTTTT ATGGTGCGCC GGCCCTCGGA GGCAGGGCGC TCGGGGAGGC CTAGCGGCCA ATCTGCGGTG GCAGGAGGCG
2901    GGGCCGAAGG CCGTGCCTGA CCAATCCGGA GCACATAGGA GTCTCAGCCC CCCGCCCCAA AGCAAGGGGA AGTCACGCGC CTGTAGCGCC AGCGTGTTGT
3001    GAAATGGGGG CTTGGGGGGG TTGGGGCCCT GACTAGTCAA AACAAACTCC CATTGACGTC AATGGGGTGG AGACTTGGAA ATCCCCGTGA GTCAAACCGC
3101    TATCCACGCC CATTGATGTA CTGCCAAAAC CGCATCATCA TGGTAATAGC GATGACTAAT ACGTAGATGT ACTGCCAAGT AGGAAAGTCC CATAAGGTCA
3201    TGTACTGGGC ATAATGCCAG GCGGGCCATT TACCGTCATT GACGTCAATA GGGGGCGTAC TTGGCATATG ATACACTTGA TGTACTGCCA AGTGGGCAGT
3301    TTACCGTAAA TACTCCACCC ATTGACGTCA ATGGAAAGTC CCTATTGGCG TTACTATGGG AACATACGTC ATTATTGACG TCAATGGGCG GGGGTCGTTG
3401    GGCGGTCAGC CAGGCGGGCC ATTTACCGTA AGTTATGTAA CGCCTGCAGG TTAATTAAGA ACATGTGAGC AAAAGGCCAG CAAAAGGCCA GGAACCGTAA
3501    AAAGGCCGCG TTGCTGGCGT TTTTCCATAG GCTCCGCCCC CCTGACGAGC ATCACAAAAA TCGACGCTCA AGTCAGAGGT GGCGAAACCC GACAGGACTA
3601    TAAAGATACC AGGCGTTTCC CCCTGGAAGC TCCCTCGTGC GCTCTCCTGT TCCGACCCTG CCGCTTACCG GATACCTGTC CGCCTTTCTC CCTTCGGGAA
3701    GCGTGGCGCT TTCTCATAGC TCACGCTGTA GGTATCTCAG TTCGGTGTAG GTCGTTCGCT CCAAGCTGGG CTGTGTGCAC GAACCCCCCG TTCAGCCCGA
3801    CCGCTGCGCC TTATCCGGTA ACTATCGTCT TGAGTCCAAC CCGGTAAGAC ACGACTTATC GCCACTGGCA GCAGCCACTG GTAACAGGAT TAGCAGAGCG
3901    AGGTATGTAG GCGGTGCTAC AGAGTTCTTG AAGTGGTGGC CTAACTACGG CTACACTAGA AGAACAGTAT TTGGTATCTG CGCTCTGCTG AAGCCAGTTA
4001    CCTTCGGAAA AAGAGTTGGT AGCTCTTGAT CCGGCAAACA AACCACCGCT GGTAGCGGTG GTTTTTTTGT TTGCAAGCAG CAGATTACGC GCAGAAAAAA
4101    AGGATCTCAA GAAGATCCTT TGATCTTTTC TACGGGGTCT GACGCTCAGT GGAACGAAAA CTCACGTTAA GGGATTTTGG TCATGGCTAG TTAATTAACA
4201    TTTAAATCAG CGGCCGCAAT AAAATATCTT TATTTTCATT ACATCTGTGT GTTGGTTTTT TGTGTGAATC GTAACTAACA TACGCTCTCC ATCAAAACAA
4301    AACGAAACAA AACAAACTAG CAAAATAGGC TGTCCCCAGT GCAAGTGCAG GTGCCAGAAC ATTTCTCTAT CGAA  (SEQ ID NO:98)
```

IL2ss.CXCL11(4-73).hIgG4Fc sequence [Alanine substitutions for GAG binding sites – Arg, Lys & His]

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                          KasI
                                          SfoI
                                          NarI
                                          BbeI
                                         ~~~~~~~                                     IL-2 secretion signal
                                                                                     MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                             EcoRI
                             ~~~~~~~ CXCL11 (4-73)
         AlaLeuSer LeuAlaLeu ValThrAsnSer PheLysArg GlyArgCys LeuCysIleGly ProGlyVal LysAlaVal LysValAlaAsp IleGluAla
 601   TTGCACTAAG TCTTGCACTT GTCACGAATT CGTTCAAAAG AGGACGCTGT CTTTGCATAG GCCCTGGGGT AAAAGCAGTG AAAGTGGCAG ATATTGAGgc
        AlaSerIle MetTyrProSer AsnAsnCys AspLysIle GluValIleIle ThrLeuAla GluAsnAla GlyGlnAlaCys LeuAsnPro AlaSerAla
 701   cGCCTCCATA ATGTACCCAA GTAACAACTG TGACAAAATA GAAGTGATTA TTACCCTGgc aGAAAATgcc GGACAAgcaT GCCTAAATCC CgccTCGgca
                                                 human IgG4 Fc (constant region)
       GlnAlaAlaLeu IleIleAla AlaValGlu AlaAlaAsnPhe ProProCys ProSerCys ProAlaProGlu PheLeuGly GlyProSer ValPheLeuPhe
 801   CAAGCAgccC TTATAATCgc agccGTTGAA gcagccAATT TTCCCCCATG CCCATCATGC CCAGCACCTG AGTTCCTGGG GGGACCATCA GTCTTCCTGT
         ProProLys ProLysAsp ThrLeuMetIle SerArgThr ProGluVal ThrCysValVal ValAspVal SerGlnGlu AspProGluVal GlnPheAsn
 901   TCCCCCCAAA ACCCAAGGAC ACTCTCATGA TCTCCCGGAC CCCTGAGGTC ACGTGCGTGG TGGTGGACGT GAGCCAGGAA GACCCCGAGG TCCAGTTCAA
        TrpTyrVal AspGlyValGlu ValHisAsn AlaLysThr LysProArgGlu GluGlnPhe AsnSerThr TyrArgValVal SerValLeu ThrValLeu
1001   CTGGTACGTG GATGGCGTGG AGGTGCATAA TGCCAAGACA AAGCCGCGGG AGGAGCAGTT CAACAGCACG TACCGTGTGG TCAGCGTCCT CACCGTCCTG
       HisGlnAspTrp LeuAsnGly LysGluTyr LysCysLysVal SerAsnLys GlyLeuPro SerSerIleGlu LysThrIle SerLysAla LysGlyGlnPro
1101   CACCAGGACT GGCTGAACGG CAAGGAGTAC AAGTGCAAGG TCTCCAACAA AGGCCTCCCG TCCTCCATCG AGAAAACCAT CTCCAAAGCC AAAGGGCAGC
         ArgGluPro GlnValTyr ThrLeuProPro SerGlnGlu GluMetThr LysAsnGlnVal SerLeuThr CysLeuVal LysGlyPheTyr ProSerAsp
1201   CCCGAGAGCC ACAGGTGTAC ACCCTGCCCC CATCCCAGGA GGAGATGACC AAGAACCAGG TCAGCCTGAC CTGCCTGGTC AAAGGCTTCT ACCCCAGCGA
        IleAlaVal GluTrpGluSer AsnGlyGln ProGluAsn AsnTyrLysThr ThrProPro ValLeuAsp SerAspGlySer PhePheLeu TyrSerArg
1301   CATCGCCGTG GAGTGGGAGA GCAATGGGCA GCCGGAGAAC AACTACAAGA CCACGCCTCC CGTGCTGGAC TCCGACGGCT CCTTCTTCCT CTACAGCAGG
       LeuThrValAsp LysSerArg TrpGlnGlu GlyAsnValPhe SerCysSer ValMetHis GluAlaLeuHis AsnHisTyr ThrGlnLys SerLeuSerLeu
1401   CTAACCGTGG ACAAGAGCAG GTGGCAGGAG GGGAATGTCT TCTCATGCTC CGTGATGCAT GAGGCTCTGC ACAACCACTA CACACAGAAG AGCCTCTCCC
                           BmtI
                           NheI
                          ~~~~~~~
         SerProGly Lys***(SEQ ID NO:72)
1501   TGTCTCCGGG TAAATGAGTG CTAGCTGGCC AGACATGATA AGATACATTG ATGAGTTTGG ACAAACCACA ACTAGAATGC AGTGAAAAAA ATGCTTTATT
1601   TGTGAAATTT GTGATGCTAT TGCTTTATTT GTAACCATTA TAAGCTGCAA TAAACAAGTT AACAACAACA ATTGCATTCA TTTTATGTTT CAGGTTCAGG
                                                                   AseI
                                                                  ~~~~~~~
```

```
1701   GGGAGGTGTG GGAGGTTTTT TAAAGCAAGT AAAACCTCTA CAAATGTGGT ATGGAATTAA TTCTAAAATA CAGCATAGCA AAACTTTAAC CTCCAAATCA
1801   AGCCTCTACT TGAATCCTTT TCTGAGGGAT GAATAAGGCA TAGGCATCAG GGGCTGTTGC CAATGTGCAT TAGCTGTTTG CAGCCTCACC TTCTTTCATG
1901   GAGTTTAAGA TATAGTGTAT TTTCCCAAGG TTTGAACTAG CTCTTCATTT CTTTATGTTT TAAATGCACT GACCTCCCAC ATTCCCTTTT TAGTAAAATA
2001   TTCAGAAATA ATTTAAATAC ATCATTGCAA TGAAAATAAA TGTTTTTTAT TAGGCAGAAT CCAGATGCTC AAGGCCCTTC ATAATATCCC CCAGTTTAGT
2101   AGTTGGACTT AGGGAACAAA GGAACCTTTA ATAGAAATTG GACAGCAAGA AAGCGAGCTT CTAGCTTATC CTCAGTCCTG CTCCTCTGCC ACAAAGTGCA
2201   CGCAGTTGCC GGCCGGGTCG CGCAGGGCGA ACTCCCGCCC CCACGGCTGC TCGCCGATCT CGGTCATGGC CGGCCCGGAG GCGTCCCGGA AGTTCGTGGA
2301   CACGACCTCC GACCACTCGG CGTACAGCTC GTCCAGGCCG CGCACCCACA CCCAGGCCAG GGTGTTGTCC GGCACCACCT GGTCCTGGAC CGCGCTGATG
2401   AACAGGGTCA CGTCGTCCCG GACCACACCG GCGAAGTCGT CCTCCACGAA GTCCCGGGAG AACCCGAGCC GGTCGGTCCA GAACTCGACC GCTCCGGCGA
2501   CGTCGCGCGC GGTGAGCACC GGAACGGCAC TGGTCAACTT GGCCATGATG GCTCCTCCTG TCAGGAGAGG AAAGAGAAGA AGGTTAGTAC AATTGCTATA
                                                 AseI
                                               ~~~~~~~
2601   GTGAGTTGTA TTATACTATG CAGATATACT ATGCCAATGA TTAATTGTCA AACTAGGGCT GCAGGGTTCA TAGTGCCACT TTTCCTGCAC TGCCCCATCT
2701   CCTGCCCACC CTTTCCCAGG CATAGACAGT CAGTGACTTA CCAAACTCAC AGGAGGGAGA AGGCAGAAGC TTGAGACAGA CCCGCGGGAC CGCCGAACTG
2801   CGAGGGGACG TGGCTAGGGC GGCTTCTTTT ATGGTGCGCC GGCCCTCGGA GGCAGGGCGC TCGGGGAGGC CTAGCGGCCA ATCTGCGGTG GCAGGAGGCG
2901   GGGCCGAAGG CCGTGCCTGA CCAATCCGGA GCACATAGGA GTCTCAGCCC CCCGCCCCAA AGCAAGGGGA AGTCACGCGC CTGTAGCGCC AGCGTGTTGT
3001   GAAATGGGGG CTTGGGGGGG TTGGGGCCCT GACTAGTCAA AACAAACTCC CATTGACGTC AATGGGGTGG AGACTTGGAA ATCCCCGTGA GTCAAACCGC
3101   TATCCACGCC CATTGATGTA CTCCCAAAAC CGCATCATCA TGGTAATAGC GATGACTAAT ACGTAGATCT ACTGCCAAGT AGGAAAGTCC CATAAGGTCA
3201   TGTACTGGGC ATAATGCCAG GCGGGCCATT TACCGTCATT GACGTCAATA GGGGGCGTAC TTGGCATATG ATACACTTGA TGTACTGCCA AGTGGGCAGT
3301   TTACCGTAAA TACTCCACCC ATTGACGTCA ATGGAAAGTC CCTATTGGCG TTACTATGGG AACATACGTC ATTATTGACG TCAATGGGCG GGGGTCGTTG
3401   GGCGGTCAGC CAGGCGGGCC ATTTACCGTA AGTTATGTAA CGCCTGCAGG TTAATTAAGA ACATGTGAGC AAAAGGCCAG CAAAAGGCCA GGAACCGTAA
3501   AAAGGCCGCG TTGCTGGCGT TTTTCCATAG GCTCCGCCCC CCTGACGAGC ATCACAAAAA TCGACGCTCA AGTCAGAGGT GGCGAAACCC GACAGGACTA
3601   TAAAGATACC AGGCGTTTCC CCCTGGAAGC TCCCTCGTGC GCTCTCCTGT TCCGACCCTG CCGCTTACCG GATACCTGTC CGCCTTTCTC CCTTCGGGAA
3701   GCGTGGCGCT TTCTCATAGC TCACGCTGTA GGTATCTCAG TTCGGTGTAG GTCGTTCGCT CCAAGCTGGG CTGTGTGCAC GAACCCCCCG TTCAGCCCGA
3801   CCGCTGCGCC TTATCCGGTA ACTATCGTCT TGAGTCCAAC CCGGTAAGAC ACGACTTATC GCCACTGGCA GCAGCCACTG GTAACAGGAT TAGCAGAGCG
3901   AGGTATGTAG GCGGTGCTAC AGAGTTCTTG AAGTGGTGGC CTAACTACGG CTACACTAGA AGAACAGTAT TTGGTATCTG CGCTCTGCTG AAGCCAGTTA
4001   CCTTCGGAAA AAGAGTTGGT AGCTCTTGAT CCGGCAAACA AACCACCGCT GGTAGCGGTG GTTTTTTTGT TTGCAAGCAG CAGATTACGC GCAGAAAAAA
4101   AGGATCTCAA GAAGATCCTT TGATCTTTTC TACGGGGTCT GACGCTCAGT GGAACGAAAA CTCACGTTAA GGGATTTTGG TCATGGCTAG TTAATTAACA
4201   TTTAAATCAG CGGCCGCAAT AAAATATCTT TATTTTCATT ACATCTGTGT GTTGGTTTTT TGTGTGAATC GTAACTAACA TACGCTCTCC ATCAAAACAA
4301   AACGAAACAA AACAAACTAG CAAAATAGGC TGTCCCCAGT GCAAGTGCAG GTGCCAGAAC ATTTCTCTAT CGAA  (SEQ ID NO:99)
```

FIG.7E (CONT)

FIG. 8A
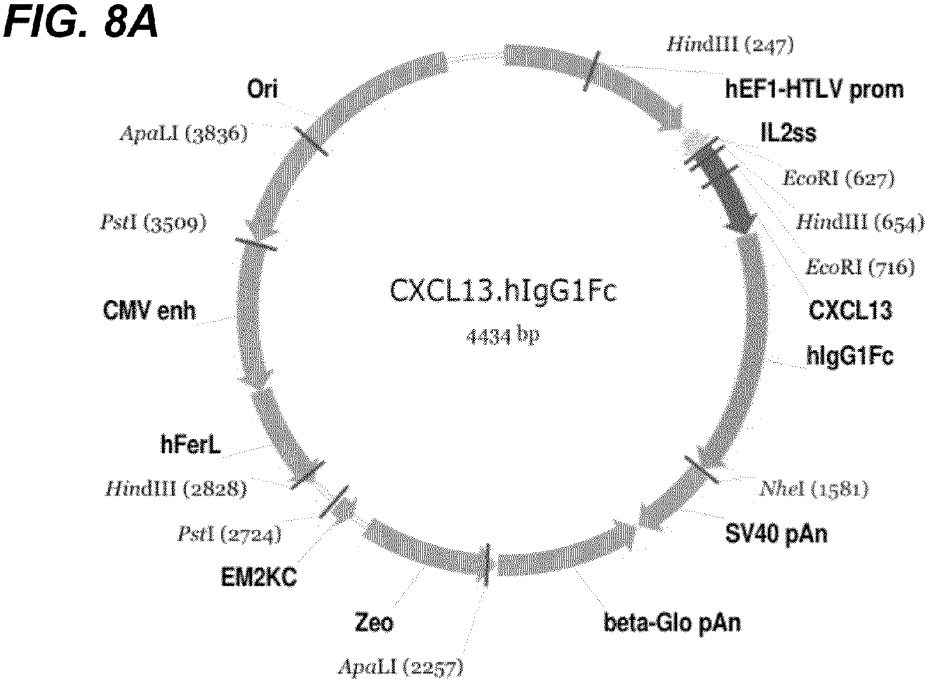
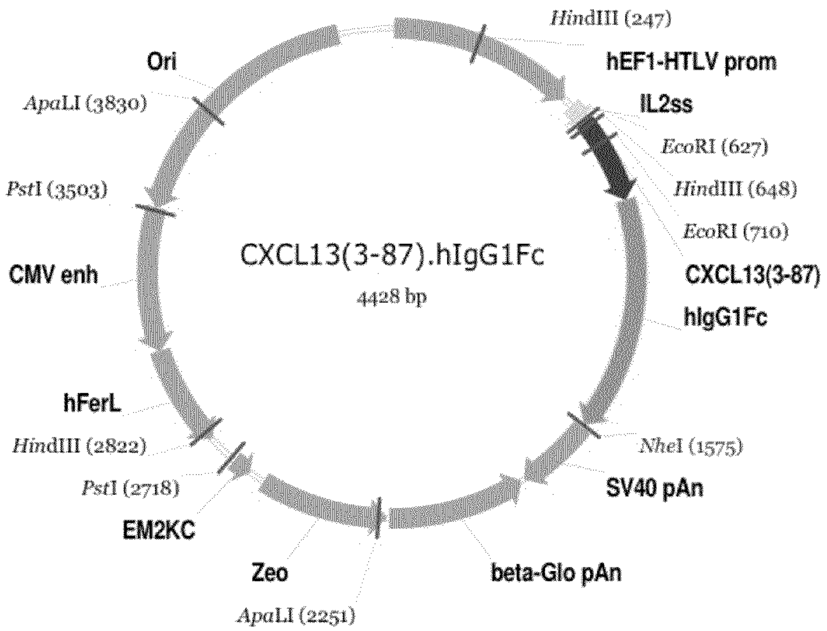
FIG.8B

FIG. 8C

IL2ss.CXCL13.hIgG1Fc sequence

```
   1     GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101     GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201     GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301     GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401     GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                              KasI
                                              NarI
                                              SfoI
                                              BbeI
                                             ~~~~~~~                                   IL-2 secretion signal
                                                                                       MetTyrArg MetGlnLeu LeuSerCysIle
 501     TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                   EcoRI
                                         CXCL13 (1-87)
           AlaLeuSer LeuAlaLeu ValThrAsnSer ValLeuGlu ValTyrTyr ThrSerLeuArg CysArgCys ValGlnGlu SerSerValPhe IleProArg
 601     TTGCACTAAG TCTTGCACTT GTCACGAATT CGGTTCTGGA GGTCTATTAC ACAAGCTTGA GGTGTAGATG TGTCCAAGAG AGCTCAGTCT TTATCCCTAG
                      EcoRI
          ArgPheIle AspArgIleGln IleLeuPro ArgGlyAsn GlyCysProArg LysGluIle IleValTrp LysLysAsnLys SerIleVal CysValAsp
 701     ACGCTTCATT GATCGAATTC AAATCTTGCC CCGTGGGAAT GGTTGTCCAA GAAAAGAAAT CATAGTCTGG AAGAAGAACA AGTCAATTGT GTGTGTGGAC
                                                                                                     human IgG1 Fc
                                                                                                  (constant region)
         ProGlnAlaGlu TrpIleGln ArgMetMet GluValLeuArg LysArgSer SerSerThr LeuProValPro ValPheLys ArgLysIle ProAspLysThr
 801     CCTCAAGCTG AATGGATACA AAGAATGATG GAAGTATTGA GAAAAAGAAG TTCTTCAACT CTACCAGTTC CAGTGTTTAA GAGAAAGATT CCCGACAAAA
           HisThrCys ProProCys ProAlaProGlu LeuLeuGly GlyProSer ValPheLeuPhe ProProLys ProLysAsp ThrLeuMetIle SerArgThr
 901     CTCACACATG CCCACCGTGC CCAGCACCTG AACTCCTGGG GGGACCGTCA GTCTTCCTCT TCCCCCCAAA ACCCAAGGAC ACCCTCATGA TCTCCCGGAC
          ProGluVal ThrCysValVal ValAspVal SerHisGlu AspProGluVal LysPheAsn TrpTyrVal AspGlyValGlu ValHisAsn AlaLysThr
1001     CCCTGAGGTC ACATGCGTGG TGGTGGACGT GAGCCACGAA GACCCTGAGG TCAAGTTCAA CTGGTACGTG GACGGCGTGG AGGTGCATAA TGCCAAGACA
         LysProArgGlu GluGlnTyr AsnSerThr TyrArgValVal SerValLeu ThrValLeu HisGlnAspTrp LeuAsnGly LysGluTyr LysCysLysVal
1101     AAGCCGCGGG AGGAGCAGTA CAACAGCACG TACCGTGTGG TCAGCGTCCT CACCGTCCTG CACCAGGACT GGCTGAATGG CAAGGAGTAC AAGTGCAAGG
           SerAsnLys AlaLeuPro AlaProIleGlu LysThrIle SerLysAla LysGlyGlnPro ArgGluPro GlnValTyr ThrLeuProPro SerArgGlu
1201     TCTCCAACAA AGCCCTCCCA GCCCCCATCG AGAAAACCAT CTCCAAAGCC AAAGGGCAGC CCCGAGAACC ACAGGTGTAC ACCCTGCCCC CATCCCGGGA
          GluMetThr LysAsnGlnVal SerLeuThr CysLeuVal LysGlyPheTyr ProSerAsp IleAlaVal GluTrpGluSer AsnGlyGln ProGluAsn
1301     GGAGATGACC AAGAACCAGG TCAGCCTGAC CTGCCTGGTC AAAGGCTTCT ATCCCAGCGA CATCGCCGTG GAGTGGGAGA GCAATGGGCA GCCGGAGAAC
         AsnTyrLysThr ThrProPro ValLeuAsp SerAspGlySer PhePheLeu TyrSerLys LeuThrValAsp LysSerArg TrpGlnGln GlyAsnValPhe
1401     AACTACAAGA CCACGCCTCC CGTGCTGGAC TCCGACGGCT CCTTCTTCCT CTACAGCAAG CTCACCGTGG ACAAGAGCAG GTGGCAGCAG GGGAACGTCT
                                                                                                BmtI
                                                                                                NheI
           SerCysSer ValMetHis GluAlaLeuHis AsnHisTyr ThrGlnLys SerLeuSerLeu SerProGly Lys***(SEQ ID NO:73)
1501     TCTCATGCTC CGTGATGCAC GAGGCTCTGC ACAACCACTA CACGCAGAAG AGCCTCTCCC TGTCTCCGGG TAAATGAGTG CTAGCTGGCC AGACATGATA
1601     AGATACATTG ATGAGTTTGG ACAAACCACA ACTAGAATGC AGTGAAAAAA ATGCTTTATT TGTGAAATTT GTGATGCTAT TGCTTTATTT GTAACCATTA
1701     TAAGCTGCAA TAAACAAGTT AACAACAACA ATTGCATTCA TTTTATGTTT CAGGTTCAGG GGGAGGTGTG GGAGGTTTTT TAAAGCAAGT AAAACCTCTA
```

Figure 8C:
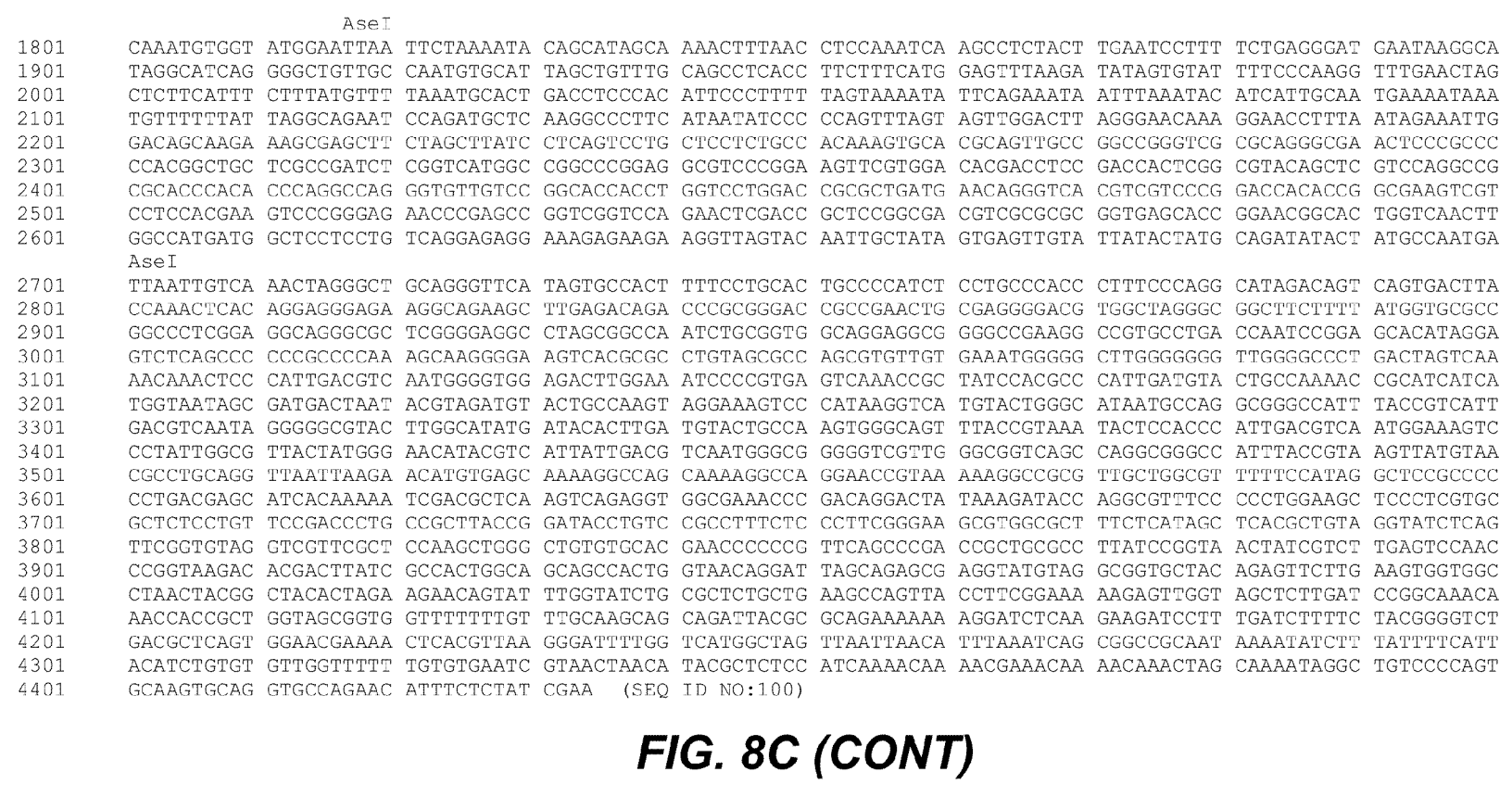

```
                      AseI
1801   CAAATGTGGT ATGGAATTAA TTCTAAAATA CAGCATAGCA AAACTTTAAC CTCCAAATCA AGCCTCTACT TGAATCCTTT TCTGAGGGAT CAATAAGGCA
1901   TAGGCATCAG GGGCTGTTGC CAATGTGCAT TAGCTGTTTG CAGCCTCACC TTCTTTCATG GAGTTTAAGA TATAGTGTAT TTTCCCAAGG TTTGAACTAG
2001   CTCTTCATTT CTTTATGTTT TAAATGCACT GACCTCCCAC ATTCCCTTTT TAGTAAAATA TTCAGAAATA ATTTAAATAC ATCATTGCAA TGAAAATAAA
2101   TGTTTTTTAT TAGGCAGAAT CCAGATGCTC AAGGCCCTTC ATAATATCCC CCAGTTTAGT AGTTGGACTT AGGGAACAAA GGAACCTTTA ATAGAAATTG
2201   GACAGCAAGA AAGCGAGCTT CTAGCTTATC CTCAGTCCTG CTCCTCTGCC ACAAAGTGCA CGCAGTTGCC GGCCGGGTCG CGCAGGGCGA ACTCCCGCCC
2301   CCACGGCTGC TCGCCGATCT CGGTCATGGC CGGCCCGGAG GCGTCCCGGA AGTTCGTGGA CACGACCTCC GACCACTCGG CGTACAGCTC GTCCAGGCCG
2401   CGCACCCACA CCCAGGCCAG GGTGTTGTCC GGCACCACCT GGTCCTGGAC CGCGCTGATG AACAGGGTCA CGTCGTCCCG GACCACACCG GCGAAGTCGT
2501   CCTCCACGAA GTCCCGGGAG AACCCGAGCC GGTCGGTCCA GAACTCGACC GCTCCGGCGA CGTCGCGCGC GGTGAGCACC GGAACGGCAC TGGTCAACTT
2601   GGCCATGATG GCTCCTCCTG TCAGGAGAGG AAAGAGAAGA AGGTTAGTAC AATTGCTATA GTGAGTTGTA TTATACTATG CAGATATACT ATGCCAATGA
       AseI
2701   TTAATTGTCA AACTAGGGCT GCAGGGTTCA TAGTGCCACT TTTCCTGCAC TGCCCCATCT CCTGCCCACC CTTTCCCAGG CATAGACAGT CAGTGACTTA
2801   CCAAACTCAC AGGAGGGAGA AGGCAGAAGC TTGAGACAGA CCCGCGGGAC CGCCGAACTG CGAGGGGACG TGGCTAGGGC GGCTTCTTTT ATGGTGCGCC
2901   GGCCCTCGGA GGCAGGGCGC TCGGGGAGGC CTAGCGGCCA ATCTGCGGTG GCAGGAGGCG GGGCCGAAGG CCGTGCCTGA CCAATCCGGA GCACATAGGA
3001   GTCTCAGCCC CCCGCCCCAA AGCAAGGGGA AGTCACGCGC CTGTAGCGCC AGCGTGTTGT GAAATGGGGG CTTGGGGGGG TTGGGGCCCT GACTAGTCAA
3101   AACAAACTCC CATTGACGTC AATGGGGTGG AGACTTGGAA ATCCCCGTGA GTCAAACCGC TATCCACGCC CATTGATGTA CTGCCAAAAC CGCATCATCA
3201   TGGTAATAGC GATGACTAAT ACGTAGATGT ACTGCCAAGT AGGAAAGTCC CATAAGGTCA TGTACTGGGC ATAATGCCAG GCGGGCCATT TACCGTCATT
3301   GACGTCAATA GGGGGCGTAC TTGGCATATG ATACACTTGA TGTACTGCCA AGTGGGCAGT TTACCGTAAA TACTCCACCC ATTGACGTCA ATGGAAAGTC
3401   CCTATTGGCG TTACTATGGG AACATACGTC ATTATTGACG TCAATGGGCG GGGGTCGTTG GGCGGTCAGC CAGGCGGGCC ATTTACCGTA AGTTATGTAA
3501   CGCCTGCAGG TTAATTAAGA ACATGTGAGC AAAAGGCCAG CAAAAGGCCA GGAACCGTAA AAAGGCCGCG TTGCTGGCGT TTTTCCATAG GCTCCGCCCC
3601   CCTGACGAGC ATCACAAAAA TCGACGCTCA AGTCAGAGGT GGCGAAACCC GACAGGACTA TAAAGATACC AGGCGTTTCC CCCTGGAAGC TCCCTCGTGC
3701   GCTCTCCTGT TCCGACCCTG CCGCTTACCG GATACCTGTC CGCCTTTCTC CCTTCGGGAA GCGTGGCGCT TTCTCATAGC TCACGCTGTA GGTATCTCAG
3801   TTCGGTGTAG GTCGTTCGCT CCAAGCTGGG CTGTGTGCAC GAACCCCCCG TTCAGCCCGA CCGCTGCGCC TTATCCGGTA ACTATCGTCT TGAGTCCAAC
3901   CCGGTAAGAC ACGACTTATC GCCACTGGCA GCAGCCACTG GTAACAGGAT TAGCAGAGCG AGGTATGTAG GCGGTGCTAC AGAGTTCTTG AAGTGGTGGC
4001   CTAACTACGG CTACACTAGA AGAACAGTAT TTGGTATCTG CGCTCTGCTG AAGCCAGTTA CCTTCGGAAA AAGAGTTGGT AGCTCTTGAT CCGGCAAACA
4101   AACCACCGCT GGTAGCGGTG GTTTTTTTGT TTGCAAGCAG CAGATTACGC GCAGAAAAAA AGGATCTCAA GAAGATCCTT TGATCTTTTC TACGGGGTCT
4201   GACGCTCAGT GGAACGAAAA CTCACGTTAA GGGATTTTGG TCATGGCTAG TTAATTAACA TTTAAATCAG CGGCCGCAAT AAAATATCTT TATTTTCATT
4301   ACATCTGTGT GTTGGTTTTT TGTGTGAATC GTAACTAACA TACGCTCTCC ATCAAAACAA AACGAAACAA AACAAACTAG CAAAATAGGC TGTCCCCAGT
4401   GCAAGTGCAG GTGCCAGAAC ATTTCTCTAT CGAA  (SEQ ID NO:100)
```

IL2ss.CXCL13(3-87).hIgG1Fc sequence

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                                 KasI
                                                 NarI
                                                 SfoI
                                                 BbeI
                                                ~~~~~~~                                    IL-2 secretion signal
                                                                                           MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                 EcoRI
                                 ~~~~~~~ CXCL13 (3-87)
        AlaLeuSer LeuAlaLeu ValThrAsnSer GluValTyr TyrThrSer LeuArgCysArg CysValGln GluSerSer ValPheIlePro ArgArgPhe
 601   TTGCACTAAG TCTTGCACTT GTCACGAATT CGGAGGTCTA TTACACAAGC TTGAGGTGTA GATGTGTCCA AGAGAGCTCA GTCTTTATCC CTAGACGCTT
        IleAspArg IleGlnIleLeu ProArgGly AsnGlyCys ProArgLysGlu IleIleVal TrpLysLys AsnLysSerIle ValCysVal AspProGln
 701   CATTGATCGA ATTCAAATCT TGCCCCGTGG GAATGGTTGT CCAAGAAAAG AAATCATAGT CTGGAAGAAG AACAAGTCAA TTGTGTGTGT GGACCCTCAA
                                                                                                         human IgG1 Fc
                                                                                                       (constant region)
       AlaGluTrpIle GlnArgMet MetGluVal LeuArgLysArg SerSerSer ThrLeuPro ValProValPhe LysArgLys IleProAsp LysThrHisThr
 801   GCTGAATGGA TACAAAGAAT GATGGAAGTA TTGAGAAAAA GAAGTTCTTC AACTCTACCA GTTCCAGTGT TTAAGAGAAA GATTCCCGAC AAAACTCACA
        CysProPro CysProAla ProGluLeuLeu GlyGlyPro SerValPhe LeuPheProPro LysProLys AspThrLeu MetIleSerArg ThrProGlu
 901   CATGCCCACC GTGCCCAGCA CCTGAACTCC TGGGGGGACC GTCAGTCTTC CTCTTCCCCC CAAAACCCAA GGACACCCTC ATGATCTCCC GGACCCCTGA
        ValThrCys ValValValAsp ValSerHis GluAspPro GluValLysPhe AsnTrpTyr ValAspGly ValGluValHis AsnAlaLys ThrLysPro
1001   GGTCACATGC GTGGTGGTGG ACGTGAGCCA CGAAGACCCT GAGGTCAAGT TCAACTGGTA CGTGGACGGC GTGGAGGTGC ATAATGCCAA GACAAAGCCG
       ArgGluGluGln TyrAsnSer ThrTyrArg ValValSerVal LeuThrVal LeuHisGln AspTrpLeuAsn GlyLysGlu TyrLysCys LysValSerAsn
1101   CGGGAGGAGC AGTACAACAG CACGTACCGT GTGGTCAGCG TCCTCACCGT CCTGCACCAG GACTGGCTGA ATGGCAAGGA GTACAAGTGC AAGGTCTCCA
        LysAlaLeu ProAlaPro IleGluLysThr IleSerLys AlaLysGly GlnProArgGlu ProGlnVal TyrThrLeu ProProSerArg GluGluMet
1201   ACAAAGCCCT CCCAGCCCCC ATCGAGAAAA CCATCTCCAA AGCCAAAGGG CAGCCCCGAG AACCACAGGT GTACACCCTG CCCCCATCCC GGGAGGAGAT
        ThrLysAsn GlnValSerLeu ThrCysLeu ValLysGly PheTyrProSer AspIleAla ValGluTrp GluSerAsnGly GlnProGlu AsnAsnTyr
1301   GACCAAGAAC CAGGTCAGCC TGACCTGCCT GGTCAAAGGC TTCTATCCCA GCGACATCGC CGTGGAGTGG GAGAGCAATG GGCAGCCGGA GAACAACTAC
       LysThrThrPro ProValLeu AspSerAsp GlySerPhePhe LeuTyrSer LysLeuThr ValAspLysSer ArgTrpGln GlnGlyAsn ValPheSerCys
1401   AAGACCACGC CTCCCGTGCT GGACTCCGAC GGCTCCTTCT TCCTCTACAG CAAGCTCACC GTGGACAAGA GCAGGTGGCA GCAGGGGAAC GTCTTCTCAT
                                                                                               BmtI
                                                                                               NheI
         SerValMet HisGluAla LeuHisAsnHis TyrThrGln LysSerLeu SerLeuSerPro GlyLys***(SEQ ID NO:74)
1501   GCTCCGTGAT GCACGAGGCT CTGCACAACC ACTACACGCA GAAGAGCCTC TCCCTGTCTC CGGGTAAATG AGTGCTAGCT GGCCAGACAT GATAAGATAC
1601   ATTGATGAGT TTGGACAAAC CACAACTAGA ATGCAGTGAA AAAAATGCTT TATTTGTGAA ATTTGTGATG CTATTGCTTT ATTTGTAACC ATTATAAGCT
1701   GCAATAAACA AGTTAACAAC AACAATTGCA TTCATTTTAT GTTTCAGGTT CAGGGGGAGG TGTGGGAGGT TTTTTAAAGC AAGTAAAACC TCTACAAATG
                 AseI
```

```
1801 TGGTATGGAA TTAATTCTAA AATACAGCAT AGCAAAACTT TAACCTCCAA ATCAAGCCTC TACTTGAATC CTTTTCTGAG GGATGAATAA GGCATAGGCA
1901 TCAGGGGCTG TTGCCAATGT GCATTAGCTG TTTGCAGCCT CACCTTCTTT CATGGAGTTT AAGATATAGT GTATTTTCCC AAGGTTTGAA CTAGCTCTTC
2001 ATTTCTTTAT GTTTTAAATG CACTGACCTC CCACATTCCC TTTTTAGTAA AATATTCAGA AATAATTTAA ATACATCATT GCAATGAAAA TAAATGTTTT
2101 TTATTAGGCA GAATCCAGAT GCTCAAGGCC CTTCATAATA TCCCCCAGTT TAGTAGTTGG ACTTAGGGAA CAAAGGAACC TTTAATAGAA ATTGGACAGC
2201 AAGAAAGCGA GCTTCTAGCT TATCCTCAGT CCTGCTCCTC TGCCACAAAG TGCACGCAGT TGCCGGCCGG GTCGCGCAGG GCGAACTCCC GCCCCCACGG
2301 CTGCTCGCCG ATCTCGGTCA TGGCCGGCCC GGAGGCGTCC CGGAAGTTCG TGGACACGAC CTCCGACCAC TCGGCGTACA GCTCGTCCAG GCCGCGCACC
2401 CACACCCAGG CCAGGGTGTT GTCCGGCACC ACCTGGTCCT GGACCGCGCT GATGAACAGG GTCACGTCGT CCCGGACCAC ACCGGCGAAG TCGTCCTCCA
2501 CGAAGTCCCG GGAGAACCCG AGCCGGTCGG TCCAGAACTC GACCGCTCCG GCGACGTCGC GCGCGGTGAG CACCGGAACG GCACTGGTCA ACTTGGCCAT
                                                                                                          AseI
2601 GATGGCTCCT CCTGTCAGGA GAGGAAAGAG AAGAAGGTTA GTACAATTGC TATAGTGAGT TGTATTATAC TATGCAGATA TACTATGCCA ATGATTAATT
2701 GTCAAACTAG GGCTGCAGGG TTCATAGTGC CACTTTTCCT GCACTGCCCC ATCTCCTGCC CACCCTTTCC CAGGCATAGA CAGTCAGTGA CTTACCAAAC
2801 TCACAGGAGG GAGAAGGCAG AAGCTTGAGA CAGACCCGCG GGACCGCCGA ACTGCGAGGG GACGTGGCTA GGGCGGCTTC TTTTATGGTG CGCCGGCCCT
2901 CGGAGGCAGG GCGCTCGGGG AGGCCTAGCG GCCAATCTGC GGTGGCAGGA GGCGGGGCCG AAGGCCGTGC CTGACCAATC CGGAGCACAT AGGAGTCTCA
3001 GCCCCCCGCC CCAAAGCAAG GGGAAGTCAC GCGCCTGTAG CGCCAGCGTG TTGTGAAATG GGGGCTTGGG GGGGTTGGGG CCCTGACTAG TCAAAACAAA
3101 CTCCCATTGA CGTCAATGGG GTGGAGACTT GGAAATCCCC GTGAGTCAAA CCGCTATCCA CGCCCATTGA TGTACTGCCA AAACCGCATC ATCATGGTAA
3201 TAGCGATGAC TAATACGTAG ATGTACTGCC AAGTAGGAAA GTCCCATAAG GTCATGTACT GGGCATAATG CCAGGCGGGC CATTTACCGT CATTGACGTC
3301 AATAGGGGGC GTACTTGGCA TATGATACAC TTGATGTACT GCCAAGTGGG CAGTTTACCG TAAATACTCC ACCCATTGAC GTCAATGGAA AGTCCCTATT
3401 GGCGTTACTA TGGGAACATA CGTCATTATT GACGTCAATG GGCGGGGGTC GTTGGGCGGT CAGCCAGGCG GGCCATTTAC CGTAAGTTAT GTAACGCCTG
3501 CAGGTTAATT AAGAACATGT GAGCAAAAGG CCAGCAAAAG GCCAGGAACC GTAAAAAGGC CGCGTTGCTG GCGTTTTTCC ATAGGCTCCG CCCCCCTGAC
3601 GAGCATCACA AAAATCGACG CTCAAGTCAG AGGTGGCGAA ACCCGACAGG ACTATAAAGA TACCAGGCGT TTCCCCCTGG AAGCTCCCTC GTGCGCTCTC
3701 CTGTTCCGAC CCTGCCGCTT ACCGGATACC TGTCCGCCTT TCTCCCTTCG GGAAGCGTGG CGCTTTCTCA TAGCTCACGC TGTAGGTATC TCAGTTCGGT
3801 GTAGGTCGTT CGCTCCAAGC TGGGCTGTGT GCACGAACCC CCCGTTCAGC CCGACCGCTG CGCCTTATCC GGTAACTATC GTCTTGAGTC CAACCCGGTA
3901 AGACACGACT TATCGCCACT GGCAGCAGCC ACTGGTAACA GGATTAGCAG AGCGAGGTAT GTAGGCGGTG CTACAGAGTT CTTGAAGTGG TGGCCTAACT
4001 ACGGCTACAC TAGAAGAACA GTATTTGGTA TCTGCGCTCT GCTGAAGCCA GTTACCTTCG GAAAAAGAGT TGGTAGCTCT TGATCCGGCA AACAAACCAC
4101 CGCTGGTAGC GGTGGTTTTT TTGTTTGCAA GCAGCAGATT ACGCGCAGAA AAAAAGGATC TCAAGAAGAT CCTTTGATCT TTTCTACGGG GTCTGACGCT
4201 CAGTGGAACG AAAACTCACG TTAAGGGATT TTGGTCATGG CTAGTTAATT AACATTTAAA TCAGCGGCCG CAATAAAATA TCTTTATTTT CATTACATCT
4301 GTGTGTTGGT TTTTTGTGTG AATCGTAACT AACATACGCT CTCCATCAAA ACAAAACGAA ACAAAACAAA CTAGCAAAAT AGGCTGTCCC CAGTGCAAGT
4401 GCAGGTGCCA GAACATTTCT CTATCGAA (SEQ ID NO:101)
```

IL2ss.CXCL13(3-87).hIgG1Fc sequence [Alanine substitutions for removal of GAG binding sites – Lys & His]

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                           KasI
                                           NarI
                                           SfoI
                                           BbeI
                                           ~~~~~~~~                                        IL-2 secretion signal
                                                                                           MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                  EcoRI
                                  ~~~~~~~ CXCL13 (3-87)
         AlaLeuSer LeuAlaLeu ValThrAsnSer GluValTyr TyrThrSer LeuArgCysArg CysValGln GluSerSer ValPheIlePro ArgArgPhe
 601   TTGCACTAAG TCTTGCACTT GTCACGAATT CGGAGGTCTA TTACACAAGC TTGAGGTGTA GATGTGTCCA AGAGAGCTCA GTCTTTATCC CTAGACGCTT
              EcoRI
        IleAspAla IleGlnIleLeu ProArgGly AsnGlyCys ProArgLysGlu IleIleVal TrpAlaAla AsnAlaSerIle ValCysVal AspProGln
 701   CATTGATgcc ATTCAAATCT TGCCCCGTGG GAATGGTTGT CCAAGAAAAG AAATCATAGT CTGGgctgcg AACgctTCAA TTGTGTGTGT GGACCCTCAA
                                                                                                         human IgG1 Fc
                                                                                                       (constant region)
       AlaGluTrpIle GlnAlaMet MetGluVal LeuAlaAlaAla SerSerSer ThrLeuPro ValProValPhe AlaAlaAla IleProAsp LysThrHisThr
 801   GCTGAATGGA TACAAgccAT GATGGAAGTA TTGgctgcgg ctAGTTCTTC AACTCTACCA GTTCCAGTGT TTgccgctgc gATTCCCGAC AAAACTCACA
         CysProPro CysProAla ProGluLeuLeu GlyGlyPro SerValPhe LeuPheProPro LysProLys AspThrLeu MetIleSerArg ThrProGlu
 901   CATGCCCACC GTGCCCAGCA CCTGAACTCC TGGGGGGACC GTCAGTCTTC CTCTTCCCCC CAAAACCCAA GGACACCCTC ATGATCTCCC GGACCCCTGA
        ValThrCys ValValValAsp ValSerHis GluAspPro GluValLysPhe AsnTrpTyr ValAspGly ValGluValHis AsnAlaLys ThrLysPro
1001   GGTCACATGC GTGGTGGTGG ACGTGAGCCA CGAAGACCCT GAGGTCAAGT TCAACTGGTA CGTGGACGGC GTGGAGGTGC ATAATGCCAA GACAAAGCCG
       ArgGluGluGln TyrAsnSer ThrTyrArg ValValSerVal LeuThrVal LeuHisGln AspTrpLeuAsn GlyLysGlu TyrLysCys LysValSerAsn
1101   CGGGAGGAGC AGTACAACAG CACGTACCGT GTGGTCAGCG TCCTCACCGT CCTGCACCAG GACTGGCTGA ATGGCAAGGA GTACAAGTGC AAGGTCTCCA
         LysAlaLeu ProAlaPro IleGluLysThr IleSerLys AlaLysGly GlnProArgGlu ProGlnVal TyrThrLeu ProProSerArg GluGluMet
1201   ACAAAGCCCT CCCAGCCCCC ATCGAGAAAA CCATCTCCAA AGCCAAAGGG CAGCCCCGAG AACCACAGGT GTACACCCTG CCCCCATCCC GGGAGGAGAT
        ThrLysAsn GlnValSerLeu ThrCysLeu ValLysGly PheTyrProSer AspIleAla ValGluTrp GluSerAsnGly GlnProGlu AsnAsnTyr
1301   GACCAAGAAC CAGGTCAGCC TGACCTGCCT GGTCAAAGGC TTCTATCCCA GCGACATCGC CGTGGAGTGG GAGAGCAATG GGCAGCCGGA GAACAACTAC
       LysThrThrPro ProValLeu AspSerAsp GlySerPhePhe LeuTyrSer LysLeuThr ValAspLysSer ArgTrpGln GlnGlyAsn ValPheSerCys
1401   AAGACCACGC CTCCCGTGCT GGACTCCGAC GGCTCCTTCT TCCTCTACAG CAAGCTCACC GTGGACAAGA GCAGGTGGCA GCAGGGGAAC GTCTTCTCAT
                                                                                             BmtI
                                                                                             NheI
         SerValMet HisGluAla LeuHisAsnHis TyrThrGln LysSerLeu SerLeuSerPro GlyLys***(SEQ ID NO:75)
1501   GCTCCGTGAT GCACGAGGCT CTGCACAACC ACTACACGCA GAAGAGCCTC TCCCTGTCTC CGGGTAAATG AGTGCTAGCT GGCCAGACAT GATAAGATAC
1601   ATTGATGAGT TTGGACAAAC CACAACTAGA ATGCAGTGAA AAAAATGCTT TATTTGTGAA ATTTGTGATG CTATTGCTTT ATTTGTAACC ATTATAAGCT
1701   GCAATAAACA AGTTAACAAC AACAATTGCA TTCATTTTAT GTTTCAGGTT CAGGGGGAGG TGTGGGAGGT TTTTTAAAGC AAGTAAAACC TCTACAAATG
```

```
                 AseI
1801   TGGTATGGAA TTAATTCTAA AATACAGCAT AGCAAAACTT TAACCTCCAA ATCAAGCCTC TACTTGAATC CTTTTCTGAG GGATGAATAA GGCATAGGCA
1901   TCAGGGGCTG TTGCCAATGT GCATTAGCTG TTTGCAGCCT CACCTTCTTT CATGGAGTTT AAGATATAGT GTATTTTCCC AAGGTTTGAA CTAGCTCTTC
2001   ATTTCTTTAT GTTTTAAATG CACTGACCTC CCACATTCCC TTTTTAGTAA AATATTCAGA AATAATTTAA ATACATCATT GCAATGAAAA TAAATGTTTT
2101   TTATTAGGCA GAATCCAGAT GCTCAAGGCC CTTCATAATA TCCCCCAGTT TAGTAGTTGG ACTTAGGGAA CAAAGGAACC TTTAATAGAA ATTGGACAGC
2201   AAGAAAGCGA GCTTCTAGCT TATCCTCAGT CCTGCTCCTC TGCCACAAAG TGCACGCAGT TGCCGGCCGG GTCGCGCAGG GCGAACTCCC GCCCCCACGG
2301   CTGCTCGCCG ATCTCGGTCA TGGCCGGCCC GGAGGCGTCC CGGAAGTTCG TGGACACGAC CTCCGACCAC TCGGCGTACA GCTCGTCCAG GCCGCGCACC
2401   CACACCCAGG CCAGGGTGTT GTCCGGCACC ACCTGGTCCT GGACCGCGCT GATGAACAGG GTCACGTCGT CCCGGACCAC ACCGGCGAAG TCGTCCTCCA
2501   CGAAGTCCCG GGAGAACCCG AGCCGGTCGG TCCAGAACTC GACCGCTCCG GCGACGTCGC GCGCGGTGAG CACCGGAACG GCACTGGTCA ACTTGGCCAT
                                                                                                               AseI
2601   GATGGCTCCT CCTGTCAGGA GAGGAAAGAG AAGAAGGTTA GTACAATTGC TATAGTGAGT TGTATTATAC TATGCAGATA TACTATGCCA ATGATTAATT
2701   GTCAAACTAG GGCTGCAGGG TTCATAGTGC CACTTTTCCT GCACTGCCCC ATCTCCTGCC CACCCTTTCC CAGGCATAGA CAGTCAGTGA CTTACCAAAC
2801   TCACAGGAGG GAGAAGGCAG AAGCTTGAGA CAGACCCGCG GGACCGCCGA ACTGCGAGGG GACGTGGCTA GGGCGGCTTC TTTTATGGTG CGCCGGCCCT
2901   CGGAGGCAGG GCGCTCGGGG AGGCCTAGCG GCCAATCTGC GGTGGCAGGA GGCGGGGCCG AAGGCCGTGC CTGACCAATC CGGAGCACAT AGGAGTCTCA
3001   GCCCCCCGCC CCAAAGCAAG GGGAAGTCAC GCGCCTGTAG CGCCAGCGTG TTGTGAAATG GGGGCTTGGG GGGGTTGGGG CCCTGACTAG TCAAAACAAA
3101   CTCCCATTGA CGTCAATGGG GTGGAGACTT GGAAATCCCC GTGAGTCAAA CCGCTATCCA CGCCCATTGA TGTACTGCCA AAACCGCATC ATCATGGTAA
3201   TAGCGATGAC TAATACGTAG ATGTACTGCC AAGTAGGAAA GTCCCATAAG GTCATGTACT GGGCATAATG CCAGGCGGGC CATTTACCGT CATTGACGTC
3301   AATAGGGGGC GTACTTGGCA TATGATACAC TTGATGTACT GCCAAGTGGG CAGTTTACCG TAAATACTCC ACCCATTGAC GTCAATGGAA AGTCCCTATT
3401   GGCGTTACTA TGGGAACATA CGTCATTATT GACGTCAATG GGCGGGGGTC GTTGGGCGGT CAGCCAGGCG GGCCATTTAC CGTAAGTTAT GTAACGCCTG
3501   CAGGTTAATT AAGAACATGT GAGCAAAAGG CCAGCAAAAG GCCAGGAACC GTAAAAAGGC CGCGTTGCTG GCGTTTTTCC ATAGGCTCCG CCCCCCTGAC
3601   GAGCATCACA AAAATCGACG CTCAAGTCAG AGGTGGCGAA ACCCGACAGG ACTATAAAGA TACCAGGCGT TTCCCCCTGG AAGCTCCCTC GTGCGCTCTC
3701   CTGTTCCGAC CCTGCCGCTT ACCGGATACC TGTCCGCCTT TCTCCCTTCG GGAAGCGTGG CGCTTTCTCA TAGCTCACGC TGTAGGTATC TCAGTTCGGT
3801   GTAGGTCGTT CGCTCCAAGC TGGGCTGTGT GCACGAACCC CCCGTTCAGC CCGACCGCTG CGCCTTATCC GGTAACTATC GTCTTGAGTC CAACCCGGTA
3901   AGACACGACT TATCGCCACT GGCAGCAGCC ACTGGTAACA GGATTAGCAG AGCGAGGTAT GTAGGCGGTG CTACAGAGTT CTTGAAGTGG TGGCCTAACT
4001   ACGGCTACAC TAGAAGAACA GTATTTGGTA TCTGCGCTCT GCTGAAGCCA GTTACCTTCG GAAAAAGAGT TGGTAGCTCT TGATCCGGCA AACAAACCAC
4101   CGCTGGTAGC GGTGGTTTTT TTGTTTGCAA GCAGCAGATT ACGCGCAGAA AAAAAGGATC TCAAGAAGAT CCTTTGATCT TTTCTACGGG GTCTGACGCT
4201   CAGTGGAACG AAAACTCACG TTAAGGGATT TTGGTCATGG CTAGTTAATT AACATTTAAA TCAGCGGCCG CAATAAAATA TCTTTATTTT CATTACATCT
4301   GTGTGTTGGT TTTTTGTGTG AATCGTAACT AACATACGCT CTCCATCAAA ACAAAACGAA ACAAAACAAA CTAGCAAAAT AGGCTGTCCC CAGTGCAAGT
4401   GCAGGTGCCA GAACATTTCT CTATCGAA  (SEQ ID NO:102)
```

FIG. 8E (CONT)

FIG.9A
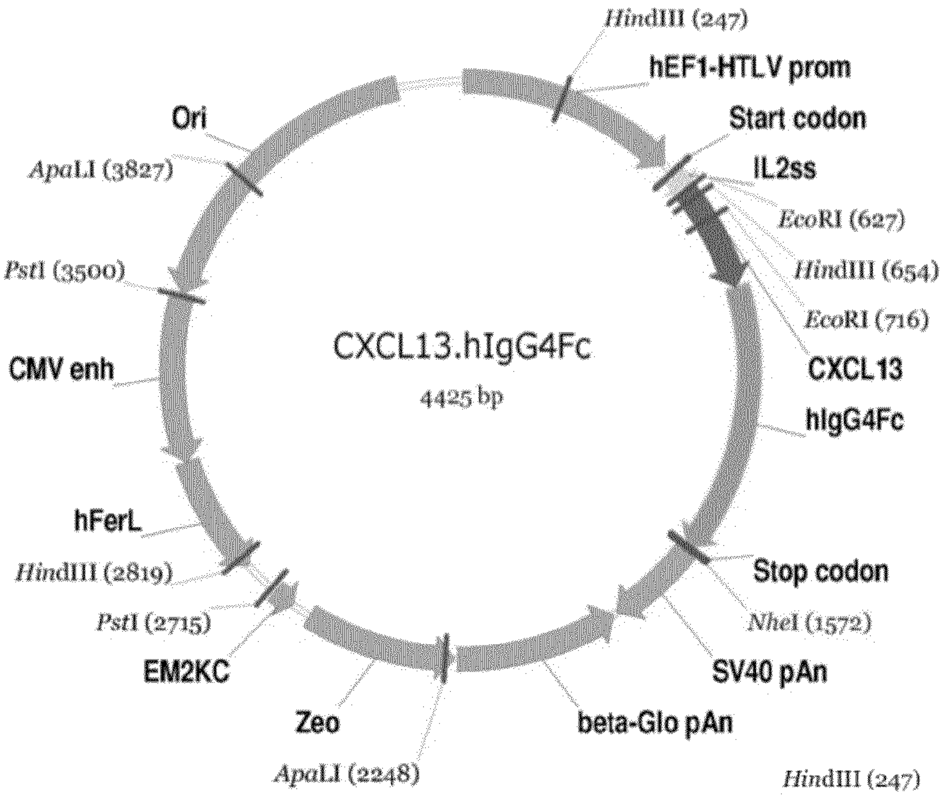
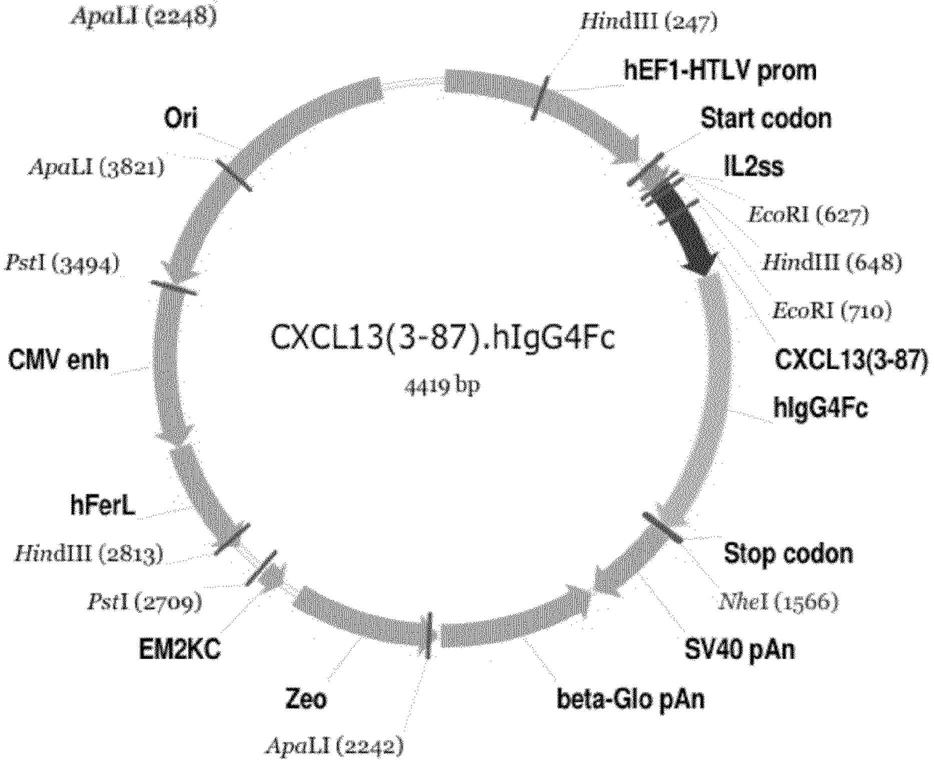
FIG.9B

FIG. 9C

IL2ss.CXCL13.hIgG4Fc sequence

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                                 KasI
                                                 NarI
                                                 SfoI
                                                 BbeI
                                                ~~~~~~~                                  IL-2 secretion signal
                                                                                         MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                      EcoRI
                                      ~~~~~~~ CXCL13 (1-87)
        AlaLeuSer LeuAlaLeu ValThrAsnSer ValLeuGlu ValTyrTyr ThrSerLeuArg CysArgCys ValGlnGlu SerSerValPhe IleProArg
 601   TTGCACTAAG TCTTGCACTT GTCACGAATT CGGTTCTGGA GGTCTATTAC ACAAGCTTGA GGTGTAGATG TGTCCAAGAG AGCTCAGTCT TTATCCCTAG
                           EcoRI
       ArgPheIle AspArgIleGln IleLeuPro ArgGlyAsn GlyCysProArg LysGluIle IleValTrp LysLysAsnLys SerIleVal CysValAsp
 701   ACGCTTCATT GATCGAATTC AAATCTTGCC CCGTGGGAAT GGTTGTCCAA GAAAAGAAAT CATAGTCTGG AAGAAGAACA AGTCAATTGT GTGTGTGGAC
                                                                                                        human IgG4 Fc
                                                                                                      (constant region)
       ProGlnAlaGlu TrpIleGln ArgMetMet GluValLeuArg LysArgSer SerSerThr LeuProValPro ValPheLys ArgLysIle ProProProCys
 801   CCTCAAGCTG AATGGATACA AAGAATGATG GAAGTATTGA GAAAAAGAAG TTCTTCAACT CTACCAGTTC CAGTGTTTAA GAGAAAGATT CCCCCCCCAT
        ProSerCys ProAlaPro GluPheLeuGly GlyProSer ValPheLeu PheProProLys ProLysAsp ThrLeuMet IleSerArgThr ProGluVal
 901   GCCCATCATG CCCAGCACCT GAGTTCCTGG GGGGACCATC AGTCTTCCTG TTCCCCCCAA AACCCAAGGA CACTCTCATG ATCTCCCGGA CCCCTGAGGT
        ThrCysVal ValValAspVal SerGlnGlu AspProGlu ValGlnPheAsn TrpTyrVal AspGlyVal GluValHisAsn AlaLysThr LysProArg
1001   CACGTGCGTG GTGGTGGACG TGAGCCAGGA AGACCCCGAG GTCCAGTTCA ACTGGTACGT GGATGGCGTG GAGGTGCATA ATGCCAAGAC AAAGCCGCGG
       GluGluGlnPhe AsnSerThr TyrArgVal ValSerValLeu ThrValLeu HisGlnAsp TrpLeuAsnGly LysGluTyr LysCysLys ValSerAsnLys
1101   GAGGAGCAGT TCAACAGCAC GTACCGTGTG GTCAGCGTCC TCACCGTCCT GCACCAGGAC TGGCTGAACG GCAAGGAGTA CAAGTGCAAG GTCTCCAACA
        GlyLeuPro SerSerIle GluLysThrIle SerLysAla LysGlyGln ProArgGluPro GlnValTyr ThrLeuPro ProSerGlnGlu GluMetThr
1201   AAGGCCTCCC GTCCTCCATC GAGAAAACCA TCTCCAAAGC CAAAGGGCAG CCCCGAGAGC CACAGGTGTA CACCCTGCCC CCATCCCAGG AGGAGATGAC
        LysAsnGln ValSerLeuThr CysLeuVal LysGlyPhe TyrProSerAsp IleAlaVal GluTrpGlu SerAsnGlyGln ProGluAsn AsnTyrLys
1301   CAAGAACCAG GTCAGCCTGA CCTGCCTGGT CAAAGGCTTC TACCCCAGCG ACATCGCCGT GGAGTGGGAG AGCAATGGGC AGCCGGAGAA CAACTACAAG
       ThrThrProPro ValLeuAsp SerAspGly SerPhePheLeu TyrSerArg LeuThrVal AspLysSerArg TrpGlnGlu GlyAsnVal PheSerCysSer
1401   ACCACGCCTC CCGTGCTGGA CTCCGACGGC TCCTTCTTCC TCTACAGCAG GCTAACCGTG GACAAGAGCA GGTGGCAGGA GGGGAATGTC TTCTCATGCT
                                                                                       BmtI
                                                                                       NheI
        ValMetHis GluAlaLeu HisAsnHisTyr ThrGlnLys SerLeuSer LeuSerProGly Lys***(SEQ ID NO:76)
1501   CCGTGATGCA TGAGGCTCTG CACAACCACT ACACACAGAA GAGCCTCTCC CTGTCTCCGG GTAAATGAGT GCTAGCTGGC CAGACATGAT AAGATACATT
1601   GATGAGTTTG GACAAACCAC AACTAGAATG CAGTGAAAAA AATGCTTTAT TTGTGAAATT TGTGATGCTA TTGCTTTATT TGTAACCATT ATAAGCTGCA
1701   ATAAACAAGT TAACAACAAC AATTGCATTC ATTTTATGTT TCAGGTTCAG GGGGAGGTGT GGGAGGTTTT TTAAAGCAAG TAAAACCTCT ACAAATGTGG
```

```
              AseI
1801   TATGGAATTA ATTCTAAAAT ACAGCATAGC AAAACTTTAA CCTCCAAATC AAGCCTCTAC TTGAATCCTT TTCTGAGGGA TGAATAAGGC ATAGGCATCA
1901   GGGGCTGTTG CCAATGTGCA TTAGCTGTTT GCAGCCTCAC CTTCTTTCAT GGAGTTTAAG ATATAGTGTA TTTTCCCAAG GTTTGAACTA GCTCTTCATT
2001   TCTTTATGTT TTAAATGCAC TGACCTCCCA CATTCCCTTT TTAGTAAAAT ATTCAGAAAT AATTTAAATA CATCATTGCA ATGAAAATAA ATGTTTTTTA
2101   TTAGGCAGAA TCCAGATGCT CAAGGCCCTT CATAATATCC CCCAGTTTAG TAGTTGGACT TAGGGAACAA AGGAACCTTT AATAGAAATT GGACAGCAAG
2201   AAAGCGAGCT TCTAGCTTAT CCTCAGTCCT GCTCCTCTGC CACAAAGTGC ACGCAGTTGC CGGCCGGGTC GCGCAGGGCG AACTCCCGCC CCCACGGCTG
2301   CTCGCCGATC TCGGTCATGG CCGGCCCGGA GGCGTCCCGG AAGTTCGTGG ACACGACCTC CGACCACTCG GCGTACAGCT CGTCCAGGCC GCGCACCCAC
2401   ACCCAGGCCA GGGTGTTGTC CGGCACCACC TGGTCCTGGA CCGCGCTGAT GAACAGGGTC ACGTCGTCCC GGACCACACC GGCGAAGTCG TCCTCCACGA
2501   AGTCCCGGGA GAACCCGAGC CGGTCGGTCC AGAACTCGAC CGCTCCGGCG ACGTCGCGCG CGGTGAGCAC CGGAACGGCA CTGGTCAACT TGGCCATGAT
                                                                                                           AseI
2601   GGCTCCTCCT GTCAGGAGAG GAAAGAGAAG AAGGTTAGTA CAATTGCTAT AGTGAGTTGT ATTATACTAT GCAGATATAC TATGCCAATG ATTAATTGTC
2701   AAACTAGGGC TGCAGGGTTC ATAGTGCCAC TTTTCCTGCA CTGCCCCATC TCCTGCCCAC CCTTTCCCAG GCATAGACAG TCAGTGACTT ACCAAACTCA
2801   CAGGAGGGAG AAGGCAGAAG CTTGAGACAG ACCCGCGGGA CCGCCGAACT GCGAGGGGAC GTGGCTAGGG CGGCTTCTTT TATGGTGCGC CGGCCCTCGG
2901   AGGCAGGGCG CTCGGGGAGG CCTAGCGGCC AATCTGCGGT GGCAGGACGC GGGGCCGAAG GCCGTGCCTG ACCAATCCGG AGCACATAGG AGTCTCAGCC
3001   CCCCGCCCCA AAGCAAGGGG AAGTCACGCG CCTGTAGCGC CAGCGTGTTG TGAAATGGGG GCTTGGGGGG GTTGGGGCCC TGACTAGTCA AAACAAACTC
3101   CCATTGACGT CAATGGGGTG GAGACTTGGA AATCCCCGTG AGTCAAACCG CTATCCACGC CCATTGATGT ACTGCCAAAA CCGCATCATC ATGGTAATAG
3201   CGATGACTAA TACGTAGATG TACTGCCAAG TAGGAAAGTC CCATAAGGTC ATGTACTGGG CATAATGCCA GGCGGGCCAT TTACCGTCAT TGACGTCAAT
3301   AGGGGGCGTA CTTGGCATAT GATACACTTG ATGTACTGCC AAGTGGGCAG TTTACCGTAA ATACTCCACC CATTGACGTC AATGGAAAGT CCCTATTGGC
3401   GTTACTATGG GAACATACGT CATTATTGAC GTCAATGGGC GGGGGTCGTT GGGCGGTCAG CCAGGCGGGC CATTTACCGT AAGTTATGTA ACGCCTGCAG
3501   GTTAATTAAG AACATGTGAG CAAAAGGCCA GCAAAAGGCC AGGAACCGTA AAAAGGCCGC GTTGCTGGCG TTTTTCCATA GGCTCCGCCC CCCTGACGAG
3601   CATCACAAAA ATCGACGCTC AAGTCAGAGG TGGCGAAACC CGACAGGACT ATAAAGATAC CAGGCGTTTC CCCCTGGAAG CTCCCTCGTG CGCTCTCCTG
3701   TTCCGACCCT GCCGCTTACC GGATACCTGT CCGCCTTTCT CCCTTCGGGA AGCGTGGCGC TTTCTCATAG CTCACGCTGT AGGTATCTCA GTTCGGTGTA
3801   GGTCGTTCGC TCCAAGCTGG GCTGTGTGCA CGAACCCCCC GTTCAGCCCG ACCGCTGCGC CTTATCCGGT AACTATCGTC TTGAGTCCAA CCCGGTAAGA
3901   CACGACTTAT CGCCACTGGC AGCAGCCACT GGTAACAGGA TTAGCAGAGC GAGGTATGTA GGCGGTGCTA CAGAGTTCTT GAAGTGGTGG CCTAACTACG
4001   GCTACACTAG AAGAACAGTA TTTGGTATCT GCGCTCTGCT GAAGCCAGTT ACCTTCGGAA AAAGAGTTGG TAGCTCTTGA TCCGGCAAAC AAACCACCGC
4101   TGGTAGCGGT GGTTTTTTTG TTTGCAAGCA GCAGATTACG CGCAGAAAAA AAGGATCTCA AGAAGATCCT TTGATCTTTT CTACGGGGTC TGACGCTCAG
4201   TGGAACGAAA ACTCACGTTA AGGGATTTTG GTCATGGCTA GTTAATTAAC ATTTAAATCA GCGGCCGCAA TAAAATATCT TTATTTTCAT TACATCTGTG
4301   TGTTGGTTTT TTGTGTGAAT CGTAACTAAC ATACGCTCTC CATCAAAACA AAACGAAACA AAACAAACTA GCAAAATAGG CTGTCCCCAG TGCAAGTGCA
4401   GGTGCCAGAA CATTTCTCTA TCGAA  (SEQ ID NO:103)
```

IL2ss.CXCL13(3-87).hIgG4Fc sequence

```
   1    GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101    GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201    GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301    GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401    GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                          NarI
                                          KasI
                                          SfoI
                                          BbeI
                                         ~~~~~~~                                    IL-2 secretion signal
                                                                                    MetTyrArg MetGlnLeu LeuSerCysIle
 501    TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                EcoRI
                                ~~~~~~~ CXCL13 (3-87)
         AlaLeuSer LeuAlaLeu ValThrAsnSer GluValTyr TyrThrSer LeuArgCysArg CysValGln GluSerSer ValPheIlePro ArgArgPhe
 601    TTGCACTAAG TCTTGCACTT GTCACGAATT CGGAGGTCTA TTACACAAGC TTGAGGTGTA GATGTGTCCA AGAGAGCTCA GTCTTTATCC CTAGACGCTT
             EcoRI
         IleAspArg IleGlnIleLeu ProArgGly AsnGlyCys ProArgLysGlu IleIleVal TrpLysLys AsnLysSerIle ValCysVal AspProGln
 701    CATTGATCGA ATTCAAATCT TGCCCCGTGG GAATGGTTGT CCAAGAAAAG AAATCATAGT CTGGAAGAAG AACAAGTCAA TTGTGTGTGT GGACCCTCAA
                                                                                   human IgG4 Fc (constant region)
        AlaGluTrpIle GlnArgMet MetGluVal LeuArgLysArg SerSerSer ThrLeuPro ValProValPhe LysArgLys IleProPro ProCysProSer
 801    GCTGAATGGA TACAAAGAAT GATGGAAGTA TTGAGAAAAA GAAGTTCTTC AACTCTACCA GTTCCAGTGT TTAAGAGAAA GATTCCCCCC CCATGCCCAT
         CysProAla ProGluPhe LeuGlyGlyPro SerValPhe LeuPhePro ProLysProLys AspThrLeu MetIleSer ArgThrProGlu ValThrCys
 901    CATGCCCAGC ACCTGAGTTC CTGGGGGGAC CATCAGTCTT CCTGTTCCCC CCAAAACCCA AGGACACTCT CATGATCTCC CGGACCCCTG AGGTCACGTG
         ValValVal AspValSerGln GluAspPro GluValGln PheAsnTrpTyr ValAspGly ValGluVal HisAsnAlaLys ThrLysPro ArgGluGlu
1001    CGTGGTGGTG GACGTGAGCC AGGAAGACCC CGAGGTCCAG TTCAACTGGT ACGTGGATGG CGTGGAGGTG CATAATGCCA AGACAAAGCC GCGGGAGGAG
        GlnPheAsnSer ThrTyrArg ValValSer ValLeuThrVal LeuHisGln AspTrpLeu AsnGlyLysGlu TyrLysCys LysValSer AsnLysGlyLeu
1101    CAGTTCAACA GCACGTACCG TGTGGTCAGC GTCCTCACCG TCCTGCACCA GGACTGGCTG AACGGCAAGG AGTACAAGTG CAAGGTCTCC AACAAAGGCC
        ProSerSer IleGluLys ThrIleSerLys AlaLysGly GlnProArg GluProGlnVal TyrThrLeu ProProSer GlnGluGluMet ThrLysAsn
1201    TCCCGTCCTC CATCGAGAAA ACCATCTCCA AAGCCAAAGG GCAGCCCCGA GAGCCACAGG TGTACACCCT GCCCCCATCC CAGGAGGAGA TGACCAAGAA
         GlnValSer LeuThrCysLeu ValLysGly PheTyrPro SerAspIleAla ValGluTrp GluSerAsn GlyGlnProGlu AsnAsnTyr LysThrThr
1301    CCAGGTCAGC CTGACCTGCC TGGTCAAAGG CTTCTACCCC AGCGACATCG CCGTGGAGTG GGAGAGCAAT GGGCAGCCGG AGAACAACTA CAAGACCACG
        ProProValLeu AspSerAsp GlySerPhe PheLeuTyrSer ArgLeuThr ValAspLys SerArgTrpGln GluGlyAsn ValPheSer CysSerValMet
1401    CCTCCCGTGC TGGACTCCGA CGGCTCCTTC TTCCTCTACA GCAGGCTAAC CGTGGACAAG AGCAGGTGGC AGGAGGGGAA TGTCTTCTCA TGCTCCGTGA
                                                                             BmtI
                                                                             NheI
        HisGluAla LeuHisAsn HisTyrThrGln LysSerLeu SerLeuSer ProGlyLys***(SEQ ID NO:77)
1501    TGCATGAGGC TCTGCACAAC CACTACACAC AGAAGAGCCT CTCCCTGTCT CCGGGTAAAT GAGTGCTAGC TGGCCAGACA TGATAAGATA CATTGATGAG
1601    TTTGGACAAA CCACAACTAG AATGCAGTGA AAAAAATGCT TTATTTGTGA AATTTGTGAT GCTATTGCTT TATTTGTAAC CATTATAAGC TGCAATAAAC
1701    AAGTTAACAA CAACAATTGC ATTCATTTTA TGTTTCAGGT TCAGGGGGAG GTGTGGGAGG TTTTTTAAAG CAAGTAAAAC CTCTACAAAT GTGGTATGGA
         AseI
```

```
1801  ATTAATTCTA AAATACAGCA TAGCAAAACT TTAACCTCCA AATCAAGCCT CTACTTGAAT CCTTTTCTGA GGGATGAATA AGGCATAGGC ATCAGGGGCT
1901  GTTGCCAATG TGCATTAGCT GTTTGCAGCC TCACCTTCTT TCATGGAGTT TAAGATATAG TGTATTTTCC CAAGGTTTGA ACTAGCTCTT CATTTCTTTA
2001  TGTTTTAAAT GCACTGACCT CCCACATTCC CTTTTTAGTA AAATATTCAG AAATAATTTA AATACATCAT TGCAATGAAA ATAAATGTTT TTTATTAGGC
2101  AGAATCCAGA TGCTCAAGGC CCTTCATAAT ATCCCCCAGT TTAGTAGTTG GACTTAGGGA ACAAAGGAAC CTTTAATAGA AATTGGACAG CAAGAAAGCG
2201  AGCTTCTAGC TTATCCTCAG TCCTGCTCCT CTGCCACAAA GTGCACGCAG TTGCCGGCCG GGTCGCGCAG GGCGAACTCC CGCCCCCACG GCTGCTCGCC
2301  GATCTCGGTC ATGGCCGGCC CGGAGGCGTC CCGGAAGTTC GTGGACACGA CCTCCGACCA CTCGGCGTAC AGCTCGTCCA GGCCGCGCAC CCACACCCAG
2401  GCCAGGGTGT TGTCCGGCAC CACCTGGTCC TGGACCGCGC TGATGAACAG GGTCACGTCG TCCCGGACCA CACCGGCGAA GTCGTCCTCC ACGAAGTCCC
2501  GGGAGAACCC GAGCCGGTCG GTCCAGAACT CGACCGCTCC GGCGACGTCG CGCGCGGTGA GCACCGGAAC GGCACTGGTC AACTTGGCCA TGATGGCTCC
                                                                                                   AseI
2601  TCCTGTCAGG AGAGGAAAGA GAAGAAGGTT AGTACAATTG CTATAGTGAG TTGTATTATA CTATGCAGAT ATACTATGCC AATGATTAAT TGTCAAACTA
2701  GGGCTGCAGG GTTCATAGTG CCACTTTTCC TGCACTGCCC CATCTCCTGC CCACCCTTTC CCAGGCATAG ACAGTCAGTG ACTTACCAAA CTCACAGGAG
2801  GGAGAAGGCA GAAGCTTGAG ACAGACCCGC GGGACCGCCG AACTGCGAGG GGACGTGGCT AGGGCGGCTT CTTTTATGGT GCGCCGGCCC TCGGAGGCAG
2901  GGCGCTCGGG GAGGCCTAGC GGCCAATCTG CGGTGGCAGG AGGCGGGGCC GAAGGCCGTG CCTGACCAAT CCGGAGCACA TAGGAGTCTC AGCCCCCCGC
3001  CCCAAAGCAA GGGGAAGTCA CGCGCCTGTA GCGCCAGCGT GTTGTGAAAT GGGGGCTTGG GGGGGTTGGG GCCCTGACTA GTCAAAACAA ACTCCCATTG
3101  ACGTCAATGG GGTGGAGACT TGGAAATCCC CGTGAGTCAA ACCGCTATCC ACGCCCATTG ATGTACTGCC AAAACCGCAT CATCATGGTA ATAGCGATGA
3201  CTAATACGTA GATGTACTGC CAAGTAGGAA AGTCCCATAA GGTCATGTAC TGGGCATAAT GCCAGGCGGG CCATTTACCG TCATTGACGT CAATAGGGGG
3301  CGTACTTGGC ATATGATACA CTTGATGTAC TGCCAAGTGG GCAGTTTACC GTAAATACTC CACCCATTGA CGTCAATGGA AAGTCCCTAT TGGCGTTACT
3401  ATGGGAACAT ACGTCATTAT TGACGTCAAT GGGCGGGGGT CGTTGGCGGG TCAGCCAGGC GGGCCATTTA CCGTAAGTTA TGTAACGCCT GCAGGTTAAT
3501  TAAGAACATG TGAGCAAAAG GCCAGCAAAA GGCCAGGAAC CGTAAAAAGG CCGCGTTGCT GGCGTTTTTC CATAGGCTCC GCCCCCCTGA CGAGCATCAC
3601  AAAAATCGAC GCTCAAGTCA GAGGTGGCGA AACCCGACAG GACTATAAAG ATACCAGGCG TTTCCCCCTG GAAGCTCCCT CGTGCGCTCT CCTGTTCCGA
3701  CCCTGCCGCT TACCGGATAC CTGTCCGCCT TTCTCCCTTC GGGAAGCGTG GCGCTTTCTC ATAGCTCACG CTGTAGGTAT CTCAGTTCGG TGTAGGTCGT
3801  TCGCTCCAAG CTGGGCTGTG TGCACGAACC CCCCGTTCAG CCCGACCGCT GCGCCTTATC CGGTAACTAT CGTCTTGAGT CCAACCCGGT AAGACACGAC
3901  TTATCGCCAC TGGCAGCAGC CACTGGTAAC AGGATTAGCA GAGCGAGGTA TGTAGGCGGT GCTACAGAGT TCTTGAAGTG GTGGCCTAAC TACGGCTACA
4001  CTAGAAGAAC ACTATTTGGT ATCTGCGCTC TGCTGAAGCC AGTTACCTTC GGAAAAAGAG TTGGTAGCTC TTGATCCGGC AAACAAACCA CCGCTGGTAG
4101  CGGTGGTTTT TTTGTTTGCA AGCAGCAGAT TACGCGCAGA AAAAAAGGAT CTCAAGAAGA TCCTTTGATC TTTTCTACGG GGTCTGACGC TCAGTGGAAC
4201  GAAAACTCAC GTTAAGGGAT TTTGGTCATG GCTAGTTAAT TAACATTTAA ATCAGCGGCC GCAATAAAAT ATCTTTATTT TCATTACATC TGTGTGTTGG
4301  TTTTTTGTGT GAATCGTAAC TAACATACGC TCTCCATCAA AACAAAACGA AACAAAACAA ACTAGCAAAA TAGGCTGTCC CCAGTGCAAG TGCAGGTGCC
4401  AGAACATTTC TCTATCGAA  (SEQ ID NO: 104)
```

IL2ss.CXCL13(3-87).hIgG4Fc sequence [Alanine substitutions for removal of GAG binding sites – Lys & His]

```
   1    GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101    GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201    GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301    GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401    GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                           NarI
                                           KasI
                                           SfoI
                                           BbeI
                                          ~~~~~~~                                       IL-2 secretion signal
                                                                                        MetTyrArg MetGlnLeu LeuSerCysIle
 501    TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                EcoRI
                                ~~~~~~~ CXCL13 (3-87)
          AlaLeuSer LeuAlaLeu ValThrAsnSer GluValTyr TyrThrSer LeuArgCysArg CysValGln GluSerSer ValPheIlePro ArgArgPhe
 601    TTGCACTAAG TCTTGCACTT GTCACGAATT CGGAGGTCTA TTACACAAGC TTGAGGTGTA GATGTGTCCA AGAGAGCTCA GTCTTTATCC CTAGACGCTT
                  EcoRI
         IleAspAla IleGlnIleLeu ProArgGly AsnGlyCys ProArgLysGlu IleIleVal TrpAlaAla AsnAlaSerIle ValCysVal AspProGln
 701    CATTGATgcc ATTCAAATCT TGCCCCGTGG GAATGGTTGT CCAAGAAAAG AAATCATAGT CTGGgctgcg AACgctTCAA TTGTGTGTGT GGACCCTCAA
                                                                                                       human IgG4 Fc
                                                                                                      (constant region)
        AlaGluTrpIle GlnAlaMet MetGluVal LeuAlaAlaAla SerSerSer ThrLeuPro ValProValPhe AlaAlaAla IleProPro ProCysProSer
 801    GCTGAATGGA TACAAgccAT GATGGAAGTA TTGgctgcgg ctAGTTCTTC AACTCTACCA GTTCCAGTGT TTgccgctgc gATTCCCCCC CCATGCCCAT
          CysProAla ProGluPhe LeuGlyGlyPro SerValPhe LeuPhePro ProLysProLys AspThrLeu MetIleSer ArgThrProGlu ValThrCys
 901    CATGCCCAGC ACCTGAGTTC CTGGGGGGAC CATCAGTCTT CCTGTTCCCC CCAAAACCCA AGGACACTCT CATGATCTCC CGGACCCCTG AGGTCACGTG
         ValValVal AspValSerGln GluAspPro GluValGln PheAsnTrpTyr ValAspGly ValGluVal HisAsnAlaLys ThrLysPro ArgGluGlu
1001    CGTGGTGGTG GACGTGAGCC AGGAAGACCC CGAGGTCCAG TTCAACTGGT ACGTGGATGG CGTGGAGGTG CATAATGCCA AGACAAAGCC GCGGGAGGAG
        GlnPheAsnSer ThrTyrArg ValValSer ValLeuThrVal LeuHisGln AspTrpLeu AsnGlyLysGlu TyrLysCys LysValSer AsnLysGlyLeu
1101    CAGTTCAACA GCACGTACCG TGTGGTCAGC GTCCTCACCG TCCTGCACCA GGACTGGCTG AACGGCAAGG AGTACAAGTG CAAGGTCTCC AACAAAGGCC
          ProSerSer IleGluLys ThrIleSerLys AlaLysGly GlnProArg GluProGlnVal TyrThrLeu ProProSer GlnGluGluMet ThrLysAsn
1201    TCCCGTCCTC CATCGAGAAA ACCATCTCCA AAGCCAAAGG GCAGCCCCGA GAGCCACAGG TGTACACCCT GCCCCCATCC CAGGAGGAGA TGACCAAGAA
         GlnValSer LeuThrCysLeu ValLysGly PheTyrPro SerAspIleAla ValGluTrp GluSerAsn GlyGlnProGlu AsnAsnTyr LysThrThr
1301    CCAGGTCAGC CTGACCTGCC TGGTCAAAGG CTTCTACCCC AGCGACATCG CCGTGGAGTG GGAGAGCAAT GGGCAGCCGG AGAACAACTA CAAGACCACG
        ProProValLeu AspSerAsp GlySerPhe PheLeuTyrSer ArgLeuThr ValAspLys SerArgTrpGln GluGlyAsn ValPheSer CysSerValMet
1401    CCTCCCGTGC TGGACTCCGA CGGCTCCTTC TTCCTCTACA GCAGGCTAAC CGTGGACAAG AGCAGGTGGC AGGAGGGGAA TGTCTTCTCA TGCTCCGTGA
                                                                             BmtI
                                                                             NheI
          HisGluAla LeuHisAsn HisTyrThrGln LysSerLeu SerLeuSer ProGlyLys***(SEQ ID NO:78)
1501    TGCATGAGGC TCTGCACAAC CACTACACAC AGAAGAGCCT CTCCCTGTCT CCGGGTAAAT GAGTGCTAGC TGGCCAGACA TGATAAGATA CATTGATGAG
1601    TTTGGACAAA CCACAACTAG AATGCAGTGA AAAAAATGCT TTATTTGTGA AATTTGTGAT GCTATTGCTT TATTTGTAAC CATTATAAGC TGCAATAAAC
1701    AAGTTAACAA CAACAATTGC ATTCATTTTA TGTTTCAGGT TCAGGGGGAG GTGTGGGAGG TTTTTTAAAG CAAGTAAAAC CTCTACAAAT GTGGTATGGA
```

```
          AseI
1801     ATTAATTCTA AAATACAGCA TAGCAAAACT TTAACCTCCA AATCAAGCCT CTACTTGAAT CCTTTTCTGA GGGATGAATA AGGCATAGGC ATCAGGGGCT
1901     GTTGCCAATG TGCATTAGCT GTTTGCAGCC TCACCTTCTT TCATGGAGTT TAAGATATAG TGTATTTTCC CAAGGTTTGA ACTAGCTCTT CATTTCTTTA
2001     TGTTTTAAAT GCACTGACCT CCCACATTCC CTTTTTAGTA AAATATTCAG AAATAATTTA AATACATCAT TGCAATGAAA ATAAATGTTT TTTATTAGGC
2101     AGAATCCAGA TGCTCAAGGC CCTTCATAAT ATCCCCCAGT TTAGTAGTTG GACTTAGGGA ACAAAGGAAC CTTTAATAGA AATTGGACAG CAAGAAAGCG
2201     AGCTTCTAGC TTATCCTCAG TCCTGCTCCT CTGCCACAAA GTGCACGCAG TTGCCGGCCG GGTCGCGCAG GGCGAACTCC CGCCCCCACG GCTGCTCGCC
2301     GATCTCGGTC ATGGCCGGCC CGGAGGCGTC CCGGAAGTTC GTGGACACGA CCTCCGACCA CTCGGCGTAC AGCTCGTCCA GGCCGCGCAC CCACACCCAG
2401     GCCAGGGTGT TGTCCGGCAC CACCTGGTCC TGGACCGCGC TGATGAACAG GGTCACGTCG TCCCGGACCA CACCGGCGAA GTCGTCCTCC ACGAAGTCCC
2501     GGGAGAACCC GAGCCGGTCG GTCCAGAACT CGACCGCTCC GGCGACGTCG CGCGCGGTGA GCACCGGAAC GGCACTGGTC AACTTGGCCA TGATGGCTCC
                                                                                                         AseI
2601     TCCTGTCAGG AGAGGAAAGA GAAGAAGGTT AGTACAATTG CTATAGTGAG TTGTATTATA CTATGCAGAT ATACTATGCC AATGATTAAT TGTCAAACTA
2701     GGGCTGCAGG GTTCATAGTG CCACTTTTCC TGCACTGCCC CATCTCCTGC CCACCCTTTC CCAGGCATAG ACAGTCAGTG ACTTACCAAA CTCACAGGAG
2801     GGAGAAGGCA GAAGCTTGAG ACAGACCCGC GGGACCGCCG AACTGCGAGG GGACGTGGCT AGGGCGGCTT CTTTTATGGT GCGCCGGCCC TCGGAGGCAG
2901     GGCGCTCGGG GAGGCCTAGC GGCCAATCTG CGGTGGCAGG AGGCGGGGCC GAAGGCCGTG CCTGACCAAT CCGGAGCACA TAGGAGTCTC AGCCCCCCGC
3001     CCCAAAGCAA GGGGAAGTCA CGCGCCTGTA GCGCCAGCGT GTTGTGAAAT GGGGGCTTGG GGGGGTTGGG GCCCTGACTA GTCAAAACAA ACTCCCATTG
3101     ACGTCAATGG GGTGGAGACT TGGAAATCCC CGTGAGTCAA ACCGCTATCC ACGCCCATTG ATGTACTGCC AAAACCGCAT CATCATGGTA ATAGCGATGA
3201     CTAATACGTA GATGTACTGC CAAGTAGGAA AGTCCCATAA GGTCATGTAC TGGGCATAAT GCCAGGCGGG CCATTTACCG TCATTGACGT CAATAGGGGG
3301     CGTACTTGGC ATATGATACA CTTGATGTAC TGCCAAGTGG GCAGTTTACC GTAAATACTC CACCCATTGA CGTCAATGGA AAGTCCCTAT TGGCGTTACT
3401     ATGGGAACAT ACGTCATTAT TGACGTCAAT GGGCGGGGGT CGTTGGGCGG TCAGCCAGGC GGGCCATTTA CCGTAAGTTA TGTAACGCCT GCAGGTTAAT
3501     TAAGAACATG TGAGCAAAAG GCCAGCAAAA GGCCAGGAAC CGTAAAAAGG CCGCGTTGCT GGCGTTTTTC CATAGGCTCC GCCCCCCTGA CGAGCATCAC
3601     AAAAATCGAC GCTCAAGTCA GAGGTGGCGA AACCCGACAG GACTATAAAG ATACCAGGCG TTTCCCCCTG GAAGCTCCCT CGTGCGCTCT CCTGTTCCGA
3701     CCCTGCCGCT TACCGGATAC CTGTCCGCCT TTCTCCCTTC GGGAAGCGTG GCGCTTTCTC ATAGCTCACG CTGTAGGTAT CTCAGTTCGG TGTAGGTCGT
3801     TCGCTCCAAG CTGGGCTGTG TGCACGAACC CCCCGTTCAG CCCGACCGCT GCGCCTTATC CGGTAACTAT CGTCTTGAGT CCAACCCGGT AAGACACGAC
3901     TTATCGCCAC TGGCAGCAGC CACTGGTAAC AGGATTAGCA GAGCGAGGTA TGTAGGCGGT GCTACAGAGT TCTTGAAGTG GTGGCCTAAC TACGGCTACA
4001     CTAGAAGAAC AGTATTTGGT ATCTGCGCTC TGCTGAAGCC AGTTACCTTC GGAAAAAGAG TTGGTAGCTC TTGATCCGGC AAACAAACCA CCGCTGGTAG
4101     CGGTGGTTTT TTTGTTTGCA AGCAGCAGAT TACGCGCAGA AAAAAAGGAT CTCAAGAAGA TCCTTTGATC TTTTCTACGG GGTCTGACGC TCAGTGGAAC
4201     GAAAACTCAC GTTAAGGGAT TTTGGTCATG GCTAGTTAAT TAACATTTAA ATCAGCGGCC GCAATAAAAT ATCTTTATTT TCATTACATC TGTGTGTTGG
4301     TTTTTTGTGT GAATCGTAAC TAACATACGC TCTCCATCAA AACAAAACGA AACAAAACAA ACTAGCAAAA TAGGCTGTCC CCAGTGCAAG TGCAGGTGCC
4401     AGAACATTTC TCTATCGAA  (SEQ ID NO:105)
```

FIG. 9E (CONT)

indicate potential sites for pegylation of CXCL11.

FIG. 12

CCL1 NP_002972 SEQ ID NO:1
mqiittalvc lllagmwped vdsksmqvpf srccfsfaeq eiplrailcy rntssicsne
glifklkrgk eacaldtvgw vqrhrkmlrh cpskrk

CCL2 NP_002973 SEQ ID NO:2
mkvsaallcl lliaatfipq glaqpdaina pvtccynftn rkisvqrlas yrritsskcp
keavifktiv akeicadpkq kwvqdsmdhl dkqtqtpkt

CCL3 NP_002974 SEQ ID NO:3
mqvstaalav llctmalcnq fsaslaadtp taccfsytsr qipqnfiady fetssqcskp
gvifltkrsr qvcadpseew vqkyvsdlel sa

CCL4 NP_002975 SEQ ID NO:4
mklcvtvlsl lmlvaafcsp alsapmgsdp ptaccfsyta rklprnfvvd yyetsslcsq
pavvfqtkrs kqvcadpses wvqeyvydle ln

CCL4L1 NP_001001435 SEQ ID NO:5
mklcvtvlsl lvlvaafcsl alsapmgsdp ptaccfsyta rklprnfvvd yyetsslcsq
pavvfqtkrg kqvcadpses wvqeyvydle ln

CCL5 NP_002976 SEQ ID NO:6
mkvsaaalav iliatalcap asaspyssdt tpccfayiar plprahikey fytsgkcsnp
avvfvtrknr qvcanpekkw vreyinslem s

CCL7 NP_006264 SEQ ID NO:7
mkasaallcl lltaaafspq glaqpvgint sttccyrfin kkipkqrles yrrttsshcp
reavifktkl dkeicadptq kwvqdfmkhl dkktqtpkl

CCL8 NP_005614 SEQ ID NO:8
mkvsaallcl llmaatfspq glaqpdsvsi pitccfnvin rkipiqrles ytritniqcp
keavifktkr gkevcadpke rwvrdsmkhl dqifqnlkp

CCL11 CAG33702 SEQ ID NO:9
mkvsaallwl lliaaafspq glagpasvpt tccfnlanrk iplqrlesyr ritsgkcpqk
avifktklak dicadpkkkw vqdsmkyldq ksptpkp

CCL13 NP_005399 SEQ ID NO:10
mkvsavllcl llmtaafnpq glaqpdalnv pstccftfss kkislqrlks yvittsrcpq
kavifrtklg keicadpkek wvqnymkhlg rkahtlkt

CCL14-1 NP_116739 SEQ ID NO:11
mkisvaaipf fllitialgt ktesssrgpy hpseccftyt tykiprqrim dyyetnsqcs
kpgivfitkr ghsvctnpsd kwvqdyikdm ken

CCL14-2 NP_116738 SEQ ID NO:12
mkisvaaipf fllitialgt ktesssqtgg kpkvvkiqlk lvggpyhpse ccftyttyki
prqrimdyye tnsqcskpgi vfitkrghsv ctnpsdkwvq dyikdmken

FIG. 12 (CONT)

CCL15 NP_116741 SEQ ID NO:13
mkvsvaalsc lmlvavlgsq aqfindaete lmmsklplen pvvlnsfhfa adcctsyisq
sipcslmksy fetssecskp gvifltkkgr qvcakpsgpg vqdcmkklkp ysi

CCL16 NP_004581 SEQ ID NO:14
mkvseaalsl lvliliitsa srsqpkvpew vntpstcclk yyekvlprrl vvgyrkalnc
hlpaiifvtk rnrevctnpn ddwvqeyikd pnlpllptrn lstvkiitak ngqpqllnsq

CCL17 NP_002978 SEQ ID NO:15
maplkmlalv tlllgaslqh ihaargtnvg reccleyfkg aiplrklktw yqtsedcsrd
aivfvtvqgr aicsdpnnkr vknavkylqs lers

CCL18 NP_002979 SEQ ID NO:16
mkglaaallv lvctmalcsc aqvgtnkelc clvytswqip qkfivdyset spqcpkpgvi
lltkrgrqic adpnkkwvqk yisdlklna

CCL19 NP_006265 SEQ ID NO:17
malllalsll vlwtspaptl sgtndaedcc lsvtqkpipg yivrnfhyll ikdgcrvpav
vfttlrgrql cappdqpwve riiqrlqrts akmkrrss

CCL20-1 NP_004582 SEQ ID NO:18
mcctksllla almsvlllhl cgeseaasnf dcclgytdri lhpkfivgft rqlanegcdi
naiifhtkkk lsvcanpkqt wvkyivrlls kkvknm

CCL20-2 NP_001123518 SEQ ID NO:19
mcctksllla almsvlllhl cgeseasnfd cclgytdril hpkfivgftr qlanegcdin
aiifhtkkkl svcanpkqtw vkyivrllsk kvknm

CCL21 NP_002980 SEQ ID NO:20
maqslalsll ilvlafgipr tqgsdggaqd cclkysqrki pakvvrsyrk qepslgcsip
ailflprkrs qaelcadpke lwvqqlmqhl dktpspqkpa qgcrkdrgas ktgkkgkgsk
gckrtersqt pkgp

CCL22 NP_002981 SEQ ID NO:21
mdrlqtallv vlvllavalq ateagpygan medsvccrdy vryrlplrvv khfywtsdsc
prpgvvlltf rdkeicadpr vpwvkmilnk lsq

CCL23-1 NP_665905 SEQ ID NO:22
mkvsvaalsc lmlvtalgsq arvtkdaete fmmsklplen pvlldrfhat sadccisytp
rsipcslles yfetnsecsk pgvifltkkg rrfcanpsdk qvqvcvrmlk ldtriktrkn

CCL23-2 NP_005055 SEQ ID NO:23
mkvsvaalsc lmlvtalgsq arvtkdaete fmmsklplen pvlldmlwrr kigpqmtlsh
aagfhatsad ccisytprsi pcsllesyfe tnsecskpgv ifltkkgrrf canpsdkqvq
vcvrmlkldt riktrkn

CCL24 NP_002982 SEQ ID NO:24
maglmtivts llflgvcahh iiptgsvvip spccmffvsk ripenrvvsy qlssrstclk
agvifttkkg qqfcgdpkqe wvqrymknld akqkkaspra ravavkgpvq rypgnqttc

FIG. 12 (CONT)

CCL25-1 NP_005615 SEQ ID NO:25
mnlwllaclv agflgawapa vhtqgvfedc clayhypigw avlrrawtyr iqevsgscnl
paaifylpkr hrkvcgnpks revqramkll darnkvfakl hhntqtfqag phavkklssg
nsklssskfs npissskrnv sllisansgl

CCL25-2 NP_683686 SEQ ID NO:26
mnlwllaclv agflgawapa vhtqgvfedc clayhypigw avlrrawtyr iqevsgscnl
paairpscck evefwklqvi ivqv

CCL25-3 EAW68951 SEQ ID NO:27
mnlwllaclv agflgawapa vhtqgvfedc clayhypigw avlrrawtyr iqevsgscnl
paairpscck evefwklqvi iiqv

CCL26 NP_006063 SEQ ID NO:28
mmglslasav llasllslhl gtatrgsdis ktccfqyshk plpwtwvrsy eftsnscsqr
avifttkrgk kvcthprkkw vqkyisllkt pkql

CCL27 NP_006655 SEQ ID NO:29
mkgpptfcsl lllslllspd ptaafllpps tacctqlyrk plsdkllrkv iqvelqeadg
dchlqafvlh laqrsicihp qnpslsqwfe hqerklhgtl pklnfgmlrk mg

CCL28 NP_683513 SEQ ID NO:30
mqqrglaiva lavcaalhas eailpiassc ctevshhisr rllervnmcr iqradgdcdl
aavilhvkrr ricvsphnht vkqwmkvqaa kkngkgnvch rkkhhgkrns nrahqgkhet
yghktpy

CXCL1 NP_001502 SEQ ID NO:31
maraalsaap snprllrval lllllvaagr raagasvate lrcqclqtlq gihpkniqsv
nvkspgphca qteviatlkn grkaclnpas pivkkiiekm lnsdksn

CXCL2 NP_002080 SEQ ID NO:32
maratlsaap snprllrval lllllvaasr raagaplate lrcqclqtlq gihlkniqsv
kvkspgphca qteviatlkn gqkaclnpas pmvkkiiekm lkngksn

CXCL3 NP_002081 SEQ ID NO:33
mahatlsaap snprllrval lllllvaasr raagasvvte lrcqclqtlq gihlkniqsv
nvrspgphca qteviatlkn gkkaclnpas pmvqkiieki lnkgstn

CXCL4 NP_002610 SEQ ID NO:34
mssaagfcas rpgllflgll llplvvafas aeaeedgdlq clcvkttsqv rprhitslev
ikagphcpta qliatlkngr kicldlqapl ykkiikklle s

CXCL5 NP_002985 SEQ ID NO:35
msllssraar vpgpssslca llvllllltq pgpiasagpa aavlrelrcv clqttqgvhp
kmisnlqvfa igpqcskvev vaslkngkei cldpeapflk kviqkildgg nken

CXCL6 NP_002984 SEQ ID NO:36
mslpssraar vpgpsgslca llalllllltp pgplasagpv savltelrct clrvtlrvnp
ktigklqvfp agpqcskvev vaslkngkqv cldpeapflk kviqkildsg nkkn

FIG. 12 (CONT)

CXCL7 NP_002695 SEQ ID NO:37
mslrldttps cnsarplhal qvlllllsll talasstkgq tkrnlakgke esldsdlyae
lrcmciktts gihpkniqsl evigkgthcn qveviatlkd grkicldpda prikkivqkk
lagdesad

CXCL8 NP_000575 SEQ ID NO:38
mtsklavall aaflisaalc egavlprsak elrcqcikty skpfhpkfik elrviesgph
canteiivkl sdgrelcldp kenwvqrvve kflkraens

CXCL9 NP_002407 SEQ ID NO:39
mkksgvlfll giillvligv qgtpvvrkgr cscistnqgt ihlqslkdlk qfapspscek
ieiiatlkng vqtclnpdsa dvkelikkwe kqvsqkkkqk ngkkhqkkkv lkvrksqrsr
qkktt

CXCL10 NP_001556 SEQ ID NO:40
mnqtailicc lifltlsgiq gvplsrtvrc tcisisnqpv nprsleklei ipasqfcprv
eiiatmkkkg ekrclnpesk aiknllkavs kerskrsp

CXCL11 NP_005400 SEQ ID NO:41
msvkgmaial avilcatvvq gfpmfkrgrc lcigpgvkav kvadiekasi mypsnncdki
eviitlkenk gqrclnpksk qarliikkve rknf

CXCL12 NP_000600 SEQ ID NO:42
mnakvvvvlv lvltalclsd gkpvslsyrc pcrffeshva ranvkhlkil ntpncalqiv
arlknnnrqv cidpklkwiq eylekalnkr fkm

CXCL13 NP_006410 SEQ ID NO:43
mkfistslll mllvsslspv qgvlevyyts lrcrcvqess vfiprrfidr iqilprgngc
prkeiivwkk nksivcvdpq aewiqrmmev lrkrssstlp vpvfkrkip

CXCL16 NP_071342 SEQ ID NO:44
msgsqsevap spqsprspem grdlrpgsrv lllllllllv yltqpgngne gsvtgscycg
krissdspps vqfmnrlrkh lrayhrclyy trfqllswsv cggnkdpwvq elmscldlke
cghaysgiva hqkhllptsp pisqasegas sdihtpaqml lstlqstqrp tlpvgslssd
keltrpnett ihtaghslaa gpeagenqkq peknagptar tsatvpvlcl laiifiltaa
lsyvlckrrr gqspqsspdl pvhyipvapd snt

XCL1 AAH69817 SEQ ID NO:45
mrllilallg icsltayive gvgsevsdkr tcvslttqrl pvsriktyti tegslravif
itkrglkvca dpqatwvrdv vrsmdrksnt rnnmiqtkpt gtqqstntav tltg

XCL2 NP_003166 SEQ ID NO:46
mrllilallg icsltayive gvgsevshrr tcvslttqrl pvsriktyti tegslravif
itkrglkvca dpqatwvrdv vrsmdrksnt rnnmiqtkpt gtqqstntav tltg

FIG. 12 (CONT)

CX3CL1 NP_002987 SEQ ID NO:47 mapislswll rlatfchltv llagqhhgvt kcnitcskmt skipvallih yqqnqascgk
raiiletrqh rlfcadpkeq wvkdamqhld rqaaaltrng gtfekqigev kprttpaagg
mdesvvlepe atgessslep tpssqeaqra lgtspelptg vtgssgtrlp ptpkaqdggp
vgtelfrvpp vstaatwqss aphqpgpslw aeaktseaps tqdpstqast asspapeena
psegqrvwgq gqsprpensl ereemgpvpa htdafqdwgp gsmahvsvvp vssegtpsre
pvasgswtpk aeepihatmd pqrlgvlitp vpdaqaatrr qavgllaflg llfclgvamf
tyqslqgcpr kmagemaegl ryiprscgsn syvlvpv

IgG1Fc CBX54381.1 SEQ ID NO:48 sepkscdkth tcppcpapel lggpsvflfp pkpkdtlmis rtpevtcvvv dvshedpevk
fnwyvdgvev hnaktkpree qynstyrvvs vltvlhqdwl ngkeykckvs nkalpapiek
tiskakgqpr epqvytlpps rdeltknqvs ltclvkgfyp sdiavewesn gqpennyktt
ppvldsdgsf flyskltvdk srwqqgnvfs csvmhealhn hytqkslsls pgk

IgG2Fc CBX54382.1 SEQ ID NO:49 erkccvecpp cpappvagps vflfppkpkd tlmisrtpev tcvvvdvshe dpevqfnwyv
dgvevhnakt kpreeqfnst frvvsvltvv hqdwlngkey kckvsnkglp apiektiskt
kgqprepqvy tlppsreemt knqvsltclv kgfypsdiav ewesngqpen nykttppmld
sdgsfflysk ltvdksrwqq gnvfscsvmh ealhnhytqk slslspgk

IgG3Fc CBX54383.1 SEQ ID NO:50 elktplgdtt htcprcpepk scdtpppcpr cpepkscdtp ppcprcpepk scdtpppcpr
cpapellggp svflfppkpk dtlmisrtpe vtcvvvdvsh edpevqfkwy vdgvevhnak
tkpreeqfns tfrvvsvltv lhqdwlngke ykckvsnkal papiektisk tkgqprepqv
ytlppsreem tknqvsltcl vkgfypsdia vewessgqpe nnynttppml dsdgsfflys
kltvdksrwq qgnifscsvm healhnrftq kslslspgk

IgG4Fc CBX54384.1 SEQ ID NO:51 eskygppcps cpapeflggp svflfppkpk dtlmisrtpe vtcvvvdvsq edpevqfnwy
vdgvevhnak tkpreeqfns tyrvvsvltv vhqdwlngke ykckvsnkgl pssiektisk
akgqprepqv ytlppsqeem tknqvsltcl vkgfypsdia vewesngqpe nnykttppvl
dsdgsfflys rltvdksrwq egnvfscsvm healhnhytq kslslslgk

CHEMOKINE-IMMUNOGLOBULIN FUSION POLYPEPTIDES, COMPOSITIONS, METHOD OF MAKING AND USE THEREOF

This application is a continuation of U.S. patent application Ser. No. 13/962,110, filed Aug. 8, 2013, which is a continuation-in-part application of U.S. patent application Ser. No. 13/480,526, filed May 25, 2012, which claims priority of U.S. Provisional Patent Application No. 61/492,260, filed on Jun. 1, 2011. The entirety of the aforementioned applications is incorporated herein by reference.

FIELD

The present application generally relates to compositions that can be used for treating chemokine receptor-mediated disorders and modulating inflammation, inflammatory cell motility, cancer cell motility, or cancer cell survival.

BACKGROUND

Chemokines are chemotactic cytokines, of molecular weight 6-15 kDa, that are released by a wide variety of cells to attract and activate, among other cell types, macrophages, T and B lymphocytes, eosinophils, basophils and neutrophils. There are four classes of chemokines, CXC, CC, C, and CX3C, depending on whether the first two cysteines in the amino acid sequence are separated by a single amino acid (CXC) or are adjacent (CC). Unlike other chemokines, C chemokines have only two cysteines; one N-terminal and one downstream cysteine. The only CX3C chemokine, CX3CL1, has three amino acids between two N-terminal cysteines. The CXC chemokines, such as interleukin-8 (IL-8/CXCL8), neutrophil-activating protein-2 (NAP-2/CXCL7) and melanoma growth stimulatory activity protein (MGSA/CXCL1) are chemotactic primarily for neutrophils and T lymphocytes, whereas the CC chemokines, such as RANTES/CCL5, MIP-1α/CCL3, MIP-1β/CCL4, the monocyte chemotactic proteins (MCP-1/CCL2, MCP-2/CCL8, MCP-3/CCL7, MCP-4/CCL13, and MCP-5/CCL12) and the eotaxins (−1/CCL11 and −2/CCL24) are chemotactic for, among other cell types, macrophages, T lymphocytes, eosinophils, dendritic cells, and basophils. There also exist the chemokines lymphotactin-1/XCL1, lymphotactin-2/XCL2 (both C chemokines), and fractalkine/CX3CL1 (a CX3C chemokine) that do not fall into either of the major chemokine subfamilies, CXC and CC.

Chemokines bind to specific cell-surface receptors belonging to the family of G-protein-coupled seven-transmembrane-domain proteins, which are termed “chemokine receptors.” On binding to their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration.

Chemokine receptors have been implicated as being important mediators of inflammatory, infectious, and immunoregulatory disorders and diseases, including cancer, asthma and allergic diseases, as well as autoimmune pathologies such as rheumatoid arthritis and atherosclerosis. For example, the chemokine receptor CCR3 plays a pivotal role in attracting eosinophils to sites of allergic inflammation and in subsequently activating these cells. The chemokine ligands for CCR3 induce a rapid increase in intracellular calcium concentration, increased expression of cellular adhesion molecules, cellular degranulation, and the promotion of eosinophil migration. Another chemokine receptor, CCR2, contributes to cancer progression and can induce tumor cell proliferation or chemotaxis. Accordingly, agents which modulate chemokine receptors would be useful in such disorders and diseases.

Chemokines have also been implicated in the pathogenesis of cell proliferative disorders, including for example induction of tumor angiogenesis and growth. Many tumor cells have also been shown to express chemokine receptors, such as CXCR1, CXCR2, CXCR3, CXCR4, CXCR5, CXCR6, CXCR7, CX3CL1, CCR2, CCR5, and CCR9, and thus tumor cells may also stimulate their own growth, migration, and/or invasion when responding to secreted chemokines.

Chemokines are critical for leukocyte recruitment to injured tissues and play an important role in the wound healing process. Impaired wound healing in diabetic patients is accompanied by decreased early inflammatory cell infiltration, but persistence of neutrophils and macrophages leading to chronic, nonhealing wounds. Chemokines may have both direct and inflammatory-mediated effects on many different aspects of diabetic wound healing, including: impairments in growth factor expression, angiogenesis, extracellular matrix formation, and reepithelialization. Certain chemokine receptor expression in wounds may accelerate healing, and be beneficial in the context of surgery, chronic ulcers, and other conditions.

Chemokine receptors therefore represent promising targets for the development of novel anti-inflammatory and anti-tumor as well as angiostatic, angiogenic, and wound healing agents. Thus, there remains a need for compositions that are capable of modulating activity of chemokine receptors.

SUMMARY

One aspect of the present application relates to an isolated chemokine-immunoglobulin fusion polypeptide having a chemokine moiety and an immunoglobulin moiety. In some embodiments, the chemokine moiety comprises a chemokine selected from the group consisting of human CCL1, CCL2, CCL3, CCL4, CCL4L1, CCL5, CCL7, CCL8, CCL11, CCL13, CCL14-1, CCL14-2, CCL15, CCL16, CCL17, CCL 18, CCL19, CCL20-1, CCL20-2, CCL21, CCL22, CCL23-1, CCL23-1, CCL24, CCL25-1, CCL25-2, CCL25-3, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof, and the immunoglobulin moiety comprises a peptide selected from the group consisting of the constant region of human Ig G1, the constant region of human Ig G2, the constant region of human Ig G3, the constant region of human Ig G4, and functional variants thereof. In one embodiment, the isolated chemokine-immunoglobulin fusion polypeptide is a pegylated chemokine-immunoglobulin fusion polypeptide.

In one particular embodiment, the chemokine-immunoglobulin fusion polypeptide is selected from the group consisting of CCL2-IgG1Fc, CCL2(5-76)-IgG1Fc, CCL2(5-76K/H→A)-IgG1Fc, CCL2-IgG4Fc, CCL2(5-76)-IgG4Fc, CCL2 (5-76K/H→A)-IgG4Fc, CCL7-IgG1Fc, CCL7(5-76)-IgG1Fc, CCL7(5-76K/H→A)-IgG1Fc, CCL7-IgG4Fc, CCL7(5-76)-IgG4Fc, CCL7(5-76K/H→A)-IgG4Fc, CCL8-IgG1Fc, CCL8(5-76)-IgG1Fc, CCL8(5-76K/H/R→A)-IgG1Fc, CCL8-IgG4Fc, CCL8(5-76)-IgG4Fc, CCL8(5-76K/H/R→A)-IgG4Fc, CCL13-IgG1Fc, CCL13(5-75)-IgG1Fc, CCL13(5-75K/H→A)-IgG1Fc, CCL13-IgG4Fc, CCL13(5-75)-IgG4Fc, CCL13(5-75K/H→A)-IgG4Fc, CCL25-IgG1Fc, CCL25(4-127)-IgG1Fc, CCL25(4-127K/

H/R→A)-IgG1Fc, CCL25-IgG4Fc, CCL25(4-127)-IgG4Fc, CCL25(4-127K/H/R→A)-IgG4Fc, CXCL11-IgG1Fc, CXCL11(4-73)-IgG1Fc, CXCL11(4-73K/R→A)-IgG1Fc, CXCL11-IgG4Fc, CXCL11(4-73)-IgG4Fc, CXCL11(4-73K/R→A)-IgG4Fc, CXCL12α-IgG1Fc, CXCL12α(3-67)-IgG1Fc, CXCL12α(3-67K/R→A)-IgG1Fc, CXCL12α-IgG4Fc, CXCL12α(3-67)-IgG4Fc, CXCL12α(3-67K/R→A)-IgG4Fc, CXCL13-IgG1Fc, CXCL13(3-87)-IgG1Fc, CXCL13(3-87K/R→A)-IgG1Fc, CXCL13-IgG4Fc, CXCL13(3-87)-IgG4Fc, and CXCL13(3-87K/R→A)-IgG4Fc.

Another aspect of the present application is directed to an isolated polynucleotide encoding a chemokine-immunoglobulin fusion polypeptide having a chemokine moiety and an immunoglobulin moiety, wherein the chemokine moiety comprises a chemokine selected from the group consisting of human CCL1, CCL2, CCL3, CCL4, CCL5, CCL7, CCL8, CCL11, CCL13, CCL14, CCL15, CCL16, CCL17, CCL19, CCL21, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, XCL1, XCL2, CX3CL1 and functional variants thereof and wherein the immunoglobulin moiety comprises a peptide selected from the group consisting of the constant regions of human IgG1 (hIgG1Fc), the constant regions of human IgG2 (hIgG2Fc), the constant regions of human IgG3 (hIgG3Fc), the constant regions of human IgG4 (hIgG4Fc), and functional variants thereof.

In a particular embodiment, the isolated polynucleotide encoding a chemokine-immunoglobulin fusion polypeptide is selected from the group consisting of CCL2-IgG1Fc, CCL2(5-76)-IgG1Fc, CCL2(5-76K/H→A)-IgG1Fc, CCL2-IgG2Fc, CCL2(5-76)-IgG2Fc, CCL2(5-76K/H→A)-IgG2Fc, CCL2-IgG3Fc, CCL2(5-76)-IgG3Fc, CCL2(5-76K/H→A)-IgG3Fc, CCL2-IgG4Fc, CCL2(5-76)-IgG4Fc, CCL2(5-76K/H→A)-IgG4Fc, CCL7-IgG1Fc, CCL7(5-76)-IgG1Fc, CCL7(5-76K/H→A)-IgG1Fc, CCL7-IgG2Fc, CCL7(5-76)-IgG2Fc, CCL7(5-76K/H→A)-IgG2Fc, CCL7-IgG3Fc, CCL7(5-76)-IgG3Fc, CCL7(5-76K/H→A)-IgG3Fc, CCL7-IgG4Fc, CCL7(5-76)-IgG4Fc, CCL7(5-76K/H→A)-IgG4Fc, CCL8-IgG1Fc, CCL8(5-76)-IgG1Fc, CCL8(5-76K/H/R→A)-IgG1Fc, CCL8-IgG1Fc, CCL8(5-76)-IgG1Fc, CCL8(5-76K/H/R→A)-IgG1Fc, CCL8-IgG2Fc, CCL8(5-76)-IgG2Fc, CCL8(5-76K/H/R→A)-IgG2Fc, CCL8-IgG3Fc, CCL8(5-76)-IgG3Fc, CCL8(5-76K/H/R→A)-IgG3Fc, CCL8-IgG4Fc, CCL8(5-76)-IgG4Fc, CCL8(5-76K/H/R→A)-IgG4Fc, CCL13-IgG1Fc, CCL13(5-75)-IgG1Fc, CCL13(5-75K/H→A)-IgG1Fc, CCL13-IgG2Fc, CCL13(5-75)-IgG2Fc, CCL13(5-75K/H→A)-IgG2Fc, CCL13-IgG3Fc, CCL13(5-75)-IgG3Fc, CCL13(5-75K/H→A)-IgG3Fc, CCL13-IgG4Fc, CCL13(5-75)-IgG4Fc, CCL13(5-75K/H→A)-IgG4Fc, CCL25-IgG1Fc, CCL25(4-127)-IgG1Fc, CCL25(4-127K/H/R→A)-IgG1Fc, CCL25-IgG2Fc, CCL25(4-127)-IgG2Fc, CCL25(4-127K/H/R→A)-IgG2Fc, CCL25-IgG3Fc, CCL25(4-127)-IgG3Fc, CCL25(4-127K/H/R→A)-IgG3Fc, CCL25-IgG4Fc, CCL25(4-127)-IgG4Fc, CCL25(4-127K/H/R→A)-IgG4Fc, CXCL11-IgG1Fc, CXCL11(4-73)-IgG1Fc, CXCL11(4-73K/R→A)-IgG1Fc, CXCL11-IgG2Fc, CXCL11(4-73)-IgG2Fc, CXCL11(4-73K/R→A)-IgG2Fc, CXCL11-IgG3Fc, CXCL11(4-73)-IgG3Fc, CXCL11(4-73K/R→A)-IgG3Fc, CXCL11-IgG4Fc, CXCL11(4-73)-IgG4Fc, CXCL11(4-73K/R→A)-IgG4Fc, CXCL12α-IgG1Fc, CXCL12α(3-67)-IgG1Fc, CXCL12α(3-67K/R→A)-IgG1Fc, CXCL12α-IgG2Fc, CXCL12α(3-67)-IgG2Fc, CXCL12α(3-67K/R→A)-IgG2Fc, CXCL12α-IgG3Fc, CXCL12α(3-67)-IgG3Fc, CXCL12α(3-67K/

R→A)-IgG3Fc, CXCL12α-IgG4Fc, CXCL12α(3-67)-IgG4Fc, CXCL12α(3-67K/R→A)-IgG4Fc, CXCL13-IgG1Fc, CXCL13(3-87)-IgG1Fc, CXCL13(3-87K/R→A)-IgG1Fc, CXCL13-IgG2Fc, CXCL13(3-87)-IgG2Fc, CXCL13(3-87K/R→A)-IgG2Fc, CXCL13-IgG3Fc, CXCL13(3-87)-IgG3Fc, CXCL13(3-87K/R→A)-IgG3Fc, CXCL13-IgG4Fc, CXCL13(3-87)-IgG4Fc, and CXCL13(3-87K/R→A)-IgG4Fc.

A further aspect of the present application is directed to a pharmaceutical composition comprising (1) a chemokine-immunoglobulin fusion polypeptide of the present application or an expression vector encoding a chemokine-immunoglobulin fusion polypeptide of the present application, and (2) a pharmaceutically acceptable carrier.

A further aspect of the present application is directed to a method for treating a chemokine receptor-mediated disorder in a subject, comprising administering to said subject an effective amount of the pharmaceutical composition of the present application.

Another aspect of the present application relates to a method for modulating inflammation in a subject, comprising administering to said subject an effective amount of the pharmaceutical composition of the present application.

Another aspect of the present application relates to a method for treating a chemokine receptor-mediated disorder in a subject, comprising administering to said subject an effective amount of a pegylated chemokine, wherein the chemokine is selected from the group consisting of human CCL1, CCL2, CCL3, CCL4, CCL5, CCL7, CCL8, CCL11, CCL13, CCL14, CCL15, CCL16, CCL17, CCL19, CCL21, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, XCL1, XCL2, CX3CL1 and functional variants thereof.

In a further embodiment, the pegylated chemokine is selected from the group consisting of CCL2-PEG, var-CCL2-PEG, CCL7-PEG, var-CCL7-PEG, CCL8-PEG, var-CCL8-PEG, CCL13-PEG, var-CCL13-PEG, CCL25-PEG, var-CCL25-PEG, CXCL11-PEG, var-CXCL11-PEG, CXCL13-PEG, var-CXCL13-PEG, CXCL16-PEG, and var-CXCL16-PEG.

BRIEF DESCRIPTION OF THE DRAWINGS

FIG. 1A depicts the expression vector pCCL2.hIgG1Fc. The Fc region comprises the CH2 and CH3 domains of the IgG heavy chain and the hinge region. The hinge serves as a flexible spacer between the two parts of the Fc-fusion protein, allowing each part of the molecule to function independently. hEF1-HTLV prom is a composite promoter comprising the Elongation Factor-1α (EF-1α) core promoter1 and the R segment and part of the U5 sequence (R-U5') of the Human T-Cell Leukemia Virus (HTLV) Type 1 Long Terminal Repeat2. The EF-1α promoter exhibits a strong activity and yields long lasting expression of a transgene in vivo. The R-U5' has been coupled to the EF-1α core promoter to enhance stability of RNA. MCS: The multiple cloning site. SV40 pAn: the Simian Virus 40 late polyadenylation signal. ori: a minimal *E. coli* origin of replication. CMV enh/hFerL prom: This composite promoter combines the human cytomegalovirus immediate-early gene 1 enhancer and the core promoter of the human ferritin light chain gene. This ubiquitous promoter drives the expression of the Zeocin™-resistance gene in mammalian cells. EM2KC is a bacterial promoter that enables the constitutive expression of the antibiotic resistance gene in *E. coli*. EM2KC is located within an intron and is spliced out in mammalian cells. Zeo: Resistance to Zeocin™ is conferred by the Sh ble gene from *Streptoalloteichus hindustanus* The same resistance gene confers selection in both mammalian cells and *E. coli*. βGlo pAn: The human beta-globin 3'UTR and polyadenylation sequence allows efficient arrest of the transgene transcription4

FIG. 1B depicts the expression vector pCCL2(5-76).hIgG1Fc.

FIG. 1C shows the nucleotide sequence of the expression vector pCCL2.hIgG1Fc.

FIG. 1D shows the nucleotide sequence of the expression vector pCCL2(5-76).hIgG1Fc.

FIG. 1E shows the nucleotide sequence of the expression vector pCCL2(5-76).hIgG1Fc with alanine substitutions for removal of GAG binding sites—lys and his.

FIG. 2A depicts the expression vector pCCL7.hIgG1Fc.

FIG. 2B depicts the expression vector pCCL7(5-76).hIgG1Fc.

FIG. 2C shows the nucleotide sequence of the expression vector pCCL7.hIgG1Fc.

FIG. 2D shows the nucleotide sequence of the expression vector pCCL7(5-76).hIgG1Fc.

FIG. 2E shows the nucleotide sequence of the expression vector pCCL7(5-76).hIgG1Fc with alanine substitutions for removal of GAG binding sites—lys and his.

FIG. 3A depicts the expression vector pCCL8.hIgG1Fc.

FIG. 3B depicts the expression vector pCCL8(5-76).hIgG1Fc.

FIG. 3C shows the nucleotide sequence of the expression vector pCCL8.hIgG1Fc.

FIG. 3D shows the nucleotide sequence of the expression vector pCCL8(5-76).hIgG1Fc.

FIG. 3E shows the nucleotide sequence of the expression vector pCCL8(5-76).hIgG1Fc with alanine substitution FIG. 4A depicts the expression vector pCCL13.hIgG1Fc.

FIG. 4B depicts the expression vector pCCL13(5-75).hIgG1Fc.

FIG. 4C shows the nucleotide sequence of the expression vector pCCL13.hIgG1Fc.

FIG. 4D shows the nucleotide sequence of the expression vector pCCL13(5-75).hIgG1Fc.

FIG. 4E shows the nucleotide sequence of the expression vector pCCL13(5-76).hIgG1Fc with alanine substitutions for removal of GAG binding sites—lys and his.

FIG. 5A depicts the expression vector pCCL25.hIgG1Fc.

FIG. 5B depicts the expression vector pCCL25(4-127).hIgG1Fc.

FIG. 5C shows the nucleotide sequence of the expression vector pCCL25.hIgG1Fc.

FIG. 5D shows the nucleotide sequence of the expression vector pCCL25(4-127).hIgG1Fc.

FIG. 5E shows the nucleotide sequence of the expression vector pCCL25(4-127).hIgG1Fc with alanine substitutions for removal of GAG binding sites—lys and his.

FIG. 6A depicts the expression vector pCXCL11.hIgG1Fc.

FIG. 6B depicts the expression vector pCXCL11(4-73).hIgG1Fc.

FIG. 6C shows the nucleotide sequence of the expression vector pCXCL11.hIgG1Fc.

FIG. 6D shows the nucleotide sequence of the expression vector pCXCL11(4-73).hIgG1Fc.

FIG. 6E shows the nucleotide sequence of the expression vector pCXCL11(4-127).hIgG1Fc with alanine substitutions for removal of GAG binding sites—lys and his.

FIG. 7A depicts the expression vector pCXCL11.hIgG4Fc.

FIG. 7B depicts the expression vector pCXCL11(4-73).hIgG4Fc.

FIG. 7C shows the nucleotide sequence of the expression vector pCXCL11.hIgG4Fc.

FIG. 7D shows the nucleotide sequence of the expression vector pCXCL11(4-73).hIgG4Fc.

FIG. 7E shows the nucleotide sequence of the expression vector pCXCL11(4-127).hIgG4Fc with alanine substitutions for removal of GAG binding sites—lys and his.

FIG. 8A depicts the expression vector pCXCL13.hIgG1Fc.

FIG. 8B depicts the expression vector pCXCL13(3-87).hIgG1Fc.

FIG. 8C shows the nucleotide sequence of the expression vector pCXCL13.hIgG1Fc.

FIG. 8D shows the nucleotide sequence of the expression vector pCXCL13(4-73).hIgG1Fc.

FIG. 8E shows the nucleotide sequence of the expression vector pCXCL13(4-127).hIgG1Fc with alanine substitutions for removal of GAG binding sites—lys and his.

FIG. 9A depicts the expression vector pCXCL13.hIgG4Fc.

FIG. 9B depicts the expression vector pCXCL13(3-87).hIgG4Fc.

FIG. 9C shows the nucleotide sequence of the expression vector pCXCL13.hIgG4Fc.

FIG. 9D shows the nucleotide sequence of the expression vector pCXCL13(3-87).hIgG4Fc.

FIG. 9E shows the nucleotide sequence of the expression vector pCXCL11(4-127).hIgG4Fc with alanine substitutions for removal of GAG binding sites—lys and his.

FIG. 12 shows the amino acid sequences of the chemokines and human IgG Fc fragments listed in Table 1.

DETAILED DESCRIPTION

Figure 10A:
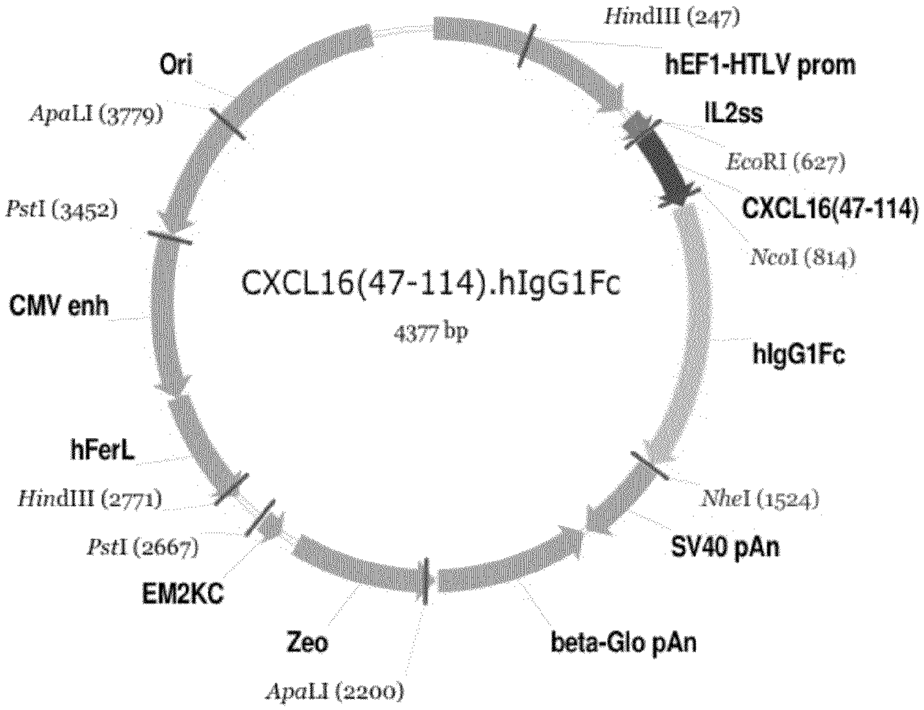
FIG. 10A depicts the expression vector pCXCL16(47-114).hIgG1Fc.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

Unless otherwise defined, scientific and technical terms used in connection with the present invention shall have the meanings that are commonly understood by those of ordinary skill in the art. Although any methods, devices, and materials similar or equivalent to those described herein can be used in the practice or testing of the presently disclosed subject matter, representative methods, devices, and materials are now described. Further, unless otherwise required by context, singular terms shall include pluralities and plural terms shall include the singular.

Unless otherwise indicated, all numbers expressing quantities of ingredients, reaction conditions, and so forth used in the specification and claims are to be understood as being modified in all instances by the term “about”. Accordingly, unless indicated to the contrary, the numerical parameters set forth in this specification and attached claims are approximations that can vary depending upon the desired properties sought to be obtained by the presently disclosed subject matter.

The present application generally relates to compositions and methods for treating chemokine receptor-mediated disorders and modulating inflammation. Particularly, the present application relates to chemokine-immunoglobulin fusion polypeptides, chemokine-polymer conjugates, and uses thereof to modulate immunity, cancer progression, and inflammation as well as treat chemokine receptor-mediated disorders, including tissue regeneration, wound repair, stem cell homeostasis, cell proliferative disorders, and inflammatory.

As used herein, the term “about,” when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The terms “treat,” “treating” or “treatment” as used herein, refers to a method of alleviating or abrogating a disorder and/or its attendant symptoms. The terms “prevent”, “preventing” or “prevention,” as used herein, refer to a method of barring a subject from acquiring a disorder and/or its attendant symptoms. In certain embodiments, the terms “prevent,” “preventing” or “prevention” refer to a method of reducing the risk of acquiring a disorder and/or its attendant symptoms.

In a pharmacological sense, in the context of the present invention, an “effective amount” of a composition refers to an amount effective in the prevention or treatment of a disorder for the treatment of which the composition is effective. A “disorder” is any condition that would benefit from treatment with the composition.

“Mammal” for purposes of treatment refers to any animal classified as a mammal, including humans, non-human primates, domestic and farm animals, and zoo, sports, or pet animals, such as dogs, horses, cats, cows, etc. Preferably, the mammal is human.

The term “inhibits” is a relative term, an agent inhibits a response or condition if the response or condition is quantitatively diminished following administration of the agent, or if it is diminished following administration of the agent, as compared to a reference agent. Similarly, the term “prevents” does not necessarily mean that an agent completely eliminates the response or condition, so long as at least one characteristic of the response or condition is eliminated. Thus, a composition that reduces or prevents an infection or a response, such as a pathological response, can, but does not necessarily completely eliminate such an infection or response, so long as the infection or response is measurably diminished, for example, by at least about 50%, such as by at least about 70%, or about 80%, or even by about 90% of (that is to 10% or less than) the infection or response in the absence of the agent, or in comparison to a reference agent.

Chemokine-Immunoglobulin Fusion Polypeptides

Chemokines have been demonstrated to mediate a number of cellular functions involving motility, invasion, adherence, proliferation, and survival. At the appropriate levels and expression, these chemotactic cytokines promote proper wound healing, neovascularization or immunity. If inappropriately expressed, these factors can dictate chronic diseases like keloid formation, angiogenesis, metastasis/drug resistance of cancer cells, autoimmunity, graft rejection, inflammation (e.g., arthritis, ulcerative colitis, Crohn’s disease, multiple sclerosis, COPD, etc.), diabetes. Both beneficial and deleterious functions are mediated by binding and activation of chemokine receptors, which are class A, G protein coupled receptors.

A number of small molecule antagonists have been constructed to block the action of these receptors. Remarkably, many of these compounds have high affinities (5-50 nM) and specificities for their target. However, these inhibitors have two major limitations: (i) hydrophobicity and possible liver retention/toxicity and (ii) relative short serum-half life or bioavailability (<6 hours).

The present application provides isolated chemokine-immunoglobulin fusion polypeptides for clinical use. The fusion polypeptides comprise a wild-type human chemokine or a variant thereof fused to the constant region (i.e., CH2 and CH3) of a human immunoglobulin (Ig) G or a variant thereof. The chemokine-immunoglobulin fusion polypeptide can bind with specificity to one or more particular chemokine receptors and thereby modulate one or more biological activities (e.g., receptor activation) of the receptor(s).

One aspect of the present invention relates to an isolated chemokine-immunoglobulin fusion polypeptide having a chemokine moiety and an immunoglobulin moiety. In some embodiments, the chemokine moiety comprises a chemokine selected from the group consisting of human CCL1, CCL2, CCL3, CCL4, CCL4L1, CCL5, CCL7, CCL8, CCL11, CCL13, CCL14, CCL15, CCL16, CCL17, CCL 18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof. In some embodiments, the chemokine moiety comprises CCL2 and functional variants thereof. In other embodiments, the chemokine moiety comprises CCL25 and functional variants thereof. In other embodiments, the chemokine moiety comprises CXCL12 and functional variants thereof. In other embodiments, the chemokine moiety comprises CXCL13 and functional variants thereof. In other embodiments, the chemokine moiety comprises CXCL16 and functional variants thereof. As used herein, each chemokine noted above refers to all isoforms of the chemokine. The immunoglobulin moiety comprises a human immunoglobulin fragment, such as a constant region of a human immunoglobulin, a Fc fragment of a human immunoglobulin, or a functional variant thereof. In certain embodiments, human immunoglobulin fragment is selected from the group consisting of the constant region (Fc) of human IgG1 (IgG1Fc), the constant region of human IgG2 (IgG2Fc), the constant region of human IgG3 (IgG3Fc), the constant region of human IgG4 (IgG4Fc), and functional variants thereof. The complete amino acid sequences of the above-described chemokines and the Fc regions of human IgG1, IgG2, IgG3 and IgG4 are listed in Table 1 below and shown in FIG. 12.

TABLE 1

| Chemokine/ Receptor | Protein Accession No. | SEQ ID NO: |
|---|---|---|
| CCL1 | NP_002972 | 1 |
| CCL2 | NP_002973 | 2 |
| CCL3 | NP_002974 | 3 |
| CCL4 | NP_002975 | 4 |
| CCL4L1 | NP_001001435 | 5 |
| CCL5 | NP_002976 | 6 |
| CCL7 | NP_006264 | 7 |
| CCL8 | NP_005614 | 8 |
| CCL11 | CAG33702 | 9 |

TABLE 1-continued

| Chemokine/ Receptor | Protein Accession No. | SEQ ID NO: |
|---|---|---|
| CCL13 | NP_005399 | 10 |
| CCL14-1 | NP_116739 | 11 |
| CCL14-2 | NP_116738 | 12 |
| CCL15 | NP_116741 | 13 |
| CCL16 | NP_004581 | 14 |
| CCL17 | NP_002978 | 15 |
| CCL18 | NP_002979 | 16 |
| CCL19 | NP_006265 | 17 |
| CCL20-1 | NP_004582 | 18 |
| CCL20-2 | NP_001123518 | 19 |
| CCL21 | NP_002980 | 20 |
| CCL22 | NP_002981 | 21 |
| CCL23-1 | NP_665905 | 22 |
| CCL23-2 | NP_005055 | 23 |
| CCL24 | NP_002982 | 24 |
| CCL25-1 | NP_005615 | 25 |
| CCL25-2 | NP_683686 | 26 |
| CCL25-3 | EAW68951 | 27 |
| CCL26 | NP_006063 | 28 |
| CCL27 | NP_006655 | 29 |
| CCL28 | NP_683513 | 30 |
| CXCL1 | NP_001502 | 31 |
| CXCL2 | NP_002080 | 32 |
| CXCL3 | NP_002081 | 33 |
| CXCL4 | NP_002610 | 34 |
| CXCL5 | NP_002985 | 35 |
| CXCL6 | NP_002984 | 36 |
| CXCL7 | NP_002695 | 37 |
| CXCL8 | NP_000575 | 38 |
| CXCL9 | NP_002407 | 39 |
| CXCL10 | NP_001556 | 40 |
| CXCL11 | NP_005400 | 41 |
| CXCL12 | NP_000600 | 42 |
| CXCL13 | NP_006410 | 43 |
| CXCL16 | NP_071342 | 44 |
| XCL1 | AAH69817 | 45 |
| XCL2 | NP_003166 | 46 |
| CX3CL1 | NP_002987 | 47 |
| IgG1Fc | CBX54381.1 | 48 |
| IgG2Fc | CBX54382.1 | 49 |
| IgG3Fc | CBX54383.1 | 50 |
| IgG4Fc | CBX54384.1 | 51 |

Without wishing to be bound by any particular theory of operation, the immunoglobulin region can increase serum-half life or bioavailability of the fusion polypeptide and the precise polypeptide sequences of the Fc portion can be selected to maximize serum-half life and/or bioavailability. In addition, Fc regions from different IgG subclasses (e.g., IgG1, IgG2, IgG3, and IgG4) exhibit different immunological activities, and therefore the IgG Fc region can be selected based on a desired immunological activity. For example, the Fc region of IgG1 can activate complement, while the Fc region of IgG4 has reduced complement activity.

Thus, a particular Fc region can be selected for a particular application based on the desired immunological activities manifested by each region. In some particular embodiments, the Fc region can be the Fc region of human IgG1, IgG2, IgG3 or IgG4. As such, the chemokine-immunoglobulin fusion polypeptide find utility in enhancing immunity, suppressing autoimmunity, suppressing inflammation, and/or inhibiting growth/metastasis of proliferative disorder cells. The present application further provides isolated polynucleotide which encode the chemokine-immunoglobulin fusion polypeptide disclosed herein and expression vectors capable of expressing the chemokine-immunoglobulin fusion polypeptide in vivo.

The term "isolated", when applied to a protein or polynucleotide, denotes that the protein or polynucleotide is essentially free of other cellular components with which it is associated in the natural state. It can be in a homogeneous state although it can be in either a dry or aqueous solution. Homogeneity and whether a molecule is isolated can be determined using analytical chemistry techniques such as polyacrylamide gel electrophoresis or high performance liquid chromatography. A protein that is the predominant species present in a preparation is substantially isolated. The term "isolated" denotes that a protein or polynucleotide gives rise to essentially one band in an electrophoretic gel. Particularly, it means that the protein or polynucleotide is in some embodiments at least about 50% pure, in some embodiments at least about 85% pure, and in some embodiments at least about 99% pure.

The term "polynucleotide" refers to deoxyribonucleotides or ribonucleotides and polymers thereof in either single- or double-stranded form. Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues. The term "polynucleotide" or "polynucleotide sequence" can also be used interchangeably with gene, open reading frame (ORF), cDNA, and mRNA encoded by a gene.

The terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The chemokine portion of the chemokine-immunoglobulin fusion polypeptide can be selected based on the chemokine receptor or receptors to which it exhibits binding specificity. This provides for the selective targeting of the chemokine-immunoglobulin fusion polypeptide to one or more specific chemokine receptors to thereby modulate activation and subsequent biological activities of the receptor(s). Table 1 (adapted from Allen et al. (2007) Annu Rev. Immunol. 25:787-820) provides an exemplary list of receptors that can be targeted by one or more chemokines, which can be incorporated into the chemokine-immunoglobulin fusion polypeptide of the presently-disclosed subject matter.

As disclosed in Table 2, certain chemokines can specifically bind more than one chemokine receptor. For example, CXCL11 can bind with specificity to chemokine receptors CXCR3-A, CXCR3-B, CXCR7, and DARC/Duffy. As such, if it is desirable to target more than one chemokine receptor, a particular chemokine, such as CXC11, can be selected for incorporation into the chemokine-immunoglobulin fusion polypeptide of the presently-disclosed subject matter. In some embodiments of the presently disclosed subject matter, the chemokine-immunoglobulin fusion polypeptide can comprise of a chemokine portion selected from the group consisting of CCL2, CCL7, CCL8, CCL13, CCL25, CXCL11, CXCL13, and mutations thereof. "Mutations" of the polypeptides include variants and fragments of the reference polypeptides.

TABLE 2

| Chemokine receptors and their ligands | |
|---|---|
| Receptor | Ligands |
| CCR1 | CCL3, CCL5, CCL7, CCL13, CCL14, CCL15, CCL16, CCL23 |
| CCR2 | CCL2, CCL7, CCL8, CCL13, CCL16 |
| CCR3 | CCL5, CCL7, CCL8, CCL11, CCL13, CCL15, CCL16, CCL24, CCL26, CCL28 |
| CCR4 | CCL17, CCL22 |
| CCR5 | CCL3, CCL4, CCL5, CCL8, CCL11, CCL14, CCL16 |
| CCR6 | CCL20 |
| CCR7 | CCL19, CCL21 |
| CCR8 | CCL1 |
| CCR9 | CCL25 |
| CCR10 | CCL27, CCL28 |
| CXCR1 | CXCL6, CXCL7, CXCL8 |
| CXCR2 | CXCL1, CXCL2, CXCL3, CXCL5, CXCL6, CXCL7, CXCL8 |
| CXCR3-A | CXCL9, CXCL10, CXCL11, CCL11 |
| CXCR3-B | CXCL4, CXCL9, CXCL10, CXCL11, CCL11 |
| CXCR4 | CXCL12 |
| CXCR5 | CXCL13 |
| CXCR6 | CXCL16 |
| CXCR7 | CXCL12, CXCL11 |
| XCR1 | XCL1, XCL2 |
| $CX_3CR1$ | $CX_3CL1$ |
| CCX-CKR | CCL19, CCL21, CCL25 |
| D6 | CCL2, CCL3L1, CCL4, CCL5, CCL7, CCL8, CCL11, CCL13, CCL14, CCL17, CCL22 |
| DARC/Duffy | CCL2, CCL7, CCL8, CCL11, CCL13, CCL14, CCL16, CCL17, CXCL1, CXCL5, CXCL6, CXCL7, CXCL8, CXCL9, CXCL11, CXCL13 |

The term "functional variant" refers to protein or polypeptide that is different from the reference protein or polypeptide by one or more amino acids, e.g., one or more amino acid substitutions, but substantially maintains the biological function of the reference protein or polypeptide. As used herein, a functional variant of a chemokine is a variant that maintains the receptor binding function of the original chemokine and a functional variant of the Fc region of IgG is a variant that maintains the immunologivla activities of the original Fc region.

A functional variant of a polypeptide may be a fragment of the original polypeptide. The term "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 3, 5, 6, 8 or 10 amino acids long, at least 14 amino acids long, at least 20, 30, 40 or 50 amino acids long, at least 75 amino acids long, or at least 100, 150, 200, or more amino acids long.

The term "functional variant" further includes conservatively substituted variants. The term "conservatively substituted variant" refers to a peptide comprising an amino acid residue sequence that differs from a reference peptide by one or more conservative amino acid substitution, and maintains some or all of the activity of the reference peptide as described herein. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another, such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. The phrase "conservatively substituted variant" also includes peptides wherein a residue is replaced with a chemically derivatized residue, provided that the resulting peptide maintains some or all of the activity of the reference peptide as described herein. In some embodiments, the functional variant of a peptide shares a sequence identity of 70%, 75%, 80%, 85%, 90%, 91%, 92%, 93%, 94%, 95%, 96%, 97%, 98% or 99% with the reference peptide. For example, a functional variant of a chemokine may shares a sequence identity of 70%, 75%, 80%, 85%, 90%, 91%, 92%, 93%, 94%, 95%, 96%, 97%, 98% and 99% with the reference chemokine; a functional variant of an immunoglobin Fc fragment may shares a sequence identity of 70%, 75%, 80%, 85%, 90%, 91%, 92%, 93%, 94%, 95%, 96%, 97%, 98% and 99% with the reference immunoglobin Fc fragment; and a functional variant of a chemokine-immunoglobin fusion protein may shares a sequence identity of 70%, 75%, 80%, 85%, 90%, 91%, 92%, 93%, 94%, 95%, 96%, 97%, 98% and 99% with the reference chemokine-immunoglobin fusion protein.

The term "sequence identity," as used herein, means that two peptide sequences are identical (i.e., on an amino acid-by-amino acid basis) over the window of comparison. The term "percentage of sequence identity" is calculated by comparing two optimally aligned sequences over the window of comparison, determining the number of positions at which the identical amino acid residue occurs in both sequences to yield the number of matched positions, dividing the number of matched positions by the total number of positions in the window of comparison (i.e., the window size), and multiplying the result by 100 to yield the percentage of sequence identity. The reference sequence may be a subset of a larger sequence, for example, as a segment of the full-length sequences of the compositions claimed in the present invention.

In some particular embodiments, the chemokine-immunoglobulin fusion polypeptides disclosed herein include functional variants to the chemokine portion that introduce amino acid substitutions to eliminate glycosaminoglycan (e.g., heparin, laminin, GAG)-binding, which can thereby increase the serum half-life of the polypeptide. For example, in some embodiments one or more alanines can be substituted for lysines, arginines and/or histidines within GAG binding sites of the chemokine portions.

Specific chemokine-immunoglobulin fusion polypeptides disclosed herein that include a chemokine variant having one or more mutations in the chemokine sequence are named accordingly to indicate the particular mutation. For example "var-" before the chemokine name (e.g., var-CCL2) is indicative of a functional variant having an engineered mutation to the chemokine portion that results in a polypeptide sequence that differs from the reference chemokine sequence (e.g., CCL2). A fragment mutation resulting from a truncation is notated be the sequence remaining after truncation. For example, a truncation of the N-terminal 4 amino acids of the 76 amino acid CCL2 chemokine would be notated as "var-CCL2" or "CCL2(5-76)". A variant mutation resulting from one or more amino acid substitutions would be notated as a parenthetical after the chemokine name in the form "X#Y" or "X→Y", wherein the amino acid X (in standard one letter amino acid code, as is known in the art) in the reference polypeptide is substituted with the amino acid Y either at a particular residue (#) or throughout the polypeptide, or a particular region of the polypeptide (X→Y), such as for example a GAG-binding region of the chemokine polypeptide. In some embodiments, a mutation can include both a variant and a fragment of the reference chemokine polypeptide. These mutants are indicated in the named polypeptide in succession in a parenthetical following the chemokine name. For example, "CCL2(5-76K/H→A)" indicates a chemokine-immunoglobulin fusion polypeptide including in the chemokine portion a mutant CCL2 polypeptide that has been truncated at the N-terminus to remove residues 1-4 and also mutated to substitute alanines (A) for lysines (K) and histidines (H) within the sequence. In some embodiments, a chemokine variant (e.g., var-CXCL13) shares a sequence identity of 70%, 75%, 80%, 85%, 90%, 91%, 92%, 93%, 94%, 95%, 96%, 97%, 98% and 99% with the reference chemokine (i.e., CXCL13). Finally, in reference to nomenclature, the chemokine-immunoglobulin fusion polypeptides disclosed herein are named according to the chemokine portion (A) and the immunoglobulin portion (B) fused together (i.e. A-B). Thus, for example, CCL2-IgG1Fc refers to a chemokine-immunoglobulin fusion polypeptide comprising a wild-type CCL2 chemokine portion fused with an Fc constant region of an IgG class 1 immunoglobulin.

In some embodiments, the present application provides a human chemokine polypeptide fused to a human immunoglobulin polypeptide. In some embodiments, the present application provides the following novel isolated chemokine-immunoglobulin fusion polypeptides: CCL2-IgG1Fc, var-CCL2-IgG1Fc, CCL2-IgG2Fc, var-CCL2-IgG2Fc, CCL2-IgG3Fc, var-CCL2-IgG3Fc, CCL2-IgG4Fc, var-CCL2-IgG4Fc, CCL7-IgG1Fc, var-CCL7-IgG1Fc, CCL7-IgG2Fc, var-CCL7-IgG2Fc, CCL7-IgG3Fc, var-CCL7-IgG3Fc, CCL7-IgG4Fc, var-CCL7-IgG4Fc, CCL8-IgG1Fc, var-CCL8-IgG1Fc, CCL8-IgG2Fc, var-CCL8-IgG2Fc, CCL8-IgG3Fc, var-CCL8-IgG3Fc, CCL8-IgG4Fc, var-CCL8-IgG4Fc, CCL13-IgG1Fc, var-CCL13-IgG1Fc, CCL13-IgG2Fc, var-CCL13-IgG2Fc, CCL13-IgG3Fc, var-CCL13-IgG3Fc, CCL13-IgG4Fc, var-CCL13-IgG4Fc, CCL25-IgG1Fc, var-CCL25-IgG1Fc, CCL25-IgG2Fc, var-CCL25-IgG2Fc, CCL25-IgG3Fc, var-CCL25-IgG3Fc, CCL25-IgG4Fc, var-CCL25-IgG4Fc, CXCL11-IgG1Fc, var-CXCL11-IgG1Fc, CXCL11-IgG2Fc, var-CXCL11-IgG2Fc, CXCL11-IgG3Fc, var-CXCL11-IgG3Fc, CXCL11-IgG4Fc, var-CXCL11-IgG4Fc, CXCL13-IgG1Fc, var-CXCL13-IgG1Fc, CXCL13-IgG2Fc, var-CXCL13-IgG2Fc, CXCL13-IgG3Fc, var-CXCL13-IgG3Fc, CXCL13-IgG4Fc, and var-CXCL13-IgG4Fc.

In particular embodiments, the present application provides the following novel isolated chemokine-immunoglobulin fusion polypeptides: CCL2-IgG1Fc (SEQ ID NO:52), CCL2(5-76)-IgG1Fc (SEQ ID NO:53), CCL2(5-76K/H→A)-IgG1Fc (SEQ ID NO:54), CCL7-IgG1Fc (SEQ ID NO:55), CCL7(5-76)-IgG1Fc (SEQ ID NO:56), CCL7(5-76K/H→A)-IgG1Fc (SEQ ID NO:57), CCL8-IgG1Fc (SEQ ID NO:58), CCL8(5-76)-IgG1Fc (SEQ ID NO:59), CCL8(5-76K/H→A)-IgG1Fc (SEQ ID NO:60), CCL13-IgG1Fc (SEQ ID NO:61), CCL13(5-75)-IgG1Fc (SEQ ID NO:62), CCL13(5-75K/H→A)-IgG1Fc (SEQ ID NO:63), CCL25-IgG1Fc (SEQ ID NO:64), CCL25(4-127)-IgG1Fc (SEQ ID NO:65), CCL25(4-127K/H→A)-IgG1Fc (SEQ ID NO:66), CXCL11-IgG1Fc (SEQ ID NO:67), CXCL11(4-73)-IgG1Fc (SEQ ID NO:68), CXCL11(4-73K/H→A)-IgG1Fc (SEQ ID NO:69), CXCL11-IgG4Fc (SEQ ID NO:70), CXCL11(4-73)-IgG4Fc (SEQ ID NO:71), CXCL11(4-73K/H→A)-IgG4Fc (SEQ ID NO:72), CXCL13-IgG1Fc (SEQ ID NO:73), CXCL13(3-87)-IgG1Fc (SEQ ID NO:74), CXCL13(3-87K/H→A)-IgG1Fc (SEQ ID NO:75), CXCL13-IgG4Fc (SEQ ID NO:76), CXCL13(3-87)-IgG4Fc (SEQ ID NO:77), and CXCL13(3-87K/H→A)-IgG4Fc (SEQ ID NO:78).

The novel chemokine-immunoglobulin fusion polypeptides disclosed herein can be produced using any of a variety of peptide production techniques generally known in the art. For example, recombinant genetic techniques can be utilized to produce the fusion polypeptides disclosed herein. As such, in some embodiments, an isolated nucleic acid molecule which encodes a chemokine-immunoglobulin fusion polypeptide selected from the group consisting of CCL2-IgG1Fc, var-CCL2-IgG1Fc, CCL2-IgG2Fc, var-CCL2-IgG2Fc, CCL2-IgG3Fc, var-CCL2-IgG3Fc, CCL2-IgG4Fc, var-CCL2-IgG4Fc, CCL7-IgG1Fc, var-CCL7-IgG1Fc, CCL7-IgG2Fc, var-CCL7-IgG2Fc, CCL7-IgG3Fc, var-CCL7-IgG3Fc, CCL7-IgG4Fc, var-CCL7-IgG4Fc, CCL8-IgG1Fc, var-CCL8-IgG1Fc, CCL8-IgG2Fc, var-CCL8-IgG2Fc, CCL8-IgG3Fc, var-CCL8-IgG3Fc, CCL8-IgG4Fc, var-CCL8-IgG4Fc, CCL13-IgG1Fc, var-CCL13-IgG1Fc, CCL13-IgG2Fc, var-CCL13-IgG2Fc, CCL13-IgG3Fc, var-CCL13-IgG3Fc, CCL13-IgG4Fc, var-CCL13-IgG4Fc, CCL25-IgG1Fc, var-CCL25-IgG1Fc, CCL25-IgG2Fc, var-CCL25-IgG2Fc, CCL25-IgG3Fc, var-CCL25-IgG3Fc, CCL25-IgG4Fc, var-CCL25-IgG4Fc, CXCL11-IgG1Fc, var-CXCL11-IgG1Fc, CXCL11-IgG2Fc, var-CXCL11-IgG2Fc, CXCL11-IgG3Fc, var-CXCL11-IgG3Fc, CXCL11-IgG4Fc, var-CXCL11-IgG4Fc, CXCL13-IgG1Fc, var-CXCL13-IgG1Fc, CXCL13-IgG2Fc, var-CXCL13-IgG2Fc, CXCL13-IgG3Fc, var-CXCL13-IgG3Fc, CXCL13-IgG4Fc, and var-CXCL13-IgG4Fc is provided.

In particular embodiments, the isolated nucleic acid molecule encodes a chemokine-immunoglobulin fusion polypeptide selected from the group consisting of CCL2-IgG1Fc, CCL2(5-76)-IgG1Fc, CCL2(5-76K/H→A)-IgG1Fc, CCL2-IgG2Fc, CCL2(5-76)-IgG2Fc, CCL2(5-76K/H→A)-IgG2Fc, CCL2-IgG3Fc, CCL2(5-76)-IgG3Fc, CCL2(5-76K/H→A)-IgG3Fc, CCL2-IgG4Fc, CCL2(5-76)-IgG4Fc, CCL2(5-76K/H→A)-IgG4Fc, CCL7-IgG1Fc, CCL7(5-76)-IgG1Fc, CCL7(5-76K/H→A)-IgG1Fc, CCL7-IgG2Fc, CCL7(5-76)-IgG2Fc, CCL7(5-76K/H→A)-IgG2Fc, CCL7-IgG3Fc, CCL7(5-76)-IgG3Fc, CCL7(5-76K/H→A)-IgG3Fc, CCL7-IgG4Fc, CCL7(5-76)-IgG4Fc, CCL7(5-76K/H→A)-IgG4Fc, CCL8-IgG1Fc, CCL8(5-76)-IgG1Fc, CCL8(5-76K/H→A)-IgG1Fc, CCL8-IgG2Fc, CCL8(5-76)-IgG2Fc, CCL8(5-76K/H→A)-IgG2Fc, CCL8-IgG3Fc, CCL8(5-76)-IgG3Fc, CCL8(5-76K/H→A)-IgG3Fc, CCL8-IgG4Fc, CCL8(5-76)-IgG4Fc, CCL8(5-76K/H→A)-IgG4Fc, CCL13-IgG1Fc, CCL13(5-75)-IgG1Fc, CCL13(5-75K/H→A)-IgG1Fc, CCL13-IgG2Fc, CCL13(5-75)-IgG2Fc, CCL13(5-75K/H→A)-IgG2Fc, CCL13-IgG3Fc, CCL13(5-75)-IgG3Fc, CCL13(5-75K/H→A)-IgG3Fc, CCL13-IgG4Fc, CCL13(5-75)-IgG4Fc, CCL13(5-75K/H→A)-IgG4Fc, CCL25-IgG1Fc, CCL25(4-127)-IgG1Fc, CCL25(4-127K/H→A)-IgG1Fc, CCL25-IgG2Fc, CCL25(4-127)-IgG2Fc, CCL25(4-127K/H→A)-IgG2Fc, CCL25-IgG3Fc, CCL25(4-127)-IgG3Fc, CCL25(4-127K/H→A)-IgG3Fc, CCL25-IgG4Fc, CCL25(4-127)-IgG4Fc, CCL25(4-127K/H→A)-IgG4Fc, CXCL11-IgG1Fc, CXCL11(4-73)-IgG1Fc, CXCL11(4-73K/H→A)-IgG1Fc, CXCL11-IgG2Fc, CXCL11(4-73)-IgG2Fc, CXCL11(4-73K/H→A)-IgG2Fc, CXCL11-IgG3Fc, CXCL11(4-73)-IgG3Fc, CXCL11(4-73K/H→A)-IgG3Fc, CXCL11-IgG4Fc, CXCL11(4-73)-IgG4Fc, CXCL11(4-73K/H→A)-IgG4Fc, CXCL13-IgG1Fc, CXCL13(3-87)-IgG1Fc, CXCL13(3-87K/H→A)-IgG1Fc, CXCL13-IgG2Fc, CXCL13(3-87)-IgG2Fc, CXCL13(3-87K/H→A)-IgG2Fc, CXCL13-IgG3Fc, CXCL13(3-87)-IgG3Fc, CXCL13(3-87K/H→A)-IgG3Fc, CXCL13-IgG4Fc, CXCL13(3-87)-IgG4Fc, and CXCL13(3-87K/H→A)-IgG4Fc. Recombinant cloning techniques may also be used to construct the heterologous gene sequences that encode for the fusion polypeptide gene product, as is known in the art.

Expression Vectors

Recombinant expression vectors comprising nucleic acid molecules which encode the polypeptides disclosed herein are also provided. Particularly useful vectors are contemplated to be those vectors in which the coding portion of the DNA segment is positioned under the control of a promoter. The promoter may be in the form of the promoter which is naturally associated with the chemokine or immunoglobulin gene, e.g., in mammalian tissues, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a chemokine or immunoglobulin gene in its natural environment. Such promoters may include promoters isolated from plant, insect, bacterial, viral, eukaryotic, fish, avian or mammalian cells. Naturally, it will be important to employ a promoter that effectively directs the expression of the DNA segment in the cell type chosen for expression. The use of promoter and cell type combinations for protein expression is generally known to those of skill in the art of molecular biology. The promoters employed may be constitutive, or inducible, and can be used under the appropriate conditions to direct high level expression of the introduced DNA segment, such as is advantageous in the large-scale production of recombinant proteins or peptides.

Expression vectors generally contain sequences for transcriptional termination, and may additionally contain one or more elements positively affecting mRNA stability. An expression vector may further include an internal ribosome entry site (IRES) between adjacent protein coding regions to facilitate expression two or more proteins from a common mRNA in an infected or transfected cell. Additionally, the expression vectors may further include nucleic acid sequence encoding a marker product. This marker product may be used to determine if the gene has been delivered to the cell and is being expressed. Preferred marker genes are the *E. coli* lacZ gene, which encodes β-galactosidase, and green fluorescent protein (GFP).

In some embodiments, the expression vectors of the present application are plasmid expression vectors that are capable of expressing the chemokine-immunoglobulin fusion polypeptides of the present application in an in vitro setting. The expressed fusion polypeptide is then isolated and purified using methods well known to a person skilled in the art.

In other embodiments, the expression vectors of the present application are plasmid expression vectors that are capable of expressing the chemokine-immunoglobulin fusion polypeptides of the present application in an in vivo setting. These expression vectors may be introduced into a subject using delivery systems such as liposomes, including cationic liposomes (e.g., DOTMA, DOPE, DC-cholesterol) and anionic liposomes, microcapsules, nanoparticles and electroporation. In some embodiments, the expression vectors are targeted to a particular cell type via antibodies, receptors, or receptor ligands. Vehicles such as "stealth" and other antibody conjugated liposomes (including lipid mediated drug targeting to cells of interest), receptor mediated targeting of DNA through cell specific ligands or viral vectors targeting e.g., lymphoid, epithelial or endothelial cells. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor level regulation. Many receptors follow more than one intracellular pathway, depending on the cell type, receptor concentration, type of ligand, ligand valency, and ligand concentration.

In yet other embodiments, the expression vectors of the present application are virus-based expression vectors that are capable of expressing the chemokine-immunoglobulin fusion polypeptides of the present application in an in vivo setting. Exemplary viral vectors may include or be derived from adenovirus, adeno-associated virus, herpesvirus, vaccinia virus, poliovirus, poxvirus, HIV virus, lentivirus, retrovirus, Sindbis and other RNA viruses, and the like. Also preferred are any viral families which share the properties of these viruses which make them suitable for use as vectors. Retroviruses include Murine Moloney Leukemia virus (MMLV), HIV and other lentivirus vectors. Adenovirus vectors are relatively stable and easy to work with, have high titers, and can be delivered in aerosol formulation, and can transfect non-dividing cells. Poxyiral vectors are large and have several sites for inserting genes, they are thermostable and can be stored at room temperature. Viral delivery systems typically utilize viral vectors having one or more genes removed and with and an exogenous gene and/or gene/promotor cassette being inserted into the viral genome in place of the removed viral DNA. The necessary functions of the removed gene(s) may be supplied by cell lines which have been engineered to express the gene products of the early genes in trans.

In other embodiments, the expression vectors are phage DNA, yeast plasmids or baculovirus.

Exemplary expression vector constructs comprising polynucleotides which encode chemokine-immunoglobulin fusion polypeptides disclosed herein are shown in FIGS. 1-10. These expression vectors include pCCL2-IgG1Fc (SEQ ID NO:79), pCCL2(5-76)-IgG1Fc (SEQ ID NO:80), pCCL2 (5-76K/H→A)-IgG1Fc (SEQ ID NO:81), pCCL7-IgG1Fc (SEQ ID NO:82), pCCL7(5-76)-IgG1Fc (SEQ ID NO:83), pCCL7(5-76K/H→A)-IgG1Fc (SEQ ID NO:84), pCCL8-IgG1Fc (SEQ ID NO:85), pCCL8(5-76)-IgG1Fc (SEQ ID NO:86), pCCL8(5-76K/H→A)-IgG1Fc (SEQ ID NO:87), pCCL13-IgG1Fc (SEQ ID NO:88), pCCL13(5-75)-IgG1Fc (SEQ ID NO:89), pCCL13(5-75K/H→A)-IgG1Fc (SEQ ID NO:90), pCCL25-IgG1Fc (SEQ ID NO:91), pCCL25(4-127)-IgG1Fc (SEQ ID NO:92), pCCL25(4-127K/H→A)-IgG1Fc (SEQ ID NO:93), pCXCL11-IgG1Fc (SEQ ID NO:94), pCXCL11(4-73)-IgG1Fc (SEQ ID NO:95), pCXCL11(4-73K/H→A)-IgG1Fc (SEQ ID NO:96), pCXCL11-IgG4Fc (SEQ ID NO:97), pCXCL11(4-73)-IgG4Fc (SEQ ID NO:98), pCXCL11(4-73K/H→A)-IgG4Fc (SEQ ID NO:99), pCXCL13-IgG1Fc (SEQ ID NO:100), pCXCL13(3-87)-IgG1Fc (SEQ ID NO:101), pCXCL13(3-87K/H→A)-IgG1Fc (SEQ ID NO:102), pCXCL13-IgG4Fc (SEQ ID NO:103), pCXCL13(3-87)-IgG4Fc (SEQ ID NO:104), and CXCL13(3-87K/H→A)-IgG4Fc (SEQ ID NO:105). It is understood that additional combinations of vectors and genes than those specifically disclosed above are contemplated by the presently-disclosed subject matter, as would be understood by one of ordinary skill in the art.

Protein Conjugates

In some embodiments, the chemokine-immunglobulin fusion polypeptides of the present application, as well as certain chemokines and variants thereof, are conjugated to a non-protein polymer to form protein-polymer conjugates. Unless specifically indicated to the contrary, the term "non-protein polymer" is defined as a molecule formed by covalent linkage of two or more monomers, wherein none of the monomers is contained in the group consisting of alanine (Ala), cysteine (Cys), aspartic acid (Asp), glutamic acid (Glu), phenylalanine (Phe), glycine (Gly), histidine (H is), isoleucine (Ile), lysine (Lys), leucine (Leu), methionine (Met), asparagine (Asn), proline (Pro), glutamine (Gln), arginine (Arg), serine (Ser), threonine (Thr), valine (Val), tryptophan (Trp), and tyrosine (Tyr) residues. Serum soluble non-protein polymers, such as polyethylene glycol, and tissue or fat soluble polymers, such as polycaprolactone, can be used for delivery, release, and/or retention of polypeptides. In some embodiments, the protein-polymer conjugate is a pegylated chemokine-immunglobulin fusion polypeptide, chemokine or a variant thereof.

In one aspect, the present application encompass a conjugate having any molar ratio of polymer to chemokine or fragment thereof that endows the conjugate with an apparent size in the desired range as taught herein. The apparent size of the conjugate will depend in part upon the size and shape of the polymer used, the size and shape of the chemokine or fragment thereof used, the number of polymer molecules attached to the chemokine or fragment thereof, and the location of such attachment site(s) on the chemokine or fragment thereof. These parameters can easily be identified and maximized to obtain the conjugate with the desired apparent size for any type of chemokine or fragment thereof, polymer and linkage system.

In some embodiments, the protein-polymer conjugate of the present application has an effective size of at least about 500,000 D, or at least about 800,000 D, or at least about 900,000 D, or at least about 1,000,000 D, or at least about 1,200,000 D, or at least about 1,400,000 D, or at least about 1,500,000 D, or at least about 1,800,000 D, or at least about 2,000,000 D, or at least about 2,500,000 D. In one embodiment, the polymer is PEG.

In other embodiments, the protein-polymer conjugate of the present application has an effective size of at or about 500,000 D to at or about 10,000,000 D, or an effective size of at or about 500,000 D to at or about 8,000,000 D, or an effective size of at or about 500,000 D to at or about 5,000,000 D, or an effective size of at or about 500,000 D to at or about 4,000,000 D, or an effective size of at or about 500,000 D to at or about 3,000,000 D, or an effective size of at or about 500,000 D to at or about 2,500,000 D, or an effective size of at or about 500,000 D to at or about 2,000,000 D, or an effective size of at or about 500,000 D to at or about 1,800,000 D, or an effective size of at or about 500,000 D to at or about 1,600,000 D, or an effective size of at or about 500,000 D to at or about 1,500,000 D, or an effective size of at or about 500,000 D to at or about 1,000,000 D. In one embodiment, the polymer is PEG.

In a further embodiment, the protein-polymer conjugate has an effective size that is at least about 8 fold greater, or at least about 10 fold greater, or at least about 12 fold greater, or at least about 15 fold greater, or at least about 18 fold greater, or at least about 20 fold greater, or at least about 25 fold greater, or at least about 28 fold greater, or at least about 30 fold greater, or at least about 40 fold greater, than the effective size of the unconjugated chemokine-immunglobulin fusion polypeptide, chemokine or variant thereof. In one embodiment, the polymer is PEG.

In another embodiment, the protein-polymer conjugate has an effective size that is about 8 fold to about 100 fold greater, or is about 8 fold to about 80 fold greater, or is about 8 fold to about 50 fold greater, or is about 8 fold to about 40 fold greater, or is about 8 fold to about 30 fold greater, or is about 8 fold to about 28 fold greater, or is about 8 fold to about 25 fold greater, or is about 8 fold to about 20 fold greater, or is about 8 fold to about 18 fold greater, or is about 8 fold to about 15 fold greater, than the effective size of the unconjugated chemokine-immunglobulin fusion polypeptide, chemokine or variant thereof. In one embodiment, the polymer is PEG.

In another embodiment, the protein-polymer conjugate has an effective size that is about 25 fold to about 100 fold greater, or is about 25 fold to about 80 fold greater, or is about 25 fold to about 50 fold greater, or is about 25 fold to about 40 fold greater, or is about 25 fold to about 30 fold greater, or is about 25 fold to about 28 fold greater, than the effective size of the unconjugated chemokine-immunglobulin fusion polypeptide, chemokine or variant thereof. In one embodiment, the polymer is PEG.

In another embodiment, the protein-polymer conjugate has a polymer-to-protein molar ratio of no more than about 10:1, or no more than about 5:1, or no more than about 4:1, or no more than about 3:1, or no more than about 2:1, or no more than 1:1. In one embodiment, the polymer is PEG.

In still another embodiment, the protein-polymer conjugate is a chemokine-immunglobulin fusion polypeptide, chemokine or variant thereof covalently attached to at least one polymer having an actual MW of at least about 20,000 D. In one embodiment, the polymer is PEG.

In a further embodiment, the conjugate is a chemokine-immunglobulin fusion polypeptide, chemokine or variant thereof covalently attached to at least one polymer having an actual MW of at least about 30,000 D. In one embodiment, the polymer is PEG.

In yet another embodiment, the conjugate is a chemokine-immunglobulin fusion polypeptide, chemokine or variant thereof covalently attached to at least one polymer having an actual MW of at least about 40,000 D. In one embodiment, the polymer is PEG.

In another embodiment, the conjugate is a chemokine-immunglobulin fusion polypeptide, chemokine or variant thereof covalently attached to at least one polymer having an actual MW that is at or about 20,000 D to at or about 300,000 D, or is at or about 30,000 D to at or about 300,000 D, or is at or about 40,000 D to at or about 300,000 D. In one embodiment, the polymer is PEG.

The conjugates of the present application can be made using any suitable technique now known or hereafter developed for derivatizing chemokines or fragments thereof with polymers. It will be appreciated that the invention is not limited to conjugates utilizing any particular type of linkage between a chemokine or fragment thereof and a polymer.

The conjugates of the present application include species wherein a polymer is covalently attached to a non-specific site or non-specific sites on a chemokine-immunoglobulin fusion polypeptide, a chemokine or a variant thereof (i.e. the polymer attachment is not targeted to a particular region or a particular amino acid residue in the unconjugated chemokine or fragment thereof). In such embodiments, the coupling chemistry can, for example, utilize the free epsilon amino groups of lysine residues in the unconjugated antibody as attachment sites for the polymer, wherein such lysine residue amino groups are randomly derivatized with polymer.

Figure 11:
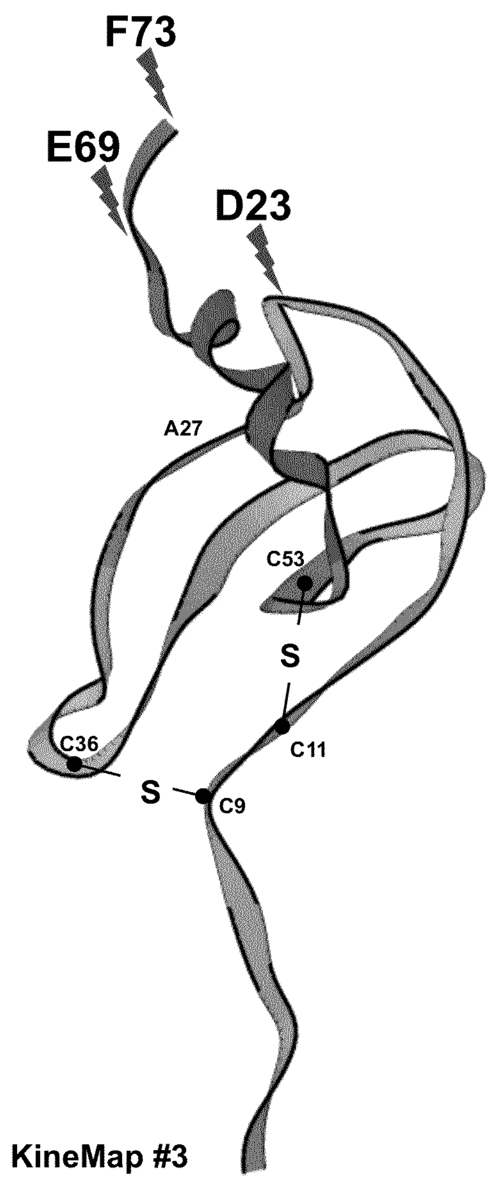
FIG. 11 depicts a cartoon of the structure of CXCL11 indication potential pegylation sites.

In addition, the conjugates of the invention include species wherein a polymer is covalently attached to a specific site or specific sites on the unconjugated chemokine or fragment thereof (i.e. a polymer attachment is targeted to a particular region or a particular amino acid residue or residues in the unconjugated chemokine or fragment thereof). FIG. 11 depicts a cartoon of the structure of CXCL11 indication potential pegylation sites. In such embodiments, the coupling chemistry can, for example, utilize the free sulfhydryl group of a cysteine residue not in a disulfide bridge in the unconjugated chemokine or fragment thereof. In one embodiment, one or more cysteine residue(s) is (are) engineered into a selected site or sites in the unconjugated chemokine or fragment thereof for the purpose of providing a specific attachment site or sites for polymer. The polymer can be activated with any functional group that is capable of reacting specifically with the free sulfhydryl or thiol group(s) on the unconjugated antibody, such as maleimide, sulfhydryl, thiol, triflate, tesylate, aziridine, oxirane, and 5-pyridyl functional groups. The polymer can be coupled to the unconjugated chemokine or fragment thereof using any protocol suitable for the chemistry of the coupling system selected.

In another embodiment, polymer attachment is targeted to the receptor binding site of the unconjugated chemokine or fragment thereof. In another embodiment, polymer attachment is targeted to a site on the chemokine or fragment thereof away from the receptor binding site of the unconjugated chemokine or fragment thereof.

In certain embodiments, the protein portion of the protein-polymer conjugate is selected from the group consisting of human CCL1, CCL2, CCL3, CCL4, CCL4L1, CCL5, CCL7, CCL8, CCL11, CCL13, CCL14, CCL15, CCL16, CCL17, CCL 18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof and the polymer portion of the protein-polymer conjugate is PEG. FIG. 11 depicts a cartoon of the structure of CXCL11 indication potential pegylation sites.

In other embodiments, the protein portion of the protein-polymer conjugate is a chemokine-immunoglobulin fusion polypeptide wherein the chemokine moiety is selected from the group consisting of a human CCL1, CCL2, CCL3, CCL4, CCL4L1, CCL5, CCL7, CCL8, CCL11, CCL13, CCL14, CCL15, CCL16, CCL17, CCL 18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof and the immunoglobulin moiety is selected from the group consisting of the Fc region of human IgG1, the Fc region of human IgG2, the Fc region of human IgG3, the Fc region of human IgG4 and variants thereof.

In some embodiments, the protein-polymer conjugate is a serum labile polypeptide selected from the group consisting of CCL2-PEG, var-CCL2-PEG, CCL7-PEG, var-CCL7-PEG, CCL8-PEG, var-CCL8-PEG, CCL13-PEG, var-CCL13-PEG, CCL25-PEG, var-CCL25-PEG, CXCL11-PEG, var-CXCL11-PEG, CXCL13-PEG, var-CXCL13-PEG, CXCL16-PEG, and var-CXCL16-PEG.

In particular embodiments, the protein-polymer conjugate is a serum labile polypeptide selected from the group consisting of CCL2-PEG, CCL2(5-76)-PEG, CCL2(5-76K/H→A)-PEG, CCL7-PEG, CCL7(5-76)-PEG, CCL7(5-76K/H→A)-PEG, CCL8-PEG, CCL8(5-76)-PEG, CCL8(5-76K/H→A)-PEG, CCL13-PEG, CCL13(5-75)-PEG, CCL13(5-75K/H→A)-PEG, CCL25-PEG, CCL25(4-127)-PEG, CCL25(4-127K/H→A)-PEG, CXCL11-PEG, CXCL11(4-73)-PEG, CXCL11(4-73K/H→A)-PEG, CXCL11-IgG4Fc, CXCL11(4-73)-IgG4Fc, CXCL11(4-73K/H→A)-IgG4Fc, CXCL13-PEG, CXCL13(3-87)-PEG, CXCL13(3-87K/H→A)-PEG, CXCL16-PEG, CXCL16(3-87)-PEG, and CXCL16(3-87K/H→A)-PEG.

It is believed that the serum half-life, MRT and/or serum clearance rate of any chemokine or fragment thereof can be greatly improved by derivatizing the chemokine or fragment thereof with polymer as taught herein. In a preferred embodiment, the conjugate contains a chemokine or fragment thereof selected from the group consisting of CCL2, CCL7, CCL8, CCL13, CCL25, CXCL11, CXCL12α, CXCL13, and mutations, variants and fragments thereof.

Methods of Producing Chemokine-Immunoglobulin Fusion Polypeptides

The chemokine-immunglobulin fusion polypeptides or variants thereof may be produced using methods well known in the art. In certain embodiments, the chemokine-immunglobulin fusion polypeptide or variants thereof are produced by chemical synthesis. Briefly, a chemokine-immunglobulin fusion polypeptide may be synthesized by coupling the carboxyl group or C-terminus of one amino acid to the amino group or N-terminus of another. Due to the possibility of unintended reactions, protecting groups are usually necessary. Chemical peptide synthesis starts at the C-terminal end of the peptide and ends at the N-terminus. This is the opposite of protein biosynthesis, which starts at the N-terminal end.

In some embodiments, the chemokine-immunglobulin fusion polypeptide may be synthesized using traditional liquid- or solid-phase synthesis. Fmoc and t-Boc solid phase peptide synthesis (SPPS) can be employed to grow the peptides from carboxy to amino-terminus. In certain embodiments, the last "amino acid" added to the reaction is pegylated. This last amino acid is often referred to as a carboxyl-PEG-amine, carboxyl-PEO-amine, or amine-PEG-acid, whereby the amine is blocked to protect against reaction and the acid is free to react with the amine group from the previously added amino acid in the reaction.

In other embodiments, the chemokine-immunglobulin fusion polypeptides or variants thereof are produced using recombinant DNA technologies. Procedures for the expression and purification of recombinant proteins are well established.

In certain embodiments, the chemokine-immunglobulin fusion polypeptides are expressed using the expression vectors such as bacterial plasmids; phage DNA; baculovirus; yeast plasmids; vectors derived from combinations of plasmids and phage DNA, and viral vectors such as vaccinia, adenovirus, fowl pox virus, pseudorabies, adenovirus, adeno-associated virus, retroviruses and many others viruses.

Expression vectors carrying the chemokine-immunglobulin fusion polypeptides can be introduced into host cells by any of a variety of well-known procedures, such as electroporation, liposome mediated transfection, calcium phosphate precipitation, infection, transfection and the like, depending on the selection of vectors and host cells.

Host cells that contain expression vectors of chemokine-immunglobulin fusion polypeptides are, thus, also a feature of this disclosure. Favorable host cells include prokaryotic (i.e., bacterial) host cells, such as *E. coli*, as well as numerous eukaryotic host cells, including fungal (e.g., yeast, such as *Saccharomyces cerevisiae* and *Picchia pastoris*) cells, insect cells, plant cells, and mammalian cells (such as CHO cells). Examples of appropriate expression hosts include: bacterial cells, such as *E. coli, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as 3T3, COS, CHO, BHK, HEK 293 or Bowes melanoma; plant cells, including algae cells, etc.

The host cells can be cultured in conventional nutrient media modified as appropriate for activating promoters, selecting transformants, or amplifying the inserted polynucleotide sequences. The culture conditions, such as temperature, pH and the like, are typically those previously used with the host cell selected for expression, and will be apparent to those skilled in the art and in the references cited herein. The chemokine-immunglobulin fusion polypeptides can also be produced in non-animal cells such as plants, yeast, fungi, bacteria and the like. In bacterial systems, a number of expression vectors can be selected depending upon the use intended for the expressed product. For example, when large quantities of a polypeptide or fragments thereof are needed for the production of antibodies, vectors which direct high level expression of fusion polypeptides that are readily purified are favorably employed. Such vectors include, but are not limited to, multifunctional *E. coli* cloning and expression vectors such as BLUESCRIPT (Stratagene), in which the coding sequence of interest, e.g., a polynucleotide of the invention as described above, can be ligated into the vector in-frame with sequences for the amino-terminal translation initiating Methionine and the subsequent 7 residues of beta-galactosidase producing a catalytically active beta galactosidase fusion polypeptide; pIN vectors (Van Heeke & Schuster (1989) J Biol Chem 264:5503-5509); pET vectors (Novagen, Madison Wis.), in which the amino-terminal methionine is ligated in frame with a histidine tag; and the like.

Similarly, in yeast, such as *Saccharomyces cerevisiae*, a number of vectors containing constitutive or inducible promoters such as alpha factor, alcohol oxidase and PGH can be used for production of the desired expression products. In mammalian host cells, a number expression systems, including both plasmids and viral-based systems, can be utilized.

For long-term, high-yield production of the chemokine-immunglobulin fusion polypeptides, stable expression systems are typically used. For example, polynucleotides encoding a the chemokine-immunglobulin fusion polypeptide are introduced into the host cell using expression vectors which contain viral origins of replication or endogenous expression elements and a selectable marker gene. Following the introduction of the vector, cells are allowed to grow for 1-2 days in an enriched media before they are switched to selective media. The purpose of the selectable marker is to confer resistance to selection, and its presence allows growth and recovery of cells, which successfully express the introduced sequences. For example, resistant groups or colonies of stably transformed cells can be proliferated using tissue culture techniques appropriate to the cell type. Host cells transformed with a nucleic acid encoding a c the chemokine-immunglobulin fusion polypeptide are optionally cultured under conditions suitable for the expression and recovery of the encoded protein from cell culture.

Following transduction of a suitable host cell line and growth of the host cells to an appropriate cell density, the selected promoter is induced by appropriate means (e.g., temperature shift or chemical induction) and cells are cultured for an additional period. The secreted polypeptide product is then recovered from the culture medium. Alternatively, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption, or use of cell lysing agents, or other methods, which are well know to those skilled in the art.

Expressed the chemokine-immunglobulin fusion polypeptides can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature protein. Finally, high performance liquid chromatography (HPLC) can be employed in the final purification steps. In addition to the references noted above, a variety of purification methods are well known in the art.

In another example, a polynucleotide sequence that encodes the chemokine-immunglobulin fusion polypeptide is introduced into insect cells using a Baculovirus Expression Vector System (BEVS). Recombinant baculovirus capable of infecting insect cells can be generated using commercially available vectors, kits and/or systems, such as the BD BaculoGold system from BD BioScience. Briefly, the polynucleotide sequence encoding the chemokine-immunglobulin fusion polypeptide is inserted into the pAcSG2 transfer vector. Then, host cells SF9 (*Spodoptera frugiperda*) are co-transfected by pAcSG2-chimer plasmid and BD BaculoGold, containing the linearized genomic DNA of the baculovirus *Autographa californica* nuclear polyhedrosis virus (AcNPV). Following transfection, homologous recombination occurs between the pACSG2 plasmid and the Baculovirus genome to generate the recombinant virus. In one example, the chemokine-immunglobulin fusion polypeptide is expressed under the regulatory control of the polyhedrin promoter (pH). Similar transfer vectors can be produced using other promoters, such as the basic (Ba) and p10 promoters. Similarly, alternative insect cells can be employed, such as SF21, which is closely related to the Sf9, and the High Five (Hi5) cell line derived from a cabbage looper, *Trichoplusia ni*. Following transfection and induction of expression (according to the selected promoter and/or enhancers or other regulatory elements), the expressed the chemokine-immunglobulin fusion polypeptides are recovered (e.g., purified or enriched) and renatured to ensure folding into a biologically active conformation.

In yet other embodiments, the chemokine-immunglobulin fusion polypeptides are expressed in vivo by a plasmid vector or a viral vector.

Treatment Methods

The present application further provides methods of using the chemokine-immunoglobulin fusion polypeptides disclosed herein to modulate inflammation and/or treat chemokine receptor-mediated disorders. In some embodiments, a method for treating a chemokine receptor-mediated disorder in a subject is provided. In some embodiments, the method comprises administering an effective amount of a chemokine-immunoglobulin fusion polypeptide disclosed herein to a subject in need thereof.

As used herein, the terms “treatment” or “treating” relate to any treatment of a chemokine receptor-mediated disorder, including but not limited to prophylactic treatment and therapeutic treatment. As such, the terms “treatment” or “treating” include, but are not limited to: preventing a chemokine receptor-mediated disorder or the development of a chemokine receptor-mediated disorder; inhibiting the progression of a chemokine receptor-mediated disorder; arresting or preventing the development of a chemokine receptor-mediated disorder; reducing the severity of a chemokine receptor-mediated disorder; ameliorating or relieving symptoms associated with a chemokine receptor-mediated disorder; and causing a regression of the chemokine receptor-mediated disorder or one or more of the symptoms associated with the chemokine receptor-mediated disorder.

The embodiments of the therapeutic compounds exhibit activity in the treatment of chemokine receptor-mediated disorders and inflammation, when administered in effective amounts. An effective amount of a composition disclosed herein is a nontoxic, but sufficient amount of the composition, such that the desired prophylactic or therapeutic effect is produced. The exact amount of the composition that is required will vary from subject to subject, depending on the species, age, condition of the animal, severity of the inflammation or chemokine receptor-mediated disorder in the animal, the particular carrier or adjuvant being used, its mode of administration, and the like. Accordingly, the effective amount of any particular therapeutic composition disclosed herein will vary based on the particular circumstances, and an appropriate effective amount can be determined in each case of application by one of ordinary skill in the art using only routine experimentation. The compositions disclosed herein can be administered in amounts ranging from about 0.1 μg to about 100 mg per kilogram of body weight. For example, the dosage regimen could be from about 1 μg to about 10 mg per kilogram of body weight, and such dosage units could be employed so that a total of from about 7 μg to about 700 mg of the composition is administered to a subject of about 70 kg of body weight.

A dosage regimen can be adjusted to provide an optimum therapeutic response and can be administered daily, biweekly, weekly, bimonthly, monthly, or at other appropriate time intervals. For example, compositions disclosed herein can be administered from once a day to once a week in dosages of about 5-250 mg per administration. For another example, several divided doses can be administered daily or the dose can be proportionally reduced as indicated by the exigencies of the therapeutic situation. One practical advantage is that the compound can be administered in a convenient manner such as intravenously, intratumorally, subcutaneously, transdermally, intraperitoneally or orally.

In some embodiments, the active composition is administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. The form should be sterile and fluid to the extent that easy syringability exists. It should be stable under the conditions of manufacture and storage and should be preserved against the contaminating action of microorganisms, such as bacteria and fungi. The pharmaceutical carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, the inclusion of isotonic agents can be desirable, for example, sugars or sodium chloride. Prolonged absorption of the injectable compositions can be brought about by the use in the compositions of agents, delaying absorption, for example, aluminum monostearate and gelatin.

Sterile injectable solutions can be prepared by incorporating the composition in the required amount in the appropriate solvent with various of the other ingredients enumerated above, followed by filtered sterilization. Generally, dispersions can be prepared by incorporating the various sterilized active ingredient into a sterile vehicle containing the basic dispersion medium and the required other ingredients from those enumerated above. In the case of sterile powders for the preparation of sterile injectable solutions, methods of preparation include vacuum drying and freeze drying techniques, which yield a powder of the active ingredient plus any additional desired ingredient from previously sterile filtered solution thereof.

As used herein, “pharmaceutically acceptable carrier” and “pharmaceutical carrier” are used interchangeably and include solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Parenteral compositions may be formulated in dosage-unit form for ease of administration and uniformity of dosage. Dosage-unit form, as used herein, refers to physically discrete units suited as unitary dosages for the subjects to be treated, each unit containing a predetermined quantity of active material calculated to produce the desired therapeutic effect in association with the required pharmaceutical carrier. The specification for the dosage-unit forms of the present application can be chosen based upon: (a) the unique characteristics of the active material and the particular therapeutic effect to be achieved, and (b) the limitations inherent in the art of compounding such an active material for the treatment of conditions in living subjects having a condition in which bodily health is impaired as described herein.

The active ingredient can be compounded for convenient and effective administration in effective amounts with a suitable pharmaceutically acceptable carrier in dosage unit form as described herein. A unit dosage form can, for example, contain the principle active compound in amounts ranging from, for example, about 0.1 to about 1000 mg or, for another example, from about 5 to about 500 mg. Expressed in proportions, the compound is generally present in from about 1 to about 100 mg/ml of carrier. In the case of compositions containing supplementary active ingredients, the dosages can be determined by reference to the usual dose and manner of administration of the ingredients.

Further, with respect to the therapeutic methods of the presently disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently disclosed subject matter.

As such, the presently application provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos.

Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

In some embodiments of the presently-disclosed subject matter, the chemokine receptor-mediated disorder treated is a cell proliferative disorder, such as tumor or cancer. The present application provides chemokine-immunoglobulin fusion polypeptides that can target specific chemokine receptors expressed on cells of proliferative disorders disclosed herein. Cancer cells express functionally active chemokine receptors that may support adhesion, invasion, and cell survival. Chemokine receptor signaling and aggregation following binding of chemokines is coupled to integrin clustering, which enhances cell survival and firm cell adhesion. Without wishing to be bound by theory, the novel chemokine-immunoglobulin fusion polypeptides disclosed herein can bind chemokine receptors on these diseased cells and inhibit cellular events, including cell survival, migration, invasion, adhesion, or combinations thereof, and thereby treat the cell proliferative disorder. Table 3 lists various cancers and associations of the listed cancers with particular chemokines and chemokine receptors.

TABLE 3

Chemokine, Chemokine Receptor and Cancer Association (dependent of stage of disease)

| Cancer | Chemokine | Chemokine Receptor |
|---|---|---|
| Carcinoma | CCL1, CCL4, CCL17, CCL19, CCL21, CCL22, CCL25, CXCL1, CXCL2, CXCL5, CXCL8, CXCL11, CXCL12, CXCL13, CXCL16 | CCR7, CCR8, CCR9, CXCR1, CXCR2, CXCR3, CXCR4, CXCR5, CXCR6, CXCR7, CX3CR1 |
| Leukemia | CCL1, CCL4, CCL17, CCL19, CCL21, CCL22, CCL25, CXCL12 | CCR7, CCR8, CCR9, CXCR4 |
| Lymphoma | CXCL12, CXCL13 | CXCR4, CXCR5 |
| Melanoma | CCL25, CCL27, CXCL1, CXCL2, CXCL3, CXCL5, CXCL6, CXCL7, CXCL8, CXCL12, CXCL13, CXCL16 CX3CL1 | CCR9, CCR10, CXCR1, CXCR2, CXCR4, CXCR5, CXCR6, CX3CR1 |

TABLE 3-continued

Chemokine, Chemokine Receptor and Cancer Association (dependent of stage of disease)

| Cancer | Chemokine | Chemokine Receptor |
|---|---|---|
| Sarcoma | CCL1, CCL3, CCL4, CCL5, CCL7, CCL8, CCL11, CCL13, CCL17, CCL19, CCL22, CCL24, CXCL12, CX3CL1 | CCR3, CCR5, CCR8, CXCR4 CX3CR1, CCXCKR |

"Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. "Cancer" refers to any of various malignant neoplasms characterized by the proliferation of cells that have the capability to invade surrounding tissue and/or metastasize to new colonization sites, and includes leukemia, lymphoma, carcinoma, melanoma, sarcoma, germ cell tumor and blastoma. Examples of cancers are cancer of the brain, bladder, breast, cervix, colon, head and neck, kidney, lung, non-small cell lung, mesothelioma, ovary, prostate, stomach and uterus, leukemia, and medulloblastoma.

By "leukemia" is meant broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, leukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenia leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, thyroid cancer, neuroblastoma, esophageal cancer, genitourinary tract cancer, malignant hypercalcemia, cervical cancer, endometrial cancer, and adrenal cortical cancer.

In some embodiments, a chemokine-immunoglobulin fusion polypeptide of the present application is used for the treatment of cancer. The chemokine-immunoglobulin fusion polypeptide comprises a chemokine moiety selected from the group consisting of CCL1, CCL2, CCL3, CCL4, CCL4L1, CCL5, CCL7, CCL8, CCL11, CCL13, CCL14, CCL15, CCL16, CCL17, CCL 18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof, and an immunoglobulin moiety selected from the group consisting of the constant region of human IgG1 and functional variants thereof.

In other embodiments, the chemokine receptor-mediated disorder treated is an inflammatory disorder. Without wishing to be bound by theory, the novel chemokine-immunoglobulin fusion polypeptides disclosed herein can bind chemokine receptors on these cells and inhibit cellular events that can result in inflammation and inflammatory disorders. Table 4 lists various exemplary inflammatory disorders and associations of the listed disorders with particular chemokines and chemokine receptors. Targeting of the listed chemokine receptors with chemokine-immunoglobulin fusion polypeptides disclosed herein that act as specific ligands of the receptors can be useful for treating the listed inflammatory disorders.

In some embodiments, a chemokine-immunoglobulin fusion polypeptide of the present application is used for the treatment of an inflammatory discorder. The chemokine-immunoglobulin fusion polypeptide comprises a chemokine moiety selected from the group consisting of CCL1, CCL2, CCL3, CCL4, CCL4L1, CCL5, CCL7, CCL8, CCL11, CCL13, CCL14, CCL15, CCL16, CCL17, CCL 18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof, and an immunoglobulin moiety selected from the group consisting of the constant region of human IgG4 and functional variants thereof.

TABLE 4

Chemokine, Chemokine Receptor and Inflammatory Disorder Association (dependent of stage of disease)

| Inflammatory Disorder | Chemokine | Chemokine Receptor |
|---|---|---|
| Allergies (Skin, Food & Respiratory) | CCL1, CCL2, CCL5, CCL7, CCL8, CCL11, CCL13, CCL17, CCL22, CCL24, CCL25, CCL26 | CCR3, CCR4, CCR8, CCR9 |

TABLE 4-continued

| Chemokine, Chemokine Receptor and Inflammatory Disorder Association (dependent of stage of disease) | | |
|---|---|---|
| Inflammatory Disorder | Chemokine | Chemokine Receptor |
| Asthma | CCL3, CCL4, CCL5, CCL7, CCL8, CCL11, CCL15, CCL17, CCL22, CCL24, CCL26 | CCR3, CCR4, CCR5 |
| Septic Shock, Anaphylaxis | CXCL1, CXCL2, CXCL3, CXCL5, CXCL6, CXCL7, CXCL8, CXCL9, CXCL10, CXCL11, CCL5 | CXCR1, CXCR2, CXCR3 |
| Arthritis (septic, rheumatoid, psoriatic) | CXCL9, CXCL10, CXCL11, CXCL12, CXCL13 | CXCR3, CXCR4, CXCR5 |
| | CCL20 | CCR6 |
| | XCL1 | XCR1 |
| | CX3CL1 | CX3CR1 |
| Osteoarthritis | CXCL1, CXCL2, CXCL3, CXCL5, CXCL6, CXCL7, CXCL8, CXCL12, CXCL13 | CXCR1, CXCR2 |
| | CCL2, CCL3, CCL4, CCL7, CCL8, CCL13, CCL5, CCL18 | CCR2, CCR5 |
| Atherosclerosis | CXCL1, CXCL2, CXCL3, CXCL4, CXCL5, CXCL8 | CXCR1, CXCR2 |
| | CCL2, CCL3, CCL4, CCL8, CCL12, CCL13, CCL17, CCL22 | CCR2, CCR8 |
| | CX3CL1 | CX3CR1 |
| Dermatitis & Delayed-Typed Hypersensitivity | CXCL9, CXCL10, CXCL11 | CXCR3 |
| | CCL2, CCL3, CCL4, CCL5, CCL17, CCL20, CCL22, CCL27 | CCR4, CCR5, CCR6, CCR10 |
| Diabetes | CXCL9, CXCL10, CXCL11 | CXCR3 |
| | CCL2, CCL9 | CCR2, CCR4 |
| | CX3CL1 | CX3CR1 |
| Graft rejection | CXCL9, CXCL10, CXCL11 | CXCR3 |
| | CCL3, CCL4, CCL5 | CCR5 |
| | XCL1, XCL2 | XCR1 |
| Inflammatory Bowel Disorders | CXCL9, CXCL10, CXCL11 | CXCR3 |
| | CCL3, CCL4, CCL5, CCL25 | CCR5 |
| Interstitial Cystitis | CXCL9, CXCL10, CXCL11 | CXCR3 |
| | CCL3, CCL4, CCL5 | CCR5 |
| Multiple Sclerosis | CXCL9, CXCL10, CXCL11 | CXCR3 |
| | CCL3, CCL4, CCL5, CCL7, CCL14, CCL15, CCL23 | CCR1, CCR5 |
| Myasthemia gravis, Grave's disease, & Hashimoto thyroiditis | CXCL9, CXCL10, CXCL11 | CXCR3 |
| | CCL3, CCL4, CCL5 | CCR5 |
| | XCL1, XCL2 | XCR1 |
| Nephritis & Systemic Lupus Erthematosus | CXCL9, CXCL10, CXCL11, CXCL13 | CXCR3, CXCR5 |
| | CCL2, CCL3, CCL4, CCL5, CCL8, CCL12, CCL13 | CCR2, CCR4 |
| | CX3CL1 | CX3CR1 |
| Pneumonitis, Chronic Obstructive Pulmonary Disease, & Chronic Bronchitis | CXCL1, CXCL2, CXCL3, CXCL5, CXCL7, CXCL8 | CXCR2, CXCR3 |
| | CCL3, CCL5, CCL7, CCL8, CCL11, CCL13, CCL24, CCL26 | CCR3 |

As used herein, the term "inflammatory disorder" includes diseases or disorders which are caused, at least in part, or exacerbated, by inflammation, which is generally characterized by increased blood flow, edema, activation of immune cells (e.g., proliferation, cytokine production, or enhanced phagocytosis), heat, redness, swelling, pain and/or loss of function in the affected tissue or organ. The cause of inflammation can be due to physical damage, chemical substances, micro-organisms, tissue necrosis, cell proliferative disorders, or other agents Inflammatory disorders include acute inflammatory disorders, chronic inflammatory disorders, and recurrent inflammatory disorders. Acute inflammatory disorders are generally of relatively short duration, and last for from about a few minutes to about one to two days, although they can last several weeks. Characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or longer, and are associated histologically with the presence of lymphocytes and macrophages and with proliferation of blood vessels and connective tissue. Recurrent inflammatory disorders include disorders which recur after a period of time or which have periodic episodes. Some inflammatory disorders fall within one or more categories. Exemplary inflammatory disorders include, but are not limited to, inflammatory disorders of the central or peripheral nervous system (e.g., abscess, AIDS related infections, Alzheimer's disease, chronic fatigue syndrome, congenital infections, encephalitis, ischemia, meningitis, multiple sclerosis, traumatic brain injury, etc.); inflammatory disorders of the urogenital system (e.g., endometriosis, glomerulosclerosis, infections of the vagina and cervix, intra-amniotic infection, pelvic inflammatory disease, renal inflammation/nephritis, sexually transmitted diseases, urethritis, urinary tract infections, yeast infection, etc.); inflammatory disorders of the digestive system (e.g., colon cancer, hepatitis, inflammatory bowel disease, interstitial cystitis, irritable bowel syndrome, ulcers, etc.); inflammatory disorders of the respiratory system (e.g., chronic lung disease, asthma, tuberculosis, pneumonia, etc.); inflammatory disorders of the skin, integument and musculoskeletal system (e.g., Behçet's disease, Crohn's disease, dermatitis, gingivitis, gout, myalgias, osteoarthritis, periodontitis, psoriasis, rheumatoid arthritis, spondyloarthropathies, skin sunburn, etc.); inflammatory disorders of the cardiovascular system (e.g., atherosclerosis, pericarditis, endocarditis, Kawasaki's disease, myocarditis, rheumatic fever, vasculitis); autoimmune disorders; cat scratch disease; infections of the eye; Lyme disease; lymphadenopathy; lymphatic inflammation; radiation-induced inflammation; sarcoidosis; Sjogren's syndrome; systemic lupus erythematosus and related disorders; and inflammatory disorders resulting from infections by microorganisms and inflammatory molecules. As used herein, the term "microorganism" refers to any species or type of microorganism, including but not limited to, bacteria, viruses, archaea, fungi, protozoans, mycoplasma, prions, and parasitic organisms. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism. As noted, an inflammatory disorder is often caused, at least in part, or exacerbated by, inflammation, which may be characterized by symptoms and/or manifestations of the inflammatory disorder which may include, but are not limited to, increased blood flow, edema, activation of immune cells (e.g., proliferation, cytokine production, or enhanced phagocytosis), heat, redness, swelling, pain and loss of function in the affected tissue and organ. As such, the present application further provides methods of modulating inflammation. The term "modulating inflammation" refers to either inducement of inflammation or alleviating inflammation where inflammation is pathological, as occurs in inflammatory disorders. The term "alleviating" as used herein refers to preventing the symptoms and/or manifestations of inflammation or the development of the symptoms and/or manifestations of inflammation; inhibiting the progression of the symptoms and/or manifestations of inflammation; arresting or preventing the development of the symptoms and/or manifestations of inflammation; reducing the severity of symptoms and/or manifestations inflammation; ameliorating or relieving the symptoms and/or manifestations associated with inflammation; and/or causing a regression of the symptoms and/or manifestations of inflammation. The present invention is further illustrated by the following examples that should not be construed as limiting. The following examples may include compilations of data that are representative of data gathered at various times during the course of development and experimentation related to the present subject matter.

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Generation of Plasmid Expression Vectors

Expression vectors capable of expressing a chemokine-immunoglobulin fusion polypeptide are generated from pFUSE-hIgG1-Fc1, pFUSE-hIgG2-Fc1, pFUSE-hIgG3-Fc1 and pFUSE-hIgG4-Fc1 vectors from InvivoGen (San Diego, Calif.) using standard molecular biology procedures. Examples of the expression vectors are shown in FIGS. 1-10.

Example 2

Expression of Chemokine Receptors in Breast Cancer Cell Lines

Experiments are conducted to compare expression levels of CXCR7 and CXCR3 in breast cancer tissue of various stages, in non-neoplastic breast tissue. Non-neoplastic breast tissue does not express detectable levels of CXCR7. CXCR7 expression is significantly higher in tissues with advanced breast cancer, comparing to non-neoplastic breast tissue. CXCR7 and CXCR3 mRNAs are also elevated in breast cancer cell lines (MDA-MB-231), compared to normal breast cells (MCF-10A).

Example 3 var-CXCL11-IgG Fusion Polypeptide Inhibits CXCR7 and CXCR3 Activation in Breast Cancer Cells Using Amnis ImageStream analysis, we found that CXCL11 stimulates CXCR3 and CXCR7 aggregation and rapid desensitization, that CXCL12 modulates modest CXCR7 clustering, and that adrenomedullin (AM) stimulates CXCR3 and CXCR7 clustering. CXCL11-IgG fusion polypeptide abrogates CXCR3 and CXCR7, but not CXCR4, clustering and desensitization by CXCL11, CXCL12 and AM.

The above description is for the purpose of teaching the person of ordinary skill in the art how to practice the present invention, and is not intended to detail all those obvious modifications and variations of it that will become apparent to the skilled worker upon reading the description. It is intended, however, that all such obvious modifications and variations be included within the scope of the present invention, which is defined by the following embodiments. The embodiments are intended to cover the components and steps in any sequence that is effective to meet the objectives there intended, unless the context specifically indicates the contrary. All the references cited in the specification are herein incorporated by reference in their entirely.

What is claimed is:

1. An isolated chemokine-immunoglobulin fusion polypeptide, comprising:

a CCL25 chemokine moiety and an immunoglobulin moiety comprising a constant region of a human immunoglobulin or a functional variant thereof, wherein the chemokine-immunoglobulin fusion polypeptide comprises an amino acid sequence selected from the group consisting of SEQ ID NO:64, SEQ ID NO:65 and SEQ ID NO:66.

2. The isolated chemokine-immunoglobulin fusion polypeptide of claim 1, wherein said fusion polypeptide is a pegylated fusion polypeptide.

3. The isolated chemokine-immunoglobulin fusion polypeptide of claim 2, wherein said pegylated fusion polypeptide comprises PEG molecules having a molecular weight of at least about 20,000 Dalton.

4. The isolated chemokine-immunoglobulin fusion polypeptide of claim 2, wherein said pegylated fusion polypeptide has a molecular weight of at least 500,000 Daltons.

5. The isolated chemokine-immunoglobulin fusion polypeptide of claim 2, wherein said pegylated fusion polypeptide has a PEG-to-fusion polypeptide molar ratio of no more than about 10:1.

6. The isolated chemokine-immunoglobulin fusion polypeptide of claim 2, wherein said pegylated fusion polypeptide has a PEG-to-fusion polypeptide molar ratio of no more than about 2:1.

7. A method for treating cancer, wherein said cancer is breast cancer, comprising: administering to a subject in need of such treatment an effective amount of a pharmaceutical composition comprising the chemokine-immunoglobulin fusion polypeptide of claim 1.

8. The method of claim 7, wherein isolated chemokine-immunoglobulin fusion polypeptide is a pegylated fusion polypeptide.

9. The method of claim 8, wherein said pegylated fusion polypeptide comprises PEG molecules having a molecular weight of at least about 20,000 Dalton.

10. The method of claim 8, wherein said pegylated fusion polypeptide has a molecular weight of at least 500,000 Daltons.

11. The method of claim 8, wherein said pegylated fusion polypeptide has a PEG-to-fusion polypeptide molar ratio of no more than about 10:1.

12. The method of claim 8, wherein said pegylated fusion polypeptide has a PEG-to-fusion polypeptide molar ratio of no more than about 2:1.

13. A method for treating an inflammatory disorder, wherein said inflammatory disorder is inflammation of the digestive system, comprising:

administering to a subject in need of such treatment an effective amount of a pharmaceutical composition comprising the chemokine-immunoglobulin fusion polypeptide of claim 1.

14. The method of claim 13, wherein said isolated chemokine-immunoglobulin fusion polypeptide is a pegylated fusion polypeptide.

15. The method of claim 14, wherein said pegylated fusion polypeptide comprises PEG molecules having a molecular weight of at least about 20,000 Dalton.

16. The method of claim 14, wherein said pegylated fusion polypeptide has a molecular weight of at least 500,000 Daltons.

17. The method of claim 14, wherein said pegylated fusion polypeptide has a PEG-to-fusion polypeptide molar ratio of no more than about 10:1.

18. The method of claim 14, wherein said pegylated fusion polypeptide has a PEG-to-fusion polypeptide molar ratio of no more than about 2:1.

* * * * *

SEQUENCE LISTING

```
<160> NUMBER OF SEQ ID NOS: 106

<210> SEQ ID NO 1
<211> LENGTH: 96
<212> TYPE: PRT
<213> ORGANISM: Homo sapiens
```

-continued

<400> SEQUENCE: 1

Met Gln Ile Ile Thr Thr Ala Leu Val Cys Leu Leu Leu Ala Gly Met
1               5                   10                  15

Trp Pro Glu Asp Val Asp Ser Lys Ser Met Gln Val Pro Phe Ser Arg
            20                  25                  30

Cys Cys Phe Ser Phe Ala Glu Gln Glu Ile Pro Leu Arg Ala Ile Leu
        35                  40                  45

Cys Tyr Arg Asn Thr Ser Ser Ile Cys Ser Asn Glu Gly Leu Ile Phe
    50                  55                  60

Lys Leu Lys Arg Gly Lys Glu Ala Cys Ala Leu Asp Thr Val Gly Trp
65                  70                  75                  80

Val Gln Arg His Arg Lys Met Leu Arg His Cys Pro Ser Lys Arg Lys
                85                  90                  95

<210> SEQ ID NO 2
<211> LENGTH: 99
<212> TYPE: PRT
<213> ORGANISM: Homo sapiens

<400> SEQUENCE: 2

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 3
<211> LENGTH: 92
<212> TYPE: PRT
<213> ORGANISM: Homo sapiens

<400> SEQUENCE: 3

Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
            20                  25                  30

Cys Cys Phe Ser Tyr Thr Ser Arg Gln Ile Pro Gln Asn Phe Ile Ala
        35                  40                  45

Asp Tyr Phe Glu Thr Ser Ser Gln Cys Ser Lys Pro Gly Val Ile Phe
    50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
                85                  90

<210> SEQ ID NO 4
<211> LENGTH: 92
<212> TYPE: PRT
<213> ORGANISM: Homo sapiens

<400> SEQUENCE: 4

Met Lys Leu Cys Val Thr Val Leu Ser Leu Leu Met Leu Val Ala Ala
1 5 10 15

Phe Cys Ser Pro Ala Leu Ser Ala Pro Met Gly Ser Asp Pro Pro Thr
20 25 30

Ala Cys Cys Phe Ser Tyr Thr Ala Arg Lys Leu Pro Arg Asn Phe Val
35 40 45

Val Asp Tyr Tyr Glu Thr Ser Ser Leu Cys Ser Gln Pro Ala Val Val
50 55 60

Phe Gln Thr Lys Arg Ser Lys Gln Val Cys Ala Asp Pro Ser Glu Ser
65 70 75 80

Trp Val Gln Glu Tyr Val Tyr Asp Leu Glu Leu Asn
85 90

<210> SEQ ID NO 5
<211> LENGTH: 92
<212> TYPE: PRT
<213> ORGANISM: Homo sapiens

<400> SEQUENCE: 5

Met Lys Leu Cys Val Thr Val Leu Ser Leu Leu Val Leu Val Ala Ala
1 5 10 15

Phe Cys Ser Leu Ala Leu Ser Ala Pro Met Gly Ser Asp Pro Pro Thr
20 25 30

Ala Cys Cys Phe Ser Tyr Thr Ala Arg Lys Leu Pro Arg Asn Phe Val
35 40 45

Val Asp Tyr Tyr Glu Thr Ser Ser Leu Cys Ser Gln Pro Ala Val Val
50 55 60

Phe Gln Thr Lys Arg Gly Lys Gln Val Cys Ala Asp Pro Ser Glu Ser
65 70 75 80

Trp Val Gln Glu Tyr Val Tyr Asp Leu Glu Leu Asn
85 90

<210> SEQ ID NO 6
<211> LENGTH: 91
<212> TYPE: PRT
<213> ORGANISM: Homo sapiens

<400> SEQUENCE: 6

Met Lys Val Ser Ala Ala Ala Leu Ala Val Ile Leu Ile Ala Thr Ala
1 5 10 15

Leu Cys Ala Pro Ala Ser Ala Ser Pro Tyr Ser Ser Asp Thr Thr Pro
20 25 30

Cys Cys Phe Ala Tyr Ile Ala Arg Pro Leu Pro Arg Ala His Ile Lys
35 40 45

Glu Tyr Phe Tyr Thr Ser Gly Lys Cys Ser Asn Pro Ala Val Val Phe
50 55 60

Val Thr Arg Lys Asn Arg Gln Val Cys Ala Asn Pro Glu Lys Lys Trp
65 70 75 80

Val Arg Glu Tyr Ile Asn Ser Leu Glu Met Ser
85 90

<210> SEQ ID NO 7
<211> LENGTH: 99
<212> TYPE: PRT
<213> ORGANISM: Homo sapiens

<400> SEQUENCE: 7

Met Lys Ala Ser Ala Ala Leu Leu Cys Leu Leu Leu Thr Ala Ala Ala
1               5                   10                  15

Phe Ser Pro Gln Gly Leu Ala Gln Pro Val Gly Ile Asn Thr Ser Thr
            20                  25                  30

Thr Cys Cys Tyr Arg Phe Ile Asn Lys Lys Ile Pro Lys Gln Arg Leu
        35                  40                  45

Glu Ser Tyr Arg Arg Thr Thr Ser Ser His Cys Pro Arg Glu Ala Val
    50                  55                  60

Ile Phe Lys Thr Lys Leu Asp Lys Glu Ile Cys Ala Asp Pro Thr Gln
65                  70                  75                  80

Lys Trp Val Gln Asp Phe Met Lys His Leu Asp Lys Lys Thr Gln Thr
                85                  90                  95

Pro Lys Leu

<210> SEQ ID NO 8
<211> LENGTH: 99
<212> TYPE: PRT
<213> ORGANISM: Homo sapiens

<400> SEQUENCE: 8

Met Lys Val Ser Ala Ala Leu Leu Cys Leu Leu Leu Met Ala Ala Thr
1               5                   10                  15

Phe Ser Pro Gln Gly Leu Ala Gln Pro Asp Ser Val Ser Ile Pro Ile
            20                  25                  30

Thr Cys Cys Phe Asn Val Ile Asn Arg Lys Ile Pro Ile Gln Arg Leu
        35                  40                  45

Glu Ser Tyr Thr Arg Ile Thr Asn Ile Gln Cys Pro Lys Glu Ala Val
    50                  55                  60

Ile Phe Lys Thr Lys Arg Gly Lys Glu Val Cys Ala Asp Pro Lys Glu
65                  70                  75                  80

Arg Trp Val Arg Asp Ser Met Lys His Leu Asp Gln Ile Phe Gln Asn
                85                  90                  95

Leu Lys Pro

<210> SEQ ID NO 9
<211> LENGTH: 97
<212> TYPE: PRT
<213> ORGANISM: Homo sapiens

<400> SEQUENCE: 9

Met Lys Val Ser Ala Ala Leu Leu Trp Leu Leu Leu Ile Ala Ala Ala
1               5                   10                  15

Phe Ser Pro Gln Gly Leu Ala Gly Pro Ala Ser Val Pro Thr Thr Cys
            20                  25                  30

Cys Phe Asn Leu Ala Asn Arg Lys Ile Pro Leu Gln Arg Leu Glu Ser
        35                  40                  45

Tyr Arg Arg Ile Thr Ser Gly Lys Cys Pro Gln Lys Ala Val Ile Phe
    50                  55                  60

Lys Thr Lys Leu Ala Lys Asp Ile Cys Ala Asp Pro Lys Lys Lys Trp
65                  70                  75                  80

Val Gln Asp Ser Met Lys Tyr Leu Asp Gln Lys Ser Pro Thr Pro Lys
                85                  90                  95

Pro

<210> SEQ ID NO 10
<211> LENGTH: 98
<212> TYPE: PRT
<213> ORGANISM: Homo sapiens

<400> SEQUENCE: 10

```
Met Lys Val Ser Ala Val Leu Leu Cys Leu Leu Leu Met Thr Ala Ala
1               5                   10                  15

Phe Asn Pro Gln Gly Leu Ala Gln Pro Asp Ala Leu Asn Val Pro Ser
            20                  25                  30

Thr Cys Cys Phe Thr Phe Ser Ser Lys Lys Ile Ser Leu Gln Arg Leu
        35                  40                  45

Lys Ser Tyr Val Ile Thr Thr Ser Arg Cys Pro Gln Lys Ala Val Ile
    50                  55                  60

Phe Arg Thr Lys Leu Gly Lys Glu Ile Cys Ala Asp Pro Lys Glu Lys
65                  70                  75                  80

Trp Val Gln Asn Tyr Met Lys His Leu Gly Arg Lys Ala His Thr Leu
                85                  90                  95

Lys Thr
```

<210> SEQ ID NO 11
<211> LENGTH: 93
<212> TYPE: PRT
<213> ORGANISM: Homo sapiens

<400> SEQUENCE: 11

```
Met Lys Ile Ser Val Ala Ala Ile Pro Phe Phe Leu Leu Ile Thr Ile
1               5                   10                  15

Ala Leu Gly Thr Lys Thr Glu Ser Ser Ser Arg Gly Pro Tyr His Pro
            20                  25                  30

Ser Glu Cys Cys Phe Thr Tyr Thr Thr Tyr Lys Ile Pro Arg Gln Arg
        35                  40                  45

Ile Met Asp Tyr Tyr Glu Thr Asn Ser Gln Cys Ser Lys Pro Gly Ile
    50                  55                  60

Val Phe Ile Thr Lys Arg Gly His Ser Val Cys Thr Asn Pro Ser Asp
65                  70                  75                  80

Lys Trp Val Gln Asp Tyr Ile Lys Asp Met Lys Glu Asn
                85                  90
```

<210> SEQ ID NO 12
<211> LENGTH: 109
<212> TYPE: PRT
<213> ORGANISM: Homo sapiens

<400> SEQUENCE: 12

```
Met Lys Ile Ser Val Ala Ala Ile Pro Phe Phe Leu Leu Ile Thr Ile
1               5                   10                  15

Ala Leu Gly Thr Lys Thr Glu Ser Ser Ser Gln Thr Gly Gly Lys Pro
            20                  25                  30

Lys Val Val Lys Ile Gln Leu Lys Leu Val Gly Gly Pro Tyr His Pro
        35                  40                  45

Ser Glu Cys Cys Phe Thr Tyr Thr Thr Tyr Lys Ile Pro Arg Gln Arg
    50                  55                  60

Ile Met Asp Tyr Tyr Glu Thr Asn Ser Gln Cys Ser Lys Pro Gly Ile
65                  70                  75                  80

Val Phe Ile Thr Lys Arg Gly His Ser Val Cys Thr Asn Pro Ser Asp
                85                  90                  95
```

```
Lys Trp Val Gln Asp Tyr Ile Lys Asp Met Lys Glu Asn
            100                 105


<210> SEQ ID NO 13
<211> LENGTH: 113
<212> TYPE: PRT
<213> ORGANISM: Homo sapiens

<400> SEQUENCE: 13

Met Lys Val Ser Val Ala Ala Leu Ser Cys Leu Met Leu Val Ala Val
1               5                   10                  15

Leu Gly Ser Gln Ala Gln Phe Ile Asn Asp Ala Glu Thr Glu Leu Met
            20                  25                  30

Met Ser Lys Leu Pro Leu Glu Asn Pro Val Val Leu Asn Ser Phe His
        35                  40                  45

Phe Ala Ala Asp Cys Cys Thr Ser Tyr Ile Ser Gln Ser Ile Pro Cys
    50                  55                  60

Ser Leu Met Lys Ser Tyr Phe Glu Thr Ser Ser Glu Cys Ser Lys Pro
65                  70                  75                  80

Gly Val Ile Phe Leu Thr Lys Lys Gly Arg Gln Val Cys Ala Lys Pro
                85                  90                  95

Ser Gly Pro Gly Val Gln Asp Cys Met Lys Lys Leu Lys Pro Tyr Ser
            100                 105                 110

Ile


<210> SEQ ID NO 14
<211> LENGTH: 120
<212> TYPE: PRT
<213> ORGANISM: Homo sapiens

<400> SEQUENCE: 14

Met Lys Val Ser Glu Ala Ala Leu Ser Leu Leu Val Leu Ile Leu Ile
1               5                   10                  15

Ile Thr Ser Ala Ser Arg Ser Gln Pro Lys Val Pro Glu Trp Val Asn
            20                  25                  30

Thr Pro Ser Thr Cys Cys Leu Lys Tyr Tyr Glu Lys Val Leu Pro Arg
        35                  40                  45

Arg Leu Val Val Gly Tyr Arg Lys Ala Leu Asn Cys His Leu Pro Ala
    50                  55                  60

Ile Ile Phe Val Thr Lys Arg Asn Arg Glu Val Cys Thr Asn Pro Asn
65                  70                  75                  80

Asp Asp Trp Val Gln Glu Tyr Ile Lys Asp Pro Asn Leu Pro Leu Leu
                85                  90                  95

Pro Thr Arg Asn Leu Ser Thr Val Lys Ile Ile Thr Ala Lys Asn Gly
            100                 105                 110

Gln Pro Gln Leu Leu Asn Ser Gln
        115                 120


<210> SEQ ID NO 15
<211> LENGTH: 94
<212> TYPE: PRT
<213> ORGANISM: Homo sapiens

<400> SEQUENCE: 15

Met Ala Pro Leu Lys Met Leu Ala Leu Val Thr Leu Leu Leu Gly Ala
1               5                   10                  15

Ser Leu Gln His Ile His Ala Ala Arg Gly Thr Asn Val Gly Arg Glu
            20                  25                  30
```

```
Cys Cys Leu Glu Tyr Phe Lys Gly Ala Ile Pro Leu Arg Lys Leu Lys
        35                  40                  45

Thr Trp Tyr Gln Thr Ser Glu Asp Cys Ser Arg Asp Ala Ile Val Phe
    50                  55                  60

Val Thr Val Gln Gly Arg Ala Ile Cys Ser Asp Pro Asn Asn Lys Arg
65                  70                  75                  80

Val Lys Asn Ala Val Lys Tyr Leu Gln Ser Leu Glu Arg Ser
                85                  90


<210> SEQ ID NO 16
<211> LENGTH: 89
<212> TYPE: PRT
<213> ORGANISM: Homo sapiens

<400> SEQUENCE: 16

Met Lys Gly Leu Ala Ala Ala Leu Leu Val Leu Val Cys Thr Met Ala
1               5                   10                  15

Leu Cys Ser Cys Ala Gln Val Gly Thr Asn Lys Glu Leu Cys Cys Leu
            20                  25                  30

Val Tyr Thr Ser Trp Gln Ile Pro Gln Lys Phe Ile Val Asp Tyr Ser
        35                  40                  45

Glu Thr Ser Pro Gln Cys Pro Lys Pro Gly Val Ile Leu Leu Thr Lys
    50                  55                  60

Arg Gly Arg Gln Ile Cys Ala Asp Pro Asn Lys Lys Trp Val Gln Lys
65                  70                  75                  80

Tyr Ile Ser Asp Leu Lys Leu Asn Ala
                85


<210> SEQ ID NO 17
<211> LENGTH: 98
<212> TYPE: PRT
<213> ORGANISM: Homo sapiens

<400> SEQUENCE: 17

Met Ala Leu Leu Leu Ala Leu Ser Leu Leu Val Leu Trp Thr Ser Pro
1               5                   10                  15

Ala Pro Thr Leu Ser Gly Thr Asn Asp Ala Glu Asp Cys Cys Leu Ser
            20                  25                  30

Val Thr Gln Lys Pro Ile Pro Gly Tyr Ile Val Arg Asn Phe His Tyr
        35                  40                  45

Leu Leu Ile Lys Asp Gly Cys Arg Val Pro Ala Val Val Phe Thr Thr
    50                  55                  60

Leu Arg Gly Arg Gln Leu Cys Ala Pro Pro Asp Gln Pro Trp Val Glu
65                  70                  75                  80

Arg Ile Ile Gln Arg Leu Gln Arg Thr Ser Ala Lys Met Lys Arg Arg
                85                  90                  95

Ser Ser


<210> SEQ ID NO 18
<211> LENGTH: 96
<212> TYPE: PRT
<213> ORGANISM: Homo sapiens

<400> SEQUENCE: 18

Met Cys Cys Thr Lys Ser Leu Leu Leu Ala Ala Leu Met Ser Val Leu
1               5                   10                  15

Leu Leu His Leu Cys Gly Glu Ser Glu Ala Ala Ser Asn Phe Asp Cys
```

-continued

```
            20                  25                  30

Cys Leu Gly Tyr Thr Asp Arg Ile Leu His Pro Lys Phe Ile Val Gly
        35                  40                  45

Phe Thr Arg Gln Leu Ala Asn Glu Gly Cys Asp Ile Asn Ala Ile Ile
    50                  55                  60

Phe His Thr Lys Lys Lys Leu Ser Val Cys Ala Asn Pro Lys Gln Thr
65                  70                  75                  80

Trp Val Lys Tyr Ile Val Arg Leu Leu Ser Lys Lys Val Lys Asn Met
                85                  90                  95


<210> SEQ ID NO 19
<211> LENGTH: 95
<212> TYPE: PRT
<213> ORGANISM: Homo sapiens

<400> SEQUENCE: 19

Met Cys Cys Thr Lys Ser Leu Leu Leu Ala Ala Leu Met Ser Val Leu
1               5                   10                  15

Leu Leu His Leu Cys Gly Glu Ser Glu Ala Ser Asn Phe Asp Cys Cys
            20                  25                  30

Leu Gly Tyr Thr Asp Arg Ile Leu His Pro Lys Phe Ile Val Gly Phe
        35                  40                  45

Thr Arg Gln Leu Ala Asn Glu Gly Cys Asp Ile Asn Ala Ile Ile Phe
    50                  55                  60

His Thr Lys Lys Lys Leu Ser Val Cys Ala Asn Pro Lys Gln Thr Trp
65                  70                  75                  80

Val Lys Tyr Ile Val Arg Leu Leu Ser Lys Lys Val Lys Asn Met
                85                  90                  95


<210> SEQ ID NO 20
<211> LENGTH: 134
<212> TYPE: PRT
<213> ORGANISM: Homo sapiens

<400> SEQUENCE: 20

Met Ala Gln Ser Leu Ala Leu Ser Leu Leu Ile Leu Val Leu Ala Phe
1               5                   10                  15

Gly Ile Pro Arg Thr Gln Gly Ser Asp Gly Gly Ala Gln Asp Cys Cys
            20                  25                  30

Leu Lys Tyr Ser Gln Arg Lys Ile Pro Ala Lys Val Val Arg Ser Tyr
        35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro
    130


<210> SEQ ID NO 21
<211> LENGTH: 93
<212> TYPE: PRT
```

<213> ORGANISM: Homo sapiens

<400> SEQUENCE: 21

Met Asp Arg Leu Gln Thr Ala Leu Leu Val Val Leu Val Leu Leu Ala
1 5 10 15

Val Ala Leu Gln Ala Thr Glu Ala Gly Pro Tyr Gly Ala Asn Met Glu
20 25 30

Asp Ser Val Cys Cys Arg Asp Tyr Val Arg Tyr Arg Leu Pro Leu Arg
35 40 45

Val Val Lys His Phe Tyr Trp Thr Ser Asp Ser Cys Pro Arg Pro Gly
50 55 60

Val Val Leu Leu Thr Phe Arg Asp Lys Glu Ile Cys Ala Asp Pro Arg
65 70 75 80

Val Pro Trp Val Lys Met Ile Leu Asn Lys Leu Ser Gln
85 90

<210> SEQ ID NO 22
<211> LENGTH: 120
<212> TYPE: PRT
<213> ORGANISM: Homo sapiens

<400> SEQUENCE: 22

Met Lys Val Ser Val Ala Ala Leu Ser Cys Leu Met Leu Val Thr Ala
1 5 10 15

Leu Gly Ser Gln Ala Arg Val Thr Lys Asp Ala Glu Thr Glu Phe Met
20 25 30

Met Ser Lys Leu Pro Leu Glu Asn Pro Val Leu Leu Asp Arg Phe His
35 40 45

Ala Thr Ser Ala Asp Cys Cys Ile Ser Tyr Thr Pro Arg Ser Ile Pro
50 55 60

Cys Ser Leu Leu Glu Ser Tyr Phe Glu Thr Asn Ser Glu Cys Ser Lys
65 70 75 80

Pro Gly Val Ile Phe Leu Thr Lys Lys Gly Arg Arg Phe Cys Ala Asn
85 90 95

Pro Ser Asp Lys Gln Val Gln Val Cys Val Arg Met Leu Lys Leu Asp
100 105 110

Thr Arg Ile Lys Thr Arg Lys Asn
115 120

<210> SEQ ID NO 23
<211> LENGTH: 137
<212> TYPE: PRT
<213> ORGANISM: Homo sapiens

<400> SEQUENCE: 23

Met Lys Val Ser Val Ala Ala Leu Ser Cys Leu Met Leu Val Thr Ala
1 5 10 15

Leu Gly Ser Gln Ala Arg Val Thr Lys Asp Ala Glu Thr Glu Phe Met
20 25 30

Met Ser Lys Leu Pro Leu Glu Asn Pro Val Leu Leu Asp Met Leu Trp
35 40 45

Arg Arg Lys Ile Gly Pro Gln Met Thr Leu Ser His Ala Ala Gly Phe
50 55 60

His Ala Thr Ser Ala Asp Cys Cys Ile Ser Tyr Thr Pro Arg Ser Ile
65 70 75 80

Pro Cys Ser Leu Leu Glu Ser Tyr Phe Glu Thr Asn Ser Glu Cys Ser
85 90 95

```
Lys Pro Gly Val Ile Phe Leu Thr Lys Lys Gly Arg Arg Phe Cys Ala
            100                 105                 110

Asn Pro Ser Asp Lys Gln Val Gln Val Cys Val Arg Met Leu Lys Leu
        115                 120                 125

Asp Thr Arg Ile Lys Thr Arg Lys Asn
    130                 135


<210> SEQ ID NO 24
<211> LENGTH: 119
<212> TYPE: PRT
<213> ORGANISM: Homo sapiens

<400> SEQUENCE: 24

Met Ala Gly Leu Met Thr Ile Val Thr Ser Leu Leu Phe Leu Gly Val
1               5                   10                  15

Cys Ala His His Ile Ile Pro Thr Gly Ser Val Val Ile Pro Ser Pro
            20                  25                  30

Cys Cys Met Phe Phe Val Ser Lys Arg Ile Pro Glu Asn Arg Val Val
        35                  40                  45

Ser Tyr Gln Leu Ser Ser Arg Ser Thr Cys Leu Lys Ala Gly Val Ile
    50                  55                  60

Phe Thr Thr Lys Lys Gly Gln Gln Phe Cys Gly Asp Pro Lys Gln Glu
65                  70                  75                  80

Trp Val Gln Arg Tyr Met Lys Asn Leu Asp Ala Lys Gln Lys Lys Ala
                85                  90                  95

Ser Pro Arg Ala Arg Ala Val Ala Val Lys Gly Pro Val Gln Arg Tyr
            100                 105                 110

Pro Gly Asn Gln Thr Thr Cys
        115


<210> SEQ ID NO 25
<211> LENGTH: 150
<212> TYPE: PRT
<213> ORGANISM: Homo sapiens

<400> SEQUENCE: 25

Met Asn Leu Trp Leu Leu Ala Cys Leu Val Ala Gly Phe Leu Gly Ala
1               5                   10                  15

Trp Ala Pro Ala Val His Thr Gln Gly Val Phe Glu Asp Cys Cys Leu
            20                  25                  30

Ala Tyr His Tyr Pro Ile Gly Trp Ala Val Leu Arg Arg Ala Trp Thr
        35                  40                  45

Tyr Arg Ile Gln Glu Val Ser Gly Ser Cys Asn Leu Pro Ala Ala Ile
    50                  55                  60

Phe Tyr Leu Pro Lys Arg His Arg Lys Val Cys Gly Asn Pro Lys Ser
65                  70                  75                  80

Arg Glu Val Gln Arg Ala Met Lys Leu Leu Asp Ala Arg Asn Lys Val
                85                  90                  95

Phe Ala Lys Leu His His Asn Thr Gln Thr Phe Gln Ala Gly Pro His
            100                 105                 110

Ala Val Lys Lys Leu Ser Ser Gly Asn Ser Lys Leu Ser Ser Ser Lys
        115                 120                 125

Phe Ser Asn Pro Ile Ser Ser Ser Lys Arg Asn Val Ser Leu Leu Ile
    130                 135                 140

Ser Ala Asn Ser Gly Leu
145                 150
```

<210> SEQ ID NO 26
<211> LENGTH: 84
<212> TYPE: PRT
<213> ORGANISM: Homo sapiens

<400> SEQUENCE: 26

```
Met Asn Leu Trp Leu Leu Ala Cys Leu Val Ala Gly Phe Leu Gly Ala
1               5                   10                  15

Trp Ala Pro Ala Val His Thr Gln Gly Val Phe Glu Asp Cys Cys Leu
            20                  25                  30

Ala Tyr His Tyr Pro Ile Gly Trp Ala Val Leu Arg Arg Ala Trp Thr
        35                  40                  45

Tyr Arg Ile Gln Glu Val Ser Gly Ser Cys Asn Leu Pro Ala Ala Ile
    50                  55                  60

Arg Pro Ser Cys Cys Lys Glu Val Glu Phe Trp Lys Leu Gln Val Ile
65                  70                  75                  80

Ile Val Gln Val
```

<210> SEQ ID NO 27
<211> LENGTH: 84
<212> TYPE: PRT
<213> ORGANISM: Homo sapiens

<400> SEQUENCE: 27

```
Met Asn Leu Trp Leu Leu Ala Cys Leu Val Ala Gly Phe Leu Gly Ala
1               5                   10                  15

Trp Ala Pro Ala Val His Thr Gln Gly Val Phe Glu Asp Cys Cys Leu
            20                  25                  30

Ala Tyr His Tyr Pro Ile Gly Trp Ala Val Leu Arg Arg Ala Trp Thr
        35                  40                  45

Tyr Arg Ile Gln Glu Val Ser Gly Ser Cys Asn Leu Pro Ala Ala Ile
    50                  55                  60

Arg Pro Ser Cys Cys Lys Glu Val Glu Phe Trp Lys Leu Gln Val Ile
65                  70                  75                  80

Ile Ile Gln Val
```

<210> SEQ ID NO 28
<211> LENGTH: 94
<212> TYPE: PRT
<213> ORGANISM: Homo sapiens

<400> SEQUENCE: 28

```
Met Met Gly Leu Ser Leu Ala Ser Ala Val Leu Leu Ala Ser Leu Leu
1               5                   10                  15

Ser Leu His Leu Gly Thr Ala Thr Arg Gly Ser Asp Ile Ser Lys Thr
            20                  25                  30

Cys Cys Phe Gln Tyr Ser His Lys Pro Leu Pro Trp Thr Trp Val Arg
        35                  40                  45

Ser Tyr Glu Phe Thr Ser Asn Ser Cys Ser Gln Arg Ala Val Ile Phe
    50                  55                  60

Thr Thr Lys Arg Gly Lys Lys Val Cys Thr His Pro Arg Lys Lys Trp
65                  70                  75                  80

Val Gln Lys Tyr Ile Ser Leu Leu Lys Thr Pro Lys Gln Leu
                85                  90
```

<210> SEQ ID NO 29

-continued

<211> LENGTH: 112
<212> TYPE: PRT
<213> ORGANISM: Homo sapiens

<400> SEQUENCE: 29

```
Met Lys Gly Pro Pro Thr Phe Cys Ser Leu Leu Leu Leu Ser Leu Leu
1               5                   10                  15

Leu Ser Pro Asp Pro Thr Ala Ala Phe Leu Leu Pro Pro Ser Thr Ala
            20                  25                  30

Cys Cys Thr Gln Leu Tyr Arg Lys Pro Leu Ser Asp Lys Leu Leu Arg
        35                  40                  45

Lys Val Ile Gln Val Glu Leu Gln Glu Ala Asp Gly Asp Cys His Leu
    50                  55                  60

Gln Ala Phe Val Leu His Leu Ala Gln Arg Ser Ile Cys Ile His Pro
65                  70                  75                  80

Gln Asn Pro Ser Leu Ser Gln Trp Phe Glu His Gln Glu Arg Lys Leu
                85                  90                  95

His Gly Thr Leu Pro Lys Leu Asn Phe Gly Met Leu Arg Lys Met Gly
            100                 105                 110
```

<210> SEQ ID NO 30
<211> LENGTH: 127
<212> TYPE: PRT
<213> ORGANISM: Homo sapiens

<400> SEQUENCE: 30

```
Met Gln Gln Arg Gly Leu Ala Ile Val Ala Leu Ala Val Cys Ala Ala
1               5                   10                  15

Leu His Ala Ser Glu Ala Ile Leu Pro Ile Ala Ser Ser Cys Cys Thr
            20                  25                  30

Glu Val Ser His His Ile Ser Arg Arg Leu Leu Glu Arg Val Asn Met
        35                  40                  45

Cys Arg Ile Gln Arg Ala Asp Gly Asp Cys Asp Leu Ala Ala Val Ile
    50                  55                  60

Leu His Val Lys Arg Arg Arg Ile Cys Val Ser Pro His Asn His Thr
65                  70                  75                  80

Val Lys Gln Trp Met Lys Val Gln Ala Ala Lys Lys Asn Gly Lys Gly
                85                  90                  95

Asn Val Cys His Arg Lys Lys His His Gly Lys Arg Asn Ser Asn Arg
            100                 105                 110

Ala His Gln Gly Lys His Glu Thr Tyr Gly His Lys Thr Pro Tyr
        115                 120                 125
```

<210> SEQ ID NO 31
<211> LENGTH: 107
<212> TYPE: PRT
<213> ORGANISM: Homo sapiens

<400> SEQUENCE: 31

```
Met Ala Arg Ala Ala Leu Ser Ala Ala Pro Ser Asn Pro Arg Leu Leu
1               5                   10                  15

Arg Val Ala Leu Leu Leu Leu Leu Leu Val Ala Ala Gly Arg Arg Ala
            20                  25                  30

Ala Gly Ala Ser Val Ala Thr Glu Leu Arg Cys Gln Cys Leu Gln Thr
        35                  40                  45

Leu Gln Gly Ile His Pro Lys Asn Ile Gln Ser Val Asn Val Lys Ser
    50                  55                  60
```

```
Pro Gly Pro His Cys Ala Gln Thr Glu Val Ile Ala Thr Leu Lys Asn
65                  70                  75                  80

Gly Arg Lys Ala Cys Leu Asn Pro Ala Ser Pro Ile Val Lys Lys Ile
                85                  90                  95

Ile Glu Lys Met Leu Asn Ser Asp Lys Ser Asn
            100                 105


<210> SEQ ID NO 32
<211> LENGTH: 107
<212> TYPE: PRT
<213> ORGANISM: Homo sapiens

<400> SEQUENCE: 32

Met Ala Arg Ala Thr Leu Ser Ala Ala Pro Ser Asn Pro Arg Leu Leu
1               5                   10                  15

Arg Val Ala Leu Leu Leu Leu Leu Leu Val Ala Ala Ser Arg Arg Ala
            20                  25                  30

Ala Gly Ala Pro Leu Ala Thr Glu Leu Arg Cys Gln Cys Leu Gln Thr
        35                  40                  45

Leu Gln Gly Ile His Leu Lys Asn Ile Gln Ser Val Lys Val Lys Ser
    50                  55                  60

Pro Gly Pro His Cys Ala Gln Thr Glu Val Ile Ala Thr Leu Lys Asn
65                  70                  75                  80

Gly Gln Lys Ala Cys Leu Asn Pro Ala Ser Pro Met Val Lys Lys Ile
                85                  90                  95

Ile Glu Lys Met Leu Lys Asn Gly Lys Ser Asn
            100                 105


<210> SEQ ID NO 33
<211> LENGTH: 107
<212> TYPE: PRT
<213> ORGANISM: Homo sapiens

<400> SEQUENCE: 33

Met Ala His Ala Thr Leu Ser Ala Ala Pro Ser Asn Pro Arg Leu Leu
1               5                   10                  15

Arg Val Ala Leu Leu Leu Leu Leu Leu Val Ala Ala Ser Arg Arg Ala
            20                  25                  30

Ala Gly Ala Ser Val Val Thr Glu Leu Arg Cys Gln Cys Leu Gln Thr
        35                  40                  45

Leu Gln Gly Ile His Leu Lys Asn Ile Gln Ser Val Asn Val Arg Ser
    50                  55                  60

Pro Gly Pro His Cys Ala Gln Thr Glu Val Ile Ala Thr Leu Lys Asn
65                  70                  75                  80

Gly Lys Lys Ala Cys Leu Asn Pro Ala Ser Pro Met Val Gln Lys Ile
                85                  90                  95

Ile Glu Lys Ile Leu Asn Lys Gly Ser Thr Asn
            100                 105


<210> SEQ ID NO 34
<211> LENGTH: 101
<212> TYPE: PRT
<213> ORGANISM: Homo sapiens

<400> SEQUENCE: 34

Met Ser Ser Ala Ala Gly Phe Cys Ala Ser Arg Pro Gly Leu Leu Phe
1               5                   10                  15

Leu Gly Leu Leu Leu Leu Pro Leu Val Val Ala Phe Ala Ser Ala Glu
```

```
            20                  25                  30

Ala Glu Glu Asp Gly Asp Leu Gln Cys Leu Cys Val Lys Thr Thr Ser
        35                  40                  45

Gln Val Arg Pro Arg His Ile Thr Ser Leu Glu Val Ile Lys Ala Gly
    50                  55                  60

Pro His Cys Pro Thr Ala Gln Leu Ile Ala Thr Leu Lys Asn Gly Arg
65                  70                  75                  80

Lys Ile Cys Leu Asp Leu Gln Ala Pro Leu Tyr Lys Lys Ile Ile Lys
                85                  90                  95

Lys Leu Leu Glu Ser
            100


<210> SEQ ID NO 35
<211> LENGTH: 114
<212> TYPE: PRT
<213> ORGANISM: Homo sapiens

<400> SEQUENCE: 35

Met Ser Leu Leu Ser Ser Arg Ala Ala Arg Val Pro Gly Pro Ser Ser
1               5                   10                  15

Ser Leu Cys Ala Leu Leu Val Leu Leu Leu Leu Leu Thr Gln Pro Gly
            20                  25                  30

Pro Ile Ala Ser Ala Gly Pro Ala Ala Ala Val Leu Arg Glu Leu Arg
        35                  40                  45

Cys Val Cys Leu Gln Thr Thr Gln Gly Val His Pro Lys Met Ile Ser
    50                  55                  60

Asn Leu Gln Val Phe Ala Ile Gly Pro Gln Cys Ser Lys Val Glu Val
65                  70                  75                  80

Val Ala Ser Leu Lys Asn Gly Lys Glu Ile Cys Leu Asp Pro Glu Ala
                85                  90                  95

Pro Phe Leu Lys Lys Val Ile Gln Lys Ile Leu Asp Gly Gly Asn Lys
            100                 105                 110

Glu Asn


<210> SEQ ID NO 36
<211> LENGTH: 114
<212> TYPE: PRT
<213> ORGANISM: Homo sapiens

<400> SEQUENCE: 36

Met Ser Leu Pro Ser Ser Arg Ala Ala Arg Val Pro Gly Pro Ser Gly
1               5                   10                  15

Ser Leu Cys Ala Leu Leu Ala Leu Leu Leu Leu Leu Thr Pro Pro Gly
            20                  25                  30

Pro Leu Ala Ser Ala Gly Pro Val Ser Ala Val Leu Thr Glu Leu Arg
        35                  40                  45

Cys Thr Cys Leu Arg Val Thr Leu Arg Val Asn Pro Lys Thr Ile Gly
    50                  55                  60

Lys Leu Gln Val Phe Pro Ala Gly Pro Gln Cys Ser Lys Val Glu Val
65                  70                  75                  80

Val Ala Ser Leu Lys Asn Gly Lys Gln Val Cys Leu Asp Pro Glu Ala
                85                  90                  95

Pro Phe Leu Lys Lys Val Ile Gln Lys Ile Leu Asp Ser Gly Asn Lys
            100                 105                 110

Lys Asn
```

<210> SEQ ID NO 37
<211> LENGTH: 128
<212> TYPE: PRT
<213> ORGANISM: Homo sapiens

<400> SEQUENCE: 37

```
Met Ser Leu Arg Leu Asp Thr Thr Pro Ser Cys Asn Ser Ala Arg Pro
1               5                   10                  15

Leu His Ala Leu Gln Val Leu Leu Leu Leu Ser Leu Leu Leu Thr Ala
            20                  25                  30

Leu Ala Ser Ser Thr Lys Gly Gln Thr Lys Arg Asn Leu Ala Lys Gly
        35                  40                  45

Lys Glu Glu Ser Leu Asp Ser Asp Leu Tyr Ala Glu Leu Arg Cys Met
    50                  55                  60

Cys Ile Lys Thr Thr Ser Gly Ile His Pro Lys Asn Ile Gln Ser Leu
65                  70                  75                  80

Glu Val Ile Gly Lys Gly Thr His Cys Asn Gln Val Glu Val Ile Ala
                85                  90                  95

Thr Leu Lys Asp Gly Arg Lys Ile Cys Leu Asp Pro Asp Ala Pro Arg
            100                 105                 110

Ile Lys Lys Ile Val Gln Lys Lys Leu Ala Gly Asp Glu Ser Ala Asp
        115                 120                 125
```

<210> SEQ ID NO 38
<211> LENGTH: 99
<212> TYPE: PRT
<213> ORGANISM: Homo sapiens

<400> SEQUENCE: 38

```
Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser
```

<210> SEQ ID NO 39
<211> LENGTH: 125
<212> TYPE: PRT
<213> ORGANISM: Homo sapiens

<400> SEQUENCE: 39

```
Met Lys Lys Ser Gly Val Leu Phe Leu Leu Gly Ile Ile Leu Leu Val
1               5                   10                  15

Leu Ile Gly Val Gln Gly Thr Pro Val Val Arg Lys Gly Arg Cys Ser
            20                  25                  30

Cys Ile Ser Thr Asn Gln Gly Thr Ile His Leu Gln Ser Leu Lys Asp
        35                  40                  45

Leu Lys Gln Phe Ala Pro Ser Pro Ser Cys Glu Lys Ile Glu Ile Ile
    50                  55                  60
```

-continued

```
Ala Thr Leu Lys Asn Gly Val Gln Thr Cys Leu Asn Pro Asp Ser Ala
65                  70                  75                  80

Asp Val Lys Glu Leu Ile Lys Lys Trp Glu Lys Gln Val Ser Gln Lys
                85                  90                  95

Lys Lys Gln Lys Asn Gly Lys Lys His Gln Lys Lys Lys Val Leu Lys
            100                 105                 110

Val Arg Lys Ser Gln Arg Ser Arg Gln Lys Lys Thr Thr
        115                 120                 125


<210> SEQ ID NO 40
<211> LENGTH: 98
<212> TYPE: PRT
<213> ORGANISM: Homo sapiens

<400> SEQUENCE: 40

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro


<210> SEQ ID NO 41
<211> LENGTH: 94
<212> TYPE: PRT
<213> ORGANISM: Homo sapiens

<400> SEQUENCE: 41

Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
            20                  25                  30

Ile Gly Pro Gly Val Lys Ala Val Lys Val Ala Asp Ile Glu Lys Ala
        35                  40                  45

Ser Ile Met Tyr Pro Ser Asn Asn Cys Asp Lys Ile Glu Val Ile Ile
    50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
                85                  90


<210> SEQ ID NO 42
<211> LENGTH: 93
<212> TYPE: PRT
<213> ORGANISM: Homo sapiens

<400> SEQUENCE: 42

Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
```

```
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90


<210> SEQ ID NO 43
<211> LENGTH: 109
<212> TYPE: PRT
<213> ORGANISM: Homo sapiens

<400> SEQUENCE: 43

Met Lys Phe Ile Ser Thr Ser Leu Leu Leu Met Leu Leu Val Ser Ser
1               5                   10                  15

Leu Ser Pro Val Gln Gly Val Leu Glu Val Tyr Tyr Thr Ser Leu Arg
            20                  25                  30

Cys Arg Cys Val Gln Glu Ser Ser Val Phe Ile Pro Arg Arg Phe Ile
        35                  40                  45

Asp Arg Ile Gln Ile Leu Pro Arg Gly Asn Gly Cys Pro Arg Lys Glu
    50                  55                  60

Ile Ile Val Trp Lys Lys Asn Lys Ser Ile Val Cys Val Asp Pro Gln
65                  70                  75                  80

Ala Glu Trp Ile Gln Arg Met Met Glu Val Leu Arg Lys Arg Ser Ser
                85                  90                  95

Ser Thr Leu Pro Val Pro Val Phe Lys Arg Lys Ile Pro
            100                 105


<210> SEQ ID NO 44
<211> LENGTH: 273
<212> TYPE: PRT
<213> ORGANISM: Homo sapiens

<400> SEQUENCE: 44

Met Ser Gly Ser Gln Ser Glu Val Ala Pro Ser Pro Gln Ser Pro Arg
1               5                   10                  15

Ser Pro Glu Met Gly Arg Asp Leu Arg Pro Gly Ser Arg Val Leu Leu
            20                  25                  30

Leu Leu Leu Leu Leu Leu Leu Val Tyr Leu Thr Gln Pro Gly Asn Gly
        35                  40                  45

Asn Glu Gly Ser Val Thr Gly Ser Cys Tyr Cys Gly Lys Arg Ile Ser
    50                  55                  60

Ser Asp Ser Pro Pro Ser Val Gln Phe Met Asn Arg Leu Arg Lys His
65                  70                  75                  80

Leu Arg Ala Tyr His Arg Cys Leu Tyr Tyr Thr Arg Phe Gln Leu Leu
                85                  90                  95

Ser Trp Ser Val Cys Gly Gly Asn Lys Asp Pro Trp Val Gln Glu Leu
            100                 105                 110

Met Ser Cys Leu Asp Leu Lys Glu Cys Gly His Ala Tyr Ser Gly Ile
        115                 120                 125

Val Ala His Gln Lys His Leu Leu Pro Thr Ser Pro Pro Ile Ser Gln
    130                 135                 140

Ala Ser Glu Gly Ala Ser Ser Asp Ile His Thr Pro Ala Gln Met Leu
```

145 150 155 160

Leu Ser Thr Leu Gln Ser Thr Gln Arg Pro Thr Leu Pro Val Gly Ser
165 170 175

Leu Ser Ser Asp Lys Glu Leu Thr Arg Pro Asn Glu Thr Thr Ile His
180 185 190

Thr Ala Gly His Ser Leu Ala Ala Gly Pro Glu Ala Gly Glu Asn Gln
195 200 205

Lys Gln Pro Glu Lys Asn Ala Gly Pro Thr Ala Arg Thr Ser Ala Thr
210 215 220

Val Pro Val Leu Cys Leu Leu Ala Ile Ile Phe Ile Leu Thr Ala Ala
225 230 235 240

Leu Ser Tyr Val Leu Cys Lys Arg Arg Arg Gly Gln Ser Pro Gln Ser
245 250 255

Ser Pro Asp Leu Pro Val His Tyr Ile Pro Val Ala Pro Asp Ser Asn
260 265 270

Thr

<210> SEQ ID NO 45
<211> LENGTH: 114
<212> TYPE: PRT
<213> ORGANISM: Homo sapiens

<400> SEQUENCE: 45

Met Arg Leu Leu Ile Leu Ala Leu Leu Gly Ile Cys Ser Leu Thr Ala
1 5 10 15

Tyr Ile Val Glu Gly Val Gly Ser Glu Val Ser Asp Lys Arg Thr Cys
20 25 30

Val Ser Leu Thr Thr Gln Arg Leu Pro Val Ser Arg Ile Lys Thr Tyr
35 40 45

Thr Ile Thr Glu Gly Ser Leu Arg Ala Val Ile Phe Ile Thr Lys Arg
50 55 60

Gly Leu Lys Val Cys Ala Asp Pro Gln Ala Thr Trp Val Arg Asp Val
65 70 75 80

Val Arg Ser Met Asp Arg Lys Ser Asn Thr Arg Asn Asn Met Ile Gln
85 90 95

Thr Lys Pro Thr Gly Thr Gln Gln Ser Thr Asn Thr Ala Val Thr Leu
100 105 110

Thr Gly

<210> SEQ ID NO 46
<211> LENGTH: 114
<212> TYPE: PRT
<213> ORGANISM: Homo sapiens

<400> SEQUENCE: 46

Met Arg Leu Leu Ile Leu Ala Leu Leu Gly Ile Cys Ser Leu Thr Ala
1 5 10 15

Tyr Ile Val Glu Gly Val Gly Ser Glu Val Ser His Arg Arg Thr Cys
20 25 30

Val Ser Leu Thr Thr Gln Arg Leu Pro Val Ser Arg Ile Lys Thr Tyr
35 40 45

Thr Ile Thr Glu Gly Ser Leu Arg Ala Val Ile Phe Ile Thr Lys Arg
50 55 60

Gly Leu Lys Val Cys Ala Asp Pro Gln Ala Thr Trp Val Arg Asp Val
65 70 75 80

```
Val Arg Ser Met Asp Arg Lys Ser Asn Thr Arg Asn Asn Met Ile Gln
                85                  90                  95

Thr Lys Pro Thr Gly Thr Gln Gln Ser Thr Asn Thr Ala Val Thr Leu
            100                 105                 110

Thr Gly


<210> SEQ ID NO 47
<211> LENGTH: 397
<212> TYPE: PRT
<213> ORGANISM: Homo sapiens

<400> SEQUENCE: 47

Met Ala Pro Ile Ser Leu Ser Trp Leu Leu Arg Leu Ala Thr Phe Cys
1               5                   10                  15

His Leu Thr Val Leu Leu Ala Gly Gln His His Gly Val Thr Lys Cys
            20                  25                  30

Asn Ile Thr Cys Ser Lys Met Thr Ser Lys Ile Pro Val Ala Leu Leu
        35                  40                  45

Ile His Tyr Gln Gln Asn Gln Ala Ser Cys Gly Lys Arg Ala Ile Ile
    50                  55                  60

Leu Glu Thr Arg Gln His Arg Leu Phe Cys Ala Asp Pro Lys Glu Gln
65                  70                  75                  80

Trp Val Lys Asp Ala Met Gln His Leu Asp Arg Gln Ala Ala Ala Leu
                85                  90                  95

Thr Arg Asn Gly Gly Thr Phe Glu Lys Gln Ile Gly Glu Val Lys Pro
            100                 105                 110

Arg Thr Thr Pro Ala Ala Gly Gly Met Asp Glu Ser Val Val Leu Glu
        115                 120                 125

Pro Glu Ala Thr Gly Glu Ser Ser Ser Leu Glu Pro Thr Pro Ser Ser
    130                 135                 140

Gln Glu Ala Gln Arg Ala Leu Gly Thr Ser Pro Glu Leu Pro Thr Gly
145                 150                 155                 160

Val Thr Gly Ser Ser Gly Thr Arg Leu Pro Pro Thr Pro Lys Ala Gln
                165                 170                 175

Asp Gly Gly Pro Val Gly Thr Glu Leu Phe Arg Val Pro Pro Val Ser
            180                 185                 190

Thr Ala Ala Thr Trp Gln Ser Ser Ala Pro His Gln Pro Gly Pro Ser
        195                 200                 205

Leu Trp Ala Glu Ala Lys Thr Ser Glu Ala Pro Ser Thr Gln Asp Pro
    210                 215                 220

Ser Thr Gln Ala Ser Thr Ala Ser Ser Pro Ala Pro Glu Glu Asn Ala
225                 230                 235                 240

Pro Ser Glu Gly Gln Arg Val Trp Gly Gln Gly Gln Ser Pro Arg Pro
                245                 250                 255

Glu Asn Ser Leu Glu Arg Glu Glu Met Gly Pro Val Pro Ala His Thr
            260                 265                 270

Asp Ala Phe Gln Asp Trp Gly Pro Gly Ser Met Ala His Val Ser Val
        275                 280                 285

Val Pro Val Ser Ser Glu Gly Thr Pro Ser Arg Glu Pro Val Ala Ser
    290                 295                 300

Gly Ser Trp Thr Pro Lys Ala Glu Glu Pro Ile His Ala Thr Met Asp
305                 310                 315                 320

Pro Gln Arg Leu Gly Val Leu Ile Thr Pro Val Pro Asp Ala Gln Ala
                325                 330                 335
```

-continued

```
Ala Thr Arg Arg Gln Ala Val Gly Leu Leu Ala Phe Leu Gly Leu Leu
            340                 345                 350

Phe Cys Leu Gly Val Ala Met Phe Thr Tyr Gln Ser Leu Gln Gly Cys
        355                 360                 365

Pro Arg Lys Met Ala Gly Glu Met Ala Glu Gly Leu Arg Tyr Ile Pro
    370                 375                 380

Arg Ser Cys Gly Ser Asn Ser Tyr Val Leu Val Pro Val
385                 390                 395


<210> SEQ ID NO 48
<211> LENGTH: 233
<212> TYPE: PRT
<213> ORGANISM: Homo sapiens

<400> SEQUENCE: 48

Ser Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230


<210> SEQ ID NO 49
<211> LENGTH: 228
<212> TYPE: PRT
<213> ORGANISM: Homo sapiens

<400> SEQUENCE: 49

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30
```

```
Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225


<210> SEQ ID NO 50
<211> LENGTH: 279
<212> TYPE: PRT
<213> ORGANISM: Homo sapiens

<400> SEQUENCE: 50

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Glu
        35                  40                  45

Pro Lys Ser Cys Asp Thr Pro Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Phe
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175
```

Glu Pro Gln Val Tyr Thr Leu Pro Pro Ser Arg Glu Glu Met Thr Lys
180 185 190

Asn Gln Val Ser Leu Thr Cys Leu Val Lys Gly Phe Tyr Pro Ser Asp
195 200 205

Ile Ala Val Glu Trp Glu Ser Ser Gly Gln Pro Glu Asn Asn Tyr Asn
210 215 220

Thr Thr Pro Pro Met Leu Asp Ser Asp Gly Ser Phe Phe Leu Tyr Ser
225 230 235 240

Lys Leu Thr Val Asp Lys Ser Arg Trp Gln Gln Gly Asn Ile Phe Ser
245 250 255

Cys Ser Val Met His Glu Ala Leu His Asn Arg Phe Thr Gln Lys Ser
260 265 270

Leu Ser Leu Ser Pro Gly Lys
275

<210> SEQ ID NO 51
<211> LENGTH: 229
<212> TYPE: PRT
<213> ORGANISM: Homo sapiens

<400> SEQUENCE: 51

Glu Ser Lys Tyr Gly Pro Pro Cys Pro Ser Cys Pro Ala Pro Glu Phe
1 5 10 15

Leu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Val His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Thr Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Lys
225

<210> SEQ ID NO 52
<211> LENGTH: 303
<212> TYPE: PRT

<213> ORGANISM: Artificial Sequence
<220> FEATURE:
<223> OTHER INFORMATION: CCL2-IgG1Fc

<400> SEQUENCE: 52

```
Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr Asp Lys Thr His
65                  70                  75                  80

Thr Cys Pro Pro Cys Pro Ala Pro Glu Leu Leu Gly Gly Pro Ser Val
                85                  90                  95

Phe Leu Phe Pro Pro Lys Pro Lys Asp Thr Leu Met Ile Ser Arg Thr
            100                 105                 110

Pro Glu Val Thr Cys Val Val Val Asp Val Ser His Glu Asp Pro Glu
        115                 120                 125

Val Lys Phe Asn Trp Tyr Val Asp Gly Val Glu Val His Asn Ala Lys
    130                 135                 140

Thr Lys Pro Arg Glu Glu Gln Tyr Asn Ser Thr Tyr Arg Val Val Ser
145                 150                 155                 160

Val Leu Thr Val Leu His Gln Asp Trp Leu Asn Gly Lys Glu Tyr Lys
                165                 170                 175

Cys Lys Val Ser Asn Lys Ala Leu Pro Ala Pro Ile Glu Lys Thr Ile
            180                 185                 190

Ser Lys Ala Lys Gly Gln Pro Arg Glu Pro Gln Val Tyr Thr Leu Pro
        195                 200                 205

Pro Ser Arg Glu Glu Met Thr Lys Asn Gln Val Ser Leu Thr Cys Leu
    210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
                245                 250                 255

Asp Gly Ser Phe Phe Leu Tyr Ser Lys Leu Thr Val Asp Lys Ser Arg
            260                 265                 270

Trp Gln Gln Gly Asn Val Phe Ser Cys Ser Val Met His Glu Ala Leu
        275                 280                 285

His Asn His Tyr Thr Gln Lys Ser Leu Ser Leu Ser Pro Gly Lys
    290                 295                 300
```

<210> SEQ ID NO 53
<211> LENGTH: 309
<212> TYPE: PRT
<213> ORGANISM: Artificial Sequence
<220> FEATURE:
<223> OTHER INFORMATION: CCL2(5-76)-IgG1Fc

<400> SEQUENCE: 53

```
Ala Leu Ser Leu Ala Leu Val Thr Asn Ser Ile Asn Ala Pro Val Thr
1               5                   10                  15

Cys Cys Tyr Asn Phe Thr Asn Arg Lys Ile Ser Val Gln Arg Leu Ala
            20                  25                  30
```

```
Ser Tyr Arg Arg Ile Thr Ser Ser Lys Cys Pro Lys Glu Ala Val Ile
        35                  40                  45

Phe Lys Thr Ile Val Ala Lys Glu Ile Cys Ala Asp Pro Lys Gln Lys
    50                  55                  60

Trp Val Gln Asp Ser Met Asp His Leu Asp Lys Gln Thr Gln Thr Pro
65                  70                  75                  80

Lys Thr Asp Lys Thr His Thr Cys Pro Pro Cys Pro Ala Pro Glu Leu
                85                  90                  95

Leu Gly Gly Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser His Glu Asp Pro Glu Val Lys Phe Asn Trp Tyr Val Asp Gly Val
    130                 135                 140

Glu Val His Asn Ala Lys Thr Lys Pro Arg Glu Glu Gln Tyr Asn Ser
145                 150                 155                 160

Thr Tyr Arg Val Val Ser Val Leu Thr Val Leu His Gln Asp Trp Leu
                165                 170                 175

Asn Gly Lys Glu Tyr Lys Cys Lys Val Ser Asn Lys Ala Leu Pro Ala
            180                 185                 190

Pro Ile Glu Lys Thr Ile Ser Lys Ala Lys Gly Gln Pro Arg Glu Pro
        195                 200                 205

Gln Val Tyr Thr Leu Pro Pro Ser Arg Glu Glu Met Thr Lys Asn Gln
    210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
                245                 250                 255

Pro Pro Val Leu Asp Ser Asp Gly Ser Phe Phe Leu Tyr Ser Lys Leu
            260                 265                 270

Thr Val Asp Lys Ser Arg Trp Gln Gln Gly Asn Val Phe Ser Cys Ser
        275                 280                 285

Val Met His Glu Ala Leu His Asn His Tyr Thr Gln Lys Ser Leu Ser
    290                 295                 300

Leu Ser Pro Gly Lys
305


<210> SEQ ID NO 54
<211> LENGTH: 299
<212> TYPE: PRT
<213> ORGANISM: Artificial Sequence
<220> FEATURE:
<223> OTHER INFORMATION: CCL2(5-76K/H-A)-IgG1Fc

<400> SEQUENCE: 54

Ile Asn Ala Pro Val Thr Cys Cys Tyr Asn Phe Thr Asn Arg Lys Ile
1               5                   10                  15

Ser Val Gln Arg Leu Ala Ser Tyr Arg Arg Ile Thr Ser Ser Lys Cys
            20                  25                  30

Pro Lys Glu Ala Val Ile Phe Lys Thr Ile Val Ala Ala Glu Ile Cys
        35                  40                  45

Ala Asp Pro Ala Gln Ala Trp Val Gln Asp Ser Met Asp Ala Leu Asp
    50                  55                  60

Ala Gln Thr Gln Thr Pro Ala Thr Asp Lys Thr His Thr Cys Pro Pro
65                  70                  75                  80
```

```
Cys Pro Ala Pro Glu Leu Leu Gly Gly Pro Ser Val Phe Leu Phe Pro
                85                  90                  95

Pro Lys Pro Lys Asp Thr Leu Met Ile Ser Arg Thr Pro Glu Val Thr
            100                 105                 110

Cys Val Val Val Asp Val Ser His Glu Asp Pro Glu Val Lys Phe Asn
        115                 120                 125

Trp Tyr Val Asp Gly Val Glu Val His Asn Ala Lys Thr Lys Pro Arg
    130                 135                 140

Glu Glu Gln Tyr Asn Ser Thr Tyr Arg Val Val Ser Val Leu Thr Val
145                 150                 155                 160

Leu His Gln Asp Trp Leu Asn Gly Lys Glu Tyr Lys Cys Lys Val Ser
                165                 170                 175

Asn Lys Ala Leu Pro Ala Pro Ile Glu Lys Thr Ile Ser Lys Ala Lys
            180                 185                 190

Gly Gln Pro Arg Glu Pro Gln Val Tyr Thr Leu Pro Pro Ser Arg Glu
        195                 200                 205

Glu Met Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
                245                 250                 255

Phe Leu Tyr Ser Lys Leu Thr Val Asp Lys Ser Arg Trp Gln Gln Gly
            260                 265                 270

Asn Val Phe Ser Cys Ser Val Met His Glu Ala Leu His Asn His Tyr
        275                 280                 285

Thr Gln Lys Ser Leu Ser Leu Ser Pro Gly Lys
    290                 295


<210> SEQ ID NO 55
<211> LENGTH: 289
<212> TYPE: PRT
<213> ORGANISM: Artificial Sequence
<220> FEATURE:
<223> OTHER INFORMATION: CCL7-IgG1Fc

<400> SEQUENCE: 55

Phe Ile Asn Lys Lys Ile Pro Lys Gln Arg Leu Glu Ser Tyr Arg Arg
1               5                   10                  15

Thr Thr Ser Ser His Cys Pro Arg Glu Ala Val Ile Phe Lys Thr Lys
            20                  25                  30

Leu Asp Lys Glu Ile Cys Ala Asp Pro Thr Gln Lys Trp Val Gln Asp
        35                  40                  45

Phe Met Lys His Leu Asp Lys Lys Thr Gln Thr Pro Lys Leu Asp Lys
    50                  55                  60

Thr His Thr Cys Pro Pro Cys Pro Ala Pro Glu Leu Leu Gly Gly Pro
65                  70                  75                  80

Ser Val Phe Leu Phe Pro Pro Lys Pro Lys Asp Thr Leu Met Ile Ser
                85                  90                  95

Arg Thr Pro Glu Val Thr Cys Val Val Val Asp Val Ser His Glu Asp
            100                 105                 110

Pro Glu Val Lys Phe Asn Trp Tyr Val Asp Gly Val Glu Val His Asn
        115                 120                 125

Ala Lys Thr Lys Pro Arg Glu Glu Gln Tyr Asn Ser Thr Tyr Arg Val
    130                 135                 140
```

Val Ser Val Leu Thr Val Leu His Gln Asp Trp Leu Asn Gly Lys Glu
145 150 155 160

Tyr Lys Cys Lys Val Ser Asn Lys Ala Leu Pro Ala Pro Ile Glu Lys
165 170 175

Thr Ile Ser Lys Ala Lys Gly Gln Pro Arg Glu Pro Gln Val Tyr Thr
180 185 190

Leu Pro Pro Ser Arg Glu Glu Met Thr Lys Asn Gln Val Ser Leu Thr
195 200 205

Cys Leu Val Lys Gly Phe Tyr Pro Ser Asp Ile Ala Val Glu Trp Glu
210 215 220

Ser Asn Gly Gln Pro Glu Asn Asn Tyr Lys Thr Thr Pro Pro Val Leu
225 230 235 240

Asp Ser Asp Gly Ser Phe Phe Leu Tyr Ser Lys Leu Thr Val Asp Lys
245 250 255

Ser Arg Trp Gln Gln Gly Asn Val Phe Ser Cys Ser Val Met His Glu
260 265 270

Ala Leu His Asn His Tyr Thr Gln Lys Ser Leu Ser Leu Ser Pro Gly
275 280 285

Lys

<210> SEQ ID NO 56
<211> LENGTH: 293
<212> TYPE: PRT
<213> ORGANISM: Artificial Sequence
<220> FEATURE:
<223> OTHER INFORMATION: CCL7(5-76)-IgGFc

<400> SEQUENCE: 56

Cys Cys Tyr Arg Phe Ile Asn Lys Lys Ile Pro Lys Gln Arg Leu Glu
1 5 10 15

Ser Tyr Arg Arg Thr Thr Ser Ser His Cys Pro Arg Glu Ala Val Ile
20 25 30

Phe Lys Thr Lys Leu Asp Lys Glu Ile Cys Ala Asp Pro Thr Gln Lys
35 40 45

Trp Val Gln Asp Phe Met Lys His Leu Asp Lys Lys Thr Gln Thr Pro
50 55 60

Lys Leu Asp Lys Thr His Thr Cys Pro Pro Cys Pro Ala Pro Glu Leu
65 70 75 80

Leu Gly Gly Pro Ser Val Phe Leu Phe Pro Pro Lys Pro Lys Asp Thr
85 90 95

Leu Met Ile Ser Arg Thr Pro Glu Val Thr Cys Val Val Val Asp Val
100 105 110

Ser His Glu Asp Pro Glu Val Lys Phe Asn Trp Tyr Val Asp Gly Val
115 120 125

Glu Val His Asn Ala Lys Thr Lys Pro Arg Glu Glu Gln Tyr Asn Ser
130 135 140

Thr Tyr Arg Val Val Ser Val Leu Thr Val Leu His Gln Asp Trp Leu
145 150 155 160

Asn Gly Lys Glu Tyr Lys Cys Lys Val Ser Asn Lys Ala Leu Pro Ala
165 170 175

Pro Ile Glu Lys Thr Ile Ser Lys Ala Lys Gly Gln Pro Arg Glu Pro
180 185 190

Gln Val Tyr Thr Leu Pro Pro Ser Arg Glu Glu Met Thr Lys Asn Gln
195 200 205

Val Ser Leu Thr Cys Leu Val Lys Gly Phe Tyr Pro Ser Asp Ile Ala

```
    210                 215                 220

Val Glu Trp Glu Ser Asn Gly Gln Pro Glu Asn Asn Tyr Lys Thr Thr
225                 230                 235                 240

Pro Pro Val Leu Asp Ser Asp Gly Ser Phe Phe Leu Tyr Ser Lys Leu
                245                 250                 255

Thr Val Asp Lys Ser Arg Trp Gln Gln Gly Asn Val Phe Ser Cys Ser
            260                 265                 270

Val Met His Glu Ala Leu His Asn His Tyr Thr Gln Lys Ser Leu Ser
        275                 280                 285

Leu Ser Pro Gly Lys
    290


<210> SEQ ID NO 57
<211> LENGTH: 289
<212> TYPE: PRT
<213> ORGANISM: Artificial Sequence
<220> FEATURE:
<223> OTHER INFORMATION: CCL7(5-76K/H-A)-IgGFc

<400> SEQUENCE: 57

Phe Ile Asn Lys Lys Ile Pro Lys Gln Arg Leu Glu Ser Tyr Arg Arg
1               5                   10                  15

Thr Thr Ser Ser His Cys Pro Arg Glu Ala Val Ile Phe Ala Thr Ala
            20                  25                  30

Leu Asp Ala Glu Ile Cys Ala Asp Pro Thr Gln Ala Trp Val Gln Asp
        35                  40                  45

Phe Met Ala Ala Leu Asp Ala Ala Thr Gln Thr Pro Ala Leu Asp Lys
    50                  55                  60

Thr His Thr Cys Pro Pro Cys Pro Ala Pro Glu Leu Leu Gly Gly Pro
65                  70                  75                  80

Ser Val Phe Leu Phe Pro Pro Lys Pro Lys Asp Thr Leu Met Ile Ser
                85                  90                  95

Arg Thr Pro Glu Val Thr Cys Val Val Val Asp Val Ser His Glu Asp
            100                 105                 110

Pro Glu Val Lys Phe Asn Trp Tyr Val Asp Gly Val Glu Val His Asn
        115                 120                 125

Ala Lys Thr Lys Pro Arg Glu Glu Gln Tyr Asn Ser Thr Tyr Arg Val
    130                 135                 140

Val Ser Val Leu Thr Val Leu His Gln Asp Trp Leu Asn Gly Lys Glu
145                 150                 155                 160

Tyr Lys Cys Lys Val Ser Asn Lys Ala Leu Pro Ala Pro Ile Glu Lys
                165                 170                 175

Thr Ile Ser Lys Ala Lys Gly Gln Pro Arg Glu Pro Gln Val Tyr Thr
            180                 185                 190

Leu Pro Pro Ser Arg Glu Glu Met Thr Lys Asn Gln Val Ser Leu Thr
        195                 200                 205

Cys Leu Val Lys Gly Phe Tyr Pro Ser Asp Ile Ala Val Glu Trp Glu
    210                 215                 220

Ser Asn Gly Gln Pro Glu Asn Asn Tyr Lys Thr Thr Pro Pro Val Leu
225                 230                 235                 240

Asp Ser Asp Gly Ser Phe Phe Leu Tyr Ser Lys Leu Thr Val Asp Lys
                245                 250                 255

Ser Arg Trp Gln Gln Gly Asn Val Phe Ser Cys Ser Val Met His Glu
            260                 265                 270

Ala Leu His Asn His Tyr Thr Gln Lys Ser Leu Ser Leu Ser Pro Gly
```

```
        275                 280                 285

Lys


<210> SEQ ID NO 58
<211> LENGTH: 303
<212> TYPE: PRT
<213> ORGANISM: Artificial Sequence
<220> FEATURE:
<223> OTHER INFORMATION: CCL8-IgG1Fc

<400> SEQUENCE: 58

Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro Asp Lys Thr His
65                  70                  75                  80

Thr Cys Pro Pro Cys Pro Ala Pro Glu Leu Leu Gly Gly Pro Ser Val
                85                  90                  95

Phe Leu Phe Pro Pro Lys Pro Lys Asp Thr Leu Met Ile Ser Arg Thr
            100                 105                 110

Pro Glu Val Thr Cys Val Val Val Asp Val Ser His Glu Asp Pro Glu
        115                 120                 125

Val Lys Phe Asn Trp Tyr Val Asp Gly Val Glu Val His Asn Ala Lys
    130                 135                 140

Thr Lys Pro Arg Glu Glu Gln Tyr Asn Ser Thr Tyr Arg Val Val Ser
145                 150                 155                 160

Val Leu Thr Val Leu His Gln Asp Trp Leu Asn Gly Lys Glu Tyr Lys
                165                 170                 175

Cys Lys Val Ser Asn Lys Ala Leu Pro Ala Pro Ile Glu Lys Thr Ile
            180                 185                 190

Ser Lys Ala Lys Gly Gln Pro Arg Glu Pro Gln Val Tyr Thr Leu Pro
        195                 200                 205

Pro Ser Arg Glu Glu Met Thr Lys Asn Gln Val Ser Leu Thr Cys Leu
    210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
                245                 250                 255

Asp Gly Ser Phe Phe Leu Tyr Ser Lys Leu Thr Val Asp Lys Ser Arg
            260                 265                 270

Trp Gln Gln Gly Asn Val Phe Ser Cys Ser Val Met His Glu Ala Leu
        275                 280                 285

His Asn His Tyr Thr Gln Lys Ser Leu Ser Leu Ser Pro Gly Lys
    290                 295                 300


<210> SEQ ID NO 59
<211> LENGTH: 299
<212> TYPE: PRT
<213> ORGANISM: Artificial Sequence
<220> FEATURE:
<223> OTHER INFORMATION: CCL8(5-76)-IgG1Fc
```

<400> SEQUENCE: 59

```
Val Ser Ile Pro Ile Thr Cys Cys Phe Asn Val Ile Asn Arg Lys Ile
1               5                   10                  15

Pro Ile Gln Arg Leu Glu Ser Tyr Thr Arg Ile Thr Asn Ile Gln Cys
            20                  25                  30

Pro Lys Glu Ala Val Ile Phe Lys Thr Lys Arg Gly Lys Glu Val Cys
        35                  40                  45

Ala Asp Pro Lys Glu Arg Trp Val Arg Asp Ser Met Lys His Leu Asp
    50                  55                  60

Gln Ile Phe Gln Asn Leu Lys Pro Asp Lys Thr His Thr Cys Pro Pro
65                  70                  75                  80

Cys Pro Ala Pro Glu Leu Leu Gly Gly Pro Ser Val Phe Leu Phe Pro
                85                  90                  95

Pro Lys Pro Lys Asp Thr Leu Met Ile Ser Arg Thr Pro Glu Val Thr
            100                 105                 110

Cys Val Val Val Asp Val Ser His Glu Asp Pro Glu Val Lys Phe Asn
        115                 120                 125

Trp Tyr Val Asp Gly Val Glu Val His Asn Ala Lys Thr Lys Pro Arg
    130                 135                 140

Glu Glu Gln Tyr Asn Ser Thr Tyr Arg Val Val Ser Val Leu Thr Val
145                 150                 155                 160

Leu His Gln Asp Trp Leu Asn Gly Lys Glu Tyr Lys Cys Lys Val Ser
                165                 170                 175

Asn Lys Ala Leu Pro Ala Pro Ile Glu Lys Thr Ile Ser Lys Ala Lys
            180                 185                 190

Gly Gln Pro Arg Glu Pro Gln Val Tyr Thr Leu Pro Pro Ser Arg Glu
        195                 200                 205

Glu Met Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
                245                 250                 255

Phe Leu Tyr Ser Lys Leu Thr Val Asp Lys Ser Arg Trp Gln Gln Gly
            260                 265                 270

Asn Val Phe Ser Cys Ser Val Met His Glu Ala Leu His Asn His Tyr
        275                 280                 285

Thr Gln Lys Ser Leu Ser Leu Ser Pro Gly Lys
    290                 295
```

<210> SEQ ID NO 60
<211> LENGTH: 265
<212> TYPE: PRT
<213> ORGANISM: Artificial Sequence
<220> FEATURE:
<223> OTHER INFORMATION: CCL8(5-76K/H-A)-IgG1Fc

<400> SEQUENCE: 60

```
Val Ser Ile Pro Ile Thr Cys Cys Phe Asn Val Ile Asn Arg Lys Ile
1               5                   10                  15

Pro Ile Gln Arg Leu Glu Ser Tyr Thr Arg Ile Thr Asn Ile Gln Cys
            20                  25                  30

Pro Lys Glu Ala Val Ile Phe Lys Thr Ala Ala Gly Ala Glu Val Cys
        35                  40                  45

Ala Asp Pro Ala Glu Ala Trp Val Ala Asp Ser Met Ala Ala Leu Asp
```

```
    50                  55                  60

Gln Ile Phe Gln Asn Leu Ala Pro Asp Lys Thr His Thr Cys Pro Pro
65                  70                  75                  80

Cys Pro Ala Pro Glu Leu Leu Gly Gly Pro Ser Val Phe Leu Phe Pro
                85                  90                  95

Pro Lys Pro Lys Asp Thr Leu Met Ile Ser Arg Thr Pro Glu Val Thr
            100                 105                 110

Cys Val Val Val Asp Val Ser His Glu Asp Pro Glu Val Lys Phe Asn
        115                 120                 125

Trp Tyr Val Asp Gly Val Glu Val His Asn Ala Lys Thr Lys Pro Arg
    130                 135                 140

Glu Glu Gln Tyr Asn Ser Thr Tyr Arg Val Val Ser Val Leu Thr Val
145                 150                 155                 160

Leu His Gln Asp Trp Leu Asn Gly Lys Glu Tyr Lys Cys Lys Val Ser
                165                 170                 175

Asn Lys Ala Leu Pro Ala Pro Ile Glu Lys Thr Ile Ser Lys Ala Lys
            180                 185                 190

Gly Gln Pro Arg Glu Pro Gln Val Tyr Thr Leu Pro Pro Ser Arg Glu
        195                 200                 205

Glu Met Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
                245                 250                 255

Lys Ser Leu Ser Leu Ser Pro Gly Lys
            260                 265


<210> SEQ ID NO 61
<211> LENGTH: 302
<212> TYPE: PRT
<213> ORGANISM: Artificial Sequence
<220> FEATURE:
<223> OTHER INFORMATION: CCL13-IgG1Fc

<400> SEQUENCE: 61

Gln Pro Asp Ala Leu Asn Val Pro Ser Thr Cys Cys Phe Thr Phe Ser
1               5                   10                  15

Ser Lys Lys Ile Ser Leu Gln Arg Leu Lys Ser Tyr Val Ile Thr Thr
            20                  25                  30

Ser Arg Cys Pro Gln Lys Ala Val Ile Phe Arg Thr Lys Leu Gly Lys
        35                  40                  45

Glu Ile Cys Ala Asp Pro Lys Glu Lys Trp Val Gln Asn Tyr Met Lys
    50                  55                  60

His Leu Gly Arg Lys Ala His Thr Leu Lys Thr Asp Lys Thr His Thr
65                  70                  75                  80

Cys Pro Pro Cys Pro Ala Pro Glu Leu Leu Gly Gly Pro Ser Val Phe
                85                  90                  95

Leu Phe Pro Pro Lys Pro Lys Asp Thr Leu Met Ile Ser Arg Thr Pro
            100                 105                 110

Glu Val Thr Cys Val Val Val Asp Val Ser His Glu Asp Pro Glu Val
        115                 120                 125

Lys Phe Asn Trp Tyr Val Asp Gly Val Glu Val His Asn Ala Lys Thr
    130                 135                 140

Lys Pro Arg Glu Glu Gln Tyr Asn Ser Thr Tyr Arg Val Val Ser Val
```

```
145                 150                 155                 160

Leu Thr Val Leu His Gln Asp Trp Leu Asn Gly Lys Glu Tyr Lys Cys
                165                 170                 175

Lys Val Ser Asn Lys Ala Leu Pro Ala Pro Ile Glu Lys Thr Ile Ser
            180                 185                 190

Lys Ala Lys Gly Gln Pro Arg Glu Pro Gln Val Tyr Thr Leu Pro Pro
        195                 200                 205

Ser Arg Glu Glu Met Thr Lys Asn Gln Val Ser Leu Thr Cys Leu Val
    210                 215                 220

Lys Gly Phe Tyr Pro Ser Asp Ile Ala Val Glu Trp Glu Ser Asn Gly
225                 230                 235                 240

Gln Pro Glu Asn Asn Tyr Lys Thr Thr Pro Pro Val Leu Asp Ser Asp
                245                 250                 255

Gly Ser Phe Phe Leu Tyr Ser Lys Leu Thr Val Asp Lys Ser Arg Trp
            260                 265                 270

Gln Gln Gly Asn Val Phe Ser Cys Ser Val Met His Glu Ala Leu His
        275                 280                 285

Asn His Tyr Thr Gln Lys Ser Leu Ser Leu Ser Pro Gly Lys
    290                 295                 300


<210> SEQ ID NO 62
<211> LENGTH: 298
<212> TYPE: PRT
<213> ORGANISM: Artificial Sequence
<220> FEATURE:
<223> OTHER INFORMATION: CCL13(5-75)-IgG1Fc

<400> SEQUENCE: 62

Leu Asn Val Pro Ser Thr Cys Cys Phe Thr Phe Ser Ser Lys Lys Ile
1               5                   10                  15

Ser Leu Gln Arg Leu Lys Ser Tyr Val Ile Thr Thr Ser Arg Cys Pro
            20                  25                  30

Gln Lys Ala Val Ile Phe Arg Thr Lys Leu Gly Lys Glu Ile Cys Ala
        35                  40                  45

Asp Pro Lys Glu Lys Trp Val Gln Asn Tyr Met Lys His Leu Gly Arg
    50                  55                  60

Lys Ala His Thr Leu Lys Thr Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
    130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
        195                 200                 205

Met Thr Lys Asn Gln Val Ser Leu Thr Cys Leu Val Lys Gly Phe Tyr
```

-continued

```
    210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
        275                 280                 285

Gln Lys Ser Leu Ser Leu Ser Pro Gly Lys
    290                 295


<210> SEQ ID NO 63
<211> LENGTH: 298
<212> TYPE: PRT
<213> ORGANISM: Artificial Sequence
<220> FEATURE:
<223> OTHER INFORMATION: CCL13(5-75K/H-A)-IgG1Fc

<400> SEQUENCE: 63

Leu Asn Val Pro Ser Thr Cys Cys Phe Thr Phe Ser Ser Lys Lys Ile
1               5                   10                  15

Ser Leu Gln Arg Leu Lys Ser Tyr Val Ile Thr Thr Ser Arg Cys Pro
            20                  25                  30

Gln Lys Ala Val Ile Phe Arg Thr Ala Leu Gly Ala Glu Ile Cys Ala
        35                  40                  45

Asp Pro Ala Glu Ala Trp Val Gln Asn Tyr Met Ala Ala Leu Gly Arg
    50                  55                  60

Lys Ala Ala Thr Leu Ala Thr Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
    130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
        195                 200                 205

Met Thr Lys Asn Gln Val Ser Leu Thr Cys Leu Val Lys Gly Phe Tyr
    210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
```

```
        275                 280                 285

Gln Lys Ser Leu Ser Leu Ser Pro Gly Lys
    290                 295


<210> SEQ ID NO 64
<211> LENGTH: 345
<212> TYPE: PRT
<213> ORGANISM: Artificial Sequence
<220> FEATURE:
<223> OTHER INFORMATION: CCL25-IgG1Fc

<400> SEQUENCE: 64

Thr Gln Gly Val Phe Glu Asp Cys Cys Leu Ala Tyr His Tyr Pro Ile
1               5                   10                  15

Gly Trp Ala Val Leu Arg His Ala Trp Thr Tyr Arg Ile Gln Glu Val
            20                  25                  30

Ser Gly Ser Cys Asn Leu Pro Ala Ala Ile Phe Tyr Leu Pro Lys Arg
        35                  40                  45

His Arg Lys Val Cys Gly Asn Pro Lys Ser Arg Glu Val Gln Arg Ala
    50                  55                  60

Met Lys Leu Leu Asp Ala Arg Asn Lys Val Phe Ala Lys Leu Arg His
65                  70                  75                  80

Asn Thr Gln Thr Phe Gln Gly Pro His Ala Val Lys Lys Leu Ser Ser
                85                  90                  95

Gly Asn Ser Lys Leu Ser Ser Ser Lys Phe Ser Asn Pro Ile Ser Ser
            100                 105                 110

Ser Lys Arg Asn Val Ser Asp Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
    290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
```

-continued 340 345

<210> SEQ ID NO 65
<211> LENGTH: 342
<212> TYPE: PRT
<213> ORGANISM: Artificial Sequence
<220> FEATURE:
<223> OTHER INFORMATION: CCL25(4-127)-IgG1Fc

<400> SEQUENCE: 65

Val Phe Glu Asp Cys Cys Leu Ala Tyr His Tyr Pro Ile Gly Trp Ala
1 5 10 15

Val Leu Arg His Ala Trp Thr Tyr Arg Ile Gln Glu Val Ser Gly Ser
20 25 30

Cys Asn Leu Pro Ala Ala Ile Phe Tyr Leu Pro Lys Arg His Arg Lys
35 40 45

Val Cys Gly Asn Pro Lys Ser Arg Glu Val Gln Arg Ala Met Lys Leu
50 55 60

Leu Asp Ala Arg Asn Lys Val Phe Ala Lys Leu Arg His Asn Thr Gln
65 70 75 80

Thr Phe Gln Gly Pro His Ala Val Lys Lys Leu Ser Ser Gly Asn Ser
85 90 95

Lys Leu Ser Ser Ser Lys Phe Ser Asn Pro Ile Ser Ser Ser Lys Arg
100 105 110

Asn Val Ser Asp Lys Thr His Thr Cys Pro Pro Cys Pro Ala Pro Glu
115 120 125

Leu Leu Gly Gly Pro Ser Val Phe Leu Phe Pro Pro Lys Pro Lys Asp
130 135 140

Thr Leu Met Ile Ser Arg Thr Pro Glu Val Thr Cys Val Val Val Asp
145 150 155 160

Val Ser His Glu Asp Pro Glu Val Lys Phe Asn Trp Tyr Val Asp Gly
165 170 175

Val Glu Val His Asn Ala Lys Thr Lys Pro Arg Glu Glu Gln Tyr Asn
180 185 190

Ser Thr Tyr Arg Val Val Ser Val Leu Thr Val Leu His Gln Asp Trp
195 200 205

Leu Asn Gly Lys Glu Tyr Lys Cys Lys Val Ser Asn Lys Ala Leu Pro
210 215 220

Ala Pro Ile Glu Lys Thr Ile Ser Lys Ala Lys Gly Gln Pro Arg Glu
225 230 235 240

Pro Gln Val Tyr Thr Leu Pro Pro Ser Arg Glu Glu Met Thr Lys Asn
245 250 255

Gln Val Ser Leu Thr Cys Leu Val Lys Gly Phe Tyr Pro Ser Asp Ile
260 265 270

Ala Val Glu Trp Glu Ser Asn Gly Gln Pro Glu Asn Asn Tyr Lys Thr
275 280 285

Thr Pro Pro Val Leu Asp Ser Asp Gly Ser Phe Phe Leu Tyr Ser Lys
290 295 300

Leu Thr Val Asp Lys Ser Arg Trp Gln Gln Gly Asn Val Phe Ser Cys
305 310 315 320

Ser Val Met His Glu Ala Leu His Asn His Tyr Thr Gln Lys Ser Leu
325 330 335

Ser Leu Ser Pro Gly Lys
340

<210> SEQ ID NO 66
<211> LENGTH: 342
<212> TYPE: PRT
<213> ORGANISM: Artificial Sequence
<220> FEATURE:
<223> OTHER INFORMATION: CCL25(4-127K/H-A)-IgG1Fc

<400> SEQUENCE: 66

```
Val Phe Glu Asp Cys Cys Leu Ala Tyr His Tyr Pro Ile Gly Trp Ala
1               5                   10                  15

Val Leu Arg His Ala Trp Thr Tyr Arg Ile Gln Glu Val Ser Gly Ser
            20                  25                  30

Cys Asn Leu Pro Ala Ala Ile Phe Tyr Leu Pro Ala Ala Ala Ala Ala
        35                  40                  45

Val Cys Gly Asn Pro Ala Ser Ala Glu Val Gln Ala Ala Met Ala Leu
    50                  55                  60

Leu Asp Ala Ala Asn Ala Val Phe Ala Ala Leu Ala Ala Asn Thr Gln
65                  70                  75                  80

Thr Phe Gln Gly Pro Ala Ala Val Ala Ala Leu Ser Ser Gly Asn Ser
                85                  90                  95

Ala Leu Ser Ser Ser Ala Phe Ser Asn Pro Ile Ser Ser Ser Ala Ala
            100                 105                 110

Asn Val Ser Asp Lys Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340
```

<210> SEQ ID NO 67
<211> LENGTH: 300
<212> TYPE: PRT

<213> ORGANISM: Artificial Sequence
<220> FEATURE:
<223> OTHER INFORMATION: CXCL11-IgG1Fc

<400> SEQUENCE: 67

```
Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe Asp Lys Thr His Thr Cys Pro
65                  70                  75                  80

Pro Cys Pro Ala Pro Glu Leu Leu Gly Gly Pro Ser Val Phe Leu Phe
                85                  90                  95

Pro Pro Lys Pro Lys Asp Thr Leu Met Ile Ser Arg Thr Pro Glu Val
            100                 105                 110

Thr Cys Val Val Val Asp Val Ser His Glu Asp Pro Glu Val Lys Phe
        115                 120                 125

Asn Trp Tyr Val Asp Gly Val Glu Val His Asn Ala Lys Thr Lys Pro
    130                 135                 140

Arg Glu Glu Gln Tyr Asn Ser Thr Tyr Arg Val Val Ser Val Leu Thr
145                 150                 155                 160

Val Leu His Gln Asp Trp Leu Asn Gly Lys Glu Tyr Lys Cys Lys Val
                165                 170                 175

Ser Asn Lys Ala Leu Pro Ala Pro Ile Glu Lys Thr Ile Ser Lys Ala
            180                 185                 190

Lys Gly Gln Pro Arg Glu Pro Gln Val Tyr Thr Leu Pro Pro Ser Arg
        195                 200                 205

Glu Glu Met Thr Lys Asn Gln Val Ser Leu Thr Cys Leu Val Lys Gly
    210                 215                 220

Phe Tyr Pro Ser Asp Ile Ala Val Glu Trp Glu Ser Asn Gly Gln Pro
225                 230                 235                 240

Glu Asn Asn Tyr Lys Thr Thr Pro Pro Val Leu Asp Ser Asp Gly Ser
                245                 250                 255

Phe Phe Leu Tyr Ser Lys Leu Thr Val Asp Lys Ser Arg Trp Gln Gln
            260                 265                 270

Gly Asn Val Phe Ser Cys Ser Val Met His Glu Ala Leu His Asn His
        275                 280                 285

Tyr Thr Gln Lys Ser Leu Ser Leu Ser Pro Gly Lys
    290                 295                 300
```

<210> SEQ ID NO 68
<211> LENGTH: 297
<212> TYPE: PRT
<213> ORGANISM: Artificial Sequence
<220> FEATURE:
<223> OTHER INFORMATION: CXCL11(4-73)-IgG1Fc

<400> SEQUENCE: 68

```
Phe Lys Arg Gly Arg Cys Leu Cys Ile Gly Pro Gly Val Lys Ala Val
1               5                   10                  15

Lys Val Ala Asp Ile Glu Lys Ala Ser Ile Met Tyr Pro Ser Asn Asn
            20                  25                  30
```

```
Cys Asp Lys Ile Glu Val Ile Ile Thr Leu Lys Glu Asn Lys Gly Gln
        35                  40                  45

Arg Cys Leu Asn Pro Lys Ser Lys Gln Ala Arg Leu Ile Ile Lys Lys
    50                  55                  60

Val Glu Arg Lys Asn Phe Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
        115                 120                 125

Val Asp Gly Val Glu Val His Asn Ala Lys Thr Lys Pro Arg Glu Glu
    130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Glu Glu Met
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295


<210> SEQ ID NO 69
<211> LENGTH: 297
<212> TYPE: PRT
<213> ORGANISM: Artificial Sequence
<220> FEATURE:
<223> OTHER INFORMATION: CXCL11(4-73K/H-A)-IgG1Fc

<400> SEQUENCE: 69

Phe Lys Arg Gly Arg Cys Leu Cys Ile Gly Pro Gly Val Lys Ala Val
1               5                   10                  15

Lys Val Ala Asp Ile Glu Ala Ala Ser Ile Met Tyr Pro Ser Asn Asn
            20                  25                  30

Cys Asp Lys Ile Glu Val Ile Ile Thr Leu Ala Glu Asn Ala Gly Gln
        35                  40                  45

Ala Cys Leu Asn Pro Ala Ser Ala Gln Ala Ala Leu Ile Ile Ala Ala
    50                  55                  60

Val Glu Ala Ala Asn Phe Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95
```

-continued

```
Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
        115                 120                 125

Val Asp Gly Val Glu Val His Asn Ala Lys Thr Lys Pro Arg Glu Glu
    130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Glu Glu Met
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295


<210> SEQ ID NO 70
<211> LENGTH: 297
<212> TYPE: PRT
<213> ORGANISM: Artificial Sequence
<220> FEATURE:
<223> OTHER INFORMATION: CXCL11-IgG4Fc

<400> SEQUENCE: 70

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe Pro Pro Cys Pro Ser Cys Pro
65                  70                  75                  80

Ala Pro Glu Phe Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser Gln Glu Asp Pro Glu Val Gln Phe Asn Trp Tyr
        115                 120                 125

Val Asp Gly Val Glu Val His Asn Ala Lys Thr Lys Pro Arg Glu Glu
    130                 135                 140

Gln Phe Asn Ser Thr Tyr Arg Val Val Ser Val Leu Thr Val Leu His
145                 150                 155                 160
```

```
Gln Asp Trp Leu Asn Gly Lys Glu Tyr Lys Cys Lys Val Ser Asn Lys
                165                 170                 175

Gly Leu Pro Ser Ser Ile Glu Lys Thr Ile Ser Lys Ala Lys Gly Gln
            180                 185                 190

Pro Arg Glu Pro Gln Val Tyr Thr Leu Pro Pro Ser Gln Glu Glu Met
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Arg Leu Thr Val Asp Lys Ser Arg Trp Gln Glu Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295


<210> SEQ ID NO 71
<211> LENGTH: 294
<212> TYPE: PRT
<213> ORGANISM: Artificial Sequence
<220> FEATURE:
<223> OTHER INFORMATION: CXCL11(4-73)-IgG4Fc

<400> SEQUENCE: 71

Phe Lys Arg Gly Arg Cys Leu Cys Ile Gly Pro Gly Val Lys Ala Val
1               5                   10                  15

Lys Val Ala Asp Ile Glu Lys Ala Ser Ile Met Tyr Pro Ser Asn Asn
            20                  25                  30

Cys Asp Lys Ile Glu Val Ile Ile Thr Leu Lys Glu Asn Lys Gly Gln
        35                  40                  45

Arg Cys Leu Asn Pro Lys Ser Lys Gln Ala Arg Leu Ile Ile Lys Lys
    50                  55                  60

Val Glu Arg Lys Asn Phe Pro Pro Cys Pro Ser Cys Pro Ala Pro Glu
65                  70                  75                  80

Phe Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser Gln Glu Asp Pro Glu Val Gln Phe Asn Trp Tyr Val Asp Gly
        115                 120                 125

Val Glu Val His Asn Ala Lys Thr Lys Pro Arg Glu Glu Gln Phe Asn
    130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Gly Leu Pro
                165                 170                 175

Ser Ser Ile Glu Lys Thr Ile Ser Lys Ala Lys Gly Gln Pro Arg Glu
            180                 185                 190

Pro Gln Val Tyr Thr Leu Pro Pro Ser Gln Glu Glu Met Thr Lys Asn
        195                 200                 205

Gln Val Ser Leu Thr Cys Leu Val Lys Gly Phe Tyr Pro Ser Asp Ile
    210                 215                 220
```

```
Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Arg
                245                 250                 255

Leu Thr Val Asp Lys Ser Arg Trp Gln Glu Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys
    290


<210> SEQ ID NO 72
<211> LENGTH: 294
<212> TYPE: PRT
<213> ORGANISM: Artificial Sequence
<220> FEATURE:
<223> OTHER INFORMATION: CXCL11(4-73K/H-A)-IgG4Fc

<400> SEQUENCE: 72

Phe Lys Arg Gly Arg Cys Leu Cys Ile Gly Pro Gly Val Lys Ala Val
1               5                   10                  15

Lys Val Ala Asp Ile Glu Ala Ala Ser Ile Met Tyr Pro Ser Asn Asn
            20                  25                  30

Cys Asp Lys Ile Glu Val Ile Ile Thr Leu Ala Glu Asn Ala Gly Gln
        35                  40                  45

Ala Cys Leu Asn Pro Ala Ser Ala Gln Ala Ala Leu Ile Ile Ala Ala
    50                  55                  60

Val Glu Ala Ala Asn Phe Pro Pro Cys Pro Ser Cys Pro Ala Pro Glu
65                  70                  75                  80

Phe Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser Gln Glu Asp Pro Glu Val Gln Phe Asn Trp Tyr Val Asp Gly
        115                 120                 125

Val Glu Val His Asn Ala Lys Thr Lys Pro Arg Glu Glu Gln Phe Asn
    130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Gly Leu Pro
                165                 170                 175

Ser Ser Ile Glu Lys Thr Ile Ser Lys Ala Lys Gly Gln Pro Arg Glu
            180                 185                 190

Pro Gln Val Tyr Thr Leu Pro Pro Ser Gln Glu Glu Met Thr Lys Asn
        195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Arg
                245                 250                 255

Leu Thr Val Asp Lys Ser Arg Trp Gln Glu Gly Asn Val Phe Ser Cys
            260                 265                 270

Ser Val Met His Glu Ala Leu His Asn His Tyr Thr Gln Lys Ser Leu
        275                 280                 285
```

Ser Leu Ser Pro Gly Lys
    290

<210> SEQ ID NO 73
<211> LENGTH: 314
<212> TYPE: PRT
<213> ORGANISM: Artificial Sequence
<220> FEATURE:
<223> OTHER INFORMATION: CXCL13-IgG1Fc

<400> SEQUENCE: 73

```
Val Leu Glu Val Tyr Tyr Thr Ser Leu Arg Cys Arg Cys Val Gln Glu
1               5                   10                  15

Ser Ser Val Phe Ile Pro Arg Arg Phe Ile Asp Arg Ile Gln Ile Leu
            20                  25                  30

Pro Arg Gly Asn Gly Cys Pro Arg Lys Glu Ile Ile Val Trp Lys Lys
        35                  40                  45

Asn Lys Ser Ile Val Cys Val Asp Pro Gln Ala Glu Trp Ile Gln Arg
    50                  55                  60

Met Met Glu Val Leu Arg Lys Arg Ser Ser Ser Thr Leu Pro Val Pro
65                  70                  75                  80

Val Phe Lys Arg Lys Ile Pro Asp Lys Thr His Thr Cys Pro Pro Cys
                85                  90                  95

Pro Ala Pro Glu Leu Leu Gly Gly Pro Ser Val Phe Leu Phe Pro Pro
            100                 105                 110

Lys Pro Lys Asp Thr Leu Met Ile Ser Arg Thr Pro Glu Val Thr Cys
        115                 120                 125

Val Val Val Asp Val Ser His Glu Asp Pro Glu Val Lys Phe Asn Trp
    130                 135                 140

Tyr Val Asp Gly Val Glu Val His Asn Ala Lys Thr Lys Pro Arg Glu
145                 150                 155                 160

Glu Gln Tyr Asn Ser Thr Tyr Arg Val Val Ser Val Leu Thr Val Leu
                165                 170                 175

His Gln Asp Trp Leu Asn Gly Lys Glu Tyr Lys Cys Lys Val Ser Asn
            180                 185                 190

Lys Ala Leu Pro Ala Pro Ile Glu Lys Thr Ile Ser Lys Ala Lys Gly
        195                 200                 205

Gln Pro Arg Glu Pro Gln Val Tyr Thr Leu Pro Pro Ser Arg Glu Glu
    210                 215                 220

Met Thr Lys Asn Gln Val Ser Leu Thr Cys Leu Val Lys Gly Phe Tyr
225                 230                 235                 240

Pro Ser Asp Ile Ala Val Glu Trp Glu Ser Asn Gly Gln Pro Glu Asn
                245                 250                 255

Asn Tyr Lys Thr Thr Pro Pro Val Leu Asp Ser Asp Gly Ser Phe Phe
            260                 265                 270

Leu Tyr Ser Lys Leu Thr Val Asp Lys Ser Arg Trp Gln Gln Gly Asn
        275                 280                 285

Val Phe Ser Cys Ser Val Met His Glu Ala Leu His Asn His Tyr Thr
    290                 295                 300

Gln Lys Ser Leu Ser Leu Ser Pro Gly Lys
305                 310
```

<210> SEQ ID NO 74
<211> LENGTH: 312
<212> TYPE: PRT
<213> ORGANISM: Artificial Sequence
<220> FEATURE:

<223> OTHER INFORMATION: CXCL13(3-87)-IgG1Fc

<400> SEQUENCE: 74

```
Glu Val Tyr Tyr Thr Ser Leu Arg Cys Arg Cys Val Gln Glu Ser Ser
1               5                   10                  15

Val Phe Ile Pro Arg Arg Phe Ile Asp Arg Ile Gln Ile Leu Pro Arg
            20                  25                  30

Gly Asn Gly Cys Pro Arg Lys Glu Ile Ile Val Trp Lys Lys Asn Lys
        35                  40                  45

Ser Ile Val Cys Val Asp Pro Gln Ala Glu Trp Ile Gln Arg Met Met
    50                  55                  60

Glu Val Leu Arg Lys Arg Ser Ser Ser Thr Leu Pro Val Pro Val Phe
65                  70                  75                  80

Lys Arg Lys Ile Pro Asp Lys Thr His Thr Cys Pro Pro Cys Pro Ala
                85                  90                  95

Pro Glu Leu Leu Gly Gly Pro Ser Val Phe Leu Phe Pro Pro Lys Pro
            100                 105                 110

Lys Asp Thr Leu Met Ile Ser Arg Thr Pro Glu Val Thr Cys Val Val
        115                 120                 125

Val Asp Val Ser His Glu Asp Pro Glu Val Lys Phe Asn Trp Tyr Val
    130                 135                 140

Asp Gly Val Glu Val His Asn Ala Lys Thr Lys Pro Arg Glu Glu Gln
145                 150                 155                 160

Tyr Asn Ser Thr Tyr Arg Val Val Ser Val Leu Thr Val Leu His Gln
                165                 170                 175

Asp Trp Leu Asn Gly Lys Glu Tyr Lys Cys Lys Val Ser Asn Lys Ala
            180                 185                 190

Leu Pro Ala Pro Ile Glu Lys Thr Ile Ser Lys Ala Lys Gly Gln Pro
        195                 200                 205

Arg Glu Pro Gln Val Tyr Thr Leu Pro Pro Ser Arg Glu Glu Met Thr
    210                 215                 220

Lys Asn Gln Val Ser Leu Thr Cys Leu Val Lys Gly Phe Tyr Pro Ser
225                 230                 235                 240

Asp Ile Ala Val Glu Trp Glu Ser Asn Gly Gln Pro Glu Asn Asn Tyr
                245                 250                 255

Lys Thr Thr Pro Pro Val Leu Asp Ser Asp Gly Ser Phe Phe Leu Tyr
            260                 265                 270

Ser Lys Leu Thr Val Asp Lys Ser Arg Trp Gln Gln Gly Asn Val Phe
        275                 280                 285

Ser Cys Ser Val Met His Glu Ala Leu His Asn His Tyr Thr Gln Lys
    290                 295                 300

Ser Leu Ser Leu Ser Pro Gly Lys
305                 310
```

<210> SEQ ID NO 75
<211> LENGTH: 312
<212> TYPE: PRT
<213> ORGANISM: Artificial Sequence
<220> FEATURE:
<223> OTHER INFORMATION: CXCL13(3-87K/H-A)-IgG1Fc

<400> SEQUENCE: 75

```
Glu Val Tyr Tyr Thr Ser Leu Arg Cys Arg Cys Val Gln Glu Ser Ser
1               5                   10                  15

Val Phe Ile Pro Arg Arg Phe Ile Asp Ala Ile Gln Ile Leu Pro Arg
            20                  25                  30
```

```
Gly Asn Gly Cys Pro Arg Lys Glu Ile Ile Val Trp Ala Ala Asn Ala
        35                  40                  45

Ser Ile Val Cys Val Asp Pro Gln Ala Glu Trp Ile Gln Ala Met Met
    50                  55                  60

Glu Val Leu Ala Ala Ala Ser Ser Ser Thr Leu Pro Val Pro Val Phe
65                  70                  75                  80

Ala Ala Ala Ile Pro Asp Lys Thr His Thr Cys Pro Pro Cys Pro Ala
                85                  90                  95

Pro Glu Leu Leu Gly Gly Pro Ser Val Phe Leu Phe Pro Pro Lys Pro
            100                 105                 110

Lys Asp Thr Leu Met Ile Ser Arg Thr Pro Glu Val Thr Cys Val Val
        115                 120                 125

Val Asp Val Ser His Glu Asp Pro Glu Val Lys Phe Asn Trp Tyr Val
    130                 135                 140

Asp Gly Val Glu Val His Asn Ala Lys Thr Lys Pro Arg Glu Glu Gln
145                 150                 155                 160

Tyr Asn Ser Thr Tyr Arg Val Val Ser Val Leu Thr Val Leu His Gln
                165                 170                 175

Asp Trp Leu Asn Gly Lys Glu Tyr Lys Cys Lys Val Ser Asn Lys Ala
            180                 185                 190

Leu Pro Ala Pro Ile Glu Lys Thr Ile Ser Lys Ala Lys Gly Gln Pro
        195                 200                 205

Arg Glu Pro Gln Val Tyr Thr Leu Pro Pro Ser Arg Glu Glu Met Thr
    210                 215                 220

Lys Asn Gln Val Ser Leu Thr Cys Leu Val Lys Gly Phe Tyr Pro Ser
225                 230                 235                 240

Asp Ile Ala Val Glu Trp Glu Ser Asn Gly Gln Pro Glu Asn Asn Tyr
                245                 250                 255

Lys Thr Thr Pro Pro Val Leu Asp Ser Asp Gly Ser Phe Phe Leu Tyr
            260                 265                 270

Ser Lys Leu Thr Val Asp Lys Ser Arg Trp Gln Gln Gly Asn Val Phe
        275                 280                 285

Ser Cys Ser Val Met His Glu Ala Leu His Asn His Tyr Thr Gln Lys
    290                 295                 300

Ser Leu Ser Leu Ser Pro Gly Lys
305                 310
```

<210> SEQ ID NO 76
<211> LENGTH: 311
<212> TYPE: PRT
<213> ORGANISM: Artificial Sequence
<220> FEATURE:
<223> OTHER INFORMATION: CXCL13-IgG4Fc

<400> SEQUENCE: 76

```
Val Leu Glu Val Tyr Tyr Thr Ser Leu Arg Cys Arg Cys Val Gln Glu
1               5                   10                  15

Ser Ser Val Phe Ile Pro Arg Arg Phe Ile Asp Arg Ile Gln Ile Leu
            20                  25                  30

Pro Arg Gly Asn Gly Cys Pro Arg Lys Glu Ile Ile Val Trp Lys Lys
        35                  40                  45

Asn Lys Ser Ile Val Cys Val Asp Pro Gln Ala Glu Trp Ile Gln Arg
    50                  55                  60

Met Met Glu Val Leu Arg Lys Arg Ser Ser Ser Thr Leu Pro Val Pro
65                  70                  75                  80
```

```
Val Phe Lys Arg Lys Ile Pro Pro Pro Cys Pro Ser Cys Pro Ala Pro
                85                  90                  95

Glu Phe Leu Gly Gly Pro Ser Val Phe Leu Phe Pro Pro Lys Pro Lys
            100                 105                 110

Asp Thr Leu Met Ile Ser Arg Thr Pro Glu Val Thr Cys Val Val Val
        115                 120                 125

Asp Val Ser Gln Glu Asp Pro Glu Val Gln Phe Asn Trp Tyr Val Asp
    130                 135                 140

Gly Val Glu Val His Asn Ala Lys Thr Lys Pro Arg Glu Glu Gln Phe
145                 150                 155                 160

Asn Ser Thr Tyr Arg Val Val Ser Val Leu Thr Val Leu His Gln Asp
                165                 170                 175

Trp Leu Asn Gly Lys Glu Tyr Lys Cys Lys Val Ser Asn Lys Gly Leu
            180                 185                 190

Pro Ser Ser Ile Glu Lys Thr Ile Ser Lys Ala Lys Gly Gln Pro Arg
        195                 200                 205

Glu Pro Gln Val Tyr Thr Leu Pro Pro Ser Gln Glu Glu Met Thr Lys
    210                 215                 220

Asn Gln Val Ser Leu Thr Cys Leu Val Lys Gly Phe Tyr Pro Ser Asp
225                 230                 235                 240

Ile Ala Val Glu Trp Glu Ser Asn Gly Gln Pro Glu Asn Asn Tyr Lys
                245                 250                 255

Thr Thr Pro Pro Val Leu Asp Ser Asp Gly Ser Phe Phe Leu Tyr Ser
            260                 265                 270

Arg Leu Thr Val Asp Lys Ser Arg Trp Gln Glu Gly Asn Val Phe Ser
        275                 280                 285

Cys Ser Val Met His Glu Ala Leu His Asn His Tyr Thr Gln Lys Ser
    290                 295                 300

Leu Ser Leu Ser Pro Gly Lys
305                 310


<210> SEQ ID NO 77
<211> LENGTH: 309
<212> TYPE: PRT
<213> ORGANISM: Artificial Sequence
<220> FEATURE:
<223> OTHER INFORMATION: CXCL13(3-87)-IgG4Fc

<400> SEQUENCE: 77

Glu Val Tyr Tyr Thr Ser Leu Arg Cys Arg Cys Val Gln Glu Ser Ser
1               5                   10                  15

Val Phe Ile Pro Arg Arg Phe Ile Asp Arg Ile Gln Ile Leu Pro Arg
            20                  25                  30

Gly Asn Gly Cys Pro Arg Lys Glu Ile Ile Val Trp Lys Lys Asn Lys
        35                  40                  45

Ser Ile Val Cys Val Asp Pro Gln Ala Glu Trp Ile Gln Arg Met Met
    50                  55                  60

Glu Val Leu Arg Lys Arg Ser Ser Ser Thr Leu Pro Val Pro Val Phe
65                  70                  75                  80

Lys Arg Lys Ile Pro Pro Pro Cys Pro Ser Cys Pro Ala Pro Glu Phe
                85                  90                  95

Leu Gly Gly Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125
```

```
Ser Gln Glu Asp Pro Glu Val Gln Phe Asn Trp Tyr Val Asp Gly Val
    130                 135                 140

Glu Val His Asn Ala Lys Thr Lys Pro Arg Glu Glu Gln Phe Asn Ser
145                 150                 155                 160

Thr Tyr Arg Val Val Ser Val Leu Thr Val Leu His Gln Asp Trp Leu
                165                 170                 175

Asn Gly Lys Glu Tyr Lys Cys Lys Val Ser Asn Lys Gly Leu Pro Ser
            180                 185                 190

Ser Ile Glu Lys Thr Ile Ser Lys Ala Lys Gly Gln Pro Arg Glu Pro
        195                 200                 205

Gln Val Tyr Thr Leu Pro Pro Ser Gln Glu Glu Met Thr Lys Asn Gln
    210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
                245                 250                 255

Pro Pro Val Leu Asp Ser Asp Gly Ser Phe Phe Leu Tyr Ser Arg Leu
            260                 265                 270

Thr Val Asp Lys Ser Arg Trp Gln Glu Gly Asn Val Phe Ser Cys Ser
        275                 280                 285

Val Met His Glu Ala Leu His Asn His Tyr Thr Gln Lys Ser Leu Ser
    290                 295                 300

Leu Ser Pro Gly Lys
305


<210> SEQ ID NO 78
<211> LENGTH: 309
<212> TYPE: PRT
<213> ORGANISM: Artificial Sequence
<220> FEATURE:
<223> OTHER INFORMATION: CXCL13(3-87K/H-A)-IgG4Fc

<400> SEQUENCE: 78

Glu Val Tyr Tyr Thr Ser Leu Arg Cys Arg Cys Val Gln Glu Ser Ser
1               5                   10                  15

Val Phe Ile Pro Arg Arg Phe Ile Asp Ala Ile Gln Ile Leu Pro Arg
            20                  25                  30

Gly Asn Gly Cys Pro Arg Lys Glu Ile Ile Val Trp Ala Ala Asn Ala
        35                  40                  45

Ser Ile Val Cys Val Asp Pro Gln Ala Glu Trp Ile Gln Ala Met Met
    50                  55                  60

Glu Val Leu Ala Ala Ala Ser Ser Ser Thr Leu Pro Val Pro Val Phe
65                  70                  75                  80

Ala Ala Ala Ile Pro Pro Pro Cys Pro Ser Cys Pro Ala Pro Glu Phe
                85                  90                  95

Leu Gly Gly Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser Gln Glu Asp Pro Glu Val Gln Phe Asn Trp Tyr Val Asp Gly Val
    130                 135                 140

Glu Val His Asn Ala Lys Thr Lys Pro Arg Glu Glu Gln Phe Asn Ser
145                 150                 155                 160

Thr Tyr Arg Val Val Ser Val Leu Thr Val Leu His Gln Asp Trp Leu
                165                 170                 175
```

```
Asn Gly Lys Glu Tyr Lys Cys Lys Val Ser Asn Lys Gly Leu Pro Ser
            180                 185                 190

Ser Ile Glu Lys Thr Ile Ser Lys Ala Lys Gly Gln Pro Arg Glu Pro
        195                 200                 205

Gln Val Tyr Thr Leu Pro Pro Ser Gln Glu Glu Met Thr Lys Asn Gln
    210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
                245                 250                 255

Pro Pro Val Leu Asp Ser Asp Gly Ser Phe Phe Leu Tyr Ser Arg Leu
            260                 265                 270

Thr Val Asp Lys Ser Arg Trp Gln Glu Gly Asn Val Phe Ser Cys Ser
        275                 280                 285

Val Met His Glu Ala Leu His Asn His Tyr Thr Gln Lys Ser Leu Ser
    290                 295                 300

Leu Ser Pro Gly Lys
305


<210> SEQ ID NO 79
<211> LENGTH: 4401
<212> TYPE: DNA
<213> ORGANISM: Artificial Sequence
<220> FEATURE:
<223> OTHER INFORMATION: pCCL2-IgG1Fc

<400> SEQUENCE: 79

ggatctgcga tcgctccggt gcccgtcagt gggcagagcg cacatcgccc acagtccccg      60

agaagttggg gggaggggtc ggcaattgaa cgggtgccta gagaaggtgg cgcggggtaa     120

actgggaaag tgatgtcgtg tactggctcc gcctttttcc cgagggtggg ggagaaccgt     180

atataagtgc agtagtcgcc gtgaacgttc tttttcgcaa cgggtttgcc gccagaacac     240

agctgaagct tcgaggggct cgcatctctc cttcacgcgc ccgccgccct acctgaggcc     300

gccatccacg ccggttgagt cgcgttctgc cgcctcccgc ctgtggtgcc tcctgaactg     360

cgtccgccgt ctaggtaagt ttaaagctca ggtcgagacc gggcctttgt ccggcgctcc     420

cttggagcct acctagactc agccggctct ccacgctttg cctgaccctg cttgctcaac     480

tctacgtctt tgtttcgttt tctgttctgc gccgttacag atccaagctg tgaccggcgc     540

ctacctgaga tcaccggcga aggagggcca ccatgtacag gatgcaactc ctgtcttgca     600

ttgcactaag tcttgcactt gtcacgaatt cgcagccaga tgcaatcaat gccccagtca     660

cctgctgtta taacttcacc aataggaaga tctcagtgca gaggctcgcg agctatagaa     720

gaatcaccag cagcaagtgt cccaaagaag ctgtgatctt caagaccatt gtggccaagg     780

agatctgtgc tgaccccaag cagaagtggg ttcaggattc catggaccac ctggacaagc     840

aaacccaaac tccgaagact gacaaaactc acacatgccc accgtgccca gcacctgaac     900

tcctgggggg accgtcagtc ttcctcttcc ccccaaaacc caaggacacc ctcatgatct     960

cccggacccc tgaggtcaca tgcgtggtgg tggacgtgag ccacgaagac cctgaggtca    1020

agttcaactg gtacgtggac ggcgtggagg tgcataatgc caagacaaag ccgcgggagg    1080

agcagtacaa cagcacgtac cgtgtggtca gcgtcctcac cgtcctgcac caggactggc    1140

tgaatggcaa ggagtacaag tgcaaggtct ccaacaaagc cctcccagcc cccatcgaga    1200

aaaccatctc caaagccaaa gggcagcccc gagaaccaca ggtgtacacc ctgcccccat    1260
```

-continued

```
cccgggagga gatgaccaag aaccaggtca gcctgacctg cctggtcaaa ggcttctatc   1320
ccagcgacat cgccgtggag tgggagagca atgggcagcc ggagaacaac tacaagacca   1380
cgcctcccgt gctggactcc gacggctcct tcttcctcta cagcaagctc accgtggaca   1440
agagcaggtg gcagcagggg aacgtcttct catgctccgt gatgcacgag gctctgcaca   1500
accactacac gcagaagagc ctctccctgt ctccgggtaa atgagtgcta gctggccaga   1560
catgataaga tacattgatg agtttggaca aaccacaact agaatgcagt gaaaaaaatg   1620
ctttatttgt gaaatttgtg atgctattgc tttatttgta accattataa gctgcaataa   1680
acaagttaac aacaacaatt gcattcattt tatgtttcag gttcaggggg aggtgtggga   1740
ggttttttaa agcaagtaaa acctctacaa atgtggtatg gaattaattc taaaatacag   1800
catagcaaaa ctttaacctc caaatcaagc ctctacttga atccttttct gagggatgaa   1860
taaggcatag gcatcagggg ctgttgccaa tgtgcattag ctgtttgcag cctcaccttc   1920
tttcatggag tttaagatat agtgtatttt cccaaggttt gaactagctc ttcatttctt   1980
tatgttttaa atgcactgac ctcccacatt ccctttttag taaaatattc agaaataatt   2040
taaatacatc attgcaatga aaataaatgt tttttattag gcagaatcca gatgctcaag   2100
gcccttcata atatccccca gtttagtagt tggacttagg gaacaaagga acctttaata   2160
gaaattggac agcaagaaag cgagcttcta gcttatcctc agtcctgctc ctctgccaca   2220
aagtgcacgc agttgccggc cgggtcgcgc agggcgaact cccgccccca cggctgctcg   2280
ccgatctcgg tcatggccgg cccggaggcg tcccggaagt tcgtggacac gacctccgac   2340
cactcggcgt acagctcgtc caggccgcgc acccacaccc aggccagggt gttgtccggc   2400
accacctggt cctggaccgc gctgatgaac agggtcacgt cgtcccggac cacaccggcg   2460
aagtcgtcct ccacgaagtc ccgggagaac ccgagccggt cggtccagaa ctcgaccgct   2520
ccggcgacgt cgcgcgcggt gagcaccgga acggcactgg tcaacttggc catgatggct   2580
cctcctgtca ggagaggaaa gagaagaagg ttagtacaat tgctatagtg agttgtatta   2640
tactatgcag atatactatg ccaatgatta attgtcaaac tagggctgca gggttcatag   2700
tgccactttt cctgcactgc cccatctcct gcccaccctt tcccaggcat agacagtcag   2760
tgacttacca aactcacagg agggagaagg cagaagcttg agacagaccc gcgggaccgc   2820
cgaactgcga ggggacgtgg ctagggcggc ttcttttatg gtgcgccggc cctcggaggc   2880
agggcgctcg ggaggcctag cggccaatc tgcggtggca ggaggcgggg ccgaaggccg   2940
tgcctgacca atccggagca cataggagtc tcagcccccc gccccaaagc aaggggaagt   3000
cacgcgcctg tagcgccagc gtgttgtgaa atgggggctt ggggggggttg gggccctgac   3060
tagtcaaaac aaactcccat tgacgtcaat ggggtggaga cttggaaatc cccgtgagtc   3120
aaaccgctat ccacgcccat tgatgtactg ccaaaaccgc atcatcatgg taatagcgat   3180
gactaatacg tagatgtact gccaagtagg aaagtcccat aaggtcatgt actgggcata   3240
atgccaggcg ggccatttac cgtcattgac gtcaataggg ggcgtacttg gcatatgata   3300
cacttgatgt actgccaagt gggcagttta ccgtaaatac tccacccatt gacgtcaatg   3360
gaaagtccct attggcgtta ctatgggaac atacgtcatt attgacgtca atgggcgggg   3420
gtcgttgggc ggtcagccag gcgggccatt taccgtaagt tatgtaacgc ctgcaggtta   3480
attaagaaca tgtgagcaaa aggccagcaa aaggccagga accgtaaaaa ggccgcgttg   3540
ctggcgtttt tccataggct ccgcccccct gacgagcatc acaaaaatcg acgctcaagt   3600
```

cagaggtggc gaaacccgac aggactataa agataccagg cgtttccccc tggaagctcc 3660
ctcgtgcgct ctcctgttcc gaccctgccg cttaccggat acctgtccgc ctttctccct 3720
tcgggaagcg tggcgctttc tcatagctca cgctgtaggt atctcagttc ggtgtaggtc 3780
gttcgctcca agctgggctg tgtgcacgaa ccccccgttc agcccgaccg ctgcgcctta 3840
tccggtaact atcgtcttga gtccaacccg gtaagacacg acttatcgcc actggcagca 3900
gccactggta acaggattag cagagcgagg tatgtaggcg gtgctacaga gttcttgaag 3960
tggtggccta actacggcta cactagaaga acagtatttg gtatctgcgc tctgctgaag 4020
ccagttacct tcggaaaaag agttggtagc tcttgatccg gcaaacaaac caccgctggt 4080
agcggtggtt tttttgtttg caagcagcag attacgcgca gaaaaaaagg atctcaagaa 4140
gatcctttga tcttttctac ggggtctgac gctcagtgga acgaaaactc acgttaaggg 4200
attttggtca tggctagtta attaacattt aaatcagcgg ccgcaataaa atatctttat 4260
tttcattaca tctgtgtgtt ggttttttgt gtgaatcgta actaacatac gctctccatc 4320
aaaacaaaac gaaacaaaac aaactagcaa aataggctgt ccccagtgca agtgcaggtg 4380
ccagaacatt tctctatcga a 4401

<210> SEQ ID NO 80
<211> LENGTH: 4389
<212> TYPE: DNA
<213> ORGANISM: Artificial Sequence
<220> FEATURE:
<223> OTHER INFORMATION: pCCL2(5-76)-IgG1Fc

<400> SEQUENCE: 80
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacctgaga tcaccggcga aggagggcca ccatgtacag gatgcaactc ctgtcttgca 600
ttgcactaag tcttgcactt gtcacgaatt cgatcaatgc cccagtcacc tgctgttata 660
acttcaccaa taggaagatc tcagtgcaga ggctcgcgag ctatagaaga atcaccagca 720
gcaagtgtcc caaagaagct gtgatcttca agaccattgt ggccaaggag atctgtgctg 780
accccaagca gaagtgggtt caggattcca tggaccacct ggacaagcaa acccaaactc 840
cgaagactga caaaactcac acatgcccac cgtgcccagc acctgaactc ctggggggac 900
cgtcagtctt cctcttcccc ccaaaaccca aggacaccct catgatctcc cggacccctg 960
aggtcacatg cgtggtggtg gacgtgagcc acgaagaccc tgaggtcaag ttcaactggt 1020
acgtggacgg cgtggaggtg cataatgcca agacaaagcc gcgggaggag cagtacaaca 1080
gcacgtaccg tgtggtcagc gtcctcaccg tcctgcacca ggactggctg aatggcaagg 1140
agtacaagtg caaggtctcc aacaaagccc tcccagcccc catcgagaaa accatctcca 1200
aagccaaagg gcagccccga gaaccacagg tgtacaccct gcccccatcc cgggaggaga 1260

```
tgaccaagaa ccaggtcagc ctgacctgcc tggtcaaagg cttctatccc agcgacatcg   1320
ccgtggagtg ggagagcaat gggcagccgg agaacaacta caagaccacg cctcccgtgc   1380
tggactccga cggctccttc ttcctctaca gcaagctcac cgtggacaag agcaggtggc   1440
agcaggggaa cgtcttctca tgctccgtga tgcacgaggc tctgcacaac cactacacgc   1500
agaagagcct ctccctgtct ccgggtaaat gagtgctagc tggccagaca tgataagata   1560
cattgatgag tttggacaaa ccacaactag aatgcagtga aaaaaatgct ttatttgtga   1620
aatttgtgat gctattgctt tatttgtaac cattataagc tgcaataaac aagttaacaa   1680
caacaattgc attcatttta tgtttcaggt tcagggggag gtgtgggagg ttttttaaag   1740
caagtaaaac ctctacaaat gtggtatgga attaattcta aaatacagca tagcaaaact   1800
ttaacctcca aatcaagcct ctacttgaat ccttttctga gggatgaata aggcataggc   1860
atcaggggct gttgccaatg tgcattagct gtttgcagcc tcaccttctt tcatggagtt   1920
taagatatag tgtattttcc caaggtttga actagctctt catttcttta tgttttaaat   1980
gcactgacct cccacattcc ctttttagta aaatattcag aaataattta aatacatcat   2040
tgcaatgaaa ataaatgttt tttattaggc agaatccaga tgctcaaggc ccttcataat   2100
atcccccagt ttagtagttg gacttaggga acaaaggaac ctttaataga aattggacag   2160
caagaaagcg agcttctagc ttatcctcag tcctgctcct ctgccacaaa gtgcacgcag   2220
ttgccggccg ggtcgcgcag ggcgaactcc cgcccccacg gctgctcgcc gatctcggtc   2280
atggccggcc cggaggcgtc ccggaagttc gtggacacga cctccgacca ctcggcgtac   2340
agctcgtcca ggccgcgcac ccacacccag gccagggtgt tgtccggcac cacctggtcc   2400
tggaccgcgc tgatgaacag ggtcacgtcg tcccggacca caccggcgaa gtcgtcctcc   2460
acgaagtccc gggagaaccc gagccggtcg gtccagaact cgaccgctcc ggcgacgtcg   2520
cgcgcggtga gcaccggaac ggcactggtc aacttggcca tgatggctcc tcctgtcagg   2580
agaggaaaga gaagaaggtt agtacaattg ctatagtgag ttgtattata ctatgcagat   2640
atactatgcc aatgattaat tgtcaaacta gggctgcagg gttcatagtg ccacttttcc   2700
tgcactgccc catctcctgc ccaccctttc ccaggcatag acagtcagtg acttaccaaa   2760
ctcacaggag ggagaaggca gaagcttgag acagacccgc gggaccgccg aactgcgagg   2820
ggacgtggct agggcggctt cttttatggt gcgccggccc tcggaggcag ggcgctcggg   2880
gaggcctagc ggccaatctg cggtggcagg aggcggggcc gaaggccgtg cctgaccaat   2940
ccggagcaca taggagtctc agccccccgc cccaaagcaa ggggaagtca cgcgcctgta   3000
gcgccagcgt gttgtgaaat gggggcttgg gggggttggg gccctgacta gtcaaaacaa   3060
actcccattg acgtcaatgg ggtggagact tggaaatccc cgtgagtcaa accgctatcc   3120
acgcccattg atgtactgcc aaaaccgcat catcatggta atagcgatga ctaatacgta   3180
gatgtactgc caagtaggaa agtcccataa ggtcatgtac tgggcataat gccaggcggg   3240
ccatttaccg tcattgacgt caatagggggg cgtacttggc atatgataca cttgatgtac  3300
tgccaagtgg gcagtttacc gtaaatactc cacccattga cgtcaatgga aagtccctat   3360
tggcgttact atgggaacat acgtcattat tgacgtcaat gggcgggggt cgttgggcgg   3420
tcagccaggc gggccattta ccgtaagtta tgtaacgcct gcaggttaat taagaacatg   3480
tgagcaaaag gccagcaaaa ggccaggaac cgtaaaaagg ccgcgttgct ggcgtttttc   3540
cataggctcc gccccccctga cgagcatcac aaaaatcgac gctcaagtca gaggtggcga  3600
```

aacccgacag gactataaag ataccaggcg tttccccctg gaagctccct cgtgcgctct 3660
cctgttccga ccctgccgct taccggatac ctgtccgcct ttctcccttc gggaagcgtg 3720
gcgctttctc atagctcacg ctgtaggtat ctcagttcgg tgtaggtcgt tcgctccaag 3780
ctgggctgtg tgcacgaacc ccccgttcag cccgaccgct gcgccttatc cggtaactat 3840
cgtcttgagt ccaacccggt aagacacgac ttatcgccac tggcagcagc cactggtaac 3900
aggattagca gagcgaggta tgtaggcggt gctacagagt tcttgaagtg gtggcctaac 3960
tacggctaca ctagaagaac agtatttggt atctgcgctc tgctgaagcc agttaccttc 4020
ggaaaaagag ttggtagctc ttgatccggc aaacaaacca ccgctggtag cggtggtttt 4080
tttgtttgca agcagcagat tacgcgcaga aaaaaaggat ctcaagaaga tcctttgatc 4140
ttttctacgg ggtctgacgc tcagtggaac gaaaactcac gttaagggat tttggtcatg 4200
gctagttaat taacatttaa atcagcggcc gcaataaaat atctttattt tcattacatc 4260
tgtgtgttgg ttttttgtgt gaatcgtaac taacatacgc tctccatcaa aacaaaacga 4320
aacaaaacaa actagcaaaa taggctgtcc ccagtgcaag tgcaggtgcc agaacatttc 4380
tctatcgaa 4389

<210> SEQ ID NO 81
<211> LENGTH: 4389
<212> TYPE: DNA
<213> ORGANISM: Artificial Sequence
<220> FEATURE:
<223> OTHER INFORMATION: pCCL2(5-76K/H-A)-IgG1Fc

<400> SEQUENCE: 81
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacctgaga tcaccggcga aggagggcca ccatgtacag gatgcaactc ctgtcttgca 600
ttgcactaag tcttgcactt gtcacgaatt cgatcaatgc cccagtcacc tgctgttata 660
acttcaccaa taggaagatc tcagtgcaga ggctcgcgag ctatagaaga atcaccagca 720
gcaagtgtcc caaagaagct gtgatcttca agaccattgt ggccgcggag atctgtgctg 780
accccgctca ggcctgggtt caggattcca tggacgctct ggacgcccaa acccaaactc 840
cggcgactga caaaactcac acatgcccac cgtgcccagc acctgaactc ctggggggac 900
cgtcagtctt cctcttcccc ccaaaaccca aggacaccct catgatctcc cggacccctg 960
aggtcacatg cgtggtggtg gacgtgagcc acgaagaccc tgaggtcaag ttcaactggt 1020
acgtggacgg cgtggaggtg cataatgcca agacaaagcc gcgggaggag cagtacaaca 1080
gcacgtaccg tgtggtcagc gtcctcaccg tcctgcacca ggactggctg aatggcaagg 1140
agtacaagtg caaggtctcc aacaaagccc tcccagcccc catcgagaaa accatctcca 1200
aagccaaagg gcagccccga gaaccacagg tgtacaccct gcccccatcc cgggaggaga 1260

-continued

```
tgaccaagaa ccaggtcagc ctgacctgcc tggtcaaagg cttctatccc agcgacatcg   1320
ccgtggagtg ggagagcaat gggcagccgg agaacaacta caagaccacg cctcccgtgc   1380
tggactccga cggctccttc ttcctctaca gcaagctcac cgtggacaag agcaggtggc   1440
agcaggggaa cgtcttctca tgctccgtga tgcacgaggc tctgcacaac cactacacgc   1500
agaagagcct ctccctgtct ccgggtaaat gagtgctagc tggccagaca tgataagata   1560
cattgatgag tttggacaaa ccacaactag aatgcagtga aaaaaatgct ttatttgtga   1620
aatttgtgat gctattgctt tatttgtaac cattataagc tgcaataaac aagttaacaa   1680
caacaattgc attcatttta tgtttcaggt tcagggggag gtgtgggagg ttttttaaag   1740
caagtaaaac ctctacaaat gtggtatgga attaattcta aaatacagca tagcaaaact   1800
ttaacctcca aatcaagcct ctacttgaat ccttttctga gggatgaata aggcataggc   1860
atcaggggct gttgccaatg tgcattagct gtttgcagcc tcaccttctt tcatggagtt   1920
taagatatag tgtattttcc caaggtttga actagctctt catttcttta tgttttaaat   1980
gcactgacct cccacattcc ctttttagta aaatattcag aaataattta aatacatcat   2040
tgcaatgaaa ataaatgttt tttattaggc agaatccaga tgctcaaggc ccttcataat   2100
atcccccagt ttagtagttg gacttaggga acaaaggaac ctttaataga aattggacag   2160
caagaaagcg agcttctagc ttatcctcag tcctgctcct ctgccacaaa gtgcacgcag   2220
ttgccggccg ggtcgcgcag ggcgaactcc cgcccccacg gctgctcgcc gatctcggtc   2280
atggccggcc cggaggcgtc ccggaagttc gtggacacga cctccgacca ctcggcgtac   2340
agctcgtcca ggccgcgcac ccacacccag gccagggtgt tgtccggcac cacctggtcc   2400
tggaccgcgc tgatgaacag ggtcacgtcg tcccggacca caccggcgaa gtcgtcctcc   2460
acgaagtccc gggagaaccc gagccggtcg gtccagaact cgaccgctcc ggcgacgtcg   2520
cgcgcggtga gcaccggaac ggcactggtc aacttggcca tgatggctcc tcctgtcagg   2580
agaggaaaga gaagaaggtt agtacaattg ctatagtgag ttgtattata ctatgcagat   2640
atactatgcc aatgattaat tgtcaaacta gggctgcagg gttcatagtg ccacttttcc   2700
tgcactgccc catctcctgc ccaccctttc ccaggcatag acagtcagtg acttaccaaa   2760
ctcacaggag ggagaaggca gaagcttgag acagacccgc gggaccgccg aactgcgagg   2820
ggacgtggct agggcggctt cttttatggt gcgccggccc tcggaggcag ggcgctcggg   2880
gaggcctagc ggccaatctg cggtggcagg aggcggggcc gaaggccgtg cctgaccaat   2940
ccggagcaca taggagtctc agccccccgc cccaaagcaa ggggaagtca cgcgcctgta   3000
gcgccagcgt gttgtgaaat gggggcttgg gggggttggg gccctgacta gtcaaaacaa   3060
actcccattg acgtcaatgg ggtggagact tggaaatccc cgtgagtcaa accgctatcc   3120
acgcccattg atgtactgcc aaaaccgcat catcatggta atagcgatga ctaatacgta   3180
gatgtactgc caagtaggaa agtcccataa ggtcatgtac tgggcataat gccaggcggg   3240
ccatttaccg tcattgacgt caatgggggg cgtacttggc atatgataca cttgatgtac   3300
tgccaagtgg gcagtttacc gtaaatactc cacccattga cgtcaatgga aagtccctat   3360
tggcgttact atgggaacat acgtcattat tgacgtcaat gggcgggggt cgttgggcgg   3420
tcagccaggc gggccattta ccgtaagtta tgtaacgcct gcaggttaat taagaacatg   3480
tgagcaaaag gccagcaaaa ggccaggaac cgtaaaaagg ccgcgttgct ggcgtttttc   3540
cataggctcc gcccccctga cgagcatcac aaaaatcgac gctcaagtca gaggtggcga   3600
```

-continued

```
aacccgacag gactataaag ataccaggcg tttccccctg gaagctccct cgtgcgctct   3660
cctgttccga ccctgccgct taccggatac ctgtccgcct ttctcccttc gggaagcgtg   3720
gcgctttctc atagctcacg ctgtaggtat ctcagttcgg tgtaggtcgt tcgctccaag   3780
ctgggctgtg tgcacgaacc ccccgttcag cccgaccgct gcgccttatc cggtaactat   3840
cgtcttgagt ccaacccggt aagacacgac ttatcgccac tggcagcagc cactggtaac   3900
aggattagca gagcgaggta tgtaggcggt gctacagagt tcttgaagtg gtggcctaac   3960
tacggctaca ctagaagaac agtatttggt atctgcgctc tgctgaagcc agttaccttc   4020
ggaaaaagag ttggtagctc ttgatccggc aaacaaacca ccgctggtag cggtggtttt   4080
tttgtttgca agcagcagat tacgcgcaga aaaaaaggat ctcaagaaga tcctttgatc   4140
ttttctacgg ggtctgacgc tcagtggaac gaaaactcac gttaagggat tttggtcatg   4200
gctagttaat taacatttaa atcagcggcc gcaataaaat atctttattt tcattacatc   4260
tgtgtgttgg tttttgtgt gaatcgtaac taacatacgc tctccatcaa aacaaaacga   4320
aacaaaacaa actagcaaaa taggctgtcc ccagtgcaag tgcaggtgcc agaacatttc   4380
tctatcgaa                                                           4389

<210> SEQ ID NO 82
<211> LENGTH: 4371
<212> TYPE: DNA
<213> ORGANISM: Artificial Sequence
<220> FEATURE:
<223> OTHER INFORMATION: pCCL7-IgG1Fc

<400> SEQUENCE: 82

ggatctgcga tcgctccggt gcccgtcagt gggcagagcg cacatcgccc acagtccccg     60
agaagttggg gggaggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cgtgctgcta cagatttatc aataagaaaa    660
tccctaagca gaggctggag agctacagaa ggaccaccag tagccactgt ccccgggaag    720
ctgtaatctt caagaccaaa ctggacaagg agatctgtgc tgaccccaca cagaagtggg    780
tccaggactt tatgaagcac ctggacaaga aaacccaaac tccaaagctt gacaaaactc    840
acacatgccc accgtgccca gcacctgaac tcctgggggg accgtcagtc ttcctcttcc    900
ccccaaaacc caaggacacc ctcatgatct cccggacccc tgaggtcaca tgcgtggtgg    960
tggacgtgag ccacgaagac cctgaggtca agttcaactg gtacgtggac ggcgtggagg   1020
tgcataatgc caagacaaag ccgcgggagg agcagtacaa cagcacgtac cgtgtggtca   1080
gcgtcctcac cgtcctgcac caggactggc tgaatggcaa ggagtacaag tgcaaggtct   1140
ccaacaaagc cctcccagcc cccatcgaga aaaccatctc caaagccaaa gggcagcccc   1200
gagaaccaca ggtgtacacc ctgcccccat cccgggagga gatgaccaag aaccaggtca   1260
```

-continued gcctgacctg cctggtcaaa ggcttctatc ccagcgacat cgccgtggag tgggagagca 1320
atgggcagcc ggagaacaac tacaagacca cgcctcccgt gctggactcc gacggctcct 1380
tcttcctcta cagcaagctc accgtggaca agagcaggtg gcagcagggg aacgtcttct 1440
catgctccgt gatgcacgag gctctgcaca accactacac gcagaagagc ctctccctgt 1500
ctccgggtaa atgagtgcta gctggccaga catgataaga tacattgatg agtttggaca 1560
aaccacaact agaatgcagt gaaaaaaatg ctttatttgt gaaatttgtg atgctattgc 1620
tttatttgta accattataa gctgcaataa acaagttaac aacaacaatt gcattcattt 1680
tatgtttcag gttcaggggg aggtgtggga ggttttttaa agcaagtaaa acctctacaa 1740
atgtggtatg gaattaattc taaaatacag catagcaaaa ctttaacctc caaatcaagc 1800
ctctacttga atccttttct gagggatgaa taaggcatag gcatcagggg ctgttgccaa 1860
tgtgcattag ctgtttgcag cctcaccttc tttcatggag tttaagatat agtgtatttt 1920
cccaaggttt gaactagctc ttcatttctt tatgttttaa atgcactgac ctcccacatt 1980
ccctttttag taaaatattc agaaataatt taaatacatc attgcaatga aaataaatgt 2040
tttttattag gcagaatcca gatgctcaag gcccttcata atatccccca gtttagtagt 2100
tggacttagg gaacaaagga acctttaata gaaattggac agcaagaaag cgagcttcta 2160
gcttatcctc agtcctgctc ctctgccaca aagtgcacgc agttgccggc cgggtcgcgc 2220
agggcgaact cccgccccca cggctgctcg ccgatctcgg tcatggccgg cccggaggcg 2280
tcccggaagt tcgtggacac gacctccgac cactcggcgt acagctcgtc caggccgcgc 2340
acccacaccc aggccagggt gttgtccggc accacctggt cctggaccgc gctgatgaac 2400
agggtcacgt cgtcccggac cacaccggcg aagtcgtcct ccacgaagtc ccgggagaac 2460
ccgagccggt cggtccagaa ctcgaccgct ccggcgacgt cgcgcgcggt gagcaccgga 2520
acggcactgg tcaacttggc catgatggct cctcctgtca ggagaggaaa gagaagaagg 2580
ttagtacaat tgctatagtg agttgtatta tactatgcag atatactatg ccaatgatta 2640
attgtcaaac tagggctgca gggttcatag tgccactttt cctgcactgc cccatctcct 2700
gcccaccctt tcccaggcat agacagtcag tgacttacca aactcacagg agggagaagg 2760
cagaagcttg agacagaccc gcgggaccgc cgaactgcga ggggacgtgg ctagggcggc 2820
ttcttttatg gtgcgccggc cctcggaggc agggcgctcg gggaggccta gcggccaatc 2880
tgcggtggca ggaggcgggg ccgaaggccg tgcctgacca atccggagca cataggagtc 2940
tcagcccccc gccccaaagc aaggggaagt cacgcgcctg tagcgccagc gtgttgtgaa 3000
atgggggctt gggggggttg gggccctgac tagtcaaaac aaactcccat tgacgtcaat 3060
ggggtggaga cttggaaatc cccgtgagtc aaaccgctat ccacgcccat tgatgtactg 3120
ccaaaaccgc atcatcatgg taatagcgat gactaatacg tagatgtact gccaagtagg 3180
aaagtcccat aaggtcatgt actgggcata atgccaggcg ggccatttac cgtcattgac 3240
gtcaataggg ggcgtacttg gcatatgata cacttgatgt actgccaagt gggcagttta 3300
ccgtaaatac tccacccatt gacgtcaatg gaaagtccct attggcgtta ctatgggaac 3360
atacgtcatt attgacgtca atgggcgggg gtcgttgggc ggtcagccag gcgggccatt 3420
taccgtaagt tatgtaacgc ctgcaggtta attaagaaca tgtgagcaaa aggccagcaa 3480
aaggccagga accgtaaaaa ggccgcgttg ctggcgtttt tccataggct ccgcccccct 3540
gacgagcatc acaaaaatcg acgctcaagt cagaggtggc gaaacccgac aggactataa 3600
agataccagg cgtttccccc tggaagctcc ctcgtgcgct ctcctgttcc gaccctgccg 3660
cttaccggat acctgtccgc ctttctccct tcgggaagcg tggcgctttc tcatagctca 3720
cgctgtaggt atctcagttc ggtgtaggtc gttcgctcca agctgggctg tgtgcacgaa 3780
ccccccgttc agcccgaccg ctgcgcctta tccggtaact atcgtcttga gtccaacccg 3840
gtaagacacg acttatcgcc actggcagca gccactggta acaggattag cagagcgagg 3900
tatgtaggcg gtgctacaga gttcttgaag tggtggccta actacggcta cactagaaga 3960
acagtatttg gtatctgcgc tctgctgaag ccagttacct tcggaaaaag agttggtagc 4020
tcttgatccg gcaaacaaac caccgctggt agcggtggtt tttttgtttg caagcagcag 4080
attacgcgca gaaaaaaagg atctcaagaa gatcctttga tcttttctac ggggtctgac 4140
gctcagtgga acgaaaactc acgttaaggg attttggtca tggctagtta attaacattt 4200
aaatcagcgg ccgcaataaa atatctttat tttcattaca tctgtgtgtt ggttttttgt 4260
gtgaatcgta actaacatac gctctccatc aaaacaaaac gaaacaaaac aaactagcaa 4320
aataggctgt ccccagtgca agtgcaggtg ccagaacatt tctctatcga a 4371

<210> SEQ ID NO 83
<211> LENGTH: 4359
<212> TYPE: DNA
<213> ORGANISM: Artificial Sequence
<220> FEATURE:
<223> OTHER INFORMATION: pCCL7(5-76)-IgG1Fc

<400> SEQUENCE: 83
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacctgaga tcaccggcga aggagggcca ccatgtacag gatgcaactc ctgtcttgca 600
ttgcactaag tcttgcactt gtcacgaatt cgtttatcaa taagaaaatc cctaagcaga 660
ggctggagag ctacagaagg accaccagta gccactgtcc ccgggaagct gtaatcttca 720
agaccaaact ggacaaggag atctgtgctg accccacaca gaagtgggtc caggacttta 780
tgaagcacct ggacaagaaa acccaaactc caaagcttga caaaactcac acatgcccac 840
cgtgcccagc acctgaactc ctggggggac cgtcagtctt cctcttcccc ccaaaaccca 900
aggacaccct catgatctcc cggacccctg aggtcacatg cgtggtggtg gacgtgagcc 960
acgaagaccc tgaggtcaag ttcaactggt acgtggacgg cgtggaggtg cataatgcca 1020
agacaaagcc gcgggaggag cagtacaaca gcacgtaccg tgtggtcagc gtcctcaccg 1080
tcctgcacca ggactggctg aatggcaagg agtacaagtg caaggtctcc aacaaagccc 1140
tcccagcccc catcgagaaa accatctcca aagccaaagg gcagccccga gaaccacagg 1200
tgtacaccct gcccccatcc cgggaggaga tgaccaagaa ccaggtcagc ctgacctgcc 1260
tggtcaaagg cttctatccc agcgacatcg ccgtggagtg ggagagcaat gggcagccgg 1320
agaacaacta caagaccacg cctcccgtgc tggactccga cggctccttc ttcctctaca 1380
gcaagctcac cgtggacaag agcaggtggc agcaggggaa cgtcttctca tgctccgtga 1440
tgcacgaggc tctgcacaac cactacacgc agaagagcct ctccctgtct ccgggtaaat 1500
gagtgctagc tggccagaca tgataagata cattgatgag tttggacaaa ccacaactag 1560
aatgcagtga aaaaaatgct ttatttgtga aatttgtgat gctattgctt tatttgtaac 1620
cattataagc tgcaataaac aagttaacaa caacaattgc attcatttta tgtttcaggt 1680
tcagggggag gtgtgggagg ttttttaaag caagtaaaac ctctacaaat gtggtatgga 1740
attaattcta aaatacagca tagcaaaact ttaacctcca aatcaagcct ctacttgaat 1800
ccttttctga gggatgaata aggcataggc atcaggggct gttgccaatg tgcattagct 1860
gtttgcagcc tcaccttctt tcatggagtt taagatatag tgtattttcc caaggtttga 1920
actagctctt catttcttta tgttttaaat gcactgacct cccacattcc ctttttagta 1980
aaatattcag aaataattta aatacatcat tgcaatgaaa ataaatgttt tttattaggc 2040
agaatccaga tgctcaaggc ccttcataat atcccccagt ttagtagttg gacttaggga 2100
acaaaggaac ctttaataga aattggacag caagaaagcg agcttctagc ttatcctcag 2160
tcctgctcct ctgccacaaa gtgcacgcag ttgccggccg ggtcgcgcag ggcgaactcc 2220
cgcccccacg gctgctcgcc gatctcggtc atggccggcc cggaggcgtc ccggaagttc 2280
gtggacacga cctccgacca ctcggcgtac agctcgtcca ggccgcgcac ccacacccag 2340
gccagggtgt tgtccggcac cacctggtcc tggaccgcgc tgatgaacag ggtcacgtcg 2400
tcccggacca caccggcgaa gtcgtcctcc acgaagtccc gggagaaccc gagccggtcg 2460
gtccagaact cgaccgctcc ggcgacgtcg cgcgcggtga gcaccggaac ggcactggtc 2520
aacttggcca tgatggctcc tcctgtcagg agaggaaaga gaagaaggtt agtacaattg 2580
ctatagtgag ttgtattata ctatgcagat atactatgcc aatgattaat tgtcaaacta 2640
gggctgcagg gttcatagtg ccacttttcc tgcactgccc catctcctgc ccaccctttc 2700
ccaggcatag acagtcagtg acttaccaaa ctcacaggag ggagaaggca gaagcttgag 2760
acagacccgc gggaccgccg aactgcgagg ggacgtggct agggcggctt cttttatggt 2820
gcgccggccc tcggaggcag ggcgctcggg gaggcctagc ggccaatctg cggtggcagg 2880
aggcggggcc gaaggccgtg cctgaccaat ccggagcaca taggagtctc agccccccgc 2940
cccaaagcaa ggggaagtca cgcgcctgta gcgccagcgt gttgtgaaat gggggcttgg 3000
gggggttggg gccctgacta gtcaaaacaa actcccattg acgtcaatgg ggtggagact 3060
tggaaatccc cgtgagtcaa accgctatcc acgcccattg atgtactgcc aaaaccgcat 3120
catcatggta atagcgatga ctaatacgta gatgtactgc caagtaggaa agtcccataa 3180
ggtcatgtac tgggcataat gccaggcggg ccatttaccg tcattgacgt caatagggggg 3240
cgtacttggc atatgataca cttgatgtac tgccaagtgg gcagtttacc gtaaatactc 3300
cacccattga cgtcaatgga aagtccctat tggcgttact atgggaacat acgtcattat 3360
tgacgtcaat gggcgggggt cgttgggcgg tcagccaggc gggccattta ccgtaagtta 3420
tgtaacgcct gcaggttaat taagaacatg tgagcaaaag gccagcaaaa ggccaggaac 3480
cgtaaaaagg ccgcgttgct ggcgtttttc cataggctcc gcccccctga cgagcatcac 3540
aaaaatcgac gctcaagtca gaggtggcga aacccgacag gactataaag ataccaggcg 3600
tttccccctg gaagctccct cgtgcgctct cctgttccga ccctgccgct taccggatac 3660
ctgtccgcct ttctcccttc gggaagcgtg gcgctttctc atagctcacg ctgtaggtat 3720
ctcagttcgg tgtaggtcgt tcgctccaag ctgggctgtg tgcacgaacc ccccgttcag 3780
cccgaccgct gcgccttatc cggtaactat cgtcttgagt ccaacccggt aagacacgac 3840
ttatcgccac tggcagcagc cactggtaac aggattagca gagcgaggta tgtaggcggt 3900
gctacagagt tcttgaagtg gtggcctaac tacggctaca ctagaagaac agtatttggt 3960
atctgcgctc tgctgaagcc agttaccttc ggaaaaagag ttggtagctc ttgatccggc 4020
aaacaaacca ccgctggtag cggtggtttt tttgtttgca agcagcagat tacgcgcaga 4080
aaaaaaggat ctcaagaaga tcctttgatc ttttctacgg ggtctgacgc tcagtggaac 4140
gaaaactcac gttaagggat tttggtcatg gctagttaat taacatttaa atcagcggcc 4200
gcaataaaat atctttattt tcattacatc tgtgtgttgg ttttttgtgt gaatcgtaac 4260
taacatacgc tctccatcaa aacaaaacga aacaaaacaa actagcaaaa taggctgtcc 4320
ccagtgcaag tgcaggtgcc agaacatttc tctatcgaa 4359

<210> SEQ ID NO 84
<211> LENGTH: 4359
<212> TYPE: DNA
<213> ORGANISM: Artificial Sequence
<220> FEATURE:
<223> OTHER INFORMATION: pCCL7(5-76K/H-A)-IgG1Fc

<400> SEQUENCE: 84
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacctgaga tcaccggcga aggagggcca ccatgtacag gatgcaactc ctgtcttgca 600
ttgcactaag tcttgcactt gtcacgaatt cgtttatcaa taagaaaatc cctaagcaga 660
ggctggagag ctacagaagg accaccagta gccactgtcc ccgggaagct gtaatcttcg 720
ccaccgcgct ggacgctgag atctgtgctg accccacaca ggcctgggtc caggacttta 780
tggctgccct ggacgcggct acccaaactc cagcccttga caaaactcac acatgcccac 840
cgtgcccagc acctgaactc ctggggggac cgtcagtctt cctcttcccc ccaaaaccca 900
aggacaccct catgatctcc cggacccctg aggtcacatg cgtggtggtg gacgtgagcc 960
acgaagaccc tgaggtcaag ttcaactggt acgtggacgg cgtggaggtg cataatgcca 1020
agacaaagcc gcgggaggag cagtacaaca gcacgtaccg tgtggtcagc gtcctcaccg 1080
tcctgcacca ggactggctg aatggcaagg agtacaagtg caaggtctcc aacaaagccc 1140
tcccagcccc catcgagaaa accatctcca aagccaaagg gcagccccga gaaccacagg 1200
tgtacaccct gcccccatcc cgggaggaga tgaccaagaa ccaggtcagc ctgacctgcc 1260
tggtcaaagg cttctatccc agcgacatcg ccgtggagtg ggagagcaat gggcagccgg 1320
agaacaacta caagaccacg cctcccgtgc tggactccga cggctccttc ttcctctaca 1380

-continued

```
gcaagctcac cgtggacaag agcaggtggc agcaggggaa cgtcttctca tgctccgtga   1440
tgcacgaggc tctgcacaac cactacacgc agaagagcct ctccctgtct ccgggtaaat   1500
gagtgctagc tggccagaca tgataagata cattgatgag tttggacaaa ccacaactag   1560
aatgcagtga aaaaaatgct ttatttgtga aatttgtgat gctattgctt tatttgtaac   1620
cattataagc tgcaataaac aagttaacaa caacaattgc attcatttta tgtttcaggt   1680
tcagggggag gtgtgggagg ttttttaaag caagtaaaac ctctacaaat gtggtatgga   1740
attaattcta aaatacagca tagcaaaact ttaacctcca aatcaagcct ctacttgaat   1800
ccttttctga gggatgaata aggcataggc atcaggggct gttgccaatg tgcattagct   1860
gtttgcagcc tcaccttctt tcatggagtt taagatatag tgtattttcc caaggtttga   1920
actagctctt catttcttta tgttttaaat gcactgacct cccacattcc ctttttagta   1980
aaatattcag aaataattta aatacatcat tgcaatgaaa ataaatgttt tttattaggc   2040
agaatccaga tgctcaaggc ccttcataat atcccccagt ttagtagttg gacttaggga   2100
acaaaggaac ctttaataga aattggacag caagaaagcg agcttctagc ttatcctcag   2160
tcctgctcct ctgccacaaa gtgcacgcag ttgccggccg ggtcgcgcag ggcgaactcc   2220
cgcccccacg gctgctcgcc gatctcggtc atggccggcc cggaggcgtc ccggaagttc   2280
gtggacacga cctccgacca ctcggcgtac agctcgtcca ggccgcgcac ccacacccag   2340
gccagggtgt tgtccggcac cacctggtcc tggaccgcgc tgatgaacag ggtcacgtcg   2400
tcccggacca caccggcgaa gtcgtcctcc acgaagtccc gggagaaccc gagccggtcg   2460
gtccagaact cgaccgctcc ggcgacgtcg cgcgcggtga gcaccggaac ggcactggtc   2520
aacttggcca tgatggctcc tcctgtcagg agaggaaaga gaagaaggtt agtacaattg   2580
ctatagtgag ttgtattata ctatgcagat atactatgcc aatgattaat tgtcaaacta   2640
gggctgcagg gttcatagtg ccacttttcc tgcactgccc catctcctgc ccaccctttc   2700
ccaggcatag acagtcagtg acttaccaaa ctcacaggag ggagaaggca gaagcttgag   2760
acagacccgc gggaccgccg aactgcgagg ggacgtggct agggcggctt cttttatggt   2820
gcgccggccc tcggaggcag ggcgctcggg gaggcctagc ggccaatctg cggtggcagg   2880
aggcggggcc gaaggccgtg cctgaccaat ccggagcaca taggagtctc agccccccgc   2940
cccaaagcaa ggggaagtca cgcgcctgta gcgccagcgt gttgtgaaat gggggcttgg   3000
gggggttggg gccctgacta gtcaaaacaa actcccattg acgtcaatgg ggtggagact   3060
tggaaatccc cgtgagtcaa accgctatcc acgcccattg atgtactgcc aaaaccgcat   3120
catcatggta atagcgatga ctaatacgta gatgtactgc caagtaggaa agtcccataa   3180
ggtcatgtac tgggcataat gccaggcggg ccatttaccg tcattgacgt caataggggg   3240
cgtacttggc atatgataca cttgatgtac tgccaagtgg gcagtttacc gtaaatactc   3300
cacccattga cgtcaatgga aagtccctat tggcgttact atgggaacat acgtcattat   3360
tgacgtcaat gggcgggggt cgttgggcgg tcagccaggc gggccattta ccgtaagtta   3420
tgtaacgcct gcaggttaat taagaacatg tgagcaaaag gccagcaaaa ggccaggaac   3480
cgtaaaaagg ccgcgttgct ggcgtttttc cataggctcc gcccccctga cgagcatcac   3540
aaaaatcgac gctcaagtca gaggtggcga aacccgacag gactataaag ataccaggcg   3600
tttccccctg gaagctccct cgtgcgctct cctgttccga ccctgccgct taccggatac   3660
ctgtccgcct ttctcccttc gggaagcgtg gcgctttctc atagctcacg ctgtaggtat   3720
```

ctcagttcgg tgtaggtcgt tcgctccaag ctgggctgtg tgcacgaacc ccccgttcag 3780
cccgaccgct gcgccttatc cggtaactat cgtcttgagt ccaacccggt aagacacgac 3840
ttatcgccac tggcagcagc cactggtaac aggattagca gagcgaggta tgtaggcggt 3900
gctacagagt tcttgaagtg gtggcctaac tacggctaca ctagaagaac agtatttggt 3960
atctgcgctc tgctgaagcc agttaccttc ggaaaaagag ttggtagctc ttgatccggc 4020
aaacaaacca ccgctggtag cggtggtttt tttgtttgca agcagcagat tacgcgcaga 4080
aaaaaaggat ctcaagaaga tcctttgatc ttttctacgg ggtctgacgc tcagtggaac 4140
gaaaactcac gttaagggat tttggtcatg gctagttaat taacatttaa atcagcggcc 4200
gcaataaaat atctttattt tcattacatc tgtgtgttgg tttttgtgt gaatcgtaac 4260 taacatacgc tctccatcaa aacaaaacga aacaaaacaa actagcaaaa taggctgtcc 4320
ccagtgcaag tgcaggtgcc agaacatttc tctatcgaa 4359

<210> SEQ ID NO 85
<211> LENGTH: 4401
<212> TYPE: DNA
<213> ORGANISM: Artificial Sequence
<220> FEATURE:
<223> OTHER INFORMATION: pCCL8-IgG1Fc

<400> SEQUENCE: 85
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacctgaga tcaccggcga aggagggcca ccatgtacag gatgcaactc ctgtcttgca 600
ttgcactaag tcttgcactt gtcacgaatt cgcagccaga ttcagtttcc attccaatca 660
cctgctgctt taacgtgatc aataggaaaa ttcctatcca gaggctggag agctacacaa 720
gaatcaccaa catccaatgt cccaaggaag ctgtgatctt caagaccaaa cggggcaagg 780
aggtctgtgc tgaccccaag gagagatggg tcagggattc catgaagcat ctggaccaaa 840
tatttcaaaa tctgaagcca gacaaaactc acacatgccc accgtgccca gcacctgaac 900
tcctgggggg accgtcagtc ttcctcttcc ccccaaaacc caaggacacc ctcatgatct 960
cccggacccc tgaggtcaca tgcgtggtgg tggacgtgag ccacgaagac cctgaggtca 1020
agttcaactg gtacgtggac ggcgtggagg tgcataatgc caagacaaag ccgcgggagg 1080
agcagtacaa cagcacgtac cgtgtggtca gcgtcctcac cgtcctgcac caggactggc 1140
tgaatggcaa ggagtacaag tgcaaggtct ccaacaaagc cctcccagcc cccatcgaga 1200
aaaccatctc caaagccaaa gggcagcccc gagaaccaca ggtgtacacc ctgcccccat 1260
cccgggagga gatgaccaag aaccaggtca gcctgacctg cctggtcaaa ggcttctatc 1320
ccagcgacat cgccgtggag tgggagagca atgggcagcc ggagaacaac tacaagacca 1380
cgcctcccgt gctggactcc gacggctcct tcttcctcta cagcaagctc accgtggaca 1440
agagcaggtg gcagcagggg aacgtcttct catgctccgt gatgcacgag gctctgcaca 1500
accactacac gcagaagagc ctctccctgt ctccgggtaa atgagtgcta gctggccaga 1560
catgataaga tacattgatg agtttggaca aaccacaact agaatgcagt gaaaaaaatg 1620
ctttatttgt gaaatttgtg atgctattgc tttatttgta accattataa gctgcaataa 1680
acaagttaac aacaacaatt gcattcattt tatgtttcag gttcaggggg aggtgtggga 1740
ggttttttaa agcaagtaaa acctctacaa atgtggtatg gaattaattc taaaatacag 1800
catagcaaaa ctttaacctc caaatcaagc ctctacttga atccttttct gagggatgaa 1860
taaggcatag gcatcagggg ctgttgccaa tgtgcattag ctgtttgcag cctcaccttc 1920
tttcatggag tttaagatat agtgtatttt cccaaggttt gaactagctc ttcatttctt 1980
tatgttttaa atgcactgac ctcccacatt ccctttttag taaaatattc agaaataatt 2040
taaatacatc attgcaatga aaataaatgt tttttattag gcagaatcca gatgctcaag 2100
gcccttcata atatccccca gtttagtagt tggacttagg gaacaaagga acctttaata 2160
gaaattggac agcaagaaag cgagcttcta gcttatcctc agtcctgctc ctctgccaca 2220
aagtgcacgc agttgccggc cgggtcgcgc agggcgaact cccgccccca cggctgctcg 2280
ccgatctcgg tcatggccgg cccggaggcg tcccggaagt tcgtggacac gacctccgac 2340
cactcggcgt acagctcgtc caggccgcgc acccacaccc aggccagggt gttgtccggc 2400
accacctggt cctggaccgc gctgatgaac agggtcacgt cgtcccggac cacaccggcg 2460
aagtcgtcct ccacgaagtc ccgggagaac ccgagccggt cggtccagaa ctcgaccgct 2520
ccggcgacgt cgcgcgcggt gagcaccgga acggcactgg tcaacttggc catgatggct 2580
cctcctgtca ggagaggaaa gagaagaagg ttagtacaat tgctatagtg agttgtatta 2640
tactatgcag atatactatg ccaatgatta attgtcaaac tagggctgca gggttcatag 2700
tgccactttt cctgcactgc cccatctcct gcccaccctt tcccaggcat agacagtcag 2760
tgacttacca aactcacagg agggagaagg cagaagcttg agacagaccc gcgggaccgc 2820
cgaactgcga ggggacgtgg ctagggcggc ttcttttatg gtgcgccggc cctcggaggc 2880
agggcgctcg ggaggcctag gcggccaatc tgcggtggca ggaggcgggg ccgaaggccg 2940
tgcctgacca atccggagca cataggagtc tcagcccccc gccccaaagc aaggggaagt 3000
cacgcgcctg tagcgccagc gtgttgtgaa atgggggctt ggggggttg gggccctgac 3060
tagtcaaaac aaactcccat tgacgtcaat ggggtggaga cttggaaatc cccgtgagtc 3120
aaaccgctat ccacgcccat tgatgtactg ccaaaaccgc atcatcatgg taatagcgat 3180
gactaatacg tagatgtact gccaagtagg aaagtcccat aaggtcatgt actgggcata 3240
atgccaggcg ggccatttac cgtcattgac gtcaataggg ggcgtacttg gcatatgata 3300
cacttgatgt actgccaagt gggcagttta ccgtaaatac tccacccatt gacgtcaatg 3360
gaaagtccct attggcgtta ctatgggaac atacgtcatt attgacgtca atgggcgggg 3420
gtcgttgggc ggtcagccag gcgggccatt taccgtaagt tatgtaacgc ctgcaggtta 3480
attaagaaca tgtgagcaaa aggccagcaa aaggccagga accgtaaaaa ggccgcgttg 3540
ctggcgtttt tccataggct ccgcccccct gacgagcatc acaaaaatcg acgctcaagt 3600
cagaggtggc gaaacccgac aggactataa agataccagg cgtttccccc tggaagctcc 3660
ctcgtgcgct ctcctgttcc gaccctgccg cttaccggat acctgtccgc ctttctccct 3720
tcgggaagcg tggcgctttc tcatagctca cgctgtaggt atctcagttc ggtgtaggtc 3780

```
gttcgctcca agctgggctg tgtgcacgaa ccccccgttc agcccgaccg ctgcgcctta   3840
tccggtaact atcgtcttga gtccaacccg gtaagacacg acttatcgcc actggcagca   3900
gccactggta acaggattag cagagcgagg tatgtaggcg gtgctacaga gttcttgaag   3960
tggtggccta actacggcta cactagaaga acagtatttg gtatctgcgc tctgctgaag   4020
ccagttacct tcggaaaaag agttggtagc tcttgatccg gcaaacaaac caccgctggt   4080
agcggtggtt tttttgtttg caagcagcag attacgcgca gaaaaaaagg atctcaagaa   4140
gatcctttga tcttttctac ggggtctgac gctcagtgga acgaaaactc acgttaaggg   4200
attttggtca tggctagtta attaacattt aaatcagcgg ccgcaataaa atatctttat   4260
tttcattaca tctgtgtgtt ggttttttgt gtgaatcgta actaacatac gctctccatc   4320
aaaacaaaac gaaacaaaac aaactagcaa aataggctgt ccccagtgca agtgcaggtg   4380
ccagaacatt tctctatcga a                                             4401
```

<210> SEQ ID NO 86
<211> LENGTH: 4389
<212> TYPE: DNA
<213> ORGANISM: Artificial Sequence
<220> FEATURE:
<223> OTHER INFORMATION: pCCL8(5-76)-IgG1Fc

<400> SEQUENCE: 86

```
ggatctgcga tcgctccggt gcccgtcagt gggcagagcg cacatcgccc acagtccccg     60
agaagttggg gggaggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cggtttccat tccaatcacc tgctgcttta    660
acgtgatcaa taggaaaatt cctatccaga ggctggagag ctacacaaga atcaccaaca    720
tccaatgtcc caaggaagct gtgatcttca agaccaaacg ggcaaggag gtctgtgctg    780
accccaagga gagatgggtc agggattcca tgaagcatct ggaccaaata tttcaaaatc    840
tgaagccaga caaaactcac acatgcccac cgtgcccagc acctgaactc ctggggggac    900
cgtcagtctt cctcttcccc ccaaaaccca aggacaccct catgatctcc cggacccctg    960
aggtcacatg cgtggtggtg gacgtgagcc acgaagaccc tgaggtcaag ttcaactggt   1020
acgtggacgg cgtggaggtg cataatgcca agacaaagcc gcgggaggag cagtacaaca   1080
gcacgtaccg tgtggtcagc gtcctcaccg tcctgcacca ggactggctg aatggcaagg   1140
agtacaagtg caaggtctcc aacaaagccc tcccagcccc catcgagaaa accatctcca   1200
aagccaaagg gcagccccga gaaccacagg tgtacaccct gcccccatcc cgggaggaga   1260
tgaccaagaa ccaggtcagc ctgacctgcc tggtcaaagg cttctatccc agcgacatcg   1320
ccgtggagtg ggagagcaat gggcagccgg agaacaacta caagaccacg cctcccgtgc   1380
tggactccga cggctccttc ttcctctaca gcaagctcac cgtggacaag agcaggtggc   1440
```

-continued agcaggggaa cgtcttctca tgctccgtga tgcacgaggc tctgcacaac cactacacgc 1500
agaagagcct ctccctgtct ccgggtaaat gagtgctagc tggccagaca tgataagata 1560
cattgatgag tttggacaaa ccacaactag aatgcagtga aaaaaatgct ttatttgtga 1620
aatttgtgat gctattgctt tatttgtaac cattataagc tgcaataaac aagttaacaa 1680
caacaattgc attcatttta tgtttcaggt tcagggggag gtgtgggagg tttttaaag 1740
caagtaaaac ctctacaaat gtggtatgga attaattcta aaatacagca tagcaaaact 1800
ttaacctcca aatcaagcct ctacttgaat ccttttctga gggatgaata aggcataggc 1860
atcaggggct gttgccaatg tgcattagct gtttgcagcc tcaccttctt tcatggagtt 1920
taagatatag tgtattttcc caaggtttga actagctctt catttcttta tgttttaaat 1980
gcactgacct cccacattcc ctttttagta aaatattcag aaataattta aatacatcat 2040
tgcaatgaaa ataaatgttt tttattaggc agaatccaga tgctcaaggc ccttcataat 2100
atcccccagt ttagtagttg gacttaggga acaaaggaac ctttaataga aattggacag 2160
caagaaagcg agcttctagc ttatcctcag tcctgctcct ctgccacaaa gtgcacgcag 2220
ttgccggccg ggtcgcgcag ggcgaactcc cgcccccacg gctgctcgcc gatctcggtc 2280
atggccggcc cggaggcgtc ccggaagttc gtggacacga cctccgacca ctcggcgtac 2340
agctcgtcca ggccgcgcac ccacacccag gccagggtgt tgtccggcac cacctggtcc 2400
tggaccgcgc tgatgaacag ggtcacgtcg tcccggacca caccggcgaa gtcgtcctcc 2460
acgaagtccc gggagaaccc gagccggtcg gtccagaact cgaccgctcc ggcgacgtcg 2520
cgcgcggtga gcaccggaac ggcactggtc aacttggcca tgatggctcc tcctgtcagg 2580
agaggaaaga gaagaaggtt agtacaattg ctatagtgag ttgtattata ctatgcagat 2640
atactatgcc aatgattaat tgtcaaacta gggctgcagg gttcatagtg ccacttttcc 2700
tgcactgccc catctcctgc ccaccctttc ccaggcatag acagtcagtg acttaccaaa 2760
ctcacaggag ggagaaggca gaagcttgag acagacccgc gggaccgccg aactgcgagg 2820
ggacgtggct agggcggctt cttttatggt gcgccggccc tcggaggcag ggcgctcggg 2880
gaggcctagc ggccaatctg cggtggcagg aggcggggcc gaaggccgtg cctgaccaat 2940
ccggagcaca taggagtctc agccccccgc cccaaagcaa ggggaagtca cgcgcctgta 3000
gcgccagcgt gttgtgaaat gggggcttgg gggggttggg gccctgacta gtcaaaacaa 3060
actcccattg acgtcaatgg ggtggagact tggaaatccc cgtgagtcaa accgctatcc 3120
acgcccattg atgtactgcc aaaaccgcat catcatggta atagcgatga ctaatacgta 3180
gatgtactgc caagtaggaa agtcccataa ggtcatgtac tgggcataat gccaggcggg 3240
ccatttaccg tcattgacgt caatagggggg cgtacttggc atatgataca cttgatgtac 3300
tgccaagtgg gcagtttacc gtaaatactc cacccattga cgtcaatgga aagtccctat 3360
tggcgttact atgggaacat acgtcattat tgacgtcaat gggcgggggt cgttgggcgg 3420
tcagccaggc gggccattta ccgtaagtta tgtaacgcct gcaggttaat taagaacatg 3480
tgagcaaaag gccagcaaaa ggccaggaac cgtaaaaagg ccgcgttgct ggcgtttttc 3540
cataggctcc gcccccctga cgagcatcac aaaaatcgac gctcaagtca gaggtggcga 3600
aacccgacag gactataaag ataccaggcg tttccccctg gaagctccct cgtgcgctct 3660
cctgttccga ccctgccgct taccggatac ctgtccgcct ttctcccttc gggaagcgtg 3720
gcgctttctc atagctcacg ctgtaggtat ctcagttcgg tgtaggtcgt tcgctccaag 3780

-continued

```
ctgggctgtg tgcacgaacc ccccgttcag cccgaccgct gcgccttatc cggtaactat   3840

cgtcttgagt ccaacccggt aagacacgac ttatcgccac tggcagcagc cactggtaac   3900

aggattagca gagcgaggta tgtaggcggt gctacagagt tcttgaagtg gtggcctaac   3960

tacggctaca ctagaagaac agtatttggt atctgcgctc tgctgaagcc agttaccttc   4020

ggaaaaagag ttggtagctc ttgatccggc aaacaaacca ccgctggtag cggtggtttt   4080

tttgtttgca agcagcagat tacgcgcaga aaaaaaggat ctcaagaaga tcctttgatc   4140

ttttctacgg ggtctgacgc tcagtggaac gaaaactcac gttaagggat tttggtcatg   4200

gctagttaat taacatttaa atcagcggcc gcaataaaat atctttattt tcattacatc   4260

tgtgtgttgg ttttttgtgt gaatcgtaac taacatacgc tctccatcaa aacaaaacga   4320

aacaaaacaa actagcaaaa taggctgtcc ccagtgcaag tgcaggtgcc agaacatttc   4380

tctatcgaa                                                           4389
```

<210> SEQ ID NO 87
<211> LENGTH: 4389
<212> TYPE: DNA
<213> ORGANISM: Artificial Sequence
<220> FEATURE:
<223> OTHER INFORMATION: pCCL8(5-76K/H-A)-IgG1Fc

<400> SEQUENCE: 87

```
ggatctgcga tcgctccggt gcccgtcagt gggcagagcg cacatcgccc acagtccccg     60

agaagttggg gggaggggtc ggcaattgaa cgggtgccta gagaaggtgg cgcggggtaa    120

actgggaaag tgatgtcgtg tactggctcc gcctttttcc cgagggtggg ggagaaccgt    180

atataagtgc agtagtcgcc gtgaacgttc tttttcgcaa cgggtttgcc gccagaacac    240

agctgaagct tcgaggggct cgcatctctc cttcacgcgc ccgccgccct acctgaggcc    300

gccatccacg ccggttgagt cgcgttctgc cgcctcccgc ctgtggtgcc tcctgaactg    360

cgtccgccgt ctaggtaagt ttaaagctca ggtcgagacc gggcctttgt ccggcgctcc    420

cttggagcct acctagactc agccggctct ccacgctttg cctgaccctg cttgctcaac    480

tctacgtctt tgtttcgttt tctgttctgc gccgttacag atccaagctg tgaccggcgc    540

ctacctgaga tcaccggcga aggagggcca ccatgtacag gatgcaactc ctgtcttgca    600

ttgcactaag tcttgcactt gtcacgaatt cggtttccat tccaatcacc tgctgcttta    660

acgtgatcaa taggaaaatt cctatccaga ggctggagag ctacacaaga atcaccaaca    720

tccaatgtcc caaggaagct gtgatcttca agaccgccgc gggcgctgag gtctgtgctg    780

accccgccga ggcgtgggtc gctgattcca tggccgcgct ggaccaaata tttcaaaatc    840

tggctccaga caaaactcac acatgcccac cgtgcccagc acctgaactc ctggggggac    900

cgtcagtctt cctcttcccc ccaaaaccca aggacaccct catgatctcc cggacccctg    960

aggtcacatg cgtggtggtg gacgtgagcc acgaagaccc tgaggtcaag ttcaactggt   1020

acgtggacgg cgtggaggtg cataatgcca agacaaagcc gcgggaggag cagtacaaca   1080

gcacgtaccg tgtggtcagc gtcctcaccg tcctgcacca ggactggctg aatggcaagg   1140

agtacaagtg caaggtctcc aacaaagccc tcccagcccc catcgagaaa accatctcca   1200

aagccaaagg gcagccccga gaaccacagg tgtacaccct gcccccatcc cgggaggaga   1260

tgaccaagaa ccaggtcagc ctgacctgcc tggtcaaagg cttctatccc agcgacatcg   1320

ccgtggagtg ggagagcaat gggcagccgg agaacaacta caagaccacg cctcccgtgc   1380

tggactccga cggctccttc ttcctctaca gcaagctcac cgtggacaag agcaggtggc   1440
```

-continued

```
agcaggggaa cgtcttctca tgctccgtga tgcacgaggc tctgcacaac cactacacgc   1500
agaagagcct ctccctgtct ccgggtaaat gagtgctagc tggccagaca tgataagata   1560
cattgatgag tttggacaaa ccacaactag aatgcagtga aaaaaatgct ttatttgtga   1620
aatttgtgat gctattgctt tatttgtaac cattataagc tgcaataaac aagttaacaa   1680
caacaattgc attcatttta tgtttcaggt tcagggggag gtgtgggagg ttttttaaag   1740
caagtaaaac ctctacaaat gtggtatgga attaattcta aaatacagca tagcaaaact   1800
ttaacctcca aatcaagcct ctacttgaat ccttttctga gggatgaata aggcataggc   1860
atcaggggct gttgccaatg tgcattagct gtttgcagcc tcaccttctt tcatggagtt   1920
taagatatag tgtattttcc caaggtttga actagctctt catttcttta tgttttaaat   1980
gcactgacct cccacattcc ctttttagta aaatattcag aaataattta aatacatcat   2040
tgcaatgaaa ataaatgttt tttattaggc agaatccaga tgctcaaggc ccttcataat   2100
atcccccagt ttagtagttg gacttaggga acaaaggaac ctttaataga aattggacag   2160
caagaaagcg agcttctagc ttatcctcag tcctgctcct ctgccacaaa gtgcacgcag   2220
ttgccggccg ggtcgcgcag ggcgaactcc cgcccccacg gctgctcgcc gatctcggtc   2280
atggccggcc cggaggcgtc ccggaagttc gtggacacga cctccgacca ctcggcgtac   2340
agctcgtcca ggccgcgcac ccacacccag gccagggtgt tgtccggcac cacctggtcc   2400
tggaccgcgc tgatgaacag ggtcacgtcg tcccggacca caccggcgaa gtcgtcctcc   2460
acgaagtccc gggagaaccc gagccggtcg gtccagaact cgaccgctcc ggcgacgtcg   2520
cgcgcggtga gcaccggaac ggcactggtc aacttggcca tgatggctcc tcctgtcagg   2580
agaggaaaga gaagaaggtt agtacaattg ctatagtgag ttgtattata ctatgcagat   2640
atactatgcc aatgattaat tgtcaaacta gggctgcagg gttcatagtg ccacttttcc   2700
tgcactgccc catctcctgc ccaccctttc ccaggcatag acagtcagtg acttaccaaa   2760
ctcacaggag ggagaaggca gaagcttgag acagacccgc gggaccgccg aactgcgagg   2820
ggacgtggct agggcggctt cttttatggt gcgccggccc tcggaggcag ggcgctcggg   2880
gaggcctagc ggccaatctg cggtggcagg aggcggggcc gaaggccgtg cctgaccaat   2940
ccggagcaca taggagtctc agccccccgc cccaaagcaa ggggaagtca cgcgcctgta   3000
gcgccagcgt gttgtgaaat gggggcttgg gggggttggg gccctgacta gtcaaaacaa   3060
actcccattg acgtcaatgg ggtggagact tggaaatccc cgtgagtcaa accgctatcc   3120
acgcccattg atgtactgcc aaaaccgcat catcatggta atagcgatga ctaatacgta   3180
gatgtactgc caagtaggaa agtcccataa ggtcatgtac tgggcataat gccaggcggg   3240
ccatttaccg tcattgacgt caataggggg cgtacttggc atatgataca cttgatgtac   3300
tgccaagtgg gcagtttacc gtaaatactc cacccattga cgtcaatgga aagtccctat   3360
tggcgttact atgggaacat acgtcattat tgacgtcaat gggcgggggt cgttgggcgg   3420
tcagccaggc gggccattta ccgtaagtta tgtaacgcct gcaggttaat taagaacatg   3480
tgagcaaaag gccagcaaaa ggccaggaac cgtaaaaagg ccgcgttgct ggcgtttttc   3540
cataggctcc gcccccctga cgagcatcac aaaaatcgac gctcaagtca gaggtggcga   3600
aacccgacag gactataaag ataccaggcg tttccccctg gaagctccct cgtgcgctct   3660
cctgttccga ccctgccgct taccggatac ctgtccgcct ttctcccttc gggaagcgtg   3720
gcgctttctc atagctcacg ctgtaggtat ctcagttcgg tgtaggtcgt tcgctccaag   3780
```

-continued

```
ctgggctgtg tgcacgaacc ccccgttcag cccgaccgct gcgccttatc cggtaactat   3840
cgtcttgagt ccaacccggt aagacacgac ttatcgccac tggcagcagc cactggtaac   3900
aggattagca gagcgaggta tgtaggcggt gctacagagt tcttgaagtg gtggcctaac   3960
tacggctaca ctagaagaac agtatttggt atctgcgctc tgctgaagcc agttaccttc   4020
ggaaaaagag ttggtagctc ttgatccggc aaacaaacca ccgctggtag cggtggtttt   4080
tttgtttgca agcagcagat tacgcgcaga aaaaaaggat ctcaagaaga tcctttgatc   4140
ttttctacgg ggtctgacgc tcagtggaac gaaaactcac gttaagggat tttggtcatg   4200
gctagttaat taacatttaa atcagcggcc gcaataaaat atctttattt tcattacatc   4260
tgtgtgttgg ttttttgtgt gaatcgtaac taacatacgc tctccatcaa aacaaaacga   4320
aacaaaacaa actagcaaaa taggctgtcc ccagtgcaag tgcaggtgcc agaacatttc   4380
tctatcgaa                                                           4389
```

<210> SEQ ID NO 88
<211> LENGTH: 4398
<212> TYPE: DNA
<213> ORGANISM: Artificial Sequence
<220> FEATURE:
<223> OTHER INFORMATION: pCCL13-IgG1Fc

<400> SEQUENCE: 88

```
ggatctgcga tcgctccggt gcccgtcagt gggcagagcg cacatcgccc acagtccccg     60
agaagttggg gggaggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cgcagccaga tgcactcaac gtcccatcta    660
cttgctgctt cacatttagc agtaagaaga tctccttgca gaggctgaag agctatgtga    720
tcaccaccag caggtgtccc cagaaggctg tcatcttcag aaccaaactg ggcaaggaga    780
tctgtgctga cccaaaggag aagtgggtcc agaattatat gaaacacctg ggccggaaag    840
ctcacaccct gaagactgac aaaactcaca catgcccacc gtgcccagca cctgaactcc    900
tgggggggacc gtcagtcttc ctcttccccc caaaacccaa ggacaccctc atgatctccc    960
ggacccctga ggtcacatgc gtggtggtgg acgtgagcca cgaagaccct gaggtcaagt   1020
tcaactggta cgtggacggc gtggaggtgc ataatgccaa gacaaagccg cgggaggagc   1080
agtacaacag cacgtaccgt gtggtcagcg tcctcaccgt cctgcaccag gactggctga   1140
atggcaagga gtacaagtgc aaggtctcca acaaagccct cccagccccc atcgagaaaa   1200
ccatctccaa agccaaaggg cagccccgag aaccacaggt gtacaccctg cccccatccc   1260
gggaggagat gaccaagaac caggtcagcc tgacctgcct ggtcaaaggc ttctatccca   1320
gcgacatcgc cgtggagtgg gagagcaatg ggcagccgga gaacaactac aagaccacgc   1380
ctcccgtgct ggactccgac ggctccttct tcctctacag caagctcacc gtggacaaga   1440
```

-continued

```
gcaggtggca gcaggggaac gtcttctcat gctccgtgat gcacgaggct ctgcacaacc   1500
actacacgca gaagagcctc tccctgtctc cgggtaaatg agtgctagct ggccagacat   1560
gataagatac attgatgagt ttggacaaac cacaactaga atgcagtgaa aaaaatgctt   1620
tatttgtgaa atttgtgatg ctattgcttt atttgtaacc attataagct gcaataaaca   1680
agttaacaac aacaattgca ttcattttat gtttcaggtt cagggggagg tgtgggaggt   1740
tttttaaagc aagtaaaacc tctacaaatg tggtatggaa ttaattctaa aatacagcat   1800
agcaaaactt taacctccaa atcaagcctc tacttgaatc cttttctgag ggatgaataa   1860
ggcataggca tcaggggctg ttgccaatgt gcattagctg tttgcagcct caccttcttt   1920
catggagttt aagatatagt gtattttccc aaggtttgaa ctagctcttc atttctttat   1980
gttttaaatg cactgacctc ccacattccc tttttagtaa aatattcaga aataatttaa   2040
atacatcatt gcaatgaaaa taaatgtttt ttattaggca gaatccagat gctcaaggcc   2100
cttcataata tcccccagtt tagtagttgg acttagggaa caaaggaacc tttaatagaa   2160
attggacagc aagaaagcga gcttctagct tatcctcagt cctgctcctc tgccacaaag   2220
tgcacgcagt tgccggccgg gtcgcgcagg gcgaactccc gcccccacgg ctgctcgccg   2280
atctcggtca tggccggccc ggaggcgtcc cggaagttcg tggacacgac ctccgaccac   2340
tcggcgtaca gctcgtccag gccgcgcacc cacacccagg ccagggtgtt gtccggcacc   2400
acctggtcct ggaccgcgct gatgaacagg gtcacgtcgt cccggaccac accggcgaag   2460
tcgtcctcca cgaagtcccg ggagaacccg agccggtcgg tccagaactc gaccgctccg   2520
gcgacgtcgc gcgcggtgag caccggaacg gcactggtca acttggccat gatggctcct   2580
cctgtcagga gaggaaagag aagaaggtta gtacaattgc tatagtgagt tgtattatac   2640
tatgcagata tactatgcca atgattaatt gtcaaactag ggctgcaggg ttcatagtgc   2700
cacttttcct gcactgcccc atctcctgcc caccctttcc caggcataga cagtcagtga   2760
cttaccaaac tcacaggagg gagaaggcag aagcttgaga cagacccgcg ggaccgccga   2820
actgcgaggg gacgtggcta gggcggcttc ttttatggtg cgccggccct cggaggcagg   2880
gcgctcgggg aggcctagcg gccaatctgc ggtggcagga ggcggggccg aaggccgtgc   2940
ctgaccaatc cggagcacat aggagtctca gccccccgcc ccaaagcaag gggaagtcac   3000
gcgcctgtag cgccagcgtg ttgtgaaatg gggcttgggg ggggttgggg ccctgactag   3060
tcaaaacaaa ctcccattga cgtcaatggg gtggagactt ggaaatcccc gtgagtcaaa   3120
ccgctatcca cgcccattga tgtactgcca aaaccgcatc atcatggtaa tagcgatgac   3180
taatacgtag atgtactgcc aagtaggaaa gtcccataag gtcatgtact gggcataatg   3240
ccaggcgggc catttaccgt cattgacgtc aatagggggc gtacttggca tatgatacac   3300
ttgatgtact gccaagtggg cagtttaccg taaatactcc acccattgac gtcaatggaa   3360
agtccctatt ggcgttacta tgggaacata cgtcattatt gacgtcaatg ggcgggggtc   3420
gttgggcggt cagccaggcg ggccatttac cgtaagttat gtaacgcctg caggttaatt   3480
aagaacatgt gagcaaaagg ccagcaaaag gccaggaacc gtaaaaaggc cgcgttgctg   3540
gcgtttttcc ataggctccg cccccctgac gagcatcaca aaaatcgacg ctcaagtcag   3600
aggtggcgaa acccgacagg actataaaga taccaggcgt ttccccctgg aagctccctc   3660
gtgcgctctc ctgttccgac cctgccgctt accggatacc tgtccgcctt tctcccttcg   3720
ggaagcgtgg cgctttctca tagctcacgc tgtaggtatc tcagttcggt gtaggtcgtt   3780
```

-continued

```
cgctccaagc tgggctgtgt gcacgaaccc cccgttcagc ccgaccgctg cgccttatcc   3840

ggtaactatc gtcttgagtc caacccggta agacacgact tatcgccact ggcagcagcc   3900

actggtaaca ggattagcag agcgaggtat gtaggcggtg ctacagagtt cttgaagtgg   3960

tggcctaact acggctacac tagaagaaca gtatttggta tctgcgctct gctgaagcca   4020

gttaccttcg gaaaaagagt tggtagctct tgatccggca aacaaaccac cgctggtagc   4080

ggtggttttt ttgtttgcaa gcagcagatt acgcgcagaa aaaaaggatc tcaagaagat   4140

cctttgatct tttctacggg gtctgacgct cagtggaacg aaaactcacg ttaagggatt   4200

ttggtcatgg ctagttaatt aacatttaaa tcagcggccg caataaaata tctttatttt   4260

cattacatct gtgtgttggt ttttgtgtg aatcgtaact aacatacgct ctccatcaaa   4320

acaaaacgaa acaaaacaaa ctagcaaaat aggctgtccc cagtgcaagt gcaggtgcca   4380

gaacatttct ctatcgaa                                                 4398
```

<210> SEQ ID NO 89
<211> LENGTH: 4386
<212> TYPE: DNA
<213> ORGANISM: Artificial Sequence
<220> FEATURE:
<223> OTHER INFORMATION: pCCL13(5-75)-IgG1Fc

<400> SEQUENCE: 89

```
ggatctgcga tcgctccggt gcccgtcagt gggcagagcg cacatcgccc acagtccccg     60

agaagttggg gggaggggtc ggcaattgaa cgggtgccta gagaaggtgg cgcggggtaa    120

actgggaaag tgatgtcgtg tactggctcc gcctttttcc cgagggtggg ggagaaccgt    180

atataagtgc agtagtcgcc gtgaacgttc tttttcgcaa cgggtttgcc gccagaacac    240

agctgaagct tcgaggggct cgcatctctc cttcacgcgc ccgccgccct acctgaggcc    300

gccatccacg ccggttgagt cgcgttctgc cgcctcccgc ctgtggtgcc tcctgaactg    360

cgtccgccgt ctaggtaagt ttaaagctca ggtcgagacc gggcctttgt ccggcgctcc    420

cttggagcct acctagactc agccggctct ccacgctttg cctgaccctg cttgctcaac    480

tctacgtctt tgtttcgttt tctgttctgc gccgttacag atccaagctg tgaccggcgc    540

ctacctgaga tcaccggcga aggagggcca ccatgtacag gatgcaactc ctgtcttgca    600

ttgcactaag tcttgcactt gtcacgaatt cgctcaacgt cccatctact tgctgcttca    660

catttagcag taagaagatc tccttgcaga ggctgaagag ctatgtgatc accaccagca    720

ggtgtcccca gaaggctgtc atcttcagaa ccaaactggg caaggagatc tgtgctgacc    780

caaaggagaa gtgggtccag aattatatga aacacctggg ccggaaagct cacaccctga    840

agactgacaa aactcacaca tgcccaccgt gcccagcacc tgaactcctg gggggaccgt    900

cagtcttcct cttcccccca aaacccaagg acaccctcat gatctcccgg acccctgagg    960

tcacatgcgt ggtggtggac gtgagccacg aagaccctga ggtcaagttc aactggtacg   1020

tggacggcgt ggaggtgcat aatgccaaga caaagccgcg ggaggagcag tacaacagca   1080

cgtaccgtgt ggtcagcgtc ctcaccgtcc tgcaccagga ctggctgaat ggcaaggagt   1140

acaagtgcaa ggtctccaac aaagccctcc cagcccccat cgagaaaacc atctccaaag   1200

ccaaagggca gccccgagaa ccacaggtgt acaccctgcc cccatcccgg gaggagatga   1260

ccaagaacca ggtcagcctg acctgcctgg tcaaaggctt ctatcccagc gacatcgccg   1320

tggagtggga gagcaatggg cagccggaga acaactacaa gaccacgcct cccgtgctgg   1380

actccgacgg ctccttcttc ctctacagca agctcaccgt ggacaagagc aggtggcagc   1440
```

-continued

```
aggggaacgt cttctcatgc tccgtgatgc acgaggctct gcacaaccac tacacgcaga   1500
agagcctctc cctgtctccg ggtaaatgag tgctagctgg ccagacatga taagatacat   1560
tgatgagttt ggacaaacca caactagaat gcagtgaaaa aaatgcttta tttgtgaaat   1620
ttgtgatgct attgctttat ttgtaaccat tataagctgc aataaacaag ttaacaacaa   1680
caattgcatt cattttatgt ttcaggttca gggggaggtg tgggaggttt tttaaagcaa   1740
gtaaaacctc tacaaatgtg gtatggaatt aattctaaaa tacagcatag caaaacttta   1800
acctccaaat caagcctcta cttgaatcct tttctgaggg atgaataagg cataggcatc   1860
aggggctgtt gccaatgtgc attagctgtt tgcagcctca ccttctttca tggagtttaa   1920
gatatagtgt attttcccaa ggtttgaact agctcttcat ttctttatgt tttaaatgca   1980
ctgacctccc acattccctt tttagtaaaa tattcagaaa taatttaaat acatcattgc   2040
aatgaaaata aatgtttttt attaggcaga atccagatgc tcaaggccct tcataatatc   2100
ccccagttta gtagttggac ttagggaaca aaggaacctt taatagaaat tggacagcaa   2160
gaaagcgagc ttctagctta tcctcagtcc tgctcctctg ccacaaagtg cacgcagttg   2220
ccggccgggt cgcgcagggc gaactcccgc ccccacggct gctcgccgat ctcggtcatg   2280
gccggcccgg aggcgtcccg gaagttcgtg gacacgacct ccgaccactc ggcgtacagc   2340
tcgtccaggc cgcgcaccca cacccaggcc agggtgttgt ccggcaccac ctggtcctgg   2400
accgcgctga tgaacagggt cacgtcgtcc cggaccacac cggcgaagtc gtcctccacg   2460
aagtcccggg agaacccgag ccggtcggtc cagaactcga ccgctccggc gacgtcgcgc   2520
gcggtgagca ccggaacggc actggtcaac ttggccatga tggctcctcc tgtcaggaga   2580
ggaaagagaa gaaggttagt acaattgcta tagtgagttg tattatacta tgcagatata   2640
ctatgccaat gattaattgt caaactaggg ctgcagggtt catagtgcca cttttcctgc   2700
actgccccat ctcctgccca ccctttccca ggcatagaca gtcagtgact taccaaactc   2760
acaggaggga gaaggcagaa gcttgagaca gacccgcggg accgccgaac tgcgagggga   2820
cgtggctagg gcggcttctt ttatggtgcg ccggccctcg gaggcagggc gctcggggag   2880
gcctagcggc caatctgcgg tggcaggagg cggggccgaa ggccgtgcct gaccaatccg   2940
gagcacatag gagtctcagc cccccgcccc aaagcaaggg gaagtcacgc gcctgtagcg   3000
ccagcgtgtt gtgaaatggg ggcttggggg ggttggggcc ctgactagtc aaaacaaact   3060
cccattgacg tcaatggggt ggagacttgg aaatccccgt gagtcaaacc gctatccacg   3120
cccattgatg tactgccaaa accgcatcat catggtaata gcgatgacta atacgtagat   3180
gtactgccaa gtaggaaagt cccataaggt catgtactgg gcataatgcc aggcgggcca   3240
tttaccgtca ttgacgtcaa tagggggcgt acttggcata tgatacactt gatgtactgc   3300
caagtgggca gtttaccgta aatactccac ccattgacgt caatggaaag tccctattgg   3360
cgttactatg ggaacatacg tcattattga cgtcaatggg cgggggtcgt tgggcggtca   3420
gccaggcggg ccatttaccg taagttatgt aacgcctgca ggttaattaa gaacatgtga   3480
gcaaaaggcc agcaaaaggc caggaaccgt aaaaaggccg cgttgctggc gtttttccat   3540
aggctccgcc cccctgacga gcatcacaaa aatcgacgct caagtcagag gtggcgaaac   3600
ccgacaggac tataaagata ccaggcgttt ccccctggaa gctccctcgt gcgctctcct   3660
gttccgaccc tgccgcttac cggatacctg tccgcctttc tcccttcggg aagcgtggcg   3720
ctttctcata gctcacgctg taggtatctc agttcggtgt aggtcgttcg ctccaagctg   3780
```

ggctgtgtgc acgaaccccc cgttcagccc gaccgctgcg ccttatccgg taactatcgt 3840
cttgagtcca acccggtaag acacgactta tcgccactgg cagcagccac tggtaacagg 3900
attagcagag cgaggtatgt aggcggtgct acagagttct tgaagtggtg gcctaactac 3960
ggctacacta gaagaacagt atttggtatc tgcgctctgc tgaagccagt taccttcgga 4020
aaaagagttg gtagctcttg atccggcaaa caaaccaccg ctggtagcgg tggttttttt 4080
gtttgcaagc agcagattac gcgcagaaaa aaaggatctc aagaagatcc tttgatcttt 4140
tctacggggt ctgacgctca gtggaacgaa aactcacgtt aagggatttt ggtcatggct 4200
agttaattaa catttaaatc agcggccgca ataaaatatc tttattttca ttacatctgt 4260
gtgttggttt tttgtgtgaa tcgtaactaa catacgctct ccatcaaaac aaaacgaaac 4320
aaaacaaact agcaaaatag gctgtcccca gtgcaagtgc aggtgccaga acatttctct 4380
atcgaa 4386

<210> SEQ ID NO 90
<211> LENGTH: 4386
<212> TYPE: DNA
<213> ORGANISM: Artificial Sequence
<220> FEATURE:
<223> OTHER INFORMATION: pCCL13(5-75K/H-A)-IgG1Fc

<400> SEQUENCE: 90
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacctgaga tcaccggcga aggagggcca ccatgtacag gatgcaactc ctgtcttgca 600
ttgcactaag tcttgcactt gtcacgaatt cgctcaacgt cccatctact tgctgcttca 660
catttagcag taagaagatc tccttgcaga ggctgaagag ctatgtgatc accaccagca 720
ggtgtcccca gaaggctgtc atcttcagaa ccgccctggg cgcggagatc tgtgctgacc 780
cagccgaggc ctgggtccag aattatatgg cggctctggg ccggaaagct gccaccctgg 840
ctactgacaa aactcacaca tgcccaccgt gcccagcacc tgaactcctg gggggaccgt 900
cagtcttcct cttcccccca aaacccaagg acaccctcat gatctcccgg acccctgagg 960
tcacatgcgt ggtggtggac gtgagccacg aagaccctga ggtcaagttc aactggtacg 1020
tggacggcgt ggaggtgcat aatgccaaga caaagccgcg ggaggagcag tacaacagca 1080
cgtaccgtgt ggtcagcgtc ctcaccgtcc tgcaccagga ctggctgaat ggcaaggagt 1140
acaagtgcaa ggtctccaac aaagccctcc cagcccccat cgagaaaacc atctccaaag 1200
ccaaagggca gccccgagaa ccacaggtgt acaccctgcc cccatcccgg gaggagatga 1260
ccaagaacca ggtcagcctg acctgcctgg tcaaaggctt ctatcccagc gacatcgccg 1320
tggagtggga gagcaatggg cagccggaga acaactacaa gaccacgcct cccgtgctgg 1380
actccgacgg ctccttcttc ctctacagca agctcaccgt ggacaagagc aggtggcagc 1440

-continued

```
aggggaacgt cttctcatgc tccgtgatgc acgaggctct gcacaaccac tacacgcaga   1500
agagcctctc cctgtctccg ggtaaatgag tgctagctgg ccagacatga taagatacat   1560
tgatgagttt ggacaaacca caactagaat gcagtgaaaa aaatgcttta tttgtgaaat   1620
ttgtgatgct attgctttat ttgtaaccat tataagctgc aataaacaag ttaacaacaa   1680
caattgcatt cattttatgt ttcaggttca gggggaggtg tgggaggttt tttaaagcaa   1740
gtaaaacctc tacaaatgtg gtatggaatt aattctaaaa tacagcatag caaaacttta   1800
acctccaaat caagcctcta cttgaatcct tttctgaggg atgaataagg cataggcatc   1860
aggggctgtt gccaatgtgc attagctgtt tgcagcctca ccttctttca tggagtttaa   1920
gatatagtgt attttcccaa ggtttgaact agctcttcat ttctttatgt tttaaatgca   1980
ctgacctccc acattccctt tttagtaaaa tattcagaaa taatttaaat acatcattgc   2040
aatgaaaata aatgtttttt attaggcaga atccagatgc tcaaggccct tcataatatc   2100
ccccagttta gtagttggac ttagggaaca aaggaacctt taatagaaat tggacagcaa   2160
gaaagcgagc ttctagctta tcctcagtcc tgctcctctg ccacaaagtg cacgcagttg   2220
ccggccgggt cgcgcagggc gaactcccgc ccccacggct gctcgccgat ctcggtcatg   2280
gccggcccgg aggcgtcccg gaagttcgtg gacacgacct ccgaccactc ggcgtacagc   2340
tcgtccaggc cgcgcaccca cacccaggcc agggtgttgt ccggcaccac ctggtcctgg   2400
accgcgctga tgaacagggt cacgtcgtcc cggaccacac cggcgaagtc gtcctccacg   2460
aagtcccggg agaacccgag ccggtcggtc cagaactcga ccgctccggc gacgtcgcgc   2520
gcggtgagca ccggaacggc actggtcaac ttggccatga tggctcctcc tgtcaggaga   2580
ggaaagagaa gaaggttagt acaattgcta tagtgagttg tattatacta tgcagatata   2640
ctatgccaat gattaattgt caaactaggg ctgcagggtt catagtgcca cttttcctgc   2700
actgccccat ctcctgccca ccctttccca ggcatagaca gtcagtgact taccaaactc   2760
acaggaggga gaaggcagaa gcttgagaca gacccgcggg accgccgaac tgcgagggga   2820
cgtggctagg gcggcttctt ttatggtgcg ccggccctcg gaggcagggc gctcggggag   2880
gcctagcggc caatctgcgg tggcaggagg cggggccgaa ggccgtgcct gaccaatccg   2940
gagcacatag gagtctcagc cccccgcccc aaagcaaggg gaagtcacgc gcctgtagcg   3000
ccagcgtgtt gtgaaatggg ggcttggggg ggttggggcc ctgactagtc aaaacaaact   3060
cccattgacg tcaatggggt ggagacttgg aaatccccgt gagtcaaacc gctatccacg   3120
cccattgatg tactgccaaa accgcatcat catggtaata gcgatgacta atacgtagat   3180
gtactgccaa gtaggaaagt cccataaggt catgtactgg gcataatgcc aggcgggcca   3240
tttaccgtca ttgacgtcaa tagggggcgt acttggcata tgatacactt gatgtactgc   3300
caagtgggca gtttaccgta aatactccac ccattgacgt caatggaaag tccctattgg   3360
cgttactatg ggaacatacg tcattattga cgtcaatggg cgggggtcgt tgggcggtca   3420
gccaggcggg ccatttaccg taagttatgt aacgcctgca ggttaattaa gaacatgtga   3480
gcaaaaggcc agcaaaaggc caggaaccgt aaaaaggccg cgttgctggc gtttttccat   3540
aggctccgcc cccctgacga gcatcacaaa aatcgacgct caagtcagag gtggcgaaac   3600
ccgacaggac tataaagata ccaggcgttt ccccctggaa gctccctcgt gcgctctcct   3660
gttccgaccc tgccgcttac cggatacctg tccgcctttc tcccttcggg aagcgtggcg   3720
ctttctcata gctcacgctg taggtatctc agttcggtgt aggtcgttcg ctccaagctg   3780
```

```
ggctgtgtgc acgaaccccc cgttcagccc gaccgctgcg ccttatccgg taactatcgt   3840
cttgagtcca acccggtaag acacgactta tcgccactgg cagcagccac tggtaacagg   3900
attagcagag cgaggtatgt aggcggtgct acagagttct tgaagtggtg gcctaactac   3960
ggctacacta gaagaacagt atttggtatc tgcgctctgc tgaagccagt taccttcgga   4020
aaaagagttg gtagctcttg atccggcaaa caaaccaccg ctggtagcgg tggttttttt   4080
gtttgcaagc agcagattac gcgcagaaaa aaaggatctc aagaagatcc tttgatcttt   4140
tctacggggt ctgacgctca gtggaacgaa aactcacgtt aagggatttt ggtcatggct   4200
agttaattaa catttaaatc agcggccgca ataaaatatc tttattttca ttacatctgt   4260
gtgttggttt tttgtgtgaa tcgtaactaa catacgctct ccatcaaaac aaaacgaaac   4320
aaaacaaact agcaaaatag gctgtcccca gtgcaagtgc aggtgccaga acatttctct   4380
atcgaa                                                              4386
```

<210> SEQ ID NO 91
<211> LENGTH: 4527
<212> TYPE: DNA
<213> ORGANISM: Artificial Sequence
<220> FEATURE:
<223> OTHER INFORMATION: pCCL25-IgG1Fc

<400> SEQUENCE: 91

```
ggatctgcga tcgctccggt gcccgtcagt gggcagagcg cacatcgccc acagtccccg     60
agaagttggg gggaggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cgacccaagg tgtctttgag gactgctgcc    660
tggcctacca ctaccccatt gggtgggctg tgctccggca cgcctggact taccggatcc    720
aggaggtgag cgggagctgc aatctgcctg ctgcgatatt ctacctcccc aagagacaca    780
ggaaggtgtg tgggaacccc aaaagcaggg aggtgcagag agccatgaag ctcctggatg    840
ctcgaaataa ggtttttgca aagctccgcc acaacacgca gaccttccaa ggccctcatg    900
ctgtaaagaa gttgagttct ggaaactcca agttatcatc gtccaagttt agcaatccca    960
tcagcagcag caagaggaat gtctccgaca aaactcacac atgcccaccg tgcccagcac   1020
ctgaactcct ggggggaccg tcagtcttcc tcttcccccc aaaacccaag gacaccctca   1080
tgatctcccg gacccctgag gtcacatgcg tggtggtgga cgtgagccac gaagaccctg   1140
aggtcaagtt caactggtac gtggacggcg tggaggtgca taatgccaag acaaagccgc   1200
gggaggagca gtacaacagc acgtaccgtg tggtcagcgt cctcaccgtc ctgcaccagg   1260
actggctgaa tggcaaggag tacaagtgca aggtctccaa caaagccctc ccagccccca   1320
tcgagaaaac catctccaaa gccaaagggc agccccgaga accacaggtg tacaccctgc   1380
ccccatcccg ggaggagatg accaagaacc aggtcagcct gacctgcctg gtcaaaggct   1440
```

-continued

```
tctatcccag cgacatcgcc gtggagtggg agagcaatgg gcagccggag aacaactaca   1500
agaccacgcc tcccgtgctg gactccgacg gctccttctt cctctacagc aagctcaccg   1560
tggacaagag caggtggcag caggggaacg tcttctcatg ctccgtgatg cacgaggctc   1620
tgcacaacca ctacacgcag aagagcctct ccctgtctcc gggtaaatga gtgctagctg   1680
gccagacatg ataagataca ttgatgagtt tggacaaacc acaactagaa tgcagtgaaa   1740
aaaatgcttt atttgtgaaa tttgtgatgc tattgcttta tttgtaacca ttataagctg   1800
caataaacaa gttaacaaca acaattgcat tcattttatg tttcaggttc agggggaggt   1860
gtgggaggtt ttttaaagca agtaaaacct ctacaaatgt ggtatggaat taattctaaa   1920
atacagcata gcaaaacttt aacctccaaa tcaagcctct acttgaatcc ttttctgagg   1980
gatgaataag gcataggcat caggggctgt tgccaatgtg cattagctgt ttgcagcctc   2040
accttctttc atggagttta agatatagtg tattttccca aggtttgaac tagctcttca   2100
tttctttatg ttttaaatgc actgacctcc cacattccct ttttagtaaa atattcagaa   2160
ataatttaaa tacatcattg caatgaaaat aaatgttttt tattaggcag aatccagatg   2220
ctcaaggccc ttcataatat cccccagttt agtagttgga cttagggaac aaaggaacct   2280
ttaatagaaa ttggacagca agaaagcgag cttctagctt atcctcagtc ctgctcctct   2340
gccacaaagt gcacgcagtt gccggccggg tcgcgcaggg cgaactcccg cccccacggc   2400
tgctcgccga tctcggtcat ggccggcccg gaggcgtccc ggaagttcgt ggacacgacc   2460
tccgaccact cggcgtacag ctcgtccagg ccgcgcaccc acacccaggc cagggtgttg   2520
tccggcacca cctggtcctg gaccgcgctg atgaacaggg tcacgtcgtc ccggaccaca   2580
ccggcgaagt cgtcctccac gaagtcccgg gagaacccga gccggtcggt ccagaactcg   2640
accgctccgg cgacgtcgcg cgcggtgagc accggaacgg cactggtcaa cttggccatg   2700
atggctcctc ctgtcaggag aggaaagaga agaaggttag tacaattgct atagtgagtt   2760
gtattatact atgcagatat actatgccaa tgattaattg tcaaactagg gctgcagggt   2820
tcatagtgcc acttttcctg cactgcccca tctcctgccc accctttccc aggcatagac   2880
agtcagtgac ttaccaaact cacaggaggg agaaggcaga agcttgagac agacccgcgg   2940
gaccgccgaa ctgcgagggg acgtggctag ggcggcttct tttatggtgc gccggccctc   3000
ggaggcaggg cgctcgggga ggcctagcgg ccaatctgcg gtggcaggag gcggggccga   3060
aggccgtgcc tgaccaatcc ggagcacata ggagtctcag ccccccgccc caaagcaagg   3120
ggaagtcacg cgcctgtagc gccagcgtgt tgtgaaatgg gggcttgggg gggttggggc   3180
cctgactagt caaaacaaac tcccattgac gtcaatgggg tggagacttg gaaatccccg   3240
tgagtcaaac cgctatccac gcccattgat gtactgccaa aaccgcatca tcatggtaat   3300
agcgatgact aatacgtaga tgtactgcca agtaggaaag tcccataagg tcatgtactg   3360
ggcataatgc caggcgggcc atttaccgtc attgacgtca atagggggcg tacttggcat   3420
atgatacact tgatgtactg ccaagtgggc agtttaccgt aaatactcca cccattgacg   3480
tcaatggaaa gtccctattg gcgttactat gggaacatac gtcattattg acgtcaatgg   3540
gcgggggtcg ttgggcggtc agccaggcgg gccatttacc gtaagttatg taacgcctgc   3600
aggttaatta agaacatgtg agcaaaaggc cagcaaaagg ccaggaaccg taaaaaggcc   3660
gcgttgctgg cgtttttcca taggctccgc ccccctgacg agcatcacaa aaatcgacgc   3720
tcaagtcaga ggtggcgaaa cccgacagga ctataaagat accaggcgtt tccccctgga   3780
```

-continued agctccctcg tgcgctctcc tgttccgacc ctgccgctta ccggatacct gtccgccttt 3840
ctcccttcgg gaagcgtggc gctttctcat agctcacgct gtaggtatct cagttcggtg 3900
taggtcgttc gctccaagct gggctgtgtg cacgaacccc ccgttcagcc cgaccgctgc 3960
gccttatccg gtaactatcg tcttgagtcc aacccggtaa gacacgactt atcgccactg 4020
gcagcagcca ctggtaacag gattagcaga gcgaggtatg taggcggtgc tacagagttc 4080
ttgaagtggt ggcctaacta cggctacact agaagaacag tatttggtat ctgcgctctg 4140
ctgaagccag ttaccttcgg aaaaagagtt ggtagctctt gatccggcaa acaaaccacc 4200
gctggtagcg gtggtttttt tgtttgcaag cagcagatta cgcgcagaaa aaaaggatct 4260
caagaagatc ctttgatctt ttctacgggg tctgacgctc agtggaacga aaactcacgt 4320
taagggattt tggtcatggc tagttaatta acatttaaat cagcggccgc aataaaatat 4380
ctttattttc attacatctg tgtgttggtt ttttgtgtga atcgtaacta acatacgctc 4440
tccatcaaaa caaaacgaaa caaaacaaac tagcaaaata ggctgtcccc agtgcaagtg 4500
caggtgccag aacatttctc tatcgaa 4527

<210> SEQ ID NO 92
<211> LENGTH: 4518
<212> TYPE: DNA
<213> ORGANISM: Artificial Sequence
<220> FEATURE:
<223> OTHER INFORMATION: pCCL25(4-127)-IgG1Fc

<400> SEQUENCE: 92
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacctgaga tcaccggcga aggagggcca ccatgtacag gatgcaactc ctgtcttgca 600
ttgcactaag tcttgcactt gtcacgaatt cggtctttga ggactgctgc ctggcctacc 660
actaccccat tgggtgggct gtgctccggc acgcctggac ttaccggatc caggaggtga 720
gcgggagctg caatctgcct gctgcgatat tctacctccc caagagacac aggaaggtgt 780
gtgggaaccc caaaagcagg gaggtgcaga gagccatgaa gctcctggat gctcgaaata 840
aggtttttgc aaagctccgc cacaacacgc agaccttcca aggccctcat gctgtaaaga 900
agttgagttc tggaaactcc aagttatcat cgtccaagtt tagcaatccc atcagcagca 960
gcaagaggaa tgtctccgac aaaactcaca catgcccacc gtgcccagca cctgaactcc 1020 tgggggggacc gtcagtcttc ctcttccccc caaaacccaa ggacaccctc atgatctccc 1080
ggacccctga ggtcacatgc gtggtggtgg acgtgagcca cgaagaccct gaggtcaagt 1140
tcaactggta cgtggacggc gtggaggtgc ataatgccaa gacaaagccg cgggaggagc 1200
agtacaacag cacgtaccgt gtggtcagcg tcctcaccgt cctgcaccag gactggctga 1260
atggcaagga gtacaagtgc aaggtctcca acaaagccct cccagccccc atcgagaaaa 1320

-continued

```
ccatctccaa agccaaaggg cagccccgag aaccacaggt gtacaccctg cccccatccc   1380
gggaggagat gaccaagaac caggtcagcc tgacctgcct ggtcaaaggc ttctatccca   1440
gcgacatcgc cgtggagtgg gagagcaatg ggcagccgga gaacaactac aagaccacgc   1500
ctcccgtgct ggactccgac ggctccttct tcctctacag caagctcacc gtggacaaga   1560
gcaggtggca gcaggggaac gtcttctcat gctccgtgat gcacgaggct ctgcacaacc   1620
actacacgca gaagagcctc tccctgtctc cgggtaaatg agtgctagct ggccagacat   1680
gataagatac attgatgagt ttggacaaac cacaactaga atgcagtgaa aaaaatgctt   1740
tatttgtgaa atttgtgatg ctattgcttt atttgtaacc attataagct gcaataaaca   1800
agttaacaac aacaattgca ttcattttat gtttcaggtt cagggggagg tgtgggaggt   1860
tttttaaagc aagtaaaacc tctacaaatg tggtatggaa ttaattctaa aatacagcat   1920
agcaaaactt taacctccaa atcaagcctc tacttgaatc cttttctgag ggatgaataa   1980
ggcataggca tcaggggctg ttgccaatgt gcattagctg tttgcagcct caccttcttt   2040
catggagttt aagatatagt gtattttccc aaggtttgaa ctagctcttc atttctttat   2100
gttttaaatg cactgacctc ccacattccc tttttagtaa aatattcaga aataatttaa   2160
atacatcatt gcaatgaaaa taaatgtttt ttattaggca gaatccagat gctcaaggcc   2220
cttcataata tcccccagtt tagtagttgg acttagggaa caaaggaacc tttaatagaa   2280
attggacagc aagaaagcga gcttctagct tatcctcagt cctgctcctc tgccacaaag   2340
tgcacgcagt tgccggccgg gtcgcgcagg gcgaactccc gcccccacgg ctgctcgccg   2400
atctcggtca tggccggccc ggaggcgtcc cggaagttcg tggacacgac ctccgaccac   2460
tcggcgtaca gctcgtccag gccgcgcacc cacacccagg ccagggtgtt gtccggcacc   2520
acctggtcct ggaccgcgct gatgaacagg gtcacgtcgt cccggaccac accggcgaag   2580
tcgtcctcca cgaagtcccg ggagaacccg agccggtcgg tccagaactc gaccgctccg   2640
gcgacgtcgc gcgcggtgag caccggaacg gcactggtca acttggccat gatggctcct   2700
cctgtcagga gaggaaagag aagaaggtta gtacaattgc tatagtgagt tgtattatac   2760
tatgcagata tactatgcca atgattaatt gtcaaactag ggctgcaggg ttcatagtgc   2820
cacttttcct gcactgcccc atctcctgcc caccctttcc caggcataga cagtcagtga   2880
cttaccaaac tcacaggagg gagaaggcag aagcttgaga cagacccgcg ggaccgccga   2940
actgcgaggg gacgtggcta gggcggcttc ttttatggtg cgccggccct cggaggcagg   3000
gcgctcgggg aggcctagcg gccaatctgc ggtggcagga ggcggggccg aaggccgtgc   3060
ctgaccaatc cggagcacat aggagtctca gcccccgcc ccaaagcaag gggaagtcac   3120
gcgcctgtag cgccagcgtg ttgtgaaatg ggggcttggg ggggttgggg ccctgactag   3180
tcaaaacaaa ctcccattga cgtcaatggg gtggagactt ggaaatcccc gtgagtcaaa   3240
ccgctatcca cgcccattga tgtactgcca aaaccgcatc atcatggtaa tagcgatgac   3300
taatacgtag atgtactgcc aagtaggaaa gtcccataag gtcatgtact gggcataatg   3360
ccaggcgggc catttaccgt cattgacgtc aatagggggc gtacttggca tatgatacac   3420
ttgatgtact gccaagtggg cagtttaccg taaatactcc acccattgac gtcaatggaa   3480
agtccctatt ggcgttacta tgggaacata cgtcattatt gacgtcaatg ggcgggggtc   3540
gttgggcggt cagccaggcg ggccatttac cgtaagttat gtaacgcctg caggttaatt   3600
aagaacatgt gagcaaaagg ccagcaaaag gccaggaacc gtaaaaaggc cgcgttgctg   3660
```

-continued gcgtttttcc ataggctccg cccccctgac gagcatcaca aaaatcgacg ctcaagtcag 3720
aggtggcgaa acccgacagg actataaaga taccaggcgt ttccccctgg aagctccctc 3780
gtgcgctctc ctgttccgac cctgccgctt accggatacc tgtccgcctt tctcccttcg 3840
ggaagcgtgg cgctttctca tagctcacgc tgtaggtatc tcagttcggt gtaggtcgtt 3900
cgctccaagc tgggctgtgt gcacgaaccc cccgttcagc ccgaccgctg cgccttatcc 3960
ggtaactatc gtcttgagtc caacccggta agacacgact tatcgccact ggcagcagcc 4020
actggtaaca ggattagcag agcgaggtat gtaggcggtg ctacagagtt cttgaagtgg 4080
tggcctaact acggctacac tagaagaaca gtatttggta tctgcgctct gctgaagcca 4140
gttaccttcg gaaaaagagt tggtagctct tgatccggca aacaaaccac cgctggtagc 4200
ggtggttttt ttgtttgcaa gcagcagatt acgcgcagaa aaaaaggatc tcaagaagat 4260
cctttgatct tttctacggg gtctgacgct cagtggaacg aaaactcacg ttaagggatt 4320
ttggtcatgg ctagttaatt aacatttaaa tcagcggccg caataaaata tctttatttt 4380
cattacatct gtgtgttggt ttttgtgtg aatcgtaact aacatacgct ctccatcaaa 4440
acaaaacgaa acaaaacaaa ctagcaaaat aggctgtccc cagtgcaagt gcaggtgcca 4500
gaacatttct ctatcgaa 4518

<210> SEQ ID NO 93
<211> LENGTH: 4518
<212> TYPE: DNA
<213> ORGANISM: Artificial Sequence
<220> FEATURE:
<223> OTHER INFORMATION: pCCL25(4-127K/H-A)-IgG1Fc

<400> SEQUENCE: 93
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacctgaga tcaccggcga aggagggcca ccatgtacag gatgcaactc ctgtcttgca 600
ttgcactaag tcttgcactt gtcacgaatt cggtctttga ggactgctgc ctggcctacc 660
actaccccat tgggtgggct gtgctccggc acgcctggac ttaccggatc caggaggtga 720
gcgggagctg caatctgcct gctgcgatat tctacctccc cgctgccgct gccgcggtgt 780
gtgggaaccc cgctagcgcc gaggtgcagg ctgccatggc cctcctggat gctgctaatg 840
ccgtttttgc agcgctcgct gccaacacgc agaccttcca aggccctgcg gctgtagccg 900
ctttgagttc tggaaactcc gccttatcat cgtccgcgtt tagcaatccc atcagcagca 960
gcgctgccaa tgtctccgac aaaactcaca catgcccacc gtgcccagca cctgaactcc 1020
tggggggacc gtcagtcttc ctcttccccc caaaacccaa ggacaccctc atgatctccc 1080
ggacccctga ggtcacatgc gtggtggtgg acgtgagcca cgaagaccct gaggtcaagt 1140
tcaactggta cgtggacggc gtggaggtgc ataatgccaa gacaaagccg cgggaggagc 1200

-continued

```
agtacaacag cacgtaccgt gtggtcagcg tcctcaccgt cctgcaccag gactggctga   1260
atggcaagga gtacaagtgc aaggtctcca acaaagccct cccagccccc atcgagaaaa   1320
ccatctccaa agccaaaggg cagccccgag aaccacaggt gtacaccctg cccccatccc   1380
gggaggagat gaccaagaac caggtcagcc tgacctgcct ggtcaaaggc ttctatccca   1440
gcgacatcgc cgtggagtgg gagagcaatg ggcagccgga gaacaactac aagaccacgc   1500
ctcccgtgct ggactccgac ggctccttct tcctctacag caagctcacc gtggacaaga   1560
gcaggtggca gcaggggaac gtcttctcat gctccgtgat gcacgaggct ctgcacaacc   1620
actacacgca gaagagcctc tccctgtctc cgggtaaatg agtgctagct ggccagacat   1680
gataagatac attgatgagt ttggacaaac cacaactaga atgcagtgaa aaaaatgctt   1740
tatttgtgaa atttgtgatg ctattgcttt atttgtaacc attataagct gcaataaaca   1800
agttaacaac aacaattgca ttcattttat gtttcaggtt cagggggagg tgtgggaggt   1860
tttttaaagc aagtaaaacc tctacaaatg tggtatggaa ttaattctaa aatacagcat   1920
agcaaaactt taacctccaa atcaagcctc tacttgaatc cttttctgag ggatgaataa   1980
ggcataggca tcaggggctg ttgccaatgt gcattagctg tttgcagcct caccttcttt   2040
catggagttt aagatatagt gtattttccc aaggtttgaa ctagctcttc atttctttat   2100
gttttaaatg cactgacctc ccacattccc tttttagtaa aatattcaga aataatttaa   2160
atacatcatt gcaatgaaaa taaatgtttt ttattaggca gaatccagat gctcaaggcc   2220
cttcataata tcccccagtt tagtagttgg acttagggaa caaaggaacc tttaatagaa   2280
attggacagc aagaaagcga gcttctagct tatcctcagt cctgctcctc tgccacaaag   2340
tgcacgcagt tgccggccgg gtcgcgcagg gcgaactccc gcccccacgg ctgctcgccg   2400
atctcggtca tggccggccc ggaggcgtcc cggaagttcg tggacacgac ctccgaccac   2460
tcggcgtaca gctcgtccag gccgcgcacc cacacccagg ccagggtgtt gtccggcacc   2520
acctggtcct ggaccgcgct gatgaacagg gtcacgtcgt cccggaccac accggcgaag   2580
tcgtcctcca cgaagtcccg ggagaacccg agccggtcgg tccagaactc gaccgctccg   2640
gcgacgtcgc gcgcggtgag caccggaacg gcactggtca acttggccat gatggctcct   2700
cctgtcagga gaggaaagag aagaaggtta gtacaattgc tatagtgagt tgtattatac   2760
tatgcagata tactatgcca atgattaatt gtcaaactag ggctgcaggg ttcatagtgc   2820
cacttttcct gcactgcccc atctcctgcc caccctttcc caggcataga cagtcagtga   2880
cttaccaaac tcacaggagg gagaaggcag aagcttgaga cagacccgcg ggaccgccga   2940
actgcgaggg gacgtggcta gggcggcttc ttttatggtg cgccggccct cggaggcagg   3000
gcgctcgggg aggcctagcg gccaatctgc ggtggcagga ggcggggccg aaggccgtgc   3060
ctgaccaatc cggagcacat aggagtctca gccccccgcc ccaaagcaag gggaagtcac   3120
gcgcctgtag cgccagcgtg ttgtgaaatg ggggcttggg ggggttgggg ccctgactag   3180
tcaaaacaaa ctcccattga cgtcaatggg gtggagactt ggaaatcccc gtgagtcaaa   3240
ccgctatcca cgcccattga tgtactgcca aaaccgcatc atcatggtaa tagcgatgac   3300
taatacgtag atgtactgcc aagtaggaaa gtcccataag gtcatgtact gggcataatg   3360
ccaggcgggc catttaccgt cattgacgtc aatagggggc gtacttggca tatgatacac   3420
ttgatgtact gccaagtggg cagtttaccg taaatactcc acccattgac gtcaatggaa   3480
agtccctatt ggcgttacta tgggaacata cgtcattatt gacgtcaatg ggcgggggtc   3540
```

-continued

```
gttgggcggt cagccaggcg ggccatttac cgtaagttat gtaacgcctg caggttaatt   3600

aagaacatgt gagcaaaagg ccagcaaaag gccaggaacc gtaaaaaggc cgcgttgctg   3660

gcgtttttcc ataggctccg cccccctgac gagcatcaca aaaatcgacg ctcaagtcag   3720

aggtggcgaa acccgacagg actataaaga taccaggcgt ttccccctgg aagctccctc   3780

gtgcgctctc ctgttccgac cctgccgctt accggatacc tgtccgcctt tctcccttcg   3840

ggaagcgtgg cgctttctca tagctcacgc tgtaggtatc tcagttcggt gtaggtcgtt   3900

cgctccaagc tgggctgtgt gcacgaaccc cccgttcagc ccgaccgctg cgccttatcc   3960

ggtaactatc gtcttgagtc caacccggta agacacgact tatcgccact ggcagcagcc   4020

actggtaaca ggattagcag agcgaggtat gtaggcggtg ctacagagtt cttgaagtgg   4080

tggcctaact acggctacac tagaagaaca gtatttggta tctgcgctct gctgaagcca   4140

gttaccttcg gaaaaagagt tggtagctct tgatccggca aacaaaccac cgctggtagc   4200

ggtggttttt ttgtttgcaa gcagcagatt acgcgcagaa aaaaaggatc tcaagaagat   4260

cctttgatct tttctacggg gtctgacgct cagtggaacg aaaactcacg ttaagggatt   4320

ttggtcatgg ctagttaatt aacatttaaa tcagcggccg caataaaata tctttatttt   4380

cattacatct gtgtgttggt ttttgtgtg aatcgtaact aacatacgct ctccatcaaa   4440

acaaaacgaa acaaaacaaa ctagcaaaat aggctgtccc cagtgcaagt gcaggtgcca   4500

gaacatttct ctatcgaa                                                  4518
```

<210> SEQ ID NO 94
<211> LENGTH: 4392
<212> TYPE: DNA
<213> ORGANISM: Artificial Sequence
<220> FEATURE:
<223> OTHER INFORMATION: pCXCL11-IgG1Fc

<400> SEQUENCE: 94

```
ggatctgcga tcgctccggt gcccgtcagt gggcagagcg cacatcgccc acagtccccg     60

agaagttggg gggaggggtc ggcaattgaa cgggtgccta gagaaggtgg cgcggggtaa    120

actgggaaag tgatgtcgtg tactggctcc gcctttttcc cgagggtggg ggagaaccgt    180

atataagtgc agtagtcgcc gtgaacgttc tttttcgcaa cgggtttgcc gccagaacac    240

agctgaagct tcgaggggct cgcatctctc cttcacgcgc ccgccgccct acctgaggcc    300

gccatccacg ccggttgagt cgcgttctgc cgcctcccgc ctgtggtgcc tcctgaactg    360

cgtccgccgt ctaggtaagt ttaaagctca ggtcgagacc gggcctttgt ccggcgctcc    420

cttggagcct acctagactc agccggctct ccacgctttg cctgaccctg cttgctcaac    480

tctacgtctt tgtttcgttt tctgttctgc gccgttacag atccaagctg tgaccggcgc    540

ctacctgaga tcaccggcga aggagggcca ccatgtacag gatgcaactc ctgtcttgca    600

ttgcactaag tcttgcactt gtcacgaatt cgttccccat gttcaaaaga ggacgctgtc    660

tttgcatagg ccctggggta aaagcagtga aagtggcaga tattgagaaa gcctccataa    720

tgtacccaag taacaactgt gacaaaatag aagtgattat taccctgaaa gaaaataaag    780

gacaacgatg cctaaatccc aaatcgaagc aagcaaggct tataatcaaa aaagttgaaa    840

gaaagaattt tgacaaaact cacacatgcc caccgtgccc agcacctgaa ctcctggggg    900

gaccgtcagt cttcctcttc cccccaaaac ccaaggacac cctcatgatc tcccggaccc    960

ctgaggtcac atgcgtggtg gtggacgtga gccacgaaga ccctgaggtc aagttcaact   1020

ggtacgtgga cggcgtggag gtgcataatg ccaagacaaa gccgcgggag gagcagtaca   1080
```

-continued

```
acagcacgta ccgtgtggtc agcgtcctca ccgtcctgca ccaggactgg ctgaatggca   1140
aggagtacaa gtgcaaggtc tccaacaaag ccctcccagc ccccatcgag aaaaccatct   1200
ccaaagccaa agggcagccc cgagaaccac aggtgtacac cctgccccca tcccgggagg   1260
agatgaccaa gaaccaggtc agcctgacct gcctggtcaa aggcttctat cccagcgaca   1320
tcgccgtgga gtgggagagc aatgggcagc cggagaacaa ctacaagacc acgcctcccg   1380
tgctggactc cgacggctcc ttcttcctct acagcaagct caccgtggac aagagcaggt   1440
ggcagcaggg gaacgtcttc tcatgctccg tgatgcacga ggctctgcac aaccactaca   1500
cgcagaagag cctctccctg tctccgggta aatgagtgct agctggccag acatgataag   1560
atacattgat gagtttggac aaaccacaac tagaatgcag tgaaaaaaat gctttatttg   1620
tgaaatttgt gatgctattg ctttatttgt aaccattata agctgcaata aacaagttaa   1680
caacaacaat tgcattcatt ttatgtttca ggttcagggg gaggtgtggg aggtttttta   1740
aagcaagtaa aacctctaca aatgtggtat ggaattaatt ctaaaataca gcatagcaaa   1800
actttaacct ccaaatcaag cctctacttg aatccttttc tgagggatga ataaggcata   1860
ggcatcaggg gctgttgcca atgtgcatta gctgtttgca gcctcacctt ctttcatgga   1920
gtttaagata tagtgtattt tcccaaggtt tgaactagct cttcatttct ttatgtttta   1980
aatgcactga cctcccacat tcccttttta gtaaaatatt cagaaataat ttaaatacat   2040
cattgcaatg aaaataaatg tttttatta ggcagaatcc agatgctcaa ggcccttcat   2100
aatatccccc agtttagtag ttggacttag ggaacaaagg aacctttaat agaaattgga   2160
cagcaagaaa gcgagcttct agcttatcct cagtcctgct cctctgccac aaagtgcacg   2220
cagttgccgg ccgggtcgcg cagggcgaac tcccgccccc acggctgctc gccgatctcg   2280
gtcatggccg gcccggaggc gtcccggaag ttcgtggaca cgacctccga ccactcggcg   2340
tacagctcgt ccaggccgcg cacccacacc caggccaggg tgttgtccgg caccacctgg   2400
tcctggaccg cgctgatgaa cagggtcacg tcgtcccgga ccacaccggc gaagtcgtcc   2460
tccacgaagt cccgggagaa cccgagccgg tcggtccaga actcgaccgc tccggcgacg   2520
tcgcgcgcgg tgagcaccgg aacggcactg gtcaacttgg ccatgatggc tcctcctgtc   2580
aggagaggaa agagaagaag gttagtacaa ttgctatagt gagttgtatt atactatgca   2640
gatatactat gccaatgatt aattgtcaaa ctagggctgc agggttcata gtgccacttt   2700
tcctgcactg ccccatctcc tgcccaccct ttcccaggca tagacagtca gtgacttacc   2760
aaactcacag gagggagaag gcagaagctt gagacagacc cgcgggaccg ccgaactgcg   2820
aggggacgtg gctagggcgg cttcttttat ggtgcgccgg ccctcggagg cagggcgctc   2880
ggggaggcct agcggccaat ctgcggtggc aggaggcggg gccgaaggcc gtgcctgacc   2940
aatccggagc acataggagt ctcagccccc cgccccaaag caaggggaag tcacgcgcct   3000
gtagcgccag cgtgttgtga aatgggggct tgggggggtt ggggccctga ctagtcaaaa   3060
caaactccca ttgacgtcaa tggggtggag acttggaaat ccccgtgagt caaaccgcta   3120
tccacgccca ttgatgtact gccaaaaccg catcatcatg gtaatagcga tgactaatac   3180
gtagatgtac tgccaagtag gaaagtccca taaggtcatg tactgggcat aatgccaggc   3240
gggccattta ccgtcattga cgtcaatagg gggcgtactt ggcatatgat acacttgatg   3300
tactgccaag tgggcagttt accgtaaata ctccacccat tgacgtcaat ggaaagtccc   3360
tattggcgtt actatgggaa catacgtcat tattgacgtc aatgggcggg ggtcgttggg   3420
```

```
cggtcagcca ggcgggccat ttaccgtaag ttatgtaacg cctgcaggtt aattaagaac   3480

atgtgagcaa aaggccagca aaaggccagg aaccgtaaaa aggccgcgtt gctggcgttt   3540

ttccataggc tccgcccccc tgacgagcat cacaaaaatc gacgctcaag tcagaggtgg   3600

cgaaacccga caggactata aagataccag gcgtttcccc ctggaagctc cctcgtgcgc   3660

tctcctgttc cgaccctgcc gcttaccgga tacctgtccg cctttctccc ttcgggaagc   3720

gtggcgcttt ctcatagctc acgctgtagg tatctcagtt cggtgtaggt cgttcgctcc   3780

aagctgggct gtgtgcacga accccccgtt cagcccgacc gctgcgcctt atccggtaac   3840

tatcgtcttg agtccaaccc ggtaagacac gacttatcgc cactggcagc agccactggt   3900

aacaggatta gcagagcgag gtatgtaggc ggtgctacag agttcttgaa gtggtggcct   3960

aactacggct acactagaag aacagtattt ggtatctgcg ctctgctgaa gccagttacc   4020

ttcggaaaaa gagttggtag ctcttgatcc ggcaaacaaa ccaccgctgg tagcggtggt   4080

tttttgttt gcaagcagca gattacgcgc agaaaaaaag gatctcaaga agatcctttg   4140

atcttttcta cggggtctga cgctcagtgg aacgaaaact cacgttaagg gattttggtc   4200

atggctagtt aattaacatt taaatcagcg gccgcaataa aatatcttta ttttcattac   4260

atctgtgtgt tggtttttg tgtgaatcgt aactaacata cgctctccat caaaacaaaa   4320

cgaaacaaaa caaactagca aaataggctg tccccagtgc aagtgcaggt gccagaacat   4380

ttctctatcg aa                                                       4392
```

```
<210> SEQ ID NO 95
<211> LENGTH: 4383
<212> TYPE: DNA
<213> ORGANISM: Artificial Sequence
<220> FEATURE:
<223> OTHER INFORMATION: pCXCL11(4-73)-IgG1Fc

<400> SEQUENCE: 95

ggatctgcga tcgctccggt gcccgtcagt gggcagagcg cacatcgccc acagtccccg     60

agaagttggg gggaggggtc ggcaattgaa cgggtgccta gagaaggtgg cgcggggtaa    120

actgggaaag tgatgtcgtg tactggctcc gcctttttcc cgagggtggg ggagaaccgt    180

atataagtgc agtagtcgcc gtgaacgttc tttttcgcaa cgggtttgcc gccagaacac    240

agctgaagct tcgaggggct cgcatctctc cttcacgcgc ccgccgccct acctgaggcc    300

gccatccacg ccggttgagt cgcgttctgc cgcctcccgc ctgtggtgcc tcctgaactg    360

cgtccgccgt ctaggtaagt ttaaagctca ggtcgagacc gggcctttgt ccggcgctcc    420

cttggagcct acctagactc agccggctct ccacgctttg cctgaccctg cttgctcaac    480

tctacgtctt tgtttcgttt tctgttctgc gccgttacag atccaagctg tgaccggcgc    540

ctacctgaga tcaccggcga aggagggcca ccatgtacag gatgcaactc ctgtcttgca    600

ttgcactaag tcttgcactt gtcacgaatt cgttcaaaag aggacgctgt ctttgcatag    660

gccctggggt aaaagcagtg aaagtggcag atattgagaa agcctccata atgtacccaa    720

gtaacaactg tgacaaaata gaagtgatta ttaccctgaa agaaaataaa ggacaacgat    780

gcctaaatcc caaatcgaag caagcaaggc ttataatcaa aaaagttgaa agaaagaatt    840

ttgacaaaac tcacacatgc ccaccgtgcc cagcacctga actcctgggg ggaccgtcag    900

tcttcctctt ccccccaaaa cccaaggaca ccctcatgat ctcccggacc cctgaggtca    960

catgcgtggt ggtggacgtg agccacgaag accctgaggt caagttcaac tggtacgtgg   1020

acggcgtgga ggtgcataat gccaagacaa agccgcggga ggagcagtac aacagcacgt   1080
```

-continued

```
accgtgtggt cagcgtcctc accgtcctgc accaggactg gctgaatggc aaggagtaca   1140
agtgcaaggt ctccaacaaa gccctcccag cccccatcga gaaaaccatc tccaaagcca   1200
aagggcagcc ccgagaacca caggtgtaca ccctgccccc atcccgggag gagatgacca   1260
agaaccaggt cagcctgacc tgcctggtca aaggcttcta tcccagcgac atcgccgtgg   1320
agtgggagag caatgggcag ccggagaaca actacaagac cacgcctccc gtgctggact   1380
ccgacggctc cttcttcctc tacagcaagc tcaccgtgga caagagcagg tggcagcagg   1440
ggaacgtctt ctcatgctcc gtgatgcacg aggctctgca caaccactac acgcagaaga   1500
gcctctccct gtctccgggt aaatgagtgc tagctggcca gacatgataa gatacattga   1560
tgagtttgga caaaccacaa ctagaatgca gtgaaaaaaa tgctttattt gtgaaatttg   1620
tgatgctatt gctttatttg taaccattat aagctgcaat aaacaagtta acaacaacaa   1680
ttgcattcat tttatgtttc aggttcaggg ggaggtgtgg gaggtttttt aaagcaagta   1740
aaacctctac aaatgtggta tggaattaat tctaaaatac agcatagcaa aactttaacc   1800
tccaaatcaa gcctctactt gaatcctttt ctgagggatg aataaggcat aggcatcagg   1860
ggctgttgcc aatgtgcatt agctgtttgc agcctcacct tctttcatgg agtttaagat   1920
atagtgtatt ttcccaaggt ttgaactagc tcttcatttc tttatgtttt aaatgcactg   1980
acctcccaca ttcccttttt agtaaaatat tcagaaataa tttaaataca tcattgcaat   2040
gaaaataaat gtttttttatt aggcagaatc cagatgctca aggcccttca taatatcccc   2100
cagtttagta gttggactta gggaacaaag gaacctttaa tagaaattgg acagcaagaa   2160
agcgagcttc tagcttatcc tcagtcctgc tcctctgcca caaagtgcac gcagttgccg   2220
gccgggtcgc gcagggcgaa ctcccgcccc cacggctgct cgccgatctc ggtcatggcc   2280
ggcccggagg cgtcccggaa gttcgtggac acgacctccg accactcggc gtacagctcg   2340
tccaggccgc gcacccacac ccaggccagg gtgttgtccg gcaccacctg gtcctggacc   2400
gcgctgatga acagggtcac gtcgtcccgg accacaccgg cgaagtcgtc ctccacgaag   2460
tcccgggaga acccgagccg gtcggtccag aactcgaccg ctccggcgac gtcgcgcgcg   2520
gtgagcaccg gaacggcact ggtcaacttg gccatgatgg ctcctcctgt caggagagga   2580
aagagaagaa ggttagtaca attgctatag tgagttgtat tatactatgc agatatacta   2640
tgccaatgat taattgtcaa actagggctg cagggttcat agtgccactt ttcctgcact   2700
gccccatctc ctgcccaccc tttcccaggc atagacagtc agtgacttac caaactcaca   2760
ggagggagaa ggcagaagct tgagacagac ccgcgggacc gccgaactgc gaggggacgt   2820
ggctagggcg gcttctttta tggtgcgccg gccctcggag gcagggcgct cggggaggcc   2880
tagcggccaa tctgcggtgg caggaggcgg ggccgaaggc cgtgcctgac caatccggag   2940
cacataggag tctcagcccc ccgccccaaa gcaaggggaa gtcacgcgcc tgtagcgcca   3000
gcgtgttgtg aaatgggggc ttgggggggt tggggccctg actagtcaaa acaaactccc   3060
attgacgtca atggggtgga gacttggaaa tccccgtgag tcaaaccgct atccacgccc   3120
attgatgtac tgccaaaacc gcatcatcat ggtaatagcg atgactaata cgtagatgta   3180
ctgccaagta ggaaagtccc ataaggtcat gtactgggca taatgccagg cgggccattt   3240
accgtcattg acgtcaatag ggggcgtact tggcatatga tacacttgat gtactgccaa   3300
gtgggcagtt taccgtaaat actccaccca ttgacgtcaa tggaaagtcc ctattggcgt   3360
tactatggga acatacgtca ttattgacgt caatgggcgg gggtcgttgg gcggtcagcc   3420
```

```
aggcgggcca tttaccgtaa gttatgtaac gcctgcaggt taattaagaa catgtgagca   3480

aaaggccagc aaaaggccag gaaccgtaaa aaggccgcgt tgctggcgtt tttccatagg   3540

ctccgccccc ctgacgagca tcacaaaaat cgacgctcaa gtcagaggtg gcgaaacccg   3600

acaggactat aaagatacca ggcgtttccc cctggaagct ccctcgtgcg ctctcctgtt   3660

ccgaccctgc cgcttaccgg atacctgtcc gcctttctcc cttcgggaag cgtggcgctt   3720

tctcatagct cacgctgtag gtatctcagt tcggtgtagg tcgttcgctc caagctgggc   3780

tgtgtgcacg aaccccccgt tcagcccgac cgctgcgcct tatccggtaa ctatcgtctt   3840

gagtccaacc cggtaagaca cgacttatcg ccactggcag cagccactgg taacaggatt   3900

agcagagcga ggtatgtagg cggtgctaca gagttcttga agtggtggcc taactacggc   3960

tacactagaa gaacagtatt tggtatctgc gctctgctga agccagttac cttcggaaaa   4020

agagttggta gctcttgatc cggcaaacaa accaccgctg gtagcggtgg tttttttgtt   4080

tgcaagcagc agattacgcg cagaaaaaaa ggatctcaag aagatccttt gatcttttct   4140

acggggtctg acgctcagtg gaacgaaaac tcacgttaag ggattttggt catggctagt   4200

taattaacat ttaaatcagc ggccgcaata aaatatcttt attttcatta catctgtgtg   4260

ttggtttttt gtgtgaatcg taactaacat acgctctcca tcaaaacaaa acgaaacaaa   4320

acaaactagc aaaataggct gtccccagtg caagtgcagg tgccagaaca tttctctatc   4380

gaa                                                                 4383
```

```
<210> SEQ ID NO 96
<211> LENGTH: 4383
<212> TYPE: DNA
<213> ORGANISM: Artificial Sequence
<220> FEATURE:
<223> OTHER INFORMATION: pCXCL11(4-73K/H-A)-IgG1Fc

<400> SEQUENCE: 96
```

```
ggatctgcga tcgctccggt gcccgtcagt gggcagagcg cacatcgccc acagtccccg     60

agaagttggg gggaggggtc ggcaattgaa cgggtgccta gagaaggtgg cgcggggtaa    120

actgggaaag tgatgtcgtg tactggctcc gcctttttcc cgagggtggg ggagaaccgt    180

atataagtgc agtagtcgcc gtgaacgttc tttttcgcaa cgggtttgcc gccagaacac    240

agctgaagct tcgaggggct cgcatctctc cttcacgcgc ccgccgccct acctgaggcc    300

gccatccacg ccggttgagt cgcgttctgc cgcctcccgc ctgtggtgcc tcctgaactg    360

cgtccgccgt ctaggtaagt ttaaagctca ggtcgagacc gggcctttgt ccggcgctcc    420

cttggagcct acctagactc agccggctct ccacgctttg cctgaccctg cttgctcaac    480

tctacgtctt tgtttcgttt tctgttctgc gccgttacag atccaagctg tgaccggcgc    540

ctacctgaga tcaccggcga aggagggcca ccatgtacag gatgcaactc ctgtcttgca    600

ttgcactaag tcttgcactt gtcacgaatt cgttcaaaag aggacgctgt ctttgcatag    660

gccctggggt aaaagcagtg aaagtggcag atattgaggc cgcctccata atgtacccaa    720

gtaacaactg tgacaaaata gaagtgatta ttaccctggc agaaaatgcc ggacaagcat    780

gcctaaatcc cgcctcggca caagcagccc ttataatcgc agccgttgaa gcagccaatt    840

ttgacaaaac tcacacatgc ccaccgtgcc cagcacctga actcctgggg ggaccgtcag    900

tcttcctctt ccccccaaaa cccaaggaca ccctcatgat ctcccggacc cctgaggtca    960

catgcgtggt ggtggacgtg agccacgaag accctgaggt caagttcaac tggtacgtgg   1020

acggcgtgga ggtgcataat gccaagacaa agccgcggga ggagcagtac aacagcacgt   1080
```

-continued

```
accgtgtggt cagcgtcctc accgtcctgc accaggactg gctgaatggc aaggagtaca   1140
agtgcaaggt ctccaacaaa gccctcccag cccccatcga gaaaaccatc tccaaagcca   1200
aagggcagcc ccgagaacca caggtgtaca ccctgccccc atcccgggag gagatgacca   1260
agaaccaggt cagcctgacc tgcctggtca aaggcttcta tcccagcgac atcgccgtgg   1320
agtgggagag caatgggcag ccggagaaca actacaagac cacgcctccc gtgctggact   1380
ccgacggctc cttcttcctc tacagcaagc tcaccgtgga caagagcagg tggcagcagg   1440
ggaacgtctt ctcatgctcc gtgatgcacg aggctctgca caaccactac acgcagaaga   1500
gcctctccct gtctccgggt aaatgagtgc tagctggcca gacatgataa gatacattga   1560
tgagtttgga caaaccacaa ctagaatgca gtgaaaaaaa tgctttattt gtgaaatttg   1620
tgatgctatt gctttatttg taaccattat aagctgcaat aaacaagtta acaacaacaa   1680
ttgcattcat tttatgtttc aggttcaggg ggaggtgtgg gaggtttttt aaagcaagta   1740
aaacctctac aaatgtggta tggaattaat tctaaaatac agcatagcaa aactttaacc   1800
tccaaatcaa gcctctactt gaatcctttt ctgagggatg aataaggcat aggcatcagg   1860
ggctgttgcc aatgtgcatt agctgtttgc agcctcacct tctttcatgg agtttaagat   1920
atagtgtatt ttcccaaggt ttgaactagc tcttcatttc tttatgtttt aaatgcactg   1980
acctcccaca ttcccttttt agtaaaatat tcagaaataa tttaaataca tcattgcaat   2040
gaaaataaat gtttttttatt aggcagaatc cagatgctca aggcccttca taatatcccc   2100
cagtttagta gttggactta gggaacaaag gaacctttaa tagaaattgg acagcaagaa   2160
agcgagcttc tagcttatcc tcagtcctgc tcctctgcca caaagtgcac gcagttgccg   2220
gccgggtcgc gcagggcgaa ctcccgcccc cacggctgct cgccgatctc ggtcatggcc   2280
ggcccggagg cgtcccggaa gttcgtggac acgacctccg accactcggc gtacagctcg   2340
tccaggccgc gcacccacac ccaggccagg gtgttgtccg gcaccacctg gtcctggacc   2400
gcgctgatga acagggtcac gtcgtcccgg accacaccgg cgaagtcgtc ctccacgaag   2460
tcccgggaga acccgagccg gtcggtccag aactcgaccg ctccggcgac gtcgcgcgcg   2520
gtgagcaccg gaacggcact ggtcaacttg gccatgatgg ctcctcctgt caggagagga   2580
aagagaagaa ggttagtaca attgctatag tgagttgtat tatactatgc agatatacta   2640
tgccaatgat taattgtcaa actagggctg cagggttcat agtgccactt ttcctgcact   2700
gccccatctc ctgcccaccc tttcccaggc atagacagtc agtgacttac caaactcaca   2760
ggagggagaa ggcagaagct tgagacagac ccgcgggacc gccgaactgc gaggggacgt   2820
ggctagggcg gcttctttta tggtgcgccg gccctcggag gcagggcgct cggggaggcc   2880
tagcggccaa tctgcggtgg caggaggcgg ggccgaaggc cgtgcctgac caatccggag   2940
cacataggag tctcagcccc ccgccccaaa gcaaggggaa gtcacgcgcc tgtagcgcca   3000
gcgtgttgtg aaatgggggc ttgggggggt tggggccctg actagtcaaa acaaactccc   3060
attgacgtca atggggtgga gacttggaaa tccccgtgag tcaaaccgct atccacgccc   3120
attgatgtac tgccaaaacc gcatcatcat ggtaatagcg atgactaata cgtagatgta   3180
ctgccaagta ggaaagtccc ataaggtcat gtactgggca taatgccagg cgggccattt   3240
accgtcattg acgtcaatag gggcgtact tggcatatga tacacttgat gtactgccaa   3300
gtgggcagtt taccgtaaat actccaccca ttgacgtcaa tggaaagtcc ctattggcgt   3360
tactatggga acatacgtca ttattgacgt caatgggcgg gggtcgttgg gcggtcagcc   3420
```

-continued

```
aggcgggcca tttaccgtaa gttatgtaac gcctgcaggt taattaagaa catgtgagca   3480
aaaggccagc aaaaggccag gaaccgtaaa aaggccgcgt tgctggcgtt tttccatagg   3540
ctccgccccc ctgacgagca tcacaaaaat cgacgctcaa gtcagaggtg gcgaaacccg   3600
acaggactat aaagatacca ggcgtttccc cctggaagct ccctcgtgcg ctctcctgtt   3660
ccgaccctgc cgcttaccgg atacctgtcc gcctttctcc cttcgggaag cgtggcgctt   3720
tctcatagct cacgctgtag gtatctcagt tcggtgtagg tcgttcgctc caagctgggc   3780
tgtgtgcacg aaccccccgt tcagcccgac cgctgcgcct tatccggtaa ctatcgtctt   3840
gagtccaacc cggtaagaca cgacttatcg ccactggcag cagccactgg taacaggatt   3900
agcagagcga ggtatgtagg cggtgctaca gagttcttga agtggtggcc taactacggc   3960
tacactagaa gaacagtatt tggtatctgc gctctgctga agccagttac cttcggaaaa   4020
agagttggta gctcttgatc cggcaaacaa accaccgctg gtagcggtgg tttttttgtt   4080
tgcaagcagc agattacgcg cagaaaaaaa ggatctcaag aagatccttt gatcttttct   4140
acggggtctg acgctcagtg gaacgaaaac tcacgttaag ggattttggt catggctagt   4200
taattaacat ttaaatcagc ggccgcaata aaatatcttt attttcatta catctgtgtg   4260
ttggtttttt gtgtgaatcg taactaacat acgctctcca tcaaaacaaa acgaaacaaa   4320
acaaactagc aaaataggct gtccccagtg caagtgcagg tgccagaaca tttctctatc   4380
gaa                                                                 4383
```

```
<210> SEQ ID NO 97
<211> LENGTH: 4383
<212> TYPE: DNA
<213> ORGANISM: Artificial Sequence
<220> FEATURE:
<223> OTHER INFORMATION: pCXCL11-IgG4Fc
```

```
<400> SEQUENCE: 97
```

```
ggatctgcga tcgctccggt gcccgtcagt gggcagagcg cacatcgccc acagtccccg     60
agaagttggg gggaggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cgttccccat gttcaaaaga ggacgctgtc    660
tttgcatagg ccctggggta aaagcagtga aagtggcaga tattgagaaa gcctccataa    720
tgtacccaag taacaactgt gacaaaatag aagtgattat taccctgaaa gaaaataaag    780
gacaacgatg cctaaatccc aaatcgaagc aagcaaggct tataatcaaa aaagttgaaa    840
gaaagaattt tcccccatgc ccatcatgcc cagcacctga gttcctgggg ggaccatcag    900
tcttcctgtt ccccccaaaa cccaaggaca ctctcatgat ctcccggacc cctgaggtca    960
cgtgcgtggt ggtggacgtg agccaggaag accccgaggt ccagttcaac tggtacgtgg   1020
atggcgtgga ggtgcataat gccaagacaa agccgcggga ggagcagttc aacagcacgt   1080
```

```
accgtgtggt cagcgtcctc accgtcctgc accaggactg gctgaacggc aaggagtaca   1140
agtgcaaggt ctccaacaaa ggcctcccgt cctccatcga gaaaaccatc tccaaagcca   1200
aagggcagcc ccgagagcca caggtgtaca ccctgccccc atcccaggag gagatgacca   1260
agaaccaggt cagcctgacc tgcctggtca aaggcttcta ccccagcgac atcgccgtgg   1320
agtgggagag caatgggcag ccggagaaca actacaagac cacgcctccc gtgctggact   1380
ccgacggctc cttcttcctc tacagcaggc taaccgtgga caagagcagg tggcaggagg   1440
ggaatgtctt ctcatgctcc gtgatgcatg aggctctgca caaccactac acacagaaga   1500
gcctctccct gtctccgggt aaatgagtgc tagctggcca gacatgataa gatacattga   1560
tgagtttgga caaaccacaa ctagaatgca gtgaaaaaaa tgctttattt gtgaaatttg   1620
tgatgctatt gctttatttg taaccattat aagctgcaat aaacaagtta acaacaacaa   1680
ttgcattcat tttatgtttc aggttcaggg ggaggtgtgg gaggtttttt aaagcaagta   1740
aaacctctac aaatgtggta tggaattaat tctaaaatac agcatagcaa aactttaacc   1800
tccaaatcaa gcctctactt gaatcctttt ccgaggcatg aataaggcat aggcatcagg   1860
ggctgttgcc aatgtgcatt agctgtttgc agcctcacct tctttcatgg agtttaagat   1920
atagtgtatt ttcccaaggt ttgaactagc tcttcatttc tttatgtttt aaatgcactg   1980
acctcccaca ttcccttttt agtaaaatat tcagaaataa tttaaataca tcattgcaat   2040
gaaaataaat gtttttattt aggcagaatc cagatgctca aggcccttca taatatcccc   2100
cagtttagta gttggactta gggaacaaag gaacctttaa tagaaattgg acagcaagaa   2160
agcgagcttc tagcttatcc tcagtcctgc tcctctgcca caaagtgcac gcagttgccg   2220
gccgggtcgc gcagggcgaa ctcccgcccc cacggctgct cgccgatctc ggtcatggcc   2280
ggcccggagg cgtcccggaa gttcgtggac acgacctccg accactcggc gtacagctcg   2340
tccaggccgc gcacccacac ccaggccagg gtgttgtccg gcaccacctg gtcctggacc   2400
gcgctgatga acagggtcac gtcgtcccgg accacaccgg cgaagtcgtc ctccacgaag   2460
tcccgggaga acccgagccg gtcggtccag aactcgaccg ctccggcgac gtcgcgcgcg   2520
gtgagcaccg gaacggcact ggtcaacttg gccatgatgg ctcctcctgt caggagagga   2580
aagagaagaa ggttagtaca attgctatag tgagttgtat tatactatgc agatatacta   2640
tgccaatgat taattgtcaa actagggctg cagggttcat agtgccactt ttcctgcact   2700
gccccatctc ctgcccaccc tttcccaggc atagacagtc agtgacttac caaactcaca   2760
ggagggagaa ggcagaagct tgagacagac ccgcgggacc gccgaactgc gaggggacgt   2820
ggctagggcg gcttctttta tggtgcgccg gccctcggag gcagggcgct cggggaggcc   2880
tagcggccaa tctgcggtgg caggaggcgg ggccgaaggc cgtgcctgac caatccggag   2940
cacataggag tctcagcccc ccgccccaaa gcaaggggaa gtcacgcgcc tgtagcgcca   3000
gcgtgttgtg aaatgggggc ttgggggggt tggggccctg actagtcaaa acaaactccc   3060
attgacgtca atggggtgga gacttggaaa tccccgtgag tcaaaccgct atccacgccc   3120
attgatgtac tgccaaaacc gcatcatcat ggtaatagcg atgactaata cgtagatgta   3180
ctgccaagta ggaaagtccc ataaggtcat gtactgggca taatgccagg cgggccattt   3240
accgtcattg acgtcaatag gggcgtact tggcatatga tacacttgat gtactgccaa   3300
gtgggcagtt taccgtaaat actccaccca ttgacgtcaa tggaaagtcc ctattggcgt   3360
tactatggga acatacgtca ttattgacgt caatgggcgg gggtcgttgg gcggtcagcc   3420
```

```
aggcgggcca tttaccgtaa gttatgtaac gcctgcaggt taattaagaa catgtgagca   3480

aaaggccagc aaaaggccag gaaccgtaaa aaggccgcgt tgctggcgtt tttccatagg   3540

ctccgccccc ctgacgagca tcacaaaaat cgacgctcaa gtcagaggtg gcgaaacccg   3600

acaggactat aaagatacca ggcgtttccc cctggaagct ccctcgtgcg ctctcctgtt   3660

ccgaccctgc cgcttaccgg atacctgtcc gcctttctcc cttcgggaag cgtggcgctt   3720

tctcatagct cacgctgtag gtatctcagt tcggtgtagg tcgttcgctc caagctgggc   3780

tgtgtgcacg aaccccccgt tcagcccgac cgctgcgcct tatccggtaa ctatcgtctt   3840

gagtccaacc cggtaagaca cgacttatcg ccactggcag cagccactgg taacaggatt   3900

agcagagcga ggtatgtagg cggtgctaca gagttcttga agtggtggcc taactacggc   3960

tacactagaa gaacagtatt tggtatctgc gctctgctga agccagttac cttcggaaaa   4020

agagttggta gctcttgatc cggcaaacaa accaccgctg gtagcggtgg tttttttgtt   4080

tgcaagcagc agattacgcg cagaaaaaaa ggatctcaag aagatccttt gatcttttct   4140

acggggtctg acgctcagtg gaacgaaaac tcacgttaag ggattttggt catggctagt   4200

taattaacat ttaaatcagc ggccgcaata aaatatcttt attttcatta catctgtgtg   4260

ttggtttttt gtgtgaatcg taactaacat acgctctcca tcaaaacaaa acgaaacaaa   4320

acaaactagc aaaataggct gtccccagtg caagtgcagg tgccagaaca tttctctatc   4380

gaa                                                                 4383
```

<210> SEQ ID NO 98
<211> LENGTH: 4374
<212> TYPE: DNA
<213> ORGANISM: Artificial Sequence
<220> FEATURE:
<223> OTHER INFORMATION: pCXCL11(4-73)-IgG4Fc

<400> SEQUENCE: 98

```
ggatctgcga tcgctccggt gcccgtcagt gggcagagcg cacatcgccc acagtccccg     60

agaagttggg gggaggggtc ggcaattgaa cgggtgccta gagaaggtgg cgcggggtaa    120

actgggaaag tgatgtcgtg tactggctcc gcctttttcc cgagggtggg ggagaaccgt    180

atataagtgc agtagtcgcc gtgaacgttc tttttcgcaa cgggtttgcc gccagaacac    240

agctgaagct tcgaggggct cgcatctctc cttcacgcgc ccgccgccct acctgaggcc    300

gccatccacg ccggttgagt cgcgttctgc cgcctcccgc ctgtggtgcc tcctgaactg    360

cgtccgccgt ctaggtaagt ttaaagctca ggtcgagacc gggcctttgt ccggcgctcc    420

cttggagcct acctagactc agccggctct ccacgctttg cctgaccctg cttgctcaac    480

tctacgtctt tgtttcgttt tctgttctgc gccgttacag atccaagctg tgaccggcgc    540

ctacctgaga tcaccggcga aggagggcca ccatgtacag gatgcaactc ctgtcttgca    600

ttgcactaag tcttgcactt gtcacgaatt cgttcaaaag aggacgctgt ctttgcatag    660

gccctggggt aaaagcagtg aaagtggcag atattgagaa agcctccata atgtacccaa    720

gtaacaactg tgacaaaata gaagtgatta ttaccctgaa agaaaataaa ggacaacgat    780

gcctaaatcc caaatcgaag caagcaaggc ttataatcaa aaaagttgaa agaaagaatt    840

ttcccccatg cccatcatgc ccagcacctg agttcctggg gggaccatca gtcttcctgt    900

tcccccccaaa acccaaggac actctcatga tctcccggac ccctgaggtc acgtgcgtgg    960

tggtggacgt gagccaggaa gaccccgagg tccagttcaa ctggtacgtg gatggcgtgg   1020

aggtgcataa tgccaagaca aagccgcggg aggagcagtt caacagcacg taccgtgtgg   1080
```

-continued

```
tcagcgtcct caccgtcctg caccaggact ggctgaacgg caaggagtac aagtgcaagg   1140
tctccaacaa aggcctcccg tcctccatcg agaaaaccat ctccaaagcc aaagggcagc   1200
cccgagagcc acaggtgtac accctgcccc catcccagga ggagatgacc aagaaccagg   1260
tcagcctgac ctgcctggtc aaaggcttct accccagcga catcgccgtg gagtgggaga   1320
gcaatgggca gccggagaac aactacaaga ccacgcctcc cgtgctggac tccgacggct   1380
ccttcttcct ctacagcagg ctaaccgtgg acaagagcag gtggcaggag gggaatgtct   1440
tctcatgctc cgtgatgcat gaggctctgc acaaccacta cacacagaag agcctctccc   1500
tgtctccggg taaatgagtg ctagctggcc agacatgata agatacattg atgagtttgg   1560
acaaaccaca actagaatgc agtgaaaaaa atgctttatt tgtgaaattt gtgatgctat   1620
tgctttattt gtaaccatta taagctgcaa taaacaagtt aacaacaaca attgcattca   1680
ttttatgttt caggttcagg gggaggtgtg ggaggttttt taaagcaagt aaaacctcta   1740
caaatgtggt atggaattaa ttctaaaata cagcatagca aaactttaac ctccaaatca   1800
agcctctact tgaatccttt tctgagggat gaataaggca taggcatcag gggctgttgc   1860
caatgtgcat tagctgtttg cagcctcacc ttctttcatg gagtttaaga tatagtgtat   1920
tttcccaagg tttgaactag ctcttcattt ctttatgttt taaatgcact gacctcccac   1980
attccctttt tagtaaaata ttcagaaata atttaaatac atcattgcaa tgaaaataaa   2040
tgttttttat taggcagaat ccagatgctc aaggcccttc ataatatccc ccagtttagt   2100
agttggactt agggaacaaa ggaaccttta atagaaattg gacagcaaga aagcgagctt   2160
ctagcttatc ctcagtcctg ctcctctgcc acaaagtgca cgcagttgcc ggccgggtcg   2220
cgcagggcga actcccgccc ccacggctgc tcgccgatct cggtcatggc cggcccggag   2280
gcgtcccgga agttcgtgga cacgacctcc gaccactcgg cgtacagctc gtccaggccg   2340
cgcacccaca cccaggccag ggtgttgtcc ggcaccacct ggtcctggac cgcgctgatg   2400
aacagggtca cgtcgtcccg gaccacaccg gcgaagtcgt cctccacgaa gtcccgggag   2460
aacccgagcc ggtcggtcca gaactcgacc gctccggcga cgtcgcgcgc ggtgagcacc   2520
ggaacggcac tggtcaactt ggccatgatg gctcctcctg tcaggagagg aaagagaaga   2580
aggttagtac aattgctata gtgagttgta ttatactatg cagatatact atgccaatga   2640
ttaattgtca aactagggct gcagggttca tagtgccact ttcctgcac tgccccatct   2700
cctgcccacc ctttcccagg catagacagt cagtgactta ccaaactcac aggagggaga   2760
aggcagaagc ttgagacaga cccgcgggac cgccgaactg cgaggggacg tggctagggc   2820
ggcttctttt atggtgcgcc ggccctcgga ggcagggcgc tcggggaggc ctagcggcca   2880
atctgcggtg gcaggaggcg gggccgaagg ccgtgcctga ccaatccgga gcacatagga   2940
gtctcagccc cccgccccaa agcaagggga agtcacgcgc ctgtagcgcc agcgtgttgt   3000
gaaatggggg cttggggggg ttggggccct gactagtcaa aacaaactcc cattgacgtc   3060
aatggggtgg agacttggaa atccccgtga gtcaaaccgc tatccacgcc cattgatgta   3120
ctgccaaaac cgcatcatca tggtaatagc gatgactaat acgtagatgt actgccaagt   3180
aggaaagtcc cataaggtca tgtactgggc ataatgccag gcgggccatt taccgtcatt   3240
gacgtcaata gggggcgtac ttggcatatg atacacttga tgtactgcca agtgggcagt   3300
ttaccgtaaa tactccaccc attgacgtca atggaaagtc cctattggcg ttactatggg   3360
aacatacgtc attattgacg tcaatgggcg ggggtcgttg ggcggtcagc caggcgggcc   3420
```

-continued

```
atttaccgta agttatgtaa cgcctgcagg ttaattaaga acatgtgagc aaaaggccag   3480

caaaaggcca ggaaccgtaa aaaggccgcg ttgctggcgt ttttccatag gctccgcccc   3540

cctgacgagc atcacaaaaa tcgacgctca agtcagaggt ggcgaaaccc gacaggacta   3600

taaagatacc aggcgtttcc ccctggaagc tccctcgtgc gctctcctgt tccgaccctg   3660

ccgcttaccg gatacctgtc cgcctttctc ccttcgggaa gcgtggcgct ttctcatagc   3720

tcacgctgta ggtatctcag ttcggtgtag gtcgttcgct ccaagctggg ctgtgtgcac   3780

gaaccccccg ttcagcccga ccgctgcgcc ttatccggta actatcgtct tgagtccaac   3840

ccggtaagac acgacttatc gccactggca gcagccactg gtaacaggat tagcagagcg   3900

aggtatgtag gcggtgctac agagttcttg aagtggtggc ctaactacgg ctacactaga   3960

agaacagtat ttggtatctg cgctctgctg aagccagtta ccttcggaaa aagagttggt   4020

agctcttgat ccggcaaaca aaccaccgct ggtagcggtg gtttttttgt ttgcaagcag   4080

cagattacgc gcagaaaaaa aggatctcaa gaagatcctt tgatcttttc tacggggtct   4140

gacgctcagt ggaacgaaaa ctcacgttaa gggattttgg tcatggctag ttaattaaca   4200

tttaaatcag cggccgcaat aaaatatctt tattttcatt acatctgtgt gttggttttt   4260

tgtgtgaatc gtaactaaca tacgctctcc atcaaaacaa aacgaaacaa aacaaactag   4320

caaaataggc tgtccccagt gcaagtgcag gtgccagaac atttctctat cgaa         4374
```

```
<210> SEQ ID NO 99
<211> LENGTH: 4374
<212> TYPE: DNA
<213> ORGANISM: Artificial Sequence
<220> FEATURE:
<223> OTHER INFORMATION: pCXCL11(4-73K/H-A)-IgG4Fc

<400> SEQUENCE: 99

ggatctgcga tcgctccggt gcccgtcagt gggcagagcg cacatcgccc acagtccccg     60

agaagttggg gggaggggtc ggcaattgaa cgggtgccta gagaaggtgg cgcggggtaa    120

actgggaaag tgatgtcgtg tactggctcc gcctttttcc cgagggtggg ggagaaccgt    180

atataagtgc agtagtcgcc gtgaacgttc tttttcgcaa cgggtttgcc gccagaacac    240

agctgaagct tcgaggggct cgcatctctc cttcacgcgc ccgccgccct acctgaggcc    300

gccatccacg ccggttgagt cgcgttctgc cgcctcccgc ctgtggtgcc tcctgaactg    360

cgtccgccgt ctaggtaagt ttaaagctca ggtcgagacc gggcctttgt ccggcgctcc    420

cttggagcct acctagactc agccggctct ccacgctttg cctgaccctg cttgctcaac    480

tctacgtctt tgtttcgttt tctgttctgc gccgttacag atccaagctg tgaccggcgc    540

ctacctgaga tcaccggcga aggagggcca ccatgtacag gatgcaactc ctgtcttgca    600

ttgcactaag tcttgcactt gtcacgaatt cgttcaaaag aggacgctgt ctttgcatag    660

gccctggggt aaaagcagtg aaagtggcag atattgaggc cgcctccata atgtacccaa    720

gtaacaactg tgacaaaata gaagtgatta ttaccctggc agaaaatgcc ggacaagcat    780

gcctaaatcc cgcctcggca caagcagccc ttataatcgc agccgttgaa gcagccaatt    840

ttcccccatg cccatcatgc ccagcacctg agttcctggg gggaccatca gtcttcctgt    900

tcccccaaa acccaaggac actctcatga tctcccggac ccctgaggtc acgtgcgtgg    960

tggtggacgt gagccaggaa gaccccgagg tccagttcaa ctggtacgtg gatggcgtgg   1020

aggtgcataa tgccaagaca aagccgcggg aggagcagtt caacagcacg taccgtgtgg   1080

tcagcgtcct caccgtcctg caccaggact ggctgaacgg caaggagtac aagtgcaagg   1140
```

-continued tctccaacaa aggcctcccg tcctccatcg agaaaaccat ctccaaagcc aaagggcagc 1200
cccgagagcc acaggtgtac accctgcccc catcccagga ggagatgacc aagaaccagg 1260
tcagcctgac ctgcctggtc aaaggcttct accccagcga catcgccgtg gagtgggaga 1320
gcaatgggca gccggagaac aactacaaga ccacgcctcc cgtgctggac tccgacggct 1380
ccttcttcct ctacagcagg ctaaccgtgg acaagagcag gtggcaggag gggaatgtct 1440
tctcatgctc cgtgatgcat gaggctctgc acaaccacta cacacagaag agcctctccc 1500
tgtctccggg taaatgagtg ctagctggcc agacatgata agatacattg atgagtttgg 1560
acaaaccaca actagaatgc agtgaaaaaa atgctttatt tgtgaaattt gtgatgctat 1620
tgctttattt gtaaccatta taagctgcaa taaacaagtt aacaacaaca attgcattca 1680
ttttatgttt caggttcagg gggaggtgtg ggaggttttt taaagcaagt aaaacctcta 1740
caaatgtggt atggaattaa ttctaaaata cagcatagca aaactttaac ctccaaatca 1800
agcctctact tgaatccttt tctgagggat gaataaggca taggcatcag gggctgttgc 1860
caatgtgcat tagctgtttg cagcctcacc ttctttcatg gagtttaaga tatagtgtat 1920
tttcccaagg tttgaactag ctcttcattt ctttatgttt taaatgcact gacctcccac 1980
attccctttt tagtaaaata ttcagaaata atttaaatac atcattgcaa tgaaaataaa 2040
tgttttttat taggcagaat ccagatgctc aaggcccttc ataatatccc ccagtttagt 2100
agttggactt agggaacaaa ggaaccttta atagaaattg gacagcaaga aagcgagctt 2160
ctagcttatc ctcagtcctg ctcctctgcc acaaagtgca cgcagttgcc ggccgggtcg 2220
cgcagggcga actcccgccc ccacggctgc tcgccgatct cggtcatggc cggcccggag 2280
gcgtcccgga agttcgtgga cacgacctcc gaccactcgg cgtacagctc gtccaggccg 2340
cgcacccaca cccaggccag ggtgttgtcc ggcaccacct ggtcctggac cgcgctgatg 2400
aacagggtca cgtcgtcccg gaccacaccg gcgaagtcgt cctccacgaa gtcccgggag 2460
aacccgagcc ggtcggtcca gaactcgacc gctccggcga cgtcgcgcgc ggtgagcacc 2520
ggaacggcac tggtcaactt ggccatgatg gctcctcctg tcaggagagg aaagagaaga 2580
aggttagtac aattgctata gtgagttgta ttatactatg cagatatact atgccaatga 2640
ttaattgtca aactagggct gcagggttca tagtgccact tttcctgcac tgccccatct 2700
cctgcccacc ctttcccagg catagacagt cagtgactta ccaaactcac aggagggaga 2760
aggcagaagc ttgagacaga cccgcgggac cgccgaactg cgaggggacg tggctagggc 2820
ggcttctttt atggtgcgcc ggccctcgga ggcagggcgc tcggggaggc ctagcggcca 2880
atctgcggtg gcaggaggcg gggccgaagg ccgtgcctga ccaatccgga gcacatagga 2940
gtctcagccc cccgccccaa agcaagggga agtcacgcgc ctgtagcgcc agcgtgttgt 3000
gaaatggggg cttggggggg ttggggccct gactagtcaa aacaaactcc cattgacgtc 3060
aatggggtgg agacttggaa atccccgtga gtcaaaccgc tatccacgcc cattgatgta 3120
ctgccaaaac cgcatcatca tggtaatagc gatgactaat acgtagatgt actgccaagt 3180
aggaaagtcc cataaggtca tgtactgggc ataatgccag gcgggccatt taccgtcatt 3240
gacgtcaata gggggcgtac ttggcatatg atacacttga tgtactgcca agtgggcagt 3300
ttaccgtaaa tactccaccc attgacgtca atggaaagtc cctattggcg ttactatggg 3360
aacatacgtc attattgacg tcaatgggcg ggggtcgttg ggcggtcagc caggcgggcc 3420
atttaccgta agttatgtaa cgcctgcagg ttaattaaga acatgtgagc aaaaggccag 3480
caaaaggcca ggaaccgtaa aaaggccgcg ttgctggcgt ttttccatag gctccgcccc 3540
cctgacgagc atcacaaaaa tcgacgctca agtcagaggt ggcgaaaccc gacaggacta 3600
taaagatacc aggcgtttcc ccctggaagc tccctcgtgc gctctcctgt tccgaccctg 3660
ccgcttaccg gatacctgtc cgcctttctc ccttcgggaa gcgtggcgct ttctcatagc 3720
tcacgctgta ggtatctcag ttcggtgtag gtcgttcgct ccaagctggg ctgtgtgcac 3780
gaaccccccg ttcagcccga ccgctgcgcc ttatccggta actatcgtct tgagtccaac 3840
ccggtaagac acgacttatc gccactggca gcagccactg gtaacaggat tagcagagcg 3900
aggtatgtag gcggtgctac agagttcttg aagtggtggc ctaactacgg ctacactaga 3960
agaacagtat ttggtatctg cgctctgctg aagccagtta ccttcggaaa aagagttggt 4020
agctcttgat ccggcaaaca aaccaccgct ggtagcggtg gtttttttgt ttgcaagcag 4080
cagattacgc gcagaaaaaa aggatctcaa gaagatcctt tgatcttttc tacggggtct 4140
gacgctcagt ggaacgaaaa ctcacgttaa gggattttgg tcatggctag ttaattaaca 4200
tttaaatcag cggccgcaat aaaatatctt tattttcatt acatctgtgt gttggttttt 4260
tgtgtgaatc gtaactaaca tacgctctcc atcaaaacaa aacgaaacaa aacaaactag 4320
caaaataggc tgtccccagt gcaagtgcag gtgccagaac atttctctat cgaa 4374

<210> SEQ ID NO 100
<211> LENGTH: 4434
<212> TYPE: DNA
<213> ORGANISM: Artificial Sequence
<220> FEATURE:
<223> OTHER INFORMATION: pCXCL13-IgG1Fc

<400> SEQUENCE: 100
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacctgaga tcaccggcga aggagggcca ccatgtacag gatgcaactc ctgtcttgca 600
ttgcactaag tcttgcactt gtcacgaatt cggttctgga ggtctattac acaagcttga 660
ggtgtagatg tgtccaagag agctcagtct ttatccctag acgcttcatt gatcgaattc 720
aaatcttgcc ccgtgggaat ggttgtccaa gaaaagaaat catagtctgg aagaagaaca 780
agtcaattgt gtgtgtggac cctcaagctg aatggataca aagaatgatg gaagtattga 840
gaaaaagaag ttcttcaact ctaccagttc cagtgtttaa gagaaagatt cccgacaaaa 900
ctcacacatg cccaccgtgc ccagcacctg aactcctggg gggaccgtca gtcttcctct 960
tccccccaaa acccaaggac accctcatga tctcccggac ccctgaggtc acatgcgtgg 1020
tggtggacgt gagccacgaa gaccctgagg tcaagttcaa ctggtacgtg gacggcgtgg 1080
aggtgcataa tgccaagaca aagccgcggg aggagcagta caacagcacg taccgtgtgg 1140
tcagcgtcct caccgtcctg caccaggact ggctgaatgg caaggagtac aagtgcaagg 1200

```
tctccaacaa agccctccca gcccccatcg agaaaaccat ctccaaagcc aaagggcagc   1260
cccgagaacc acaggtgtac accctgcccc catcccggga ggagatgacc aagaaccagg   1320
tcagcctgac ctgcctggtc aaaggcttct atcccagcga catcgccgtg gagtgggaga   1380
gcaatgggca gccggagaac aactacaaga ccacgcctcc cgtgctggac tccgacggct   1440
ccttcttcct ctacagcaag ctcaccgtgg acaagagcag gtggcagcag gggaacgtct   1500
tctcatgctc cgtgatgcac gaggctctgc acaaccacta cacgcagaag agcctctccc   1560
tgtctccggg taaatgagtg ctagctggcc agacatgata agatacattg atgagtttgg   1620
acaaaccaca actagaatgc agtgaaaaaa atgctttatt tgtgaaattt gtgatgctat   1680
tgctttattt gtaaccatta taagctgcaa taaacaagtt aacaacaaca attgcattca   1740
ttttatgttt caggttcagg gggaggtgtg ggaggttttt taaagcaagt aaaacctcta   1800
caaatgtggt atggaattaa ttctaaaata cagcatagca aaactttaac ctccaaatca   1860
agcctctact tgaatccttt tctgagggat gaataaggca taggcatcag gggctgttgc   1920
caatgtgcat tagctgtttg cagcctcacc ttctttcatg gagtttaaga tatagtgtat   1980
tttcccaagg tttgaactag ctcttcattt ctttatgttt taaatgcact gacctcccac   2040
attccctttt tagtaaaata ttcagaaata atttaaatac atcattgcaa tgaaaataaa   2100
tgttttttat taggcagaat ccagatgctc aaggcccttc ataatatccc ccagtttagt   2160
agttggactt agggaacaaa ggaaccttta atagaaattg gacagcaaga aagcgagctt   2220
ctagcttatc ctcagtcctg ctcctctgcc acaaagtgca cgcagttgcc ggccgggtcg   2280
cgcagggcga actcccgccc ccacggctgc tcgccgatct cggtcatggc cggcccggag   2340
gcgtcccgga agttcgtgga cacgacctcc gaccactcgg cgtacagctc gtccaggccg   2400
cgcacccaca cccaggccag ggtgttgtcc ggcaccacct ggtcctggac cgcgctgatg   2460
aacagggtca cgtcgtcccg gaccacaccg gcgaagtcgt cctccacgaa gtcccgggag   2520
aacccgagcc ggtcggtcca gaactcgacc gctccggcga cgtcgcgcgc ggtgagcacc   2580
ggaacggcac tggtcaactt ggccatgatg gctcctcctg tcaggagagg aaagagaaga   2640
aggttagtac aattgctata gtgagttgta ttatactatg cagatatact atgccaatga   2700
ttaattgtca aactagggct gcagggttca tagtgccact tttcctgcac tgccccatct   2760
cctgcccacc ctttcccagg catagacagt cagtgactta ccaaactcac aggagggaga   2820
aggcagaagc ttgagacaga cccgcgggac cgccgaactg cgaggggacg tggctagggc   2880
ggcttctttt atggtgcgcc ggccctcgga ggcagggcgc tcggggaggc ctagcggcca   2940
atctgcggtg gcaggaggcg gggccgaagg ccgtgcctga ccaatccgga gcacatagga   3000
gtctcagccc cccgccccaa agcaagggga agtcacgcgc ctgtagcgcc agcgtgttgt   3060
gaaatggggg cttggggggg ttggggccct gactagtcaa aacaaactcc cattgacgtc   3120
aatggggtgg agacttggaa atccccgtga gtcaaaccgc tatccacgcc cattgatgta   3180
ctgccaaaac cgcatcatca tggtaatagc gatgactaat acgtagatgt actgccaagt   3240
aggaaagtcc cataaggtca tgtactgggc ataatgccag gcgggccatt taccgtcatt   3300
gacgtcaata gggggcgtac ttggcatatg atacacttga tgtactgcca agtgggcagt   3360
ttaccgtaaa tactccaccc attgacgtca atggaaagtc cctattggcg ttactatggg   3420
aacatacgtc attattgacg tcaatgggcg ggggtcgttg ggcggtcagc caggcgggcc   3480
atttaccgta agttatgtaa cgcctgcagg ttaattaaga acatgtgagc aaaaggccag   3540
```

caaaaggcca ggaaccgtaa aaaggccgcg ttgctggcgt ttttccatag gctccgcccc 3600
cctgacgagc atcacaaaaa tcgacgctca agtcagaggt ggcgaaaccc gacaggacta 3660
taaagatacc aggcgtttcc ccctggaagc tccctcgtgc gctctcctgt tccgaccctg 3720
ccgcttaccg gatacctgtc cgcctttctc ccttcgggaa gcgtggcgct ttctcatagc 3780
tcacgctgta ggtatctcag ttcggtgtag gtcgttcgct ccaagctggg ctgtgtgcac 3840
gaaccccccg ttcagcccga ccgctgcgcc ttatccggta actatcgtct tgagtccaac 3900
ccggtaagac acgacttatc gccactggca gcagccactg gtaacaggat tagcagagcg 3960
aggtatgtag gcggtgctac agagttcttg aagtggtggc ctaactacgg ctacactaga 4020
agaacagtat ttggtatctg cgctctgctg aagccagtta ccttcggaaa aagagttggt 4080
agctcttgat ccggcaaaca aaccaccgct ggtagcggtg gtttttttgt ttgcaagcag 4140
cagattacgc gcagaaaaaa aggatctcaa gaagatcctt tgatcttttc tacggggtct 4200
gacgctcagt ggaacgaaaa ctcacgttaa gggattttgg tcatggctag ttaattaaca 4260
tttaaatcag cggccgcaat aaaatatctt tattttcatt acatctgtgt gttggttttt 4320
tgtgtgaatc gtaactaaca tacgctctcc atcaaaacaa aacgaaacaa aacaaactag 4380
caaaataggc tgtccccagt gcaagtgcag gtgccagaac atttctctat cgaa 4434

<210> SEQ ID NO 101
<211> LENGTH: 4428
<212> TYPE: DNA
<213> ORGANISM: Artificial Sequence
<220> FEATURE:
<223> OTHER INFORMATION: pCXCL13(3-87)-IgG1Fc

<400> SEQUENCE: 101
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacctgaga tcaccggcga aggagggcca ccatgtacag gatgcaactc ctgtcttgca 600
ttgcactaag tcttgcactt gtcacgaatt cggaggtcta ttacacaagc ttgaggtgta 660
gatgtgtcca agagagctca gtctttatcc ctagacgctt cattgatcga attcaaatct 720
tgccccgtgg gaatggttgt ccaagaaaag aaatcatagt ctggaagaag aacaagtcaa 780
ttgtgtgtgt ggaccctcaa gctgaatgga tacaaagaat gatggaagta ttgagaaaaa 840
gaagttcttc aactctacca gttccagtgt ttaagagaaa gattcccgac aaaactcaca 900
catgcccacc gtgcccagca cctgaactcc tggggggacc gtcagtcttc ctcttccccc 960
caaaacccaa ggacaccctc atgatctccc ggacccctga ggtcacatgc gtggtggtgg 1020
acgtgagcca cgaagaccct gaggtcaagt tcaactggta cgtggacggc gtggaggtgc 1080
ataatgccaa gacaaagccg cgggaggagc agtacaacag cacgtaccgt gtggtcagcg 1140
tcctcaccgt cctgcaccag gactggctga atggcaagga gtacaagtgc aaggtctcca 1200

-continued acaaagccct cccagccccc atcgagaaaa ccatctccaa agccaaaggg cagccccgag 1260
aaccacaggt gtacaccctg cccccatccc gggaggagat gaccaagaac caggtcagcc 1320
tgacctgcct ggtcaaaggc ttctatccca gcgacatcgc cgtggagtgg gagagcaatg 1380
ggcagccgga gaacaactac aagaccacgc ctcccgtgct ggactccgac ggctccttct 1440
tcctctacag caagctcacc gtggacaaga gcaggtggca gcaggggaac gtcttctcat 1500
gctccgtgat gcacgaggct ctgcacaacc actacacgca gaagagcctc tccctgtctc 1560
cgggtaaatg agtgctagct ggccagacat gataagatac attgatgagt ttggacaaac 1620
cacaactaga atgcagtgaa aaaaatgctt tatttgtgaa atttgtgatg ctattgcttt 1680
atttgtaacc attataagct gcaataaaca agttaacaac aacaattgca ttcattttat 1740
gtttcaggtt cagggggagg tgtgggaggt tttttaaagc aagtaaaacc tctacaaatg 1800
tggtatggaa ttaattctaa aatacagcat agcaaaactt taacctccaa atcaagcctc 1860
tacttgaatc cttttctgag ggatgaataa ggcataggca tcaggggctg ttgccaatgt 1920
gcattagctg tttgcagcct caccttcttt catggagttt aagatatagt gtattttccc 1980
aaggtttgaa ctagctcttc atttctttat gttttaaatg cactgacctc ccacattccc 2040
tttttagtaa aatattcaga aataatttaa atacatcatt gcaatgaaaa taaatgtttt 2100
ttattaggca gaatccagat gctcaaggcc cttcataata tcccccagtt tagtagttgg 2160
acttagggaa caaaggaacc tttaatagaa attggacagc aagaaagcga gcttctagct 2220
tatcctcagt cctgctcctc tgccacaaag tgcacgcagt tgccggccgg gtcgcgcagg 2280
gcgaactccc gcccccacgg ctgctcgccg atctcggtca tggccggccc ggaggcgtcc 2340
cggaagttcg tggacacgac ctccgaccac tcggcgtaca gctcgtccag gccgcgcacc 2400
cacacccagg ccagggtgtt gtccggcacc acctggtcct ggaccgcgct gatgaacagg 2460
gtcacgtcgt cccggaccac accggcgaag tcgtcctcca cgaagtcccg ggagaacccg 2520
agccggtcgg tccagaactc gaccgctccg gcgacgtcgc gcgcggtgag caccggaacg 2580
gcactggtca acttggccat gatggctcct cctgtcagga gaggaaagag aagaaggtta 2640
gtacaattgc tatagtgagt tgtattatac tatgcagata tactatgcca atgattaatt 2700
gtcaaactag ggctgcaggg ttcatagtgc cacttttcct gcactgcccc atctcctgcc 2760
cacccttcc caggcataga cagtcagtga cttaccaaac tcacaggagg gagaaggcag 2820
aagcttgaga cagacccgcg ggaccgccga actgcgaggg gacgtggcta gggcggcttc 2880
ttttatggtg cgccggccct cggaggcagg gcgctcgggg aggcctagcg gccaatctgc 2940
ggtggcagga ggcggggccg aaggccgtgc ctgaccaatc cggagcacat aggagtctca 3000
gcccccgcc ccaaagcaag gggaagtcac gcgcctgtag cgccagcgtg ttgtgaaatg 3060
gggcttggg ggggttgggg ccctgactag tcaaaacaaa ctcccattga cgtcaatggg 3120
gtggagactt ggaaatcccc gtgagtcaaa ccgctatcca cgcccattga tgtactgcca 3180
aaaccgcatc atcatggtaa tagcgatgac taatacgtag atgtactgcc aagtaggaaa 3240
gtcccataag gtcatgtact gggcataatg ccaggcgggc catttaccgt cattgacgtc 3300
aatagggggc gtacttggca tatgatacac ttgatgtact gccaagtggg cagtttaccg 3360
taaatactcc acccattgac gtcaatggaa agtccctatt ggcgttacta tgggaacata 3420
cgtcattatt gacgtcaatg ggcgggggtc gttgggcggt cagccaggcg ggccatttac 3480
cgtaagttat gtaacgcctg caggttaatt aagaacatgt gagcaaaagg ccagcaaaag 3540
gccaggaacc gtaaaaaggc cgcgttgctg gcgtttttcc ataggctccg cccccctgac 3600
gagcatcaca aaaatcgacg ctcaagtcag aggtggcgaa acccgacagg actataaaga 3660
taccaggcgt ttccccctgg aagctccctc gtgcgctctc ctgttccgac cctgccgctt 3720
accggatacc tgtccgcctt tctcccttcg ggaagcgtgg cgctttctca tagctcacgc 3780
tgtaggtatc tcagttcggt gtaggtcgtt cgctccaagc tgggctgtgt gcacgaaccc 3840
cccgttcagc ccgaccgctg cgccttatcc ggtaactatc gtcttgagtc caacccggta 3900
agacacgact tatcgccact ggcagcagcc actggtaaca ggattagcag agcgaggtat 3960
gtaggcggtg ctacagagtt cttgaagtgg tggcctaact acggctacac tagaagaaca 4020
gtatttggta tctgcgctct gctgaagcca gttaccttcg gaaaaagagt tggtagctct 4080
tgatccggca aacaaaccac cgctggtagc ggtggttttt ttgtttgcaa gcagcagatt 4140
acgcgcagaa aaaaaggatc tcaagaagat cctttgatct tttctacggg gtctgacgct 4200
cagtggaacg aaaactcacg ttaagggatt ttggtcatgg ctagttaatt aacatttaaa 4260
tcagcggccg caataaaata tctttatttt cattacatct gtgtgttggt tttttgtgtg 4320
aatcgtaact aacatacgct ctccatcaaa acaaaacgaa acaaaacaaa ctagcaaaat 4380
aggctgtccc cagtgcaagt gcaggtgcca gaacatttct ctatcgaa 4428

<210> SEQ ID NO 102
<211> LENGTH: 4428
<212> TYPE: DNA
<213> ORGANISM: Artificial Sequence
<220> FEATURE:
<223> OTHER INFORMATION: pCXCL13(3-87K/H-A)-IgG1Fc

<400> SEQUENCE: 102
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacctgaga tcaccggcga aggagggcca ccatgtacag gatgcaactc ctgtcttgca 600
ttgcactaag tcttgcactt gtcacgaatt cggaggtcta ttacacaagc ttgaggtgta 660
gatgtgtcca agagagctca gtctttatcc ctagacgctt cattgatgcc attcaaatct 720
tgccccgtgg gaatggttgt ccaagaaaag aaatcatagt ctgggctgcg aacgcttcaa 780
ttgtgtgtgt ggaccctcaa gctgaatgga tacaagccat gatggaagta ttggctgcgg 840
ctagttcttc aactctacca gttccagtgt ttgccgctgc gattcccgac aaaactcaca 900
catgcccacc gtgcccagca cctgaactcc tggggggacc gtcagtcttc ctcttccccc 960
caaaacccaa ggacaccctc atgatctccc ggacccctga ggtcacatgc gtggtggtgg 1020
acgtgagcca cgaagaccct gaggtcaagt tcaactggta cgtggacggc gtggaggtgc 1080
ataatgccaa gacaaagccg cgggaggagc agtacaacag cacgtaccgt gtggtcagcg 1140
tcctcaccgt cctgcaccag gactggctga atggcaagga gtacaagtgc aaggtctcca 1200

-continued

```
acaaagccct cccagccccc atcgagaaaa ccatctccaa agccaaaggg cagccccgag   1260
aaccacaggt gtacaccctg cccccatccc gggaggagat gaccaagaac caggtcagcc   1320
tgacctgcct ggtcaaaggc ttctatccca gcgacatcgc cgtggagtgg gagagcaatg   1380
ggcagccgga gaacaactac aagaccacgc ctcccgtgct ggactccgac ggctccttct   1440
tcctctacag caagctcacc gtggacaaga gcaggtggca gcaggggaac gtcttctcat   1500
gctccgtgat gcacgaggct ctgcacaacc actacacgca gaagagcctc tccctgtctc   1560
cgggtaaatg agtgctagct ggccagacat gataagatac attgatgagt ttggacaaac   1620
cacaactaga atgcagtgaa aaaaatgctt tatttgtgaa atttgtgatg ctattgcttt   1680
atttgtaacc attataagct gcaataaaca agttaacaac aacaattgca ttcattttat   1740
gtttcaggtt cagggggagg tgtgggaggt tttttaaagc aagtaaaacc tctacaaatg   1800
tggtatggaa ttaattctaa aatacagcat agcaaaactt taacctccaa atcaagcctc   1860
tacttgaatc cttttctgag ggatgaataa ggcataggca tcaggggctg ttgccaatgt   1920
gcattagctg tttgcagcct caccttcttt catggagttt aagatatagt gtattttccc   1980
aaggtttgaa ctagctcttc atttctttat gttttaaatg cactgacctc ccacattccc   2040
tttttagtaa aatattcaga aataatttaa atacatcatt gcaatgaaaa taaatgtttt   2100
ttattaggca gaatccagat gctcaaggcc cttcataata tcccccagtt tagtagttgg   2160
acttagggaa caaaggaacc tttaatagaa attggacagc aagaaagcga gcttctagct   2220
tatcctcagt cctgctcctc tgccacaaag tgcacgcagt tgccggccgg gtcgcgcagg   2280
gcgaactccc gcccccacgg ctgctcgccg atctcggtca tggccggccc ggaggcgtcc   2340
cggaagttcg tggacacgac ctccgaccac tcggcgtaca gctcgtccag gccgcgcacc   2400
cacacccagg ccagggtgtt gtccggcacc acctggtcct ggaccgcgct gatgaacagg   2460
gtcacgtcgt cccggaccac accggcgaag tcgtcctcca cgaagtcccg ggagaacccg   2520
agccggtcgg tccagaactc gaccgctccg gcgacgtcgc gcgcggtgag caccggaacg   2580
gcactggtca acttggccat gatggctcct cctgtcagga gaggaaagag aagaaggtta   2640
gtacaattgc tatagtgagt tgtattatac tatgcagata tactatgcca atgattaatt   2700
gtcaaactag ggctgcaggg ttcatagtgc cacttttcct gcactgcccc atctcctgcc   2760
cacccctttcc caggcataga cagtcagtga cttaccaaac tcacaggagg gagaaggcag   2820
aagcttgaga cagacccgcg ggaccgccga actgcgaggg gacgtggcta gggcggcttc   2880
ttttatggtg cgccggccct cggaggcagg gcgctcgggg aggcctagcg gccaatctgc   2940
ggtggcagga ggcggggccg aaggccgtgc ctgaccaatc cggagcacat aggagtctca   3000
gcccccccgcc ccaaagcaag gggaagtcac gcgcctgtag cgccagcgtg ttgtgaaatg   3060
gggcttggg ggggttgggg ccctgactag tcaaaacaaa ctcccattga cgtcaatggg   3120
gtggagactt ggaaatcccc gtgagtcaaa ccgctatcca cgcccattga tgtactgcca   3180
aaaccgcatc atcatggtaa tagcgatgac taatacgtag atgtactgcc aagtaggaaa   3240
gtcccataag gtcatgtact gggcataatg ccaggcgggc catttaccgt cattgacgtc   3300
aataggggggc gtacttggca tatgatacac ttgatgtact gccaagtggg cagtttaccg   3360
taaatactcc acccattgac gtcaatggaa agtccctatt ggcgttacta tgggaacata   3420
cgtcattatt gacgtcaatg ggcgggggtc gttgggcggt cagccaggcg ggccatttac   3480
cgtaagttat gtaacgcctg caggttaatt aagaacatgt gagcaaaagg ccagcaaaag   3540
```

gccaggaacc gtaaaaaggc cgcgttgctg gcgtttttcc ataggctccg cccccctgac 3600
gagcatcaca aaaatcgacg ctcaagtcag aggtggcgaa acccgacagg actataaaga 3660
taccaggcgt ttccccctgg aagctccctc gtgcgctctc ctgttccgac cctgccgctt 3720
accggatacc tgtccgcctt tctcccttcg ggaagcgtgg cgctttctca tagctcacgc 3780
tgtaggtatc tcagttcggt gtaggtcgtt cgctccaagc tgggctgtgt gcacgaaccc 3840
cccgttcagc ccgaccgctg cgccttatcc ggtaactatc gtcttgagtc caacccggta 3900
agacacgact tatcgccact ggcagcagcc actggtaaca ggattagcag agcgaggtat 3960
gtaggcggtg ctacagagtt cttgaagtgg tggcctaact acggctacac tagaagaaca 4020
gtatttggta tctgcgctct gctgaagcca gttaccttcg gaaaaagagt tggtagctct 4080
tgatccggca aacaaaccac cgctggtagc ggtggttttt ttgtttgcaa gcagcagatt 4140
acgcgcagaa aaaaaggatc tcaagaagat cctttgatct tttctacggg gtctgacgct 4200
cagtggaacg aaaactcacg ttaagggatt ttggtcatgg ctagttaatt aacatttaaa 4260
tcagcggccg caataaaata tctttatttt cattacatct gtgtgttggt tttttgtgtg 4320
aatcgtaact aacatacgct ctccatcaaa acaaaacgaa acaaaacaaa ctagcaaaat 4380
aggctgtccc cagtgcaagt gcaggtgcca gaacatttct ctatcgaa 4428

<210> SEQ ID NO 103
<211> LENGTH: 4425
<212> TYPE: DNA
<213> ORGANISM: Artificial Sequence
<220> FEATURE:
<223> OTHER INFORMATION: pCXCL13-IgG4Fc

<400> SEQUENCE: 103
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacctgaga tcaccggcga aggagggcca ccatgtacag gatgcaactc ctgtcttgca 600
ttgcactaag tcttgcactt gtcacgaatt cggttctgga ggtctattac acaagcttga 660
ggtgtagatg tgtccaagag agctcagtct ttatccctag acgcttcatt gatcgaattc 720
aaatcttgcc ccgtgggaat ggttgtccaa gaaaagaaat catagtctgg aagaagaaca 780
agtcaattgt gtgtgtggac cctcaagctg aatggataca aagaatgatg gaagtattga 840
gaaaaagaag ttcttcaact ctaccagttc cagtgtttaa gagaaagatt cccccccccat 900 gcccatcatg cccagcacct gagttcctgg ggggaccatc agtcttcctg ttccccccaa 960
aacccaagga cactctcatg atctcccgga cccctgaggt cacgtgcgtg gtggtggacg 1020
tgagccagga agaccccgag gtccagttca actggtacgt ggatggcgtg gaggtgcata 1080
atgccaagac aaagccgcgg gaggagcagt tcaacagcac gtaccgtgtg gtcagcgtcc 1140
tcaccgtcct gcaccaggac tggctgaacg gcaaggagta caagtgcaag gtctccaaca 1200

-continued

```
aaggcctccc gtcctccatc gagaaaacca tctccaaagc caaagggcag ccccgagagc   1260
cacaggtgta caccctgccc ccatcccagg aggagatgac caagaaccag gtcagcctga   1320
cctgcctggt caaaggcttc taccccagcg acatcgccgt ggagtgggag agcaatgggc   1380
agccggagaa caactacaag accacgcctc ccgtgctgga ctccgacggc tccttcttcc   1440
tctacagcag gctaaccgtg gacaagagca ggtggcagga ggggaatgtc ttctcatgct   1500
ccgtgatgca tgaggctctg cacaaccact acacacagaa gagcctctcc ctgtctccgg   1560
gtaaatgagt gctagctggc cagacatgat aagatacatt gatgagtttg gacaaaccac   1620
aactagaatg cagtgaaaaa aatgctttat ttgtgaaatt tgtgatgcta ttgctttatt   1680
tgtaaccatt ataagctgca ataaacaagt taacaacaac aattgcattc attttatgtt   1740
tcaggttcag ggggaggtgt gggaggtttt ttaaagcaag taaaacctct acaaatgtgg   1800
tatggaatta attctaaaat acagcatagc aaaactttaa cctccaaatc aagcctctac   1860
ttgaatcctt ttctgaggga tgaataaggc ataggcatca ggggctgttg ccaatgtgca   1920
ttagctgttt gcagcctcac cttctttcat ggagtttaag atatagtgta ttttcccaag   1980
gtttgaacta gctcttcatt tctttatgtt ttaaatgcac tgacctccca cattcccttt   2040
ttagtaaaat attcagaaat aatttaaata catcattgca atgaaaataa atgtttttta   2100
ttaggcagaa tccagatgct caaggccctt cataatatcc cccagtttag tagttggact   2160
tagggaacaa aggaaccttt aatagaaatt ggacagcaag aaagcgagct tctagcttat   2220
cctcagtcct gctcctctgc cacaaagtgc acgcagttgc cggccgggtc gcgcagggcg   2280
aactcccgcc cccacggctg ctcgccgatc tcggtcatgg ccggcccgga ggcgtcccgg   2340
aagttcgtgg acacgacctc cgaccactcg gcgtacagct cgtccaggcc gcgcacccac   2400
acccaggcca gggtgttgtc cggcaccacc tggtcctgga ccgcgctgat gaacagggtc   2460
acgtcgtccc ggaccacacc ggcgaagtcg tcctccacga agtcccggga gaacccgagc   2520
cggtcggtcc agaactcgac cgctccggcg acgtcgcgcg cggtgagcac cggaacggca   2580
ctggtcaact tggccatgat ggctcctcct gtcaggagag gaaagagaag aaggttagta   2640
caattgctat agtgagttgt attatactat gcagatatac tatgccaatg attaattgtc   2700
aaactagggc tgcagggttc atagtgccac ttttcctgca ctgccccatc tcctgcccac   2760
cctttcccag gcatagacag tcagtgactt accaaactca caggagggag aaggcagaag   2820
cttgagacag acccgcggga ccgccgaact gcgaggggac gtggctaggg cggcttcttt   2880
tatggtgcgc cggccctcgg aggcagggcg ctcggggagg cctagcggcc aatctgcggt   2940
ggcaggaggc ggggccgaag gccgtgcctg accaatccgg agcacatagg agtctcagcc   3000
ccccgcccca aagcaagggg aagtcacgcg cctgtagcgc cagcgtgttg tgaaatgggg   3060
gcttgggggg gttggggccc tgactagtca aaacaaactc ccattgacgt caatggggtg   3120
gagacttgga aatccccgtg agtcaaaccg ctatccacgc ccattgatgt actgccaaaa   3180
ccgcatcatc atggtaatag cgatgactaa tacgtagatg tactgccaag taggaaagtc   3240
ccataaggtc atgtactggg cataatgcca ggcgggccat ttaccgtcat tgacgtcaat   3300
agggggcgta cttggcatat gatacacttg atgtactgcc aagtgggcag tttaccgtaa   3360
atactccacc cattgacgtc aatggaaagt ccctattggc gttactatgg gaacatacgt   3420
cattattgac gtcaatgggc gggggtcgtt gggcggtcag ccaggcgggc catttaccgt   3480
aagttatgta acgcctgcag gttaattaag aacatgtgag caaaaggcca gcaaaaggcc   3540
aggaaccgta aaaaggccgc gttgctggcg tttttccata ggctccgccc ccctgacgag   3600
```

```
catcacaaaa atcgacgctc aagtcagagg tggcgaaacc cgacaggact ataaagatac   3660

caggcgtttc cccctggaag ctccctcgtg cgctctcctg ttccgaccct gccgcttacc   3720

ggatacctgt ccgcctttct cccttcggga agcgtggcgc tttctcatag ctcacgctgt   3780

aggtatctca gttcggtgta ggtcgttcgc tccaagctgg gctgtgtgca cgaacccccc   3840

gttcagcccg accgctgcgc cttatccggt aactatcgtc ttgagtccaa cccggtaaga   3900

cacgacttat cgccactggc agcagccact ggtaacagga ttagcagagc gaggtatgta   3960

ggcggtgcta cagagttctt gaagtggtgg cctaactacg gctacactag aagaacagta   4020

tttggtatct gcgctctgct gaagccagtt accttcggaa aaagagttgg tagctcttga   4080

tccggcaaac aaaccaccgc tggtagcggt ggtttttttg tttgcaagca gcagattacg   4140

cgcagaaaaa aaggatctca agaagatcct ttgatctttt ctacggggtc tgacgctcag   4200

tggaacgaaa actcacgtta agggattttg gtcatggcta gttaattaac atttaaatca   4260

gcggccgcaa taaaatatct ttattttcat tacatctgtg tgttggtttt ttgtgtgaat   4320

cgtaactaac atacgctctc catcaaaaca aaacgaaaca aaacaaacta gcaaaatagg   4380

ctgtccccag tgcaagtgca ggtgccagaa catttctcta tcgaa                   4425
```

<210> SEQ ID NO 104
<211> LENGTH: 4419
<212> TYPE: DNA
<213> ORGANISM: Artificial Sequence
<220> FEATURE:
<223> OTHER INFORMATION: pCXCL13(3-87)-IgG4Fc

<400> SEQUENCE: 104

```
ggatctgcga tcgctccggt gcccgtcagt gggcagagcg cacatcgccc acagtccccg     60

agaagttggg gggaggggtc ggcaattgaa cgggtgccta gagaaggtgg cgcggggtaa    120

actgggaaag tgatgtcgtg tactggctcc gcctttttcc cgagggtggg ggagaaccgt    180

atataagtgc agtagtcgcc gtgaacgttc tttttcgcaa cgggtttgcc gccagaacac    240

agctgaagct tcgaggggct cgcatctctc cttcacgcgc ccgccgccct acctgaggcc    300

gccatccacg ccggttgagt cgcgttctgc cgcctcccgc ctgtggtgcc tcctgaactg    360

cgtccgccgt ctaggtaagt ttaaagctca ggtcgagacc gggcctttgt ccggcgctcc    420

cttggagcct acctagactc agccggctct ccacgctttg cctgaccctg cttgctcaac    480

tctacgtctt tgtttcgttt tctgttctgc gccgttacag atccaagctg tgaccggcgc    540

ctacctgaga tcaccggcga aggagggcca ccatgtacag gatgcaactc ctgtcttgca    600

ttgcactaag tcttgcactt gtcacgaatt cggaggtcta ttacacaagc ttgaggtgta    660

gatgtgtcca agagagctca gtctttatcc ctagacgctt cattgatcga attcaaatct    720

tgccccgtgg gaatggttgt ccaagaaaag aaatcatagt ctggaagaag aacaagtcaa    780

ttgtgtgtgt ggaccctcaa gctgaatgga tacaaagaat gatggaagta ttgagaaaaa    840

gaagttcttc aactctacca gttccagtgt ttaagagaaa gattcccccc ccatgcccat    900

catgcccagc acctgagttc ctggggggac catcagtctt cctgttcccc ccaaaaccca    960

aggacactct catgatctcc cggacccctg aggtcacgtg cgtggtggtg gacgtgagcc   1020

aggaagaccc cgaggtccag ttcaactggt acgtggatgg cgtggaggtg cataatgcca   1080

agacaaagcc gcgggaggag cagttcaaca gcacgtaccg tgtggtcagc gtcctcaccg   1140

tcctgcacca ggactggctg aacggcaagg agtacaagtg caaggtctcc aacaaaggcc   1200

tcccgtcctc catcgagaaa accatctcca aagccaaagg gcagccccga gagccacagg   1260
```

-continued

```
tgtacaccct gcccccatcc caggaggaga tgaccaagaa ccaggtcagc ctgacctgcc   1320
tggtcaaagg cttctacccc agcgacatcg ccgtggagtg ggagagcaat gggcagccgg   1380
agaacaacta caagaccacg cctcccgtgc tggactccga cggctccttc ttcctctaca   1440
gcaggctaac cgtggacaag agcaggtggc aggaggggaa tgtcttctca tgctccgtga   1500
tgcatgaggc tctgcacaac cactacacac agaagagcct ctccctgtct ccgggtaaat   1560
gagtgctagc tggccagaca tgataagata cattgatgag tttggacaaa ccacaactag   1620
aatgcagtga aaaaaatgct ttatttgtga aatttgtgat gctattgctt tatttgtaac   1680
cattataagc tgcaataaac aagttaacaa caacaattgc attcatttta tgtttcaggt   1740
tcagggggag gtgtgggagg ttttttaaag caagtaaaac ctctacaaat gtggtatgga   1800
attaattcta aaatacagca tagcaaaact ttaacctcca aatcaagcct ctacttgaat   1860
ccttttctga gggatgaata aggcataggc atcaggggct gttgccaatg tgcattagct   1920
gtttgcagcc tcaccttctt tcatggagtt taagatatag tgtattttcc caaggtttga   1980
actagctctt catttcttta tgttttaaat gcactgacct cccacattcc ctttttagta   2040
aaatattcag aaataattta aatacatcat tgcaatgaaa ataaatgttt tttattaggc   2100
agaatccaga tgctcaaggc ccttcataat atcccccagt ttagtagttg gacttaggga   2160
acaaaggaac ctttaataga aattggacag caagaaagcg agcttctagc ttatcctcag   2220
tcctgctcct ctgccacaaa gtgcacgcag ttgccggccg ggtcgcgcag ggcgaactcc   2280
cgcccccacg gctgctcgcc gatctcggtc atggccggcc cggaggcgtc ccggaagttc   2340
gtggacacga cctccgacca ctcggcgtac agctcgtcca ggccgcgcac ccacacccag   2400
gccagggtgt tgtccggcac cacctggtcc tggaccgcgc tgatgaacag ggtcacgtcg   2460
tcccggacca caccggcgaa gtcgtcctcc acgaagtccc gggagaaccc gagccggtcg   2520
gtccagaact cgaccgctcc ggcgacgtcg cgcgcggtga gcaccggaac ggcactggtc   2580
aacttggcca tgatggctcc tcctgtcagg agaggaaaga gaagaaggtt agtacaattg   2640
ctatagtgag ttgtattata ctatgcagat atactatgcc aatgattaat tgtcaaacta   2700
gggctgcagg gttcatagtg ccacttttcc tgcactgccc catctcctgc ccaccctttc   2760
ccaggcatag acagtcagtg acttaccaaa ctcacaggag ggagaaggca gaagcttgag   2820
acagacccgc gggaccgccg aactgcgagg ggacgtggct agggcggctt cttttatggt   2880
gcgccggccc tcggaggcag ggcgctcggg gaggcctagc ggccaatctg cggtggcagg   2940
aggcggggcc gaaggccgtg cctgaccaat ccggagcaca taggagtctc agccccccgc   3000
cccaaagcaa ggggaagtca cgcgcctgta gcgccagcgt gttgtgaaat gggggcttgg   3060
gggggttggg gccctgacta gtcaaaacaa actcccattg acgtcaatgg ggtggagact   3120
tggaaatccc cgtgagtcaa accgctatcc acgcccattg atgtactgcc aaaaccgcat   3180
catcatggta atagcgatga ctaatacgta gatgtactgc caagtaggaa agtcccataa   3240
ggtcatgtac tgggcataat gccaggcggg ccatttaccg tcattgacgt caatagggggg   3300
cgtacttggc atatgataca cttgatgtac tgccaagtgg gcagtttacc gtaaatactc   3360
cacccattga cgtcaatgga aagtccctat tggcgttact atgggaacat acgtcattat   3420
tgacgtcaat gggcgggggt cgttgggcgg tcagccaggc gggccattta ccgtaagtta   3480
tgtaacgcct gcaggttaat taagaacatg tgagcaaaag gccagcaaaa ggccaggaac   3540
cgtaaaaagg ccgcgttgct ggcgtttttc cataggctcc gcccccctga cgagcatcac   3600
aaaaatcgac gctcaagtca gaggtggcga aacccgacag gactataaag ataccaggcg   3660
```

tttcccccctg gaagctccct cgtgcgctct cctgttccga ccctgccgct taccggatac 3720
ctgtccgcct ttctcccttc gggaagcgtg gcgctttctc atagctcacg ctgtaggtat 3780
ctcagttcgg tgtaggtcgt tcgctccaag ctgggctgtg tgcacgaacc ccccgttcag 3840
cccgaccgct gcgccttatc cggtaactat cgtcttgagt ccaacccggt aagacacgac 3900
ttatcgccac tggcagcagc cactggtaac aggattagca gagcgaggta tgtaggcggt 3960
gctacagagt tcttgaagtg gtggcctaac tacggctaca ctagaagaac agtatttggt 4020
atctgcgctc tgctgaagcc agttaccttc ggaaaaagag ttggtagctc ttgatccggc 4080
aaacaaacca ccgctggtag cggtggtttt tttgtttgca agcagcagat tacgcgcaga 4140
aaaaaaggat ctcaagaaga tcctttgatc ttttctacgg ggtctgacgc tcagtggaac 4200
gaaaactcac gttaagggat tttggtcatg gctagttaat taacatttaa atcagcggcc 4260
gcaataaaat atctttattt tcattacatc tgtgtgttgg ttttttgtgt gaatcgtaac 4320
taacatacgc tctccatcaa aacaaaacga aacaaaacaa actagcaaaa taggctgtcc 4380
ccagtgcaag tgcaggtgcc agaacatttc tctatcgaa 4419

<210> SEQ ID NO 105
<211> LENGTH: 4419
<212> TYPE: DNA
<213> ORGANISM: Artificial Sequence
<220> FEATURE:
<223> OTHER INFORMATION: pCXCL13(3-87K/H-A)-IgG4Fc

<400> SEQUENCE: 105
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacctgaga tcaccggcga aggagggcca ccatgtacag gatgcaactc ctgtcttgca 600
ttgcactaag tcttgcactt gtcacgaatt cggaggtcta ttacacaagc ttgaggtgta 660
gatgtgtcca agagagctca gtctttatcc ctagacgctt cattgatgcc attcaaatct 720
tgccccgtgg gaatggttgt ccaagaaaag aaatcatagt ctgggctgcg aacgcttcaa 780
ttgtgtgtgt ggaccctcaa gctgaatgga tacaagccat gatggaagta ttggctgcgg 840
ctagttcttc aactctacca gttccagtgt ttgccgctgc gattcccccc ccatgcccat 900
catgcccagc acctgagttc ctggggggac catcagtctt cctgttcccc ccaaaaccca 960
aggacactct catgatctcc cggacccctg aggtcacgtg cgtggtggtg gacgtgagcc 1020
aggaagaccc cgaggtccag ttcaactggt acgtggatgg cgtggaggtg cataatgcca 1080
agacaaagcc gcgggaggag cagttcaaca gcacgtaccg tgtggtcagc gtcctcaccg 1140
tcctgcacca ggactggctg aacggcaagg agtacaagtg caaggtctcc aacaaaggcc 1200
tcccgtcctc catcgagaaa accatctcca aagccaaagg gcagccccga gagccacagg 1260
tgtacaccct gcccccatcc caggaggaga tgaccaagaa ccaggtcagc ctgacctgcc 1320

-continued tggtcaaagg cttctacccc agcgacatcg ccgtggagtg ggagagcaat gggcagccgg 1380
agaacaacta caagaccacg cctcccgtgc tggactccga cggctccttc ttcctctaca 1440
gcaggctaac cgtggacaag agcaggtggc aggaggggaa tgtcttctca tgctccgtga 1500
tgcatgaggc tctgcacaac cactacacac agaagagcct ctccctgtct ccgggtaaat 1560
gagtgctagc tggccagaca tgataagata cattgatgag tttggacaaa ccacaactag 1620
aatgcagtga aaaaaatgct ttatttgtga aatttgtgat gctattgctt tatttgtaac 1680
cattataagc tgcaataaac aagttaacaa caacaattgc attcatttta tgtttcaggt 1740
tcagggggag gtgtgggagg ttttttaaag caagtaaaac ctctacaaat gtggtatgga 1800
attaattcta aaatacagca tagcaaaact ttaacctcca aatcaagcct ctacttgaat 1860
ccttttctga gggatgaata aggcataggc atcaggggct gttgccaatg tgcattagct 1920
gtttgcagcc tcaccttctt tcatggagtt taagatatag tgtattttcc caaggtttga 1980
actagctctt catttcttta tgttttaaat gcactgacct cccacattcc ctttttagta 2040
aaatattcag aaataattta aatacatcat tgcaatgaaa ataaatgttt tttattaggc 2100
agaatccaga tgctcaaggc ccttcataat atccccagt ttagtagttg gacttaggga 2160
acaaaggaac ctttaataga aattggacag caagaaagcg agcttctagc ttatcctcag 2220
tcctgctcct ctgccacaaa gtgcacgcag ttgccggccg ggtcgcgcag ggcgaactcc 2280
cgcccccacg gctgctcgcc gatctcggtc atggccggcc cggaggcgtc ccggaagttc 2340
gtggacacga cctccgacca ctcggcgtac agctcgtcca ggccgcgcac ccacacccag 2400
gccagggtgt tgtccggcac cacctggtcc tggaccgcgc tgatgaacag ggtcacgtcg 2460
tcccggacca caccggcgaa gtcgtcctcc acgaagtccc gggagaaccc gagccggtcg 2520
gtccagaact cgaccgctcc ggcgacgtcg cgcgcggtga gcaccggaac ggcactggtc 2580
aacttggcca tgatggctcc tcctgtcagg agaggaaaga gaagaaggtt agtacaattg 2640
ctatagtgag ttgtattata ctatgcagat atactatgcc aatgattaat tgtcaaacta 2700
gggctgcagg gttcatagtg ccacttttcc tgcactgccc catctcctgc ccaccctttc 2760
ccaggcatag acagtcagtg acttaccaaa ctcacaggag ggagaaggca gaagcttgag 2820
acagacccgc gggaccgccg aactgcgagg ggacgtggct agggcggctt cttttatggt 2880
gcgccggccc tcggaggcag ggcgctcggg gaggcctagc ggccaatctg cggtggcagg 2940
aggcggggcc gaaggccgtg cctgaccaat ccggagcaca taggagtctc agcccccgc 3000
cccaaagcaa ggggaagtca cgcgcctgta gcgccagcgt gttgtgaaat gggggcttgg 3060
gggggttggg gccctgacta gtcaaaacaa actcccattg acgtcaatgg ggtggagact 3120
tggaaatccc cgtgagtcaa accgctatcc acgcccattg atgtactgcc aaaaccgcat 3180
catcatggta atagcgatga ctaatacgta gatgtactgc caagtaggaa agtcccataa 3240
ggtcatgtac tgggcataat gccaggcggg ccatttaccg tcattgacgt caataggggg 3300
cgtacttggc atatgataca cttgatgtac tgccaagtgg gcagtttacc gtaaatactc 3360
cacccattga cgtcaatgga aagtccctat tggcgttact atgggaacat acgtcattat 3420
tgacgtcaat gggcgggggt cgttgggcgg tcagccaggc gggccattta ccgtaagtta 3480
tgtaacgcct gcaggttaat taagaacatg tgagcaaaag gccagcaaaa ggccaggaac 3540
cgtaaaaagg ccgcgttgct ggcgtttttc cataggctcc gcccccctga cgagcatcac 3600
aaaaatcgac gctcaagtca gaggtggcga aacccgacag gactataaag ataccaggcg 3660
tttccccctg gaagctccct cgtgcgctct cctgttccga ccctgccgct taccggatac 3720

-continued

```
ctgtccgcct ttctcccttc gggaagcgtg gcgctttctc atagctcacg ctgtaggtat   3780

ctcagttcgg tgtaggtcgt tcgctccaag ctgggctgtg tgcacgaacc ccccgttcag   3840

cccgaccgct gcgccttatc cggtaactat cgtcttgagt ccaacccggt aagacacgac   3900

ttatcgccac tggcagcagc cactggtaac aggattagca gagcgaggta tgtaggcggt   3960

gctacagagt tcttgaagtg gtggcctaac tacggctaca ctagaagaac agtatttggt   4020

atctgcgctc tgctgaagcc agttaccttc ggaaaaagag ttggtagctc ttgatccggc   4080

aaacaaacca ccgctggtag cggtggtttt tttgtttgca agcagcagat tacgcgcaga   4140

aaaaaaggat ctcaagaaga tcctttgatc ttttctacgg ggtctgacgc tcagtggaac   4200

gaaaactcac gttaagggat tttggtcatg gctagttaat taacatttaa atcagcggcc   4260

gcaataaaat atctttattt tcattacatc tgtgtgttgg tttttgtgt gaatcgtaac   4320

taacatacgc tctccatcaa aacaaaacga aacaaaacaa actagcaaaa taggctgtcc   4380

ccagtgcaag tgcaggtgcc agaacatttc tctatcgaa                          4419


<210> SEQ ID NO 106
<211> LENGTH: 20
<212> TYPE: PRT
<213> ORGANISM: Artificial Sequence
<220> FEATURE:
<223> OTHER INFORMATION: IL-2 Secretion Signal

<400> SEQUENCE: 106

Met Tyr Arg Met Gln Leu Leu Ser Cys Ile Ala Leu Ser Leu Ala Leu
1               5                   10                  15

Val Thr Asn Ser
            20
```